United States Patent
Du-Cuny et al.

(10) Patent No.: US 10,590,079 B2
(45) Date of Patent: Mar. 17, 2020

(54) CYANO-SUBSTITUTED INDOLES AS LSD1 INHIBITORS

(71) Applicant: Novartis AG, Basel (CH)

(72) Inventors: Lei Du-Cuny, Kelkheim (DE); Feng He, Shanghai (CN); Qitao Xiao, Shanghai (CN); Guoliang Xun, Taicang (CN); Qiangang Zheng, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/081,543

(22) PCT Filed: Feb. 28, 2017

(86) PCT No.: PCT/IB2017/051181
§ 371 (c)(1),
(2) Date: Aug. 31, 2018

(87) PCT Pub. No.: WO2017/149463
PCT Pub. Date: Sep. 8, 2017

(65) Prior Publication Data
US 2019/0092724 A1    Mar. 28, 2019

(30) Foreign Application Priority Data

Mar. 1, 2016    (WO) ............... PCT/CN2016/075195

(51) Int. Cl.
| | |
|---|---|
| *A61K 31/404* | (2006.01) |
| *C07D 209/42* | (2006.01) |
| *C07D 209/14* | (2006.01) |
| *C07D 401/04* | (2006.01) |
| *C07D 401/06* | (2006.01) |
| *C07D 403/04* | (2006.01) |
| *C07D 405/04* | (2006.01) |
| *C07D 405/06* | (2006.01) |
| *A61K 31/4427* | (2006.01) |
| *A61K 31/443* | (2006.01) |
| *A61K 31/4433* | (2006.01) |
| *A61K 31/4439* | (2006.01) |
| *A61K 31/454* | (2006.01) |
| *A61K 31/506* | (2006.01) |
| *A61K 45/06* | (2006.01) |

(52) U.S. Cl.
CPC .......... *C07D 209/14* (2013.01); *A61K 31/404* (2013.01); *A61K 31/443* (2013.01); *A61K 31/4427* (2013.01); *A61K 31/4433* (2013.01); *A61K 31/4439* (2013.01); *A61K 31/454* (2013.01); *A61K 31/506* (2013.01); *A61K 45/06* (2013.01); *C07D 401/04* (2013.01); *C07D 401/06* (2013.01); *C07D 403/04* (2013.01); *C07D 405/04* (2013.01); *C07D 405/06* (2013.01)

(58) Field of Classification Search
CPC ........................... A61K 31/404; C07D 209/42
USPC .......................................... 514/415; 548/469
See application file for complete search history.

(56) References Cited

U.S. PATENT DOCUMENTS 5,621,002 A    4/1997    Bosslet

FOREIGN PATENT DOCUMENTS

| WO | WO 2004/078163 | 9/2004 |
| WO | WO 2015/134973 | 9/2015 |
| WO | WO 2017/149463 | 9/2017 |

OTHER PUBLICATIONS

Jordan, V. C. Nature Reviews: Drug Discovery, 2, 2003, 205.*
Hackam, et al. JAMA, 296(14), 2006, 1731-1732.*
Bai et al., "Inhibition enhancer of zeste homologue 2 promotes senescence and apoptosis induced by doxorubicin in p53 mutant gastric cancer cells" *Cell Prolif.* 47(3):211-8, 2014.
Chen et al., "Cyclin-dependent kinases regulate epigenetic gene silencing through phosphorylation of EZH2" *Nature Cell Biology* 12(11):1108-14, 2010.
Humphrey et al., "Stable Histone Deacetylase Complexes Distinguished by the Presence of SANT Domain Proteins CoREST/kiaa0071 and Mta-L1" *J. Biol. Chem.* 276:6817-6824, 2001.
Knutson et al., "Synergistic Anti-Tumor Activity of EZH2 Inhibitors and Glucocorticoid Receptor Agonists in Models of Germinal Center Non-Hodgkin Lymphomas" *PLoS One*, DOI:10.1371/journal.pone.0111840, 2014.
Mould et al., "Reversible Inhibitors of LSD1 as Therapeutic Agents in Acute Myeloid Leukemia: Clinical Significance and Progress to Date," *Med. Res. Rev.* 35(3):586-618, 2015.

(Continued)

*Primary Examiner* — Douglas M Willis
(74) *Attorney, Agent, or Firm* — Daniel E. Raymond; Genomics Institute of the Novartis Research Foundation

(57) ABSTRACT

A compound of Formula (I), or a pharmaceutically acceptable salt thereof, is provided that has been shown to be useful for the treatment of lysine (K)-specific demethylase 1A (LSD1)-mediated diseases or disorders:

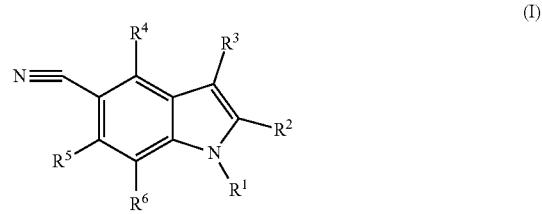

(I)

wherein $R^1$, $R^2$, $R^3$, $R^4$, $R^5$, and $R^6$ are as defined herein.

16 Claims, No Drawings
Specification includes a Sequence Listing.

(56) References Cited

OTHER PUBLICATIONS

Musch et al., "Nucleoside Drugs Induce Cellular Differentiation by Caspase-Dependent Degradation of Stem Cell Factors" *PLoS One* (5):e10726, 2010.
Shi et al., "Coordinated histone modifications mediated by a CtBP co-repressor complex" *Nature* 422:735-738, 2003.
Stazi et al., "LSD1 inhibitors: a patent review (2010-2015)" *Expert Opinion on Therapeutic Patents* 26(5):565-580, 2016.
Wu et al., "Polycomb protein EZH2 regulates cancer cell fate decision in response to DNA damage" *Cell Death Differ.* 18(11):1771-9, 2011.
Yamaguchi et al., "Histone deacetylase inhibitor (SAHA) and repression of EZH2 synergistically inhibit proliferation of gallbladder carcinoma" *Cancer Sci.* 101(2):355-62, 2010.
Zeng et al., "Phosphorylation of EZH2 by CDK1 and CDK2" *Cell Cycle* 10(4):579-83, 2011.
Zheng et al., "A Systematic Review of Histone Lysine-Specific Demethylase 1 and Its Inhibitors" *Med. Res. Rev.* 35(5):1032-1071, 2015.

\* cited by examiner

CYANO-SUBSTITUTED INDOLES AS LSD1 INHIBITORS

CROSS-REFERENCE TO RELATED APPLICATIONS

This application is the U.S. National Stage of International Application No. PCT/IB2017/051181, filed Feb. 28, 2017, which claims the benefit of priority to International Application Serial No. PCT/CN2016/075195, filed Mar. 1, 2016, the contents of which is incorporated herein by reference.

FIELD OF THE INVENTION

The present invention relates to cyano-substituted indole compounds, compositions comprising such compounds, and their use for the treatment of lysine (K)-specific demethylase 1A (LSD1)-mediated diseases or disorders.

BACKGROUND

Post-translational modifications on the lysine chains of histones are a major way by which chromatin structure is modified to regulate gene expression. Methylation and acetylation are examples of such chemical modifications. A number of enzymes that effect histone modifications have been discovered and due to their effects on gene expression and cellular function, they have been targeted for therapeutic intervention. LSD1 is a histone demethylase that uses flavin adenine dinucleotide (FAD) as cofactor. Methylated histones H3K4 and H3K9 have been shown to be targets of LSD1. Other non-histone substrates include p53, E2F1, DNMT1 and STAT3.

LSD1 consists of three major domains: The N-terminal Swi3-Rsc8-Moira (SWIRM) domain which functions in nucleosome targeting, the tower domain which participates in protein-protein interactions and the C-terminal catalytic domain that has similarity to the monoamine oxidases. LSD1 also shares homology with another lysine demethylase LSD2 but it is very distinct from the Jumomji type histone demethylases. The enzymatic activity of LSD1 is dependent on the redox process of FAD and the protonated nitrogen in the methylated lysine is thought to limit its activity to mono- and di-methylated lysines in position 4 or 9 of histone H3 (H3K4 or H3K9).

LSD1 has been reported to be involved in a number of biological processes, including cell proliferation, epithelial-mesenchymal transition, stem cell biology and malignant transformation of cells. It has also been shown to be involved in cell differentiation. LSD1 has been implicated in a number of myeloproliferative and lymphoproliferative diseases such as acute myeloid leukemia (AML) and acute lymphoblastic leukemia (ALL). It has also been shown to be linked to the aberrant function of the androgen receptor in prostate cancer as well as other cancers such as Small Cell Lung cancer. Reviews describing a variety of reversible and irreversible LSD1 inhibitors were published by Mould, Daniel P., et al., "Reversible Inhibitors of LSD1 as Therapeutic Agents in Acute Myeloid Leukemia: Clinical Significance and Progress to Date," Med. Res. Rev., 35, No. 3, 586-618, (2015); and Xheng, Yi-Choa, et. al., "A Systematic Review of Histone Lysine-Specific Demethylase 1 and Its Inhibitors" Med. Res. Rev., 35, No. 5, 1032-1071, (2015). Therefore, LSD1 has been a target for anti-cancer drug discovery.

As a drug discovery target, LSD1 has a fair degree of structural similarity to the Flavin-dependent Monoamine oxidases (MAOs). Both LSD1 and Monoamine oxidases utilize FAD as cofactor, e.g., as reported by G. W. Humphrey et. al., "Stable Histone Deacetylase Complexes Distinguished by the Presence of SANT Domain Proteins CoREST/kiaa0071 and Mta-L1" J. Biol. Chem, 276, 6817-6824 (2001) and Shi, et. al., "Coordinated histone modifications mediated by a CtBP co-repressor complex" Nature, 422, 735-738(2003). Thus a number of MAO inhibitors have been shown to inhibit LSD1 through irreversible interaction of FAD. Attempts have also been made to discover reversible inhibitors of LSD1.

In summary, LSD1 provides a pharmacological target for cancer and other disorders that associate with LSD1's activity. In particular, the need exists for novel small molecules that inhibit the activity of LSD1, which includes both irreversible and reversible inhibitors.

SUMMARY

The present invention provides a compound of Formula (I):

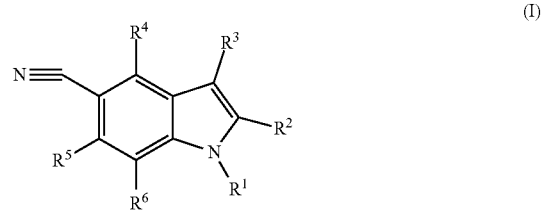

wherein $R^1$, $R^2$, $R^3$, $R^4$, $R^5$, and $R^6$ are as defined herein, including stereoisomers, tautomers, pharmaceutically acceptable salts, polymorphs, or solvates thereof, which are useful for the treatment of LSD1-mediated diseases or disorders.

The present invention also provides processes and intermediates for making the compounds of the present invention.

The present invention also provides pharmaceutical compositions comprising at least one of the compounds of the present invention and at least one pharmaceutically acceptable carrier, diluent or excipient. The pharmaceutical composition may further comprise at least one additional therapeutic agent. Of particular interest are additional therapeutic agents selected from: other anti-cancer agents, immunomodulators, anti-allergic agents, anti-nausea agents (or antiemetics), pain relievers, cytoprotective agents, and combinations thereof.

The compounds of the present invention may be used in the treatment of diseases or disorders mediated by LSD1.

The compounds of the present invention may be used in therapy.

The compounds of the present invention may be used for the manufacture of a medicament for the treatment of diseases or disorders mediated by LSD1.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is a compound of the present invention and the second therapeutic agent is one other type of therapeutic agent.

Examples of diseases or disorders mediated by LSD1 include, but are not limited to, B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is an LSD1 inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, prostate cancer and hepatocellular carcinoma.

The compounds of the present invention can be used alone, in combination with other compounds of the present invention, or in combination with one or more, preferably one to two other agent(s), simultaneously or sequentially.

Other features and advantages of the present invention will be apparent from the following detailed description and claims.

DETAILED DESCRIPTION

I. Compounds

In a first aspect, the present invention provides, inter alia, a compound of Formula (I):

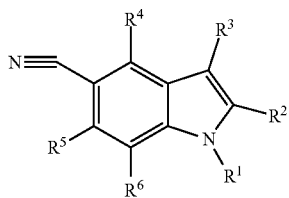
(I)

or a pharmaceutically acceptable salt thereof, wherein:

$R^1$ is independently selected from: $C_1$-$C_6$ alkyl substituted with one to two $R^a$, $C_2$-$C_6$ alkenyl substituted with one to two $R^a$, —(CH)$_n$—($C_3$-$C_6$ cycloalkyl substituted with one to two $R^d$), —(CH)$_n$-(phenyl substituted with zero to three $R^b$), —(CH)$_n$-(6-membered heteroaryl comprising carbon atoms and 1-2 heteroatoms selected from N and $NR^a$, where said heteroaryl is substituted with zero to three $R^b$),

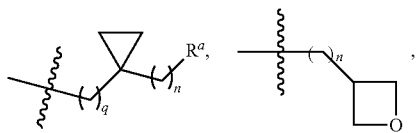

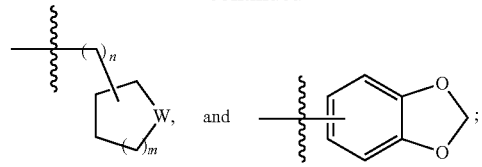

$R^2$ is independently selected from: H, halogen and $C_1$-$C_4$ alkyl;

$R^3$ is independently selected from:

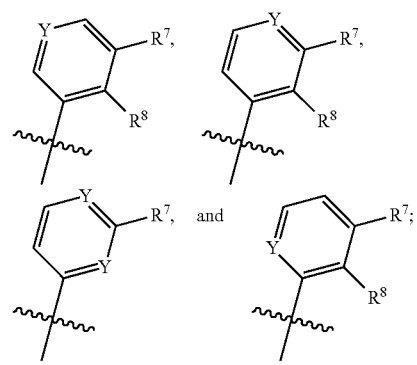

$R^4$ is independently selected from: H, halogen and $C_1$-$C_4$ alkyl;

$R^5$ is independently selected from: H, halogen, $C_1$-$C_4$ alkyl, $C_1$-$C_4$ haloalkyl and $C_3$-$C_6$ cycloalkyl;

$R^6$ is independently selected from: H, halogen and $C_1$-$C_4$ alkyl;

$R^7$ is, at each occurrence, independently selected from: NH$_2$, NH($C_1$-$C_4$ alkyl), and NHCO($C_1$-$C_4$ alkyl);

$R^8$ is, at each occurrence, independently selected from: H, halogen, $C_1$-$C_4$ alkyl, and $C_1$-$C_4$ haloalkyl;

Y is, at each occurrence, independently selected from: CH and N;

W is independently selected from: O and NH;

$R^a$ is independently selected from: OH, $C_1$-$C_4$ alkoxy, CO$_2$($C_1$-$C_4$ alkyl), CONR$^e$R$^f$, and NHR$^e$;

$R^b$ is independently selected from: halogen, $C_1$-$C_4$ haloalkoxy, OH, CN, CO$_2$($C_1$-$C_4$ alkyl), CONR$^e$R$^f$, NHR$^e$ $C_1$-$C_4$ alkyl substituted with zero to one $R^c$, and $C_1$-$C_4$ alkoxy substituted with zero to one $R^c$;

$R^c$ is independently selected from: OH, $C_1$-$C_4$ alkoxy, CO$_2$($C_1$-$C_4$ alkyl), CONR$^e$R$^f$, and NHR$^e$;

$R^d$ is independently selected from: OH, =O, and NH($C_1$-$C_4$ alkyl);

$R^e$ is independently selected from: H, $C_1$-$C_4$ alkyl, and CO($C_1$-$C_4$ alkyl);

$R^f$ is independently selected from: H and $C_1$-$C_4$ alkyl;

m is independently selected from: 1 and 2;

n, at each occurrence, is independently selected from: 0 and 1; and q is independently selected from: 1, 2 and 3.

In a second aspect, the present invention provides a compound of Formula (I) or a pharmaceutically acceptable salt thereof, within the scope of the first aspect; wherein:

$R^1$ is independently selected from: $C_1$-$C_6$ alkyl substituted with one $R^a$, $C_2$-$C_6$ alkenyl substituted with one $R^a$, —(CH)$_n$—($C_3$-$C_6$ cycloalkyl substituted with one $R^d$), —(CH)$_n$-(phenyl substituted with zero to two $R^b$), —(CH)$_n$-(6-membered heteroaryl comprising carbon atoms and 1-2 heteroatoms selected from N and NR$^a$, where said heteroaryl is substituted with zero to two R$^b$),

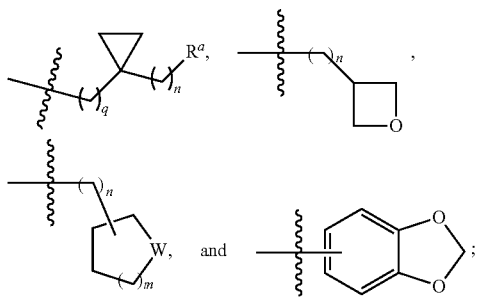

R$^2$ is independently selected from: H, halogen and C$_1$-C$_4$ alkyl;
R$^3$ is independently selected from:

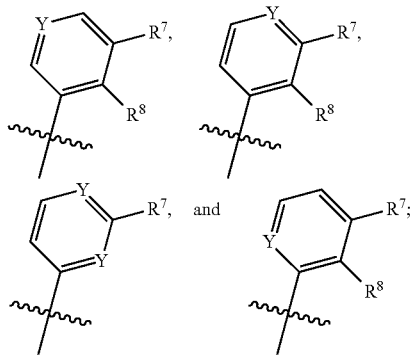

R$^4$ is independently selected from: H, halogen and C$_1$-C$_4$ alkyl;
R$^5$ is independently selected from: H, halogen, C$_1$-C$_4$ alkyl, C$_1$-C$_4$ haloalkyl and C$_3$-C$_6$ cycloalkyl;
R$^6$ is independently selected from: H, halogen and C$_1$-C$_4$ alkyl;
R$^7$ is, at each occurrence, independently selected from: NH$_2$, NH(C$_1$-C$_4$ alkyl), and NHCO(C$_1$-C$_4$ alkyl);
R$^8$ is, at each occurrence, independently selected from: H, C$_1$-C$_4$ alkyl, and C$_1$-C$_4$ haloalkyl;
Y is, at each occurrence, independently selected from: CH and N;
W is independently selected from: O and NH;
R$^a$ is independently selected from: OH, C$_1$-C$_4$ alkoxy, CO$_2$(C$_1$-C$_4$ alkyl), and CONH$_2$;
R$^b$ is independently selected from: halogen, C$_1$-C$_4$ haloalkoxy, OH, CN, CO$_2$(C$_1$-C$_4$ alkyl), CONH$_2$, C$_1$-C$_4$ alkyl substituted with zero to one R$^c$, and C$_1$-C$_4$ alkoxy substituted with zero to one R$^c$;
R$^c$ is independently selected from: OH, C$_1$-C$_4$ alkoxy, CO$_2$(C$_1$-C$_4$ alkyl), and CONH$_2$;
R$^d$ is independently selected from: OH, =O, and NH(C$_1$-C$_4$ alkyl);
m is independently selected from: 1 and 2;
n, at each occurrence, is independently selected from: 0 and 1; and
q is independently selected from: 1, 2 and 3.

In a third aspect, the present invention provides a compound of Formula (I-1):

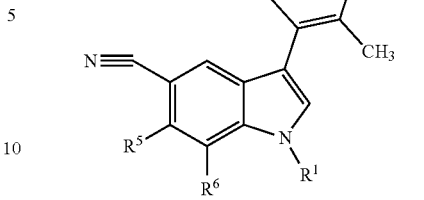

or a pharmaceutically acceptable salt thereof, within the scope of the first or second aspect; wherein:
R$^1$ is independently selected from: C$_2$-C$_6$ alkyl substituted with one R$^a$, C$_2$-C$_6$ alkenyl substituted with one R$^a$, —(CH)$_n$—(C$_4$-C$_6$ cycloalkyl substituted with one R$^d$), —(CH)$_n$-(phenyl substituted with zero to two R$^b$), —(CH)$_n$-(pyridyl substituted with zero to two R$^b$), piperidinyl,

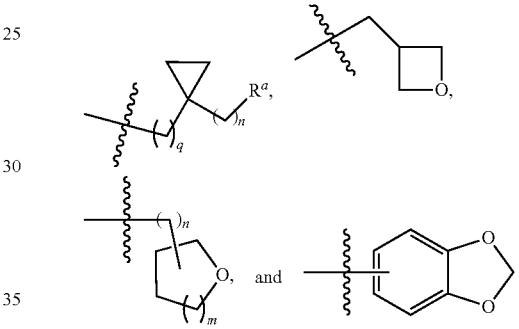

R$^5$ is independently selected from: H, halogen, C$_1$-C$_4$ alkyl, CF$_3$, and cyclopropyl;
R$^6$ is independently selected from: H and C$_1$-C$_4$ alkyl;
Y is independently selected from: CH and N;
R$^a$ is independently selected from: OH, C$_1$-C$_4$ alkoxy, CO$_2$(C$_1$-C$_4$ alkyl), and CONH$_2$;
R$^b$ is independently selected from: halogen, C$_1$-C$_4$ haloalkoxy, OH, CN, CO$_2$(C$_1$-C$_4$ alkyl), CONH$_2$, C$_1$-C$_4$ alkyl substituted with zero to one R$^c$, and C$_1$-C$_4$ alkoxy substituted with zero to one R$^c$;
R$^c$ is independently selected from: OH, C$_1$-C$_4$ alkoxy, CO$_2$(C$_1$-C$_4$ alkyl), and CONH$_2$;
R$^d$ is independently selected from: OH, =O, and NH(C$_1$-C$_4$ alkyl);
m is independently selected from: 1 and 2;
n, at each occurrence, is independently selected from: 0 and 1; and
q is independently selected from: 1, 2 and 3.

In a fourth aspect, the present invention provides a compound of Formula (I) or (I-1), or a pharmaceutically acceptable salt thereof, within the scope of any of the above aspects; wherein:
R$^1$ is independently selected from: C$_1$-C$_6$ alkyl substituted with one R$^a$, C$_2$-C$_6$ alkenyl substituted with one R$^a$, C$_4$-C$_6$ cycloalkyl substituted with one R$^d$, —(CH)$_n$-(phenyl substituted with one to two R$^b$),
—(CH)$_n$-(pyridyl substituted with one to two R$^b$), piperidinyl,

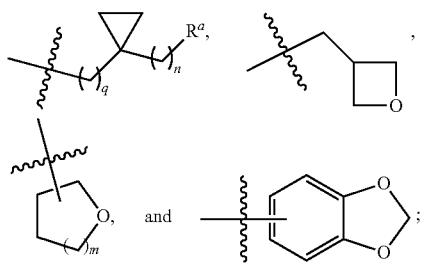

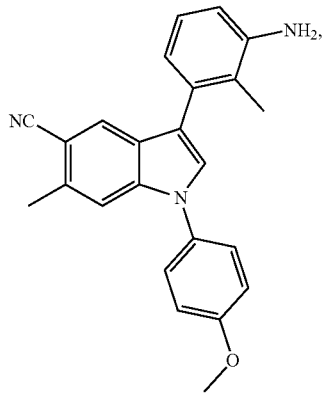

$R^5$ is independently selected from: H, F, Cl, $CH_3$, $CF_3$, and cyclopropyl;

$R^6$ is independently selected from: H and $CH_3$;

Y is independently selected from: CH and N;

$R^a$ is independently selected from: OH, $OCH_3$, $CO_2CH_3$, and $CONH_2$;

$R^b$ is independently selected from: F, Cl, OH, $OCF_3$, CN, $CO_2CH_3$, $CONH_2$, $C_1$-$C_4$ alkyl substituted with zero to one $R^c$, and $C_1$-$C_4$ alkoxy substituted with zero to one $R^c$, $R^c$ is independently selected from: OH, $OCH_3$, $CO_2CH_3$, and $CONH_2$;

$R^d$ is independently selected from: OH, =O, and $NHCH_3$;

m is independently selected from: 1 and 2;

n, at each occurrence, is independently selected from: 0 and 1; and q is independently selected from: 1 and 2.

In a fifth aspect, the present invention provides a compound of Formula (I) or (I-1), or a pharmaceutically acceptable salt thereof, within the scope of any of the above aspects; wherein:

$R^1$ is independently selected from: $C_4$-$C_6$ cycloalkyl substituted with one $R^d$, phenyl substituted with one to two $R^b$, and pyridyl substituted with one to two $R^b$;

$R^5$ is independently selected from: H, F, Cl, and $CH_3$;

$R^6$ is independently selected from: H and $CH_3$;

Y is independently selected from: CH and N;

$R^b$ is independently selected from: F, Cl, OH, $OCF_3$, CN, $CO_2CH_3$, $CONH_2$, $C_1$-$C_4$ alkyl substituted with zero to one $R^c$, and $C_1$-$C_4$ alkoxy substituted with zero to one $R^c$;

$R^c$ is independently selected from: OH, $OCH_3$, $CO_2CH_3$, and $CONH_2$; and $R^d$ is independently selected from: OH, =O, and $NHCH_3$.

In a sixth aspect, the present invention provides a compound of Formula (I) or (I-1), or a pharmaceutically acceptable salt thereof, within the scope of any of the above aspects; wherein:

$R^1$ is independently selected from: $C_4$-$C_6$ cycloalkyl substituted with one $R^d$ or phenyl substituted with one to two $R^b$;

$R^5$ is independently selected from: H, F, Cl, and $CH_3$;

$R^6$ is independently selected from: H and $CH_3$;

Y is independently selected from: CH and N;

$R^b$ is independently selected from: F, Cl, OH, $OCF_3$, $C_1$-$C_4$ alkyl and $C_1$-$C_4$ alkoxy; and $R^d$ is independently selected from: OH and $NHCH_3$.

In a seventh aspect, the present invention provides a compound selected from the exemplified examples or a pharmaceutically acceptable salt thereof, including all compounds of Examples 1 to 102.

In an eighth aspect, the present invention provides a compound selected from:

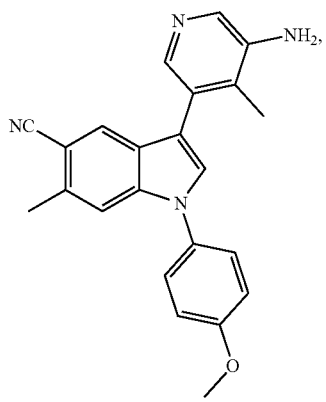

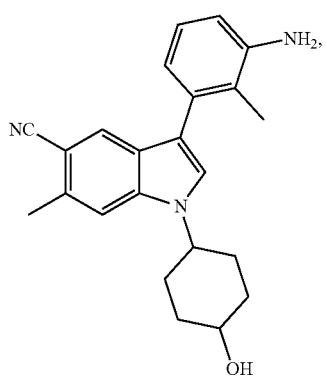

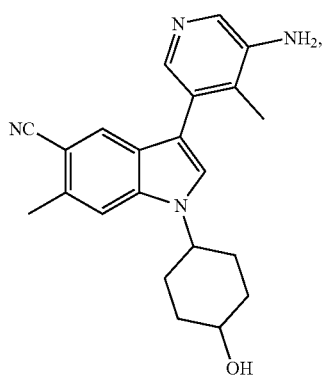

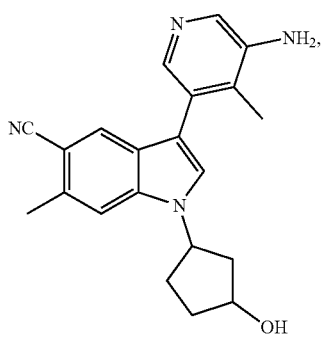
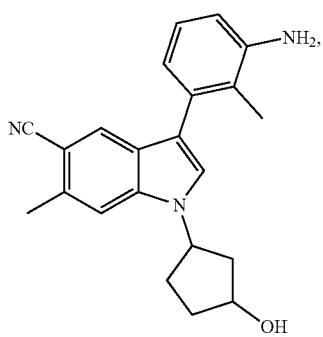
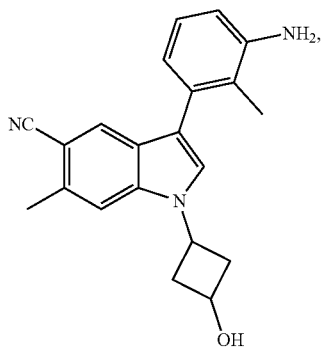
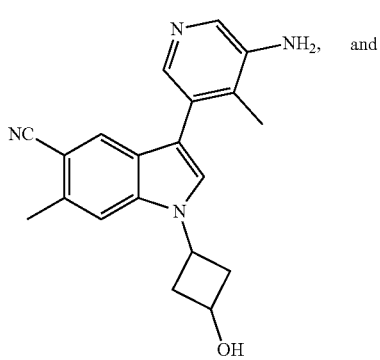
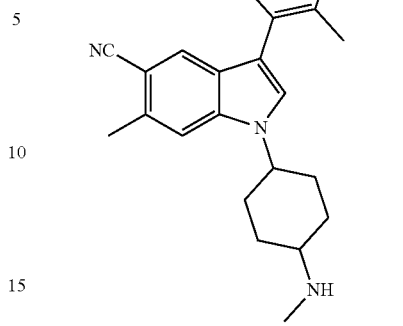
or a pharmaceutically acceptable salt thereof.
In a ninth aspect, the present invention provides a compound selected from:
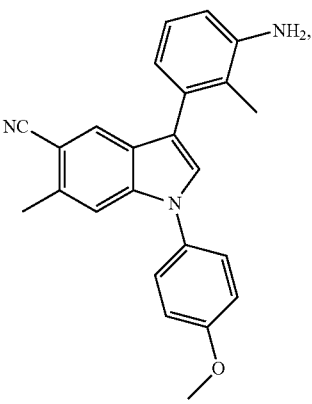
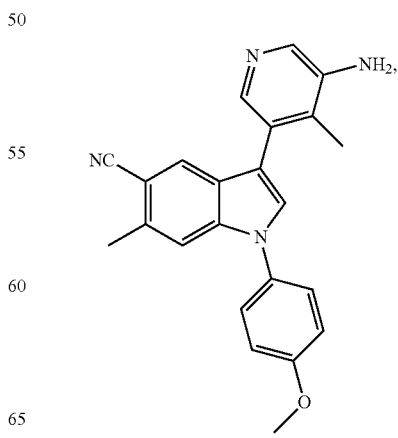

-continued
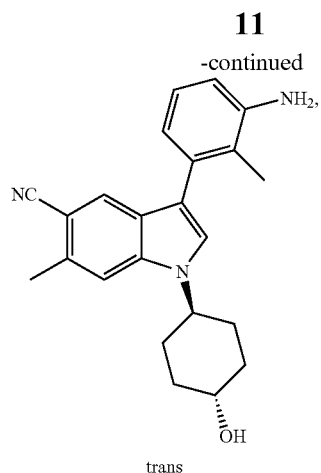
trans
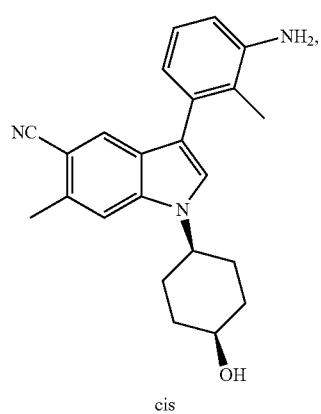
cis
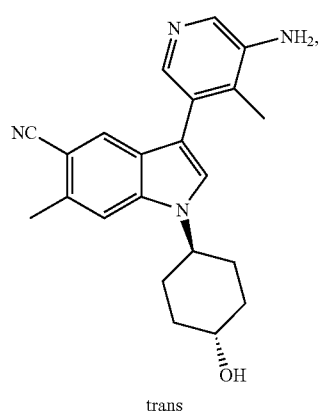
trans
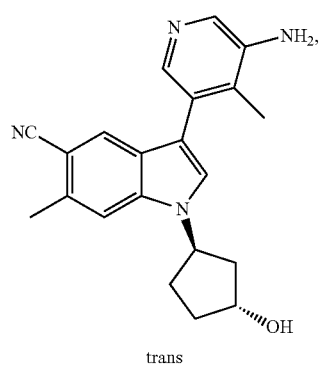
trans
-continued
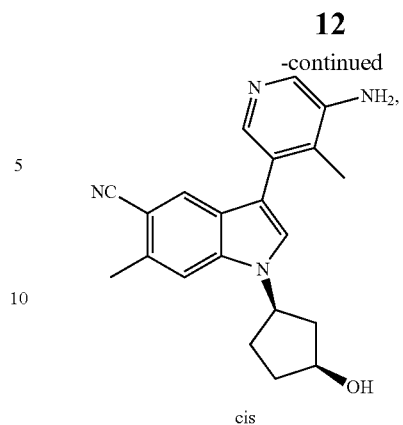
cis
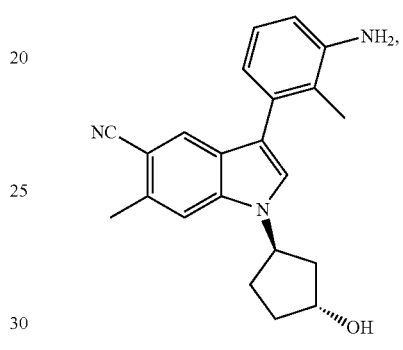
trans
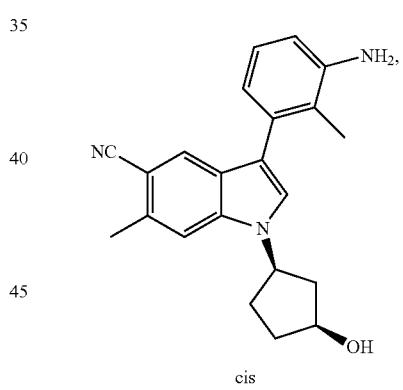
cis
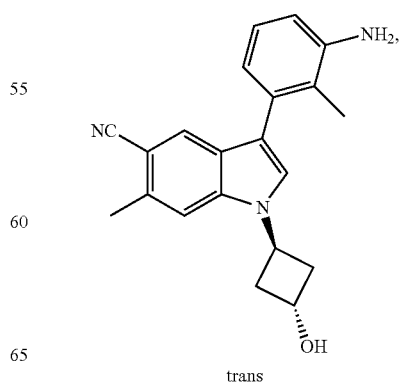
trans

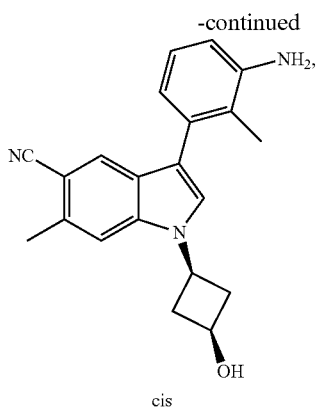
cis

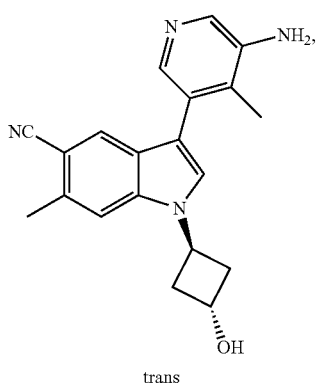
trans

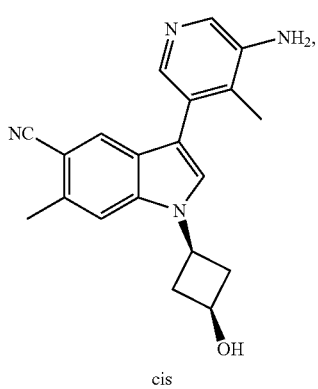
cis

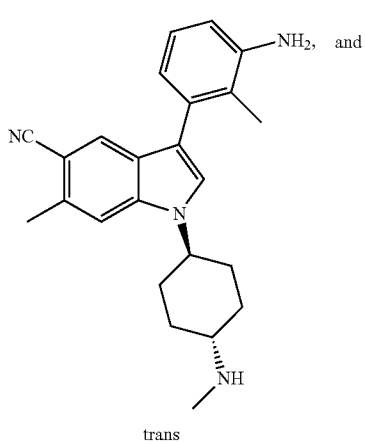
trans

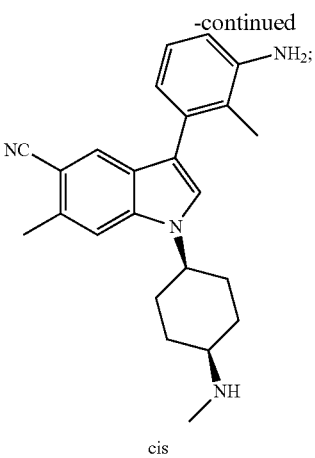
cis or a pharmaceutically acceptable salt thereof.

In another embodiment, $R^1$ is independently selected from: $C_2$-$C_6$ alkyl substituted with one $R^a$, $C_2$-$C_6$ alkenyl substituted with one $R^a$, —(CH)$_n$—($C_4$-$C_6$ cycloalkyl substituted with one $R^e$), —(CH)$_n$-(phenyl substituted with zero to two $R^b$), —(CH)$_n$-(pyridyl substituted with zero to two $R^b$), piperidinyl,

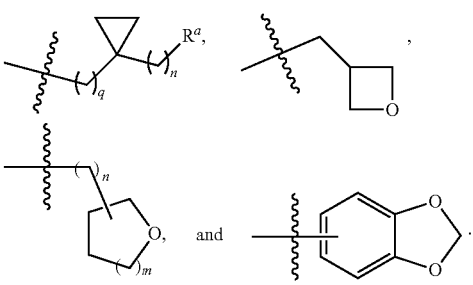

In another embodiment, $R^1$ is independently selected from: $C_1$-$C_6$ alkyl substituted with one $R^a$, $C_2$-$C_6$ alkenyl substituted with one $R^a$, cycloalkyl substituted with one $R^d$, —(CH)$_n$-(phenyl substituted with one to two $R^b$), —(CH)$_n$-(pyridyl substituted with one to two $R^b$), piperidinyl,

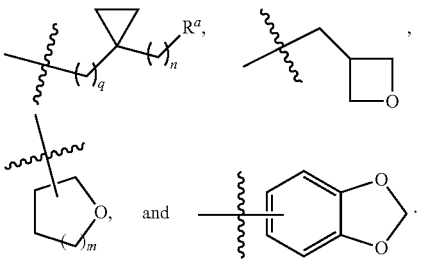

In another embodiment, $R^1$ is independently selected from: $C_4$-$C_6$ cycloalkyl substituted with one $R^d$, phenyl substituted with one to two $R^b$, and pyridyl substituted with one to two $R^b$.

In another embodiment, $R^1$ is independently selected from: $C_4$-$C_6$ cycloalkyl substituted with one $R^d$ and phenyl substituted with one to two $R^b$.

In another embodiment, $R^1$ is independently $C_4$-$C_6$ cycloalkyl substituted with one $R^d$.

In another embodiment, $R^1$ is independently phenyl substituted with one to two $R^b$ and pyridyl substituted with one to two $R^b$.

In another embodiment, $R^1$ is independently phenyl substituted with one to two $R^b$.

In another embodiment, $R^1$ is independently pyridyl substituted with one to two $R^b$.

In another embodiment, $R^5$ is independently selected from: H, halogen, $C_1$-$C_4$ alkyl, $CF_3$, and cyclopropyl.

In another embodiment, $R^5$ is independently selected from: H, F, Cl, $CH_3$, $CF_3$, and cyclopropyl.

In another embodiment, $R^5$ is independently selected from: H, F, Cl, and $CH_3$.

In another embodiment, $R^6$ is independently selected from: H and $C_1$-$C_4$ alkyl.

In another embodiment, $R^6$ is independently selected from: H and $CH_3$.

In another embodiment, Y is CH.

In another embodiment, Y is N.

In another embodiment, the compounds of the present invention have $IC_{50}$ values ≤1 µM, using the LSD1 LC-MS and/or LSD1 anti-proliferation assay disclosed herein, preferably, $IC_{50}$ values ≤0.5 µM, more preferably, $IC_{50}$ values ≤0.1 µM.

II. Other Embodiments

In another embodiment, the present invention provides a composition comprising at least one of the compounds of the present invention or a pharmaceutically acceptable salt thereof.

In another embodiment, the present invention provides a pharmaceutical composition comprising at least one of the compounds of the present invention or a pharmaceutically acceptable salt thereof and at least one pharmaceutically acceptable carrier, diluent or excipient.

In another embodiment, the present invention provides a pharmaceutical composition, comprising a therapeutically effective amount of at least one of the compounds of the present invention or a pharmaceutically acceptable salt thereof and at least one pharmaceutically acceptable carrier, diluent or excipient.

The pharmaceutical composition is useful in the treatment of diseases or disorders mediated by LSD1.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment of diseases or disorders mediated by LSD1, alone, or optionally in combination with another compound of the present invention and/or at least one other type of therapeutic agent.

In another embodiment, the present invention provides a method for the treatment of diseases or disorders mediated by LSD1, comprising administering to a patient in need of such treatment a therapeutically effective amount of at least one of the compounds of the present invention, alone, or optionally in combination with another compound of the present invention and/or at least one other type of therapeutic agent.

In another embodiment, the present invention provides a method for the treatment of diseases or disorders mediated by LSD1, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment of diseases or disorders mediated by LSD1, alone, or optionally in combination with another compound of the present invention and/or at least one other type of therapeutic agent.

In another embodiment, the present invention provides a combined preparation of a compound of the present invention and additional therapeutic agent(s) for use in therapy.

In another embodiment, the present invention provides a combination of a compound of the present invention and additional therapeutic agent(s) for simultaneous or separate use in therapy.

In another embodiment, the present invention provides a combined preparation of a compound of the present invention and additional therapeutic agent(s) for simultaneous, separate or sequential use in the treatment of diseases or disorders mediated by LSD1. The compound may be administered as a pharmaceutical composition described herein.

Examples of diseases or disorders mediated by LSD1 include, but are not limited to, B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is an LSD1 inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, prostate cancer and hepatocellular carcinoma.

In another embodiment, additional therapeutic agent(s) used in combined pharmaceutical compositions or combined methods or combined uses, are selected from one or more, preferably one to three, of the following therapeutic agents: other anti-cancer agents, immunomodulators, anti-allergic agents, anti-nausea agents (or anti-emetics), pain relievers, cytoprotective agents, and combinations thereof.

Various (enumerated) embodiments of the invention are described herein. It will be recognized that features specified in each embodiment may be combined with other specified features to provide further embodiments of the present invention. It is also understood that each individual element of the embodiments is its own independent embodiment.

Other features of the present invention should become apparent in the course of the above descriptions of exemplary embodiments that are given for illustration of the invention and are not intended to be limiting thereof.

III. Definitions

The general terms used hereinbefore and hereinafter preferably have within the context of this invention the following meanings, unless otherwise indicated, where more general terms whereever used may, independently of each other, be replaced by more specific definitions or remain, thus defining more detailed embodiments of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "a," "an," "the" and similar terms used in the context of the present invention (especially in the context of the claims) are to be construed to cover both the singular and plural unless otherwise indicated herein or clearly contradicted by the context.

As used herein, the term "heteroatoms" refers to nitrogen (N), oxygen (O) or sulfur (S) atoms, in particular nitrogen or oxygen.

Unless otherwise indicated, any heteroatom with unsatisfied valences is assumed to have hydrogen atoms sufficient to satisfy the valences.

As used herein, the terms "alkyl" refers to a hydrocarbon radical of the general formula $C_nH_{2n+1}$. The alkane radical may be straight or branched. For example, the term "$C_1$-$C_{10}$ alkyl" or "$C_1$ to $C_{10}$ alkyl" refers to a monovalent, straight, or branched aliphatic group containing 1 to 10 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like).

The term "alkylene" refers to a divalent alkyl group. For example, the term "$C_1$-$C_6$ alkylene" or "$C_1$ to $C_6$ alkylene" refers to a divalent, straight, or branched aliphatic group containing 1 to 6 carbon atoms (e.g., methylene (—$CH_2$—), ethylene (—$CH_2CH_2$—), n-propylene (—$CH_2CH_2CH_2$—), iso-propylene (—$CH(CH_3)CH_2$—), n-butylene, sec-butylene, iso-butylene, tert-butylene, n-pentylene, isopentylene, neopentylene, n-hexylene and the like).

The term "alkoxy" refers to an alkyl linked to an oxygen, which may also be represented as —O—R or —OR, wherein the R represents the alkyl group. "$C_1$-$C_6$ alkoxy" or "$C_1$ to $C_6$ alkoxy" is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halogen" or "halo" may be fluorine, chlorine, bromine or iodine (preferred halogens as substituents are fluorine and chlorine).

"Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" represents a haloalkyl group as defined above with the indicated number of carbon atoms attached through an oxygen bridge. For example, "$C_1$-$C_6$ haloalkoxy" or "$C_1$ to $C_6$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "oxo" or —C(O)— refers to a carbonyl group. For example, a ketone, aldehyde, or part of an acid, ester, amide, lactone, or lactam group.

The term "cycloalkyl" refers to nonaromatic carbocyclic ring that is fully hydrogenated ring, including mono-, bi- or poly-cyclic ring systems. "$C_3$-$C_8$ cycloalkyl" or "$C_3$ to $C_8$ cycloalkyl" is intended to include $C_3$, $C_4$, $C_5$, $C_6$, $C_7$ and $C_8$ cycloalkyl groups. Example cycloalkyl groups include, but are not limited to, cyclopropyl, cyclobutyl, cyclopentyl, cyclohexyl, and norbornyl.

The term "aryl" refers to 6- to 10-membered aromatic carbocyclic moieties having a single (e.g., phenyl) or a fused ring system (e.g., naphthalene.). A typical aryl group is phenyl group.

The term "benzyl", as used herein, refers to a methyl group on which one of the hydrogen atoms is replaced by a phenyl group.

"Heterocycloalkyl" means cycloalkyl, as defined in this application, provided that one or more of the ring carbons indicated, are replaced by a moiety selected from —O—, —N=, —NR—, —C(O)—, —S—, —S(O)— and —S(O)$_2$—, wherein R is hydrogen, $C_{1-4}$alkyl or a nitrogen protecting group (for example, carbobenzyloxy, p-methoxybenzyl carbonyl, t-butoxycarbonyl, acetyl, benzoyl, benzyl, p-methoxy-benzyl, p-methoxy-phenyl, 3,4-dimethoxybenzyl, and the like). For example, a 3 to 8 membered heterocycloalkyl includes epoxy, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholino, piperazinyl, piperidinyl, piperidinylone, pyrazolidinyl, hexahydropyrimidinyl, 1,4-dioxa-8-aza-spiro[4.5]dec-8-yl, thiomorpholino, sulfanomorpholino, sulfonomorpholino, octahydropyrrolo[3,2-b]pyrrolyl, and the like.

The term "partially saturated heterocycle" refers to a nonaromatic ring that is partially hydrogenated and may exist as a single ring, bicyclic ring (including fused rings). Unless specified otherwise, said heterocyclic ring is generally a 5- to 10-membered ring containing 1 to 3 heteroatoms selected from —O—, —N=, —NR—, and —S—, (preferably 1 or 2 heteroatoms). Partially saturated heterocyclic rings include groups such as dihydrofuranyl, dihydrooxazolyl, dihydropyridinyl, imidazolinyl, 1H-dihydroimidazolyl, 2H-pyranyl, 4H-pyranyl, 2H-chromenyl, oxazinyl and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like).

The term "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 12-membered ring containing 1 to 3 heteroatoms (preferably 1 or 2 heteroatoms) independently selected from sulfur, oxygen and/or nitrogen. When the term "partially or fully saturated heterocycle" is used, it is intended to include "heterocycloalkyl", and "partially saturated heterocycle". Examples of spiral rings include 2,6-diazaspiro[3.3]heptanyl, 3-azaspiro[5.5]undecanyl, 3,9-diazaspiro[5.5]undecanyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to four heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a heteroaryl fused to an aryl (e.g., phenyl).

When the term "heterocycle" is used, it is intended to include "heterocycloalkyl", "partially or fully saturated heterocycle", "partially saturated heterocycle", "fully saturated heterocycle" and "heteroaryl".

The term "counter ion" is used to represent a negatively charged species such as chloride, bromide, hydroxide, acetate, and sulfate or a positively charged species such as sodium (Na+), potassium (K+), ammonium ($R_nNH_m+$, where n=0-4, m=0-4 and m+n=4) and the like.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with zero to three R, then said group may be unsubstituted or substituted with up to three R, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, for example, a ketone (—CH—C=O) group in a molecule may tautomerize to its enol form (—C=C—OH). Thus, this invention is intended to cover all possible tautomers even when a structure depicts only one of them.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compounds of the present invention" or "compounds of the present invention" refers to compounds of Formula (I) or (I-1), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g, (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)— or (S)—.

Geometric isomers may occur when a compound contains a double bond or some other feature that gives the molecule a certain amount of structural rigidity. If the compound contains a double bond, the substituent may be E or Z configuration. If the compound contains a disubstituted cycloalkyl, the cycloalkyl substituent may have a cis- or trans-configuration.

Conformational isomers (or conformers) are isomers that can differ by rotations about one or more a bonds. Rotamers are conformers that differ by rotation about only a single a bond.

The term "atropisomer" refers to a structural isomer based on axial or planar chirality resulting from restricted rotation in the molecule.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation).

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers.

Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxmalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like, preferably hydrochloric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the invention of which is hereby incorporated by reference.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The present invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this present invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form (s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

"LSD1" refers to Lysine (K)-specific demethylase 1A.

The term "LSD1-mediated disease or disorder" refers to any disease or disorder which is directly or indirectly regulated by LSD1.

The term "diseases or disorders mediated by LSD1" refers to diseases or disorders which are directly or indirectly regulated by LSD1.

As used herein, the term "patient" encompasses all mammalian species.

As used herein, the term "subject" refers to an animal. Typically the animal is a mammal. A "subject" also refers to any human or non-human organism that could potentially benefit from treatment with a LSD1 inhibitor. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer disease.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease/disorder refers to the treatment of the disease/disorder in a mammal, particularly in a human, and includes: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder, either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that will elicit the biological or medical response of a subject, for example, reduction or inhibition of LSD1, or ameliorate symptoms, alleviate conditions, slow or delay disease progression, or prevent a disease or disorder mediated by LSD1. When applied to a combination, the term refers to combined amounts of the active ingredients that result in the preventive or therapeutic effect, whether administered in combination, serially, or simultaneously.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "pwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "S", "E", and "Z" are stereochemical designations familiar to one skilled in the art.

The following abbreviations used herein below have the corresponding meanings:

ACN acetonitrile
Ac acetyl
AIBN azobisisobutyronitrile
Bn benzyl
Boc tert-butoxy carbonyl
Boc$_2$O di-tert-butyl dicarbonate
BOP bis(2-oxo-3-oxazolidinyl)phosphinic
Bu butyl
Cs$_2$CO$_3$ cesium carbonate anhydrous
CHCl$_3$ chloroform
DAST diethylaminosulfurtrifluoride
DBU 2,3,4,6,7,8,9,10-octahydropyrimido[1,2-a]azepine
DCM dichloromethane
DIAD diisopropyl azodicarboxylate
DMAP 4-dimethylaminopyridine
DME 1,2-dimethoxyethane
DMF dimethylformamide
DMSO dimethylsulfoxide
DPPA diphenylphosphoryl azide
EA ethyl acetate
Et ethyl
EtOH ethanol
EtOAc ethyl acetate
HATU 2-(7-Aza-1H-benzotriazole-1-yl)-1,1,3,3-tetramethyluronium hexafluorophosphate
HCl hydrochloric acid
HOAc acetic acid
i-Bu isobutyl
i-Pr isopropyl
KOAc potassium acetate
LiAlH$_4$ lithium aluminium hydride
LiCl lithium chloride
LiHMDS lithium bis(trimethylsilyl)amide
mCPBA 3-Chloroperoxybenzoic acid
Me methyl
Me$_4$-t-BuXPhos di-tert-butyl(2',4',6-triisopropyl-3,4,5,6-tetramethyl-[1,1'-biphenyl]-2-yl)phosphane
MeCN acetonitrile
MnO$_2$ manganese dioxide
N$_2$ nitrogen
NaBH$_4$ sodium borohydride
NaHCO$_3$ sodium bicarbonate
Na$_2$SO$_4$ sodium sulfate
NBS N-bromosuccinimide
NIS N-iodosuccinimide
PE petroleum ether
Ph phenyl
PPh$_3$ triphenylphosphine
Pd(dppf)Cl$_2$ [1,1'-bis(diphenylphosphino)ferrocene]dichloropalladium(II)
Pd(PPh$_3$)$_4$ palladium(0)tetrakis(triphenylphosphine)
Ph$_3$P=O triphenylphosphine oxide
t-Bu or Bu$^t$ tert-butyl
TBAB tetra-n-butylammonium bromide
TBAF tetra-n-butylammonium fluoride
TBS t-butyldimethylsilyl
TEA triethylamine
TFA trifluoroacetic acid
THF tetrahydrofuran
Ts-Cl p-toluenesulfonyl chloride
Zn(CN)$_2$ zinc cyanide IV. Synthesis The compounds of the present invention can be prepared in a number of ways known to one skilled in the art of organic synthesis in view of the methods, reaction schemes and examples provided herein. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transforma-* tions, 2$^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this invention using conventional chemistry well known to those skilled in the art.

In the preparation of compounds of the present invention, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis,* 4th Ed., Wiley (2007). Protecting groups incorporated in making of the compounds of the present invention, such as the trityl protecting group, may be shown as one regioisomer but may also exist as a mixture of regioisomers.

Scheme 1 (below) describes potential routes for producing the compounds of the present invention which include compounds of Formula (I). Compounds of Formula (I) can be made substantially optically pure by either using substantially optically pure starting material or by separation chromatography, recrystallization or other separation techniques well-known in the art. For a more detailed description, see the Example section below.

Under Scheme 1, substituted 1H-indole-5-carbonitrile 1 was treated with bromination reagents (such as NBS or Br$_2$) to form substituted 3-bromo-1H-indole-5-carbonitrile 2, which underwent alkylation with corresponding halide to give product 3. Compound 3 coupled with boronic acid or boronate under Suzuki reactions to yield compound 4. Alternatively, substituted 1H-indole-5-carbonitrile 1 was treated with halide first to give alkylation product 5, which reacted with boronic acid or boronate to generate coupled compound 4. In some other cases, 3 was treated with bis(pinacolato)diboron to generate corresponding boronate compound 6, which was alkylated with halide to generate compound 4.

General Methods

The following methods were used in the exemplified Examples, except where noted otherwise.

Purification of intermediates and final products was carried out via either normal or reverse phase chromatography. Normal phase chromatography was carried out using prepacked SiO$_2$ cartridges eluting with either gradients of hexanes and ethyl acetate or DCM and MeOH unless otherwise indicated. For highly polar amines, gradients of DCM and 1M NH$_3$ in MeOH were used. Reverse phase preparative HPLC was carried out using C18 columns with UV 214 nm and 254 nm or prep LC-MS detection eluting with gradients of Solvent A (water with 0.1% TFA) and Solvent B (acetonitrile with 0.1% TFA) or with gradients of Solvent A (water with 0.05% TFA) and Solvent B (acetonitrile with 0.05% TFA) or with gradients of Solvent A (water with 0.05% ammonia) and Solvent B (acetonitrile with 0.05% ammonia).

LC/MS Methods Employed in Characterization of Examples

Reverse phase analytical HPLC/MS was performed on Agilent LC1200 systems coupled with 6110 (Methods A-D), or 6120 (Method E and F), or 6130 (Method G) Mass Spectrometer.

Method A: Linear gradient of 5% to 95% B over 1.2 min, with 1 min hold at 95% B;
UV visualization at 214 nm and 254 nm
Column: SunFire® C18 4.6×50 mm 3.5 µm
Flow rate: 2 mL/min
Solvent A: 0.1% trifluoroacetic acid, 99.9% water
Solvent B: 0.1% trifluoroacetic acid, 99.9% acetonitrile.

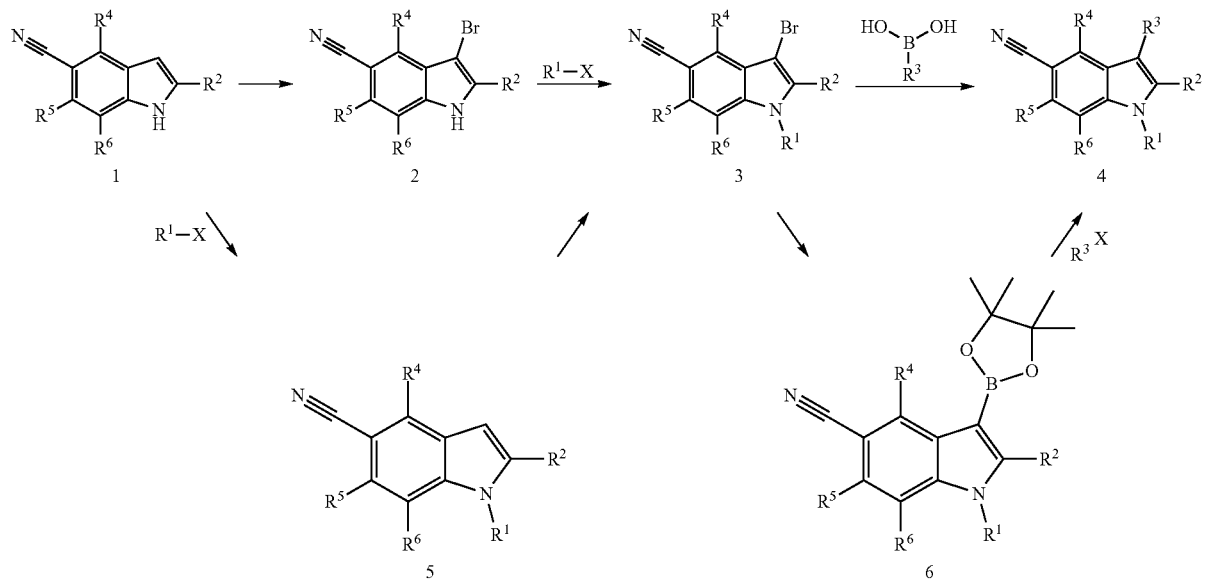

Scheme 1

Method B: Linear gradient of 5% to 95% B over 1.5 min, with 1 min hold at 95% B;
UV visualization at 214 nm and 254 nm
Column: XBridge® C18 4.6×50 mm 3.5 μm
Flow rate: 2 mL/min
Solvent A: water with 10 mM Ammonium hydrogen carbonate
Solvent B: acetonitrile.
Method C: Linear gradient of 5% to 95% B over 1.2 min, with 1.3 min hold at 95% B, 95% to 5% B over 0.01 min;
UV visualization at 214 nm and 254 nm
Column: SunFire® C18 4.6×50 mm 3.5 μm
Flow rate: 2 mL/min
Solvent A: 0.1% trifluoroacetic acid, 99.9% water
Solvent B: 0.1% trifluoroacetic acid, 99.9% acetonitrile.
Method D: Linear gradient of 5% to 95% B over 1.4 min, with 1.6 min hold at 95% B, 95% to 5% B over 0.01 min;
UV visualization at 214 nm and 254 nm
Column: XBridge® C18 4.6×50 mm 3.5 μm
Flow rate: 1.8 mL/min
Solvent A: water with 10 mM Ammonium hydrogen carbonate
Solvent B: acetonitrile.
Method E: Linear gradient of 5% to 95% B over 1.5 min, with 1 min hold at 95% B;
UV visualization at 214 nm and 254 nm
Column: XBridge® C18 4.6×50 mm 3.5 μm
Flow rate: 2 mL/min
Solvent A: water with 10 mM Ammonium hydrogen carbonate
Solvent B: acetonitrile.
Method F: Linear gradient of 5% to 95% B over 1.5 min, with 1 min hold at 95% B;
UV visualization at 214 nm and 254 nm and 300 nm
Column: XBridge® C18 4.6×30 mm 2.5 μm
Flow rate: 1.8 mL/min
Solvent A: water with 0.1% ammonia
Solvent B: acetonitrile.
Method G: Linear gradient of 10% to 95% B over 2 min, with 1 min hold at 95% B;
UV visualization at 214 nm, 254 nm and 300 nm
Column: Sunfire® C18 4.6×30 mm 2.5 μm
Flow rate: 1.8 mL/min
Solvent A: water
Solvent B: MeOH with 0.1% formic acid.

NMR Employed in Characterization of Examples $^1$H NMR spectra were obtained with Bruker Fourier transform spectrometers operating at frequencies as follows: $^1$H NMR: 400 MHz (Bruker). $^{13}$C NMR: 100 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CDCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

V. Examples

The following Examples have been prepared, isolated and characterized using the methods disclosed herein. The following examples demonstrate a partial scope of the invention and are not meant to be limiting of the scope of the invention.

Unless specified otherwise, starting materials are generally available from a non-excluding commercial sources such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia). PharmaBlock R&D Co. Ltd (Nanjing, China), Accela ChemBio Co. Ltd (Shanghai, China), Alputon Inc. (Shanghai, China), J&K Scientific Ltd. (Beijing, China).

Intermediates

Intermediate 2: 3-bromo-1H-indole-5-carbonitrile

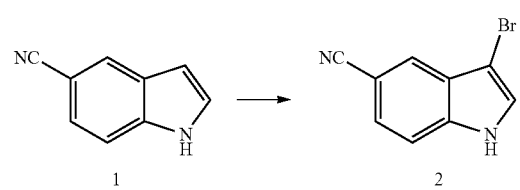 [SMILES: N#Cc1ccc2[nH]ccc2c1 ; N#Cc1ccc2[nH]cc(Br)c2c1]

To a solution of 1H-indole-5-carbonitrile (1) (1 g, 7.03 mmol) in DMF (5 mL) was added bromine (0.399 mL, 7.74 mmol). The mixture was stirred at 20° C. for 1 h. Water (15 mL) was added. The precipitate was collected and dried in high vacuum to afford the title compound (1.3 g, 71%) as a brown solid. $^1$H-NMR (400 MHz, DMSO-d$_6$) δ ppm 12.03 (s, 1H), 7.90 (s, 1H), 7.79 (s, 1H), 7.60 (d, 1H), 7.52 (d, 1H). LC-MS: [M+H]$^+$=221.0; 223.0.

Intermediate 4: 3-bromo-6-methyl-1H-indole-5-carbonitrile

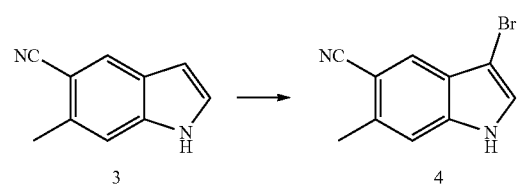

A mixture of compound 3 (2.8 g, 17.93 mmol) and NBS (3.5 g, 19.72 mmol) in DMF (60 mL) was stirred at rt for 1 h. EA and water were added to the mixture. The organic layer was separated and the aqueous layer was extracted with EA two times. The combined organic layers were washed with water and brine, dried over anhydrous Na$_2$SO$_4$, filtered and concentrated to give crude product which was purified by flash column chromatography (eluent: PE/EA, EA %=8%-20%) to give the title compound (3.1 g 74%). $^1$H NMR (300 MHz, CDCl$_3$) δ ppm 8.40 (s, 1H), 7.88 (s, 1H), 7.27 (d, 2H), 2.63 (s, 3H). LC-MS: [M+H]$^+$=235.2, 237.2.

Example 1

3-(5-isocyano-1-(4-(2-methoxyethoxy)benzyl)-1H-indol-3-yl)aniline

Intermediate 1.1:
3-(3-nitrophenyl)-1H-indole-5-carbonitrile

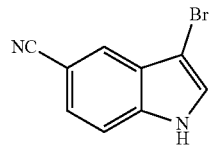

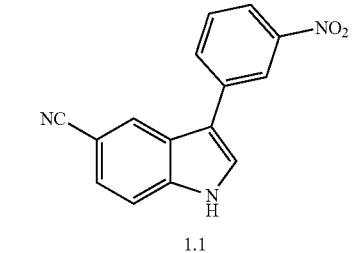

To a suspension of Pd(PPh$_3$)$_2$Cl$_2$ (66.7 mg, 0.095 mmol), sodium bicarbonate (160 mg, 1.900 mmol), 3-bromo-1H-indole-5-carbonitrile (2) (300 mg, 0.950 mmol) and (3-nitrophenyl)boronic acid (190 mg, 1.140 mmol) in 2-Propanol (10 mL) was added water (1 mL). The mixture was stirred at 90° C. under nitrogen protection for 20 h. The mixture was diluted with water (20 mL), and then extracted with DCM (10 mL×2). The organic layer was dried over Na$_2$SO$_4$, filtered and concentrated, the residue was purified by silica column to afford the title compound (160 mg, 58%) as a brown solid. $^1$H-NMR (400 MHz, DMSO-d$_6$) δ ppm 12.12 (s, 1H), 8.45 (d, 2H), 8.42 (d, 1H), 8.16 (d, 1H), 7.73 (t, 1H), 7.65 (d, 1H), 7.54 (d, 1H). LC-MS: [M+H]$^+$=264.0.

Intermediate 1.2:
1-(bromomethyl)-4-(2-methoxyethoxy)benzene

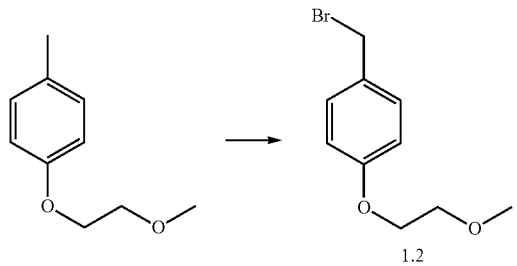

To a solution of 1-(2-methoxyethoxy)-4-methylbenzene (1 g, 6.02 mmol) and AIBN (0.049 g, 0.301 mmol) in CCl$_4$ (20 mL) was added NBS (1.285 g, 7.22 mmol). The mixture was stirred at 60° C. for 20 h and filtered. The filter residue was concentrated and purified by silica column to afford the title compound (1.1 g, 71%) as a colorless oil. $^1$H-NMR (400 MHz, CDCl$_3$) δ ppm 7.32 (d, 2H), 6.90 (d, 2H), 4.50 (s, 2H), 4.13 (t, 2H), 3.76 (t, 2H), 3.46 (s, 3H). LC-MS: [M+H]$^+$=245.0; 247.0.

Intermediate 1.3: 1-(4-(2-methoxyethoxy)benzyl)-3-(3-nitrophenyl)-1H-indole-5-carbonitrile

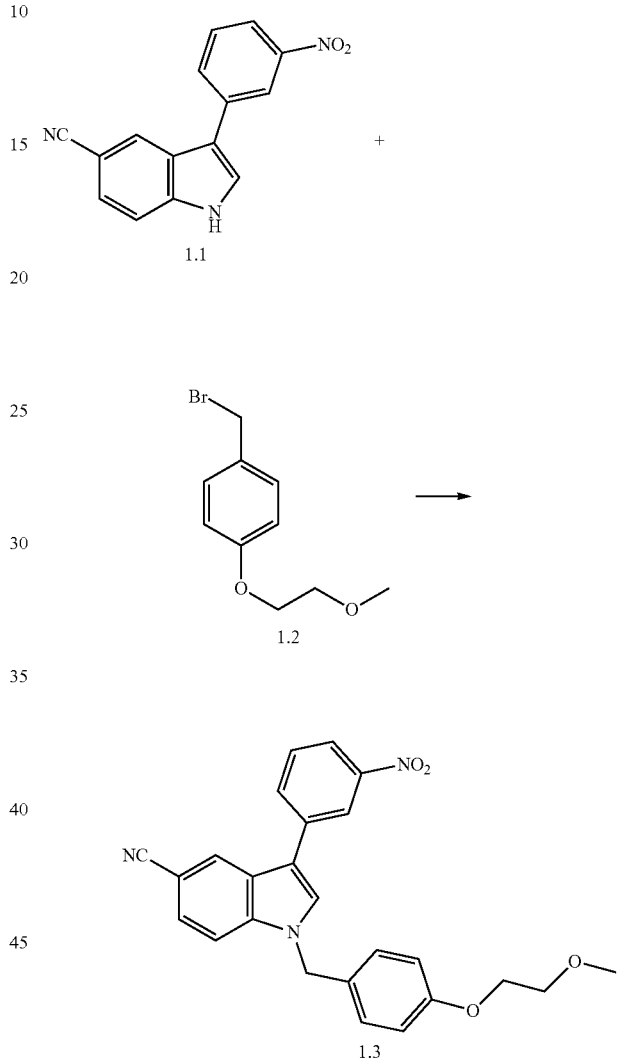

To a suspension of sodium hydride (36.5 mg, 0.912 mmol) and 1.1 (200 mg, 0.760 mmol) was added DMF (2 mL). The mixture was stirred at 20° C. for 10 min, and then a solution of 1.2 (205 mg, 0.836 mmol) in DMF (1 mL) was added. The mixture was stirred at rt for another 20 min. The mixture was diluted with water (10 mL), extracted with DCM (10 mL×2). The organic layer was dried over Na$_2$SO$_4$, filtered and concentrated, the residue was purified by silica column to afford the title compound (260 mg, 76%) as a yellow solid. $^1$H-NMR (400 MHz, DMSO-d$_6$) δ ppm 8.44-8.45 (m, 2H), 8.38 (s, 1H), 8.21 (d, 1H), 8.13 (d 1H), 7.82 (d, 1H), 7.73 (t, 1H), 7.59 (d, 1H), 7.29 (d, 2H), 6.89 (d, 2H), 5.47 (s, 2H), 4.02 (t, 2H), 3.60 (t, 2H), 3.23 (s, 3H). LC-MS: [M+H]$^+$=428.1.

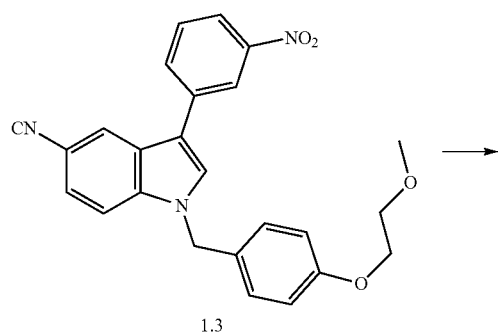

1.3

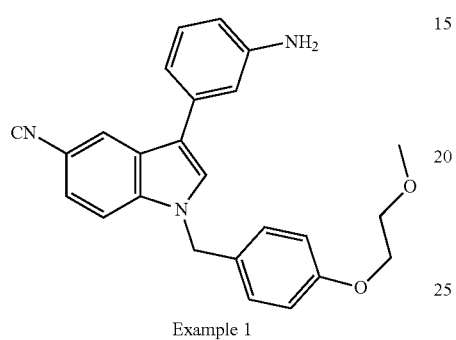

Example 1

To a suspension of intermediate 1.3 (260 mg, 0.608 mmol) and iron (272 mg, 4.87 mmol) in ethanol (10 mL) was added hydrochloric acid (0.5 mL, 6.00 mmol). The mixture was stirred at 80° C. for 3 h. The mixture was filtered off the iron. The filter diluted with water (20 mL), extracted with DCM (15 mL×2), the organic layer was dried over $Na_2SO_4$, filtered and concentrated. The residue was purified by silica column to afford the title compound (100 mg, 39%) as a white solid. $^1$H-NMR (400 MHz, DMSO-$d_6$) δ ppm 8.28 (s, 1H), 7.93 (s, 1H), 7.75 (d, 1H), 7.52 (d 1H), 7.25 (d, 2H), 7.08 (t, 1H), 6.91-6.94 (m, 3H), 6.87 (d, 1H), 6.49 (d, 1H), 5.43 (s, 2H), 4.02 (t, 2H), 3.60 (t, 2H), 3.26 (s, 3H). LC-MS: $[M+H]^+$=398.2.

Example 2

1-(4-(2-methoxyethoxy)benzyl)-3-(3-(methylamino) phenyl)-1H-indole-5-carbonitrile Intermediate 2.1: 3-bromo-1-(4-(2-methoxyethoxy) benzyl)-1H-indole-5-carbonitrile

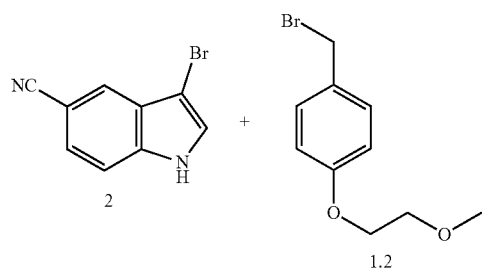

1.2

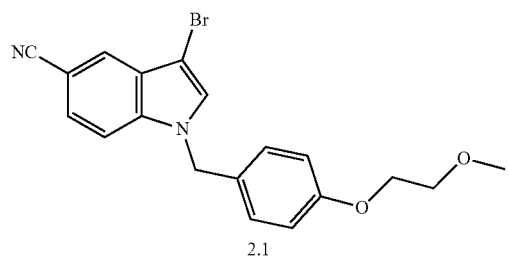

2.1

The title compound was prepared by using a procedure similar to that of intermediate 1.3 by replacing intermediate 1.1 with intermediate 2. LC-MS: $[M+H]^+$=385.0, 387.0.

Intermediate 2.2: N-methyl-3-(4,4,5,5-tetramethyl-1, 3,2-dioxaborolan-2-yl)aniline

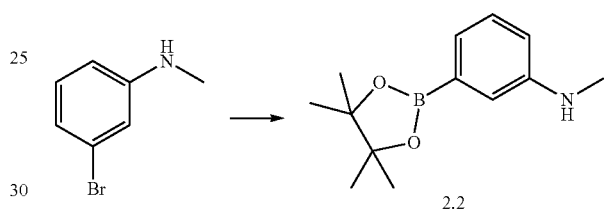

2.2

A suspension of 3-bromo-N-methylaniline (500 mg, 2.69 mmol), 4,4,4',4',5,5,5',5'-octamethyl-2,2'-bi(1,3,2-dioxaborolane) (751 mg, 2.96 mmol), $PdCl_2$(dppf).$CH_2Cl_2$ adduct (219 mg, 0.269 mmol) and potassium acetate (317 mg, 3.22 mmol) in 1,4-Dioxane (10 mL) was stirred at 100° C. for 60 h. The mixture was purified by silica column to afford the title compound (220 mg, 34%) as a brown oil. $^1$H-NMR (400 MHz, DMSO-$d_6$) δ ppm 7.07 (t, 1H), 6.82-6.88 (m, 2H), 6.63 (d, 1H), 5.57 (q, 1H), 2.65 (s, 1H), 1.29 (s, 12H). $[M+H]^+$=234.2.

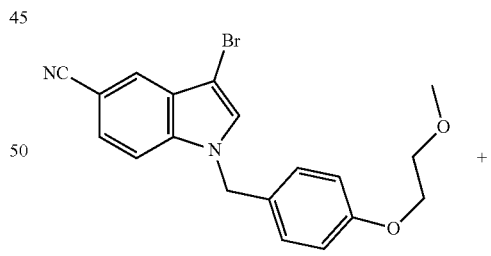

2.1

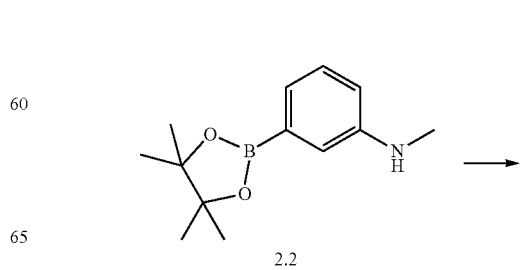

2.2

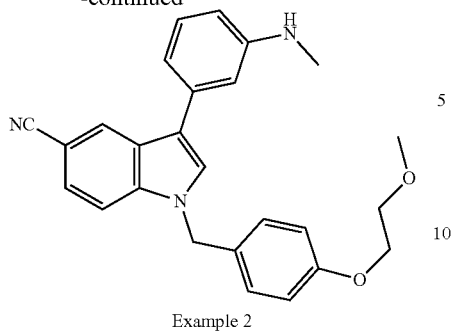

Example 2

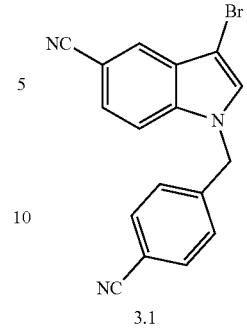

3.1

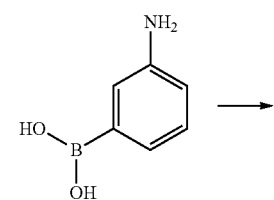

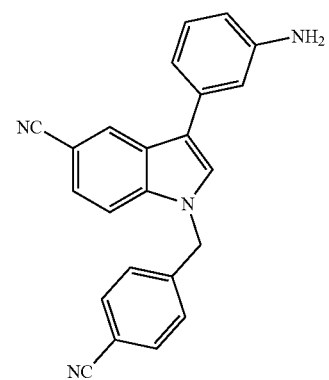

Example 3

The title compound was prepared by using a procedure similar to that of intermediate 1.1 by replacing intermediate 2 and (3-nitrophenyl)boronic acid with intermediate 2.1 and intermediate 2.2. $^1$H-NMR (400 MHz, CD$_3$OD) δ ppm 8.24 (s, 1H), 7.64 (s, 1H), 7.56 (d, 1H), 7.44 (d, 1H), 7.16-7.24 (m, 3H), 6.85-6.95 (m, 4H), 6.57-6.61 (m, 1H), 5.40 (s, 2H), 4.10 (t, 2H), 3.72 (t, 2H), 3.40 (s, 3H), 2.83 (s, 3H). LC-MS: [M+H]$^+$=412.1.

Example 3

3-(3-aminophenyl)-1-(4-cyanobenzyl)-1H-indole-5-carbonitrile

Intermediate 3.1:
3-bromo-1-(4-cyanobenzyl)-1H-indole-5-carbonitrile

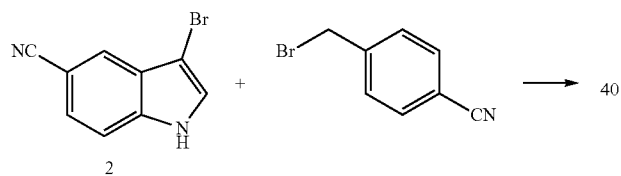

The title compound was prepared by using a procedure similar to that of intermediate 1.3 by replacing intermediate 1.1 and 1.2 with intermediate 2 and 4-(bromomethyl)benzonitrile. $^1$H-NMR (400 MHz, DMSO-d$_6$) δ ppm 8.02 (s, 1H), 7.95 (s, 1H), 7.74-7.80 (m, 3H), 7.58 (d, 1H), 7.37 (d, 2H), 5.62 (s, 2H). LC-MS: [M+H]$^+$=336.0, 338.0.

The title compound was prepared by using a procedure similar to that of intermediate 1.1 by replacing intermediate 2 and (3-nitrophenyl)boronic acid with intermediate 3.1 and (3-aminophenyl)boronic acid. $^1$H-NMR (400 MHz, CD$_3$OD) δ ppm 8.29 (s, 1H), 7.64-7.71 (m, 3H), 7.42-7.48 (m, 2H), 7.33 (d, 2H), 7.20 (t, 1H), 7.06 (s, 1H), 6.98 (d, 1H), 6.71 (d, 1H), 5.60 (s, 2H). LC-MS: [M+H]$^+$=412.1.

Example 4

4-((3-(3-aminophenyl)-5-cyano-1H-indol-1-yl)methyl)benzamide

Intermediate 4.1: methyl 4-((3-bromo-5-cyano-1H-indol-1-yl)methyl)benzoate

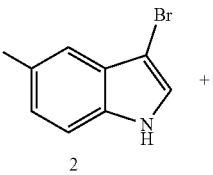

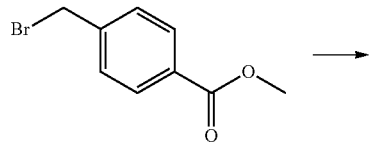

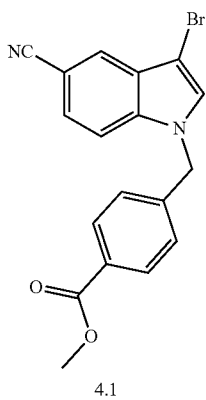

4.1

The title compound was prepared by using a procedure similar to that of intermediate 1.3 by replacing intermediate 1.1 and 1.2 with intermediate 2 and methyl 4-(bromomethyl)benzoate. $^1$H-NMR (400 MHz, DMSO-d$_6$) δ ppm 8.01 (s, 1H), 7.95 (s, 1H), 7.90 (d, 2H), 7.73 (d, 1H), 7.58 (d, 1H), 7.33 (d, 2H), 5.60 (s, 2H), 3.81 (s, 3H). LC-MS: [M+H]$^+$=369.0, 371.0.

Intermediate 4.2: 4-((3-(3-aminophenyl)-5-cyano-1H-indol-1-yl)methyl)benzoic acid

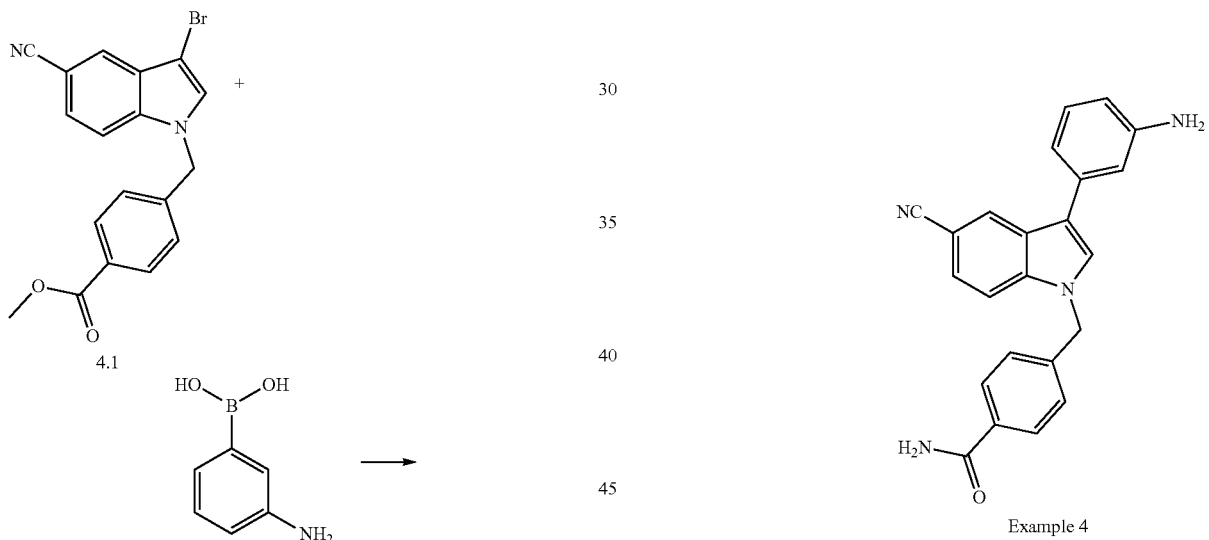

4.2

The title compound was prepared by using a procedure similar to that of intermediate 1.1 by replacing intermediate 2 and (3-nitrophenyl)boronic acid with intermediate 4.1 and (3-aminophenyl)boronic acid. $^1$H-NMR (400 MHz, CD$_3$OD) δ ppm 8.32 (s, 1H), 8.00 (s, 1H), 7.88 (d, 2H), 7.70 (d, 1H), 7.53 (d, 1H), 7.34 (d, 2H), 7.15 (t, 1H), 7.05 (s, 1H), 6.93 (d 1H), 6.60 (d, 1H), 5.62 (s, 2H). LC-MS: [M+H]$^+$=368.1.

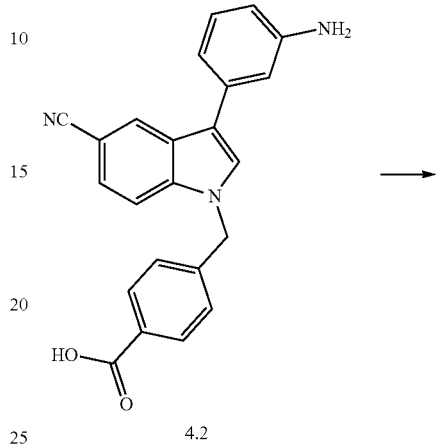

4.2

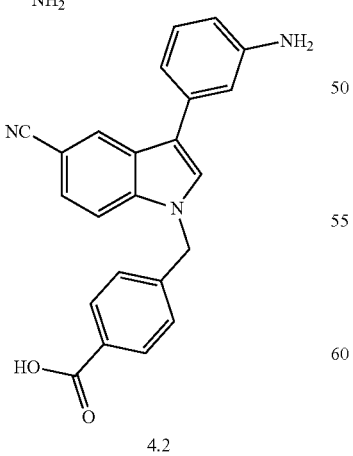

Example 4

The mixture of intermediate 4.2 (50 mg, 0.136 mmol), NH$_4$Cl (36.4 mg, 0.680 mmol), TEA (138 mg, 1.361 mmol), BOP (60.2 mg, 0.136 mmol) in DCM (6 mL) was stirred at 20° C. for 20 h. The mixture was diluted with DCM (15 mL), washed with water, brine. The organic layer was dried over Na$_2$SO$_4$, filtered and concentrated. The residue was purified by silica column to give the title compound (30 mg, 57%) as an off-white solid. $^1$H-NMR (400 MHz, DMSO-d$_6$) δ ppm 9.72 (b, 1H), 7.65-7.71 (m, 3H), 7.42-7.48 (m, 2H), 7.33 (d, 2H), 7.20 (t, 1H), 7.06 (s, 1H), 6.98 (d, 1H), 6.71 (d, 1H), 5.60 (s, 2H). LC-MS: [M+H]$^+$=412.1.

Example 5

3-((3-(3-aminophenyl)-5-cyano-1H-indol-1-yl)methyl)benzamide

Intermediate 5.1: 3-((3-bromo-5-cyano-1H-indol-1-yl)methyl)benzoic acid

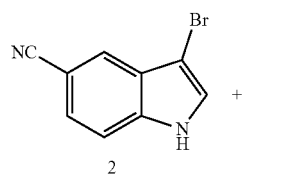

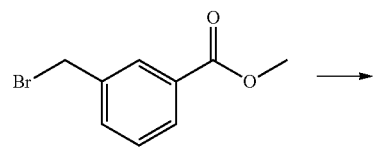

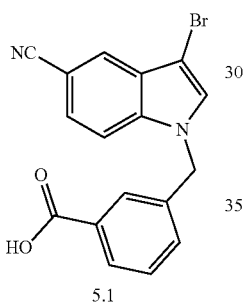

5.1

The title compound was prepared by using a procedure similar to that of intermediate 1.3 by replacing intermediate 1.1 and 1.2 with intermediate 2 and methyl 3-(bromomethyl)benzoate. LC-MS: [M−H]⁻=353.0, 355.0.

Intermediate 5.2: 3-((3-bromo-5-cyano-1H-indol-1-yl)methyl)benzamide

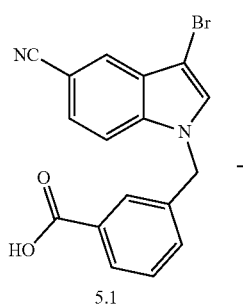 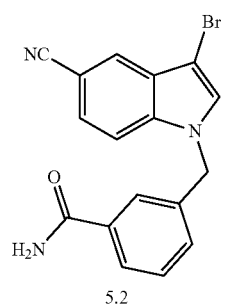

5.1       5.2

The title compound was prepared by using a procedure similar to that of Example 4 by replacing intermediate 4.2 with intermediate 5.1. LC-MS: [M+H]⁺=354.1, 356.1.

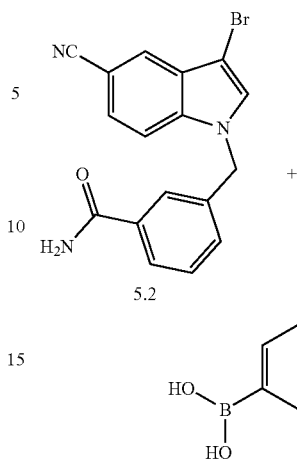

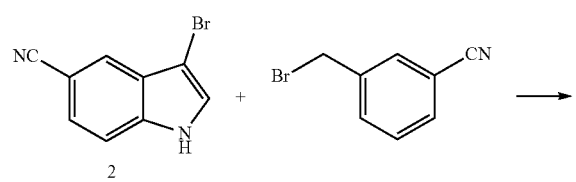

Example 5

The title compound was prepared by using a procedure similar to that of intermediate 1.1 by replacing intermediate 2 and (3-nitrophenyl)boronic acid with intermediate 5.2 and (3-aminophenyl)boronic acid. $^1$H-NMR (400 MHz, CD$_3$OD) δ ppm 8.26 (s, 1H), 7.82 (s, 1H), 7.77 (d, 1H), 7.67 (s, 1H), 7.53 (d, 1H), 7.38-7.42 (m, 2H), 7.33 (d, 1H), 7.20 (t, 1H), 7.06 (s, 1H), 6.98 (d, 1H), 6.70 (d, 1H), 5.52 (s, 2H). LC-MS: [M+H]⁺=367.2.

Example 6

3-(3-aminophenyl)-1-(3-cyanobenzyl)-1H-indole-5-carbonitrile

Intermediate 6.1:
3-bromo-1-(3-cyanobenzyl)-1H-indole-5-carbonitrile

-continued

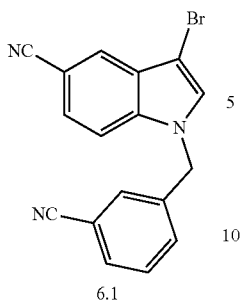

6.1

The title compound was prepared by using a procedure similar to that of intermediate 1.3 by replacing intermediate 1.1 and 1.2 with intermediate 2 and 3-(bromomethyl)benzonitrile. $^1$H-NMR (400 MHz, DMSO-d$_6$) δ ppm 8.04 (s, 1H), 7.94 (s, 1H), 7.88-7.92 (m, 2H), 7.75 (d, 1H), 7.60 (d, 1H), 7.50-7.55 (m, 2H), 5.55 (s, 2H).

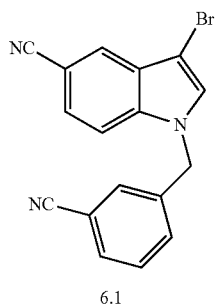

6.1

+

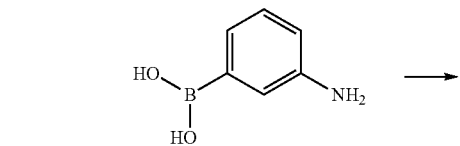

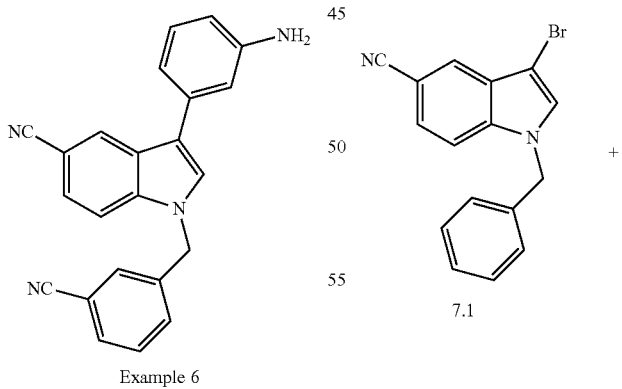

Example 6

The title compound was prepared by using a procedure similar to that of intermediate 1.1 by replacing intermediate 2 and (3-nitrophenyl)boronic acid with intermediate 6.1 and (3-aminophenyl)boronic acid. $^1$H-NMR (400 MHz, DMSO-d$_6$) δ ppm 8.24 (s, 1H), 7.65 (s, 1H), 7.40-7.60 (m, 6H), 7.19 (t, 1H), 7.04 (s, 1H), 6.96 (d, 1H), 6.69 (d, 1H), 5.51 (s, 2H). LC-MS: [M+H]$^+$=349.1.

Example 7

3-(3-aminophenyl)-1-benzyl-1H-indole-5-carbonitrile

Intermediate 7.1:
1-benzyl-3-bromo-1H-indole-5-carbonitrile

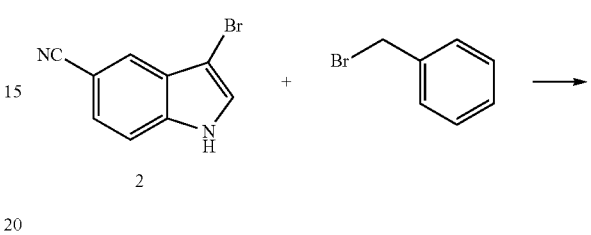

2

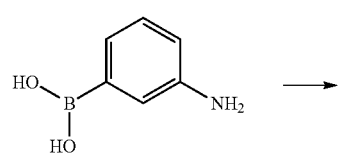

7.1

The title compound was prepared by using a procedure similar to that of intermediate 1.3 by replacing Intermediate 1.1 and 1.2 with Intermediate 2 and (bromomethyl)benzene. $^1$H-NMR (400 MHz, DMSO-d$_6$) δ ppm 8.00 (s, 1H), 7.93 (s, 1H), 7.77 (d, 1H), 7.57 (d, 1H), 7.24-7.34 (m, 5H), 5.49 (s, 2H).

7.1

+

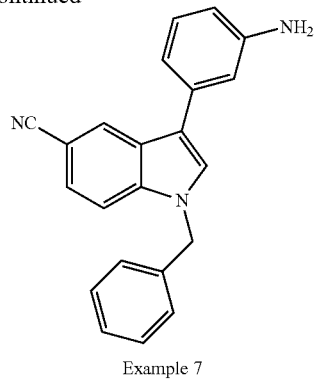

Example 7

The title compound was prepared by using a procedure similar to that of Intermediate 1.1 by replacing Intermediate 2 and (3-nitrophenyl)boronic acid with Intermediate 7.1 and (3-aminophenyl)boronic acid. $^1$H-NMR (400 MHz, CD$_3$OD) δ ppm 8.24 (s, 1H), 7.60 (s, 1H), 7.46 (d, 1H), 7.38 (d, 1H), 7.10-7.30 (m, 6H), 7.03 (s, 1H), 6.95 (d, 1H), 6.69 (d, 1H), 5.39 (s, 2H). LC-MS: [M+H]$^+$=324.2.

Example 8

3-(3-aminophenyl)-1-(2-methoxybenzyl)-1H-indole-5-carbonitrile

Intermediate 8.1: 3-bromo-1-(2-methoxybenzyl)-1H-indole-5-carbonitrile

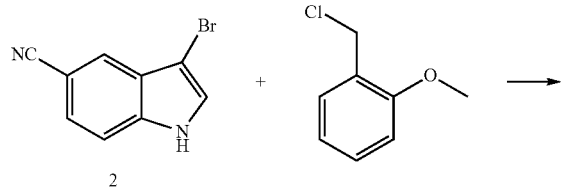

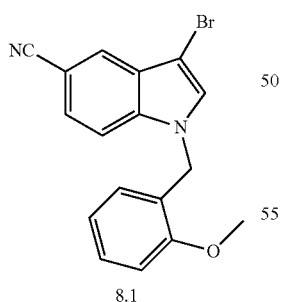

8.1

The title compound was prepared by using a procedure similar to that of Intermediate 1.3 by replacing Intermediate 1.1 and 1.2 with Intermediate 2 and 1-(chloromethyl)-2-methoxybenzene. $^1$H-NMR (400 MHz, DMSO-d$_6$) δ ppm 7.92 (s, 1H), 7.83 (s, 1H), 7.75 (d, 1H), 7.57 (d, 1H), 7.27 (t, 1H), 7.02 (d, 1H), 6.97 (d, 1H), 6.85 (t, 1H), 5.41 (s, 2H), 3.81 (s, 3H). LC-MS: [M+H]$^+$=341.0, 343.0).

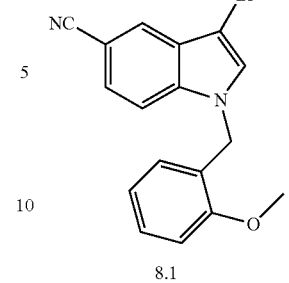

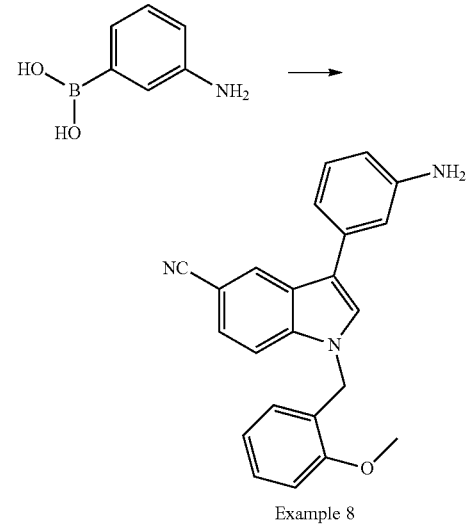

Example 8

The title compound was prepared by using a procedure similar to that of Intermediate 1.1 by replacing intermediate 2 and (3-nitrophenyl)boronic acid with intermediate 8.1 and (3-aminophenyl)boronic acid. $^1$H-NMR (400 MHz, CD$_3$OD) δ ppm 8.25 (s, 1H), 7.61 (s, 1H), 7.45 (d, 1H), 7.27 (t, 1H), 7.19 (t, 1H), 7.00-7.06 (m, 4H), 6.85 (t, 1H), 6.67 (d, 1H), 5.44 (s, 2H), 3.88 (s, 3H). LC-MS: [M+H]$^+$=354.2.

Example 9

3-(3-aminophenyl)-1-(3-methoxybenzyl)-1H-indole-5-carbonitrile

Intermediate 9.1: 3-bromo-1-(3-methoxybenzyl)-1H-indole-5-carbonitrile

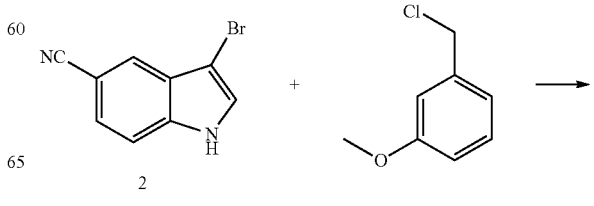

-continued

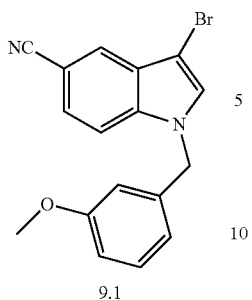

9.1

The title compound was prepared by using a procedure similar to that of intermediate 1.3 by replacing intermediate 1.1 and 1.2 with intermediate 2 and 1-(chloromethyl)-3-methoxybenzene. $^1$H-NMR (400 MHz, DMSO-d$_6$) δ ppm 7.99 (s, 1H), 7.93 (s, 1H), 7.79 (d, 1H), 7.57 (d, 1H), 7.22 (t, 1H), 6.81-6.87 (m, 2H), 6.77 (d, 1H), 5.45 (s, 2H), 3.70 (s, 3H).

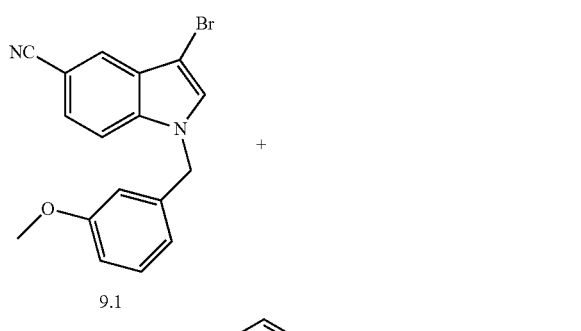

Example 9

The title compound was prepared by using a procedure similar to that of intermediate 1.1 by replacing intermediate 2 and (3-nitrophenyl)boronic acid with intermediate 9.1 and (3-aminophenyl)boronic acid. $^1$H-NMR (400 MHz, CD$_3$OD) δ ppm 8.27 (s, 1H), 7.65 (s, 1H), 7.54 (d, 1H), 7.44 (d, 1H), 7.20-7.26 (m, 2H), 7.05 (s, 1H), 6.98 (d, 1H), 6.84 (d, 1H), 6.75-7.80 (m, 2H), 6.68 (d, 1H), 5.45 (s, 2H), 3.73 (s, 3H). LC-MS: [M+H]$^+$=354.2.

Example 10

3-(3-aminophenyl)-1-(4-methoxybenzyl)-1H-indole-5-carbonitrile

Intermediate 10.1: 3-bromo-1-(4-methoxybenzyl)-1H-indole-5-carbonitrile

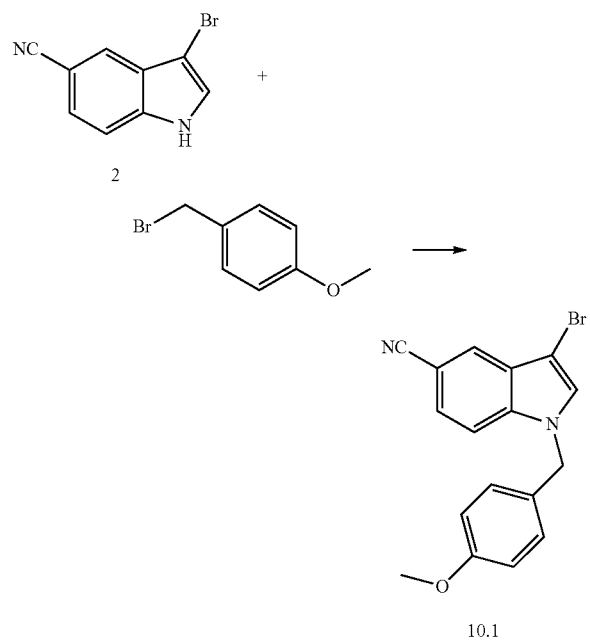

10.1

The title compound was prepared by using a procedure similar to that of intermediate 1.3 by replacing intermediate 1.1 and 1.2 with intermediate 2 and 1-(bromomethyl)-4-methoxybenzene. $^1$H-NMR (400 MHz, DMSO-d$_6$) δ ppm 7.97 (s, 1H), 7.91 (s, 1H), 7.80 (d, 1H), 7.57 (d, 1H), 7.24 (d, 2H), 6.87 (d, 2H), 5.40 (s, 2H), 3.69 (s, 3H). LC-MS: [M+H]$^+$=341.0, 343.0.

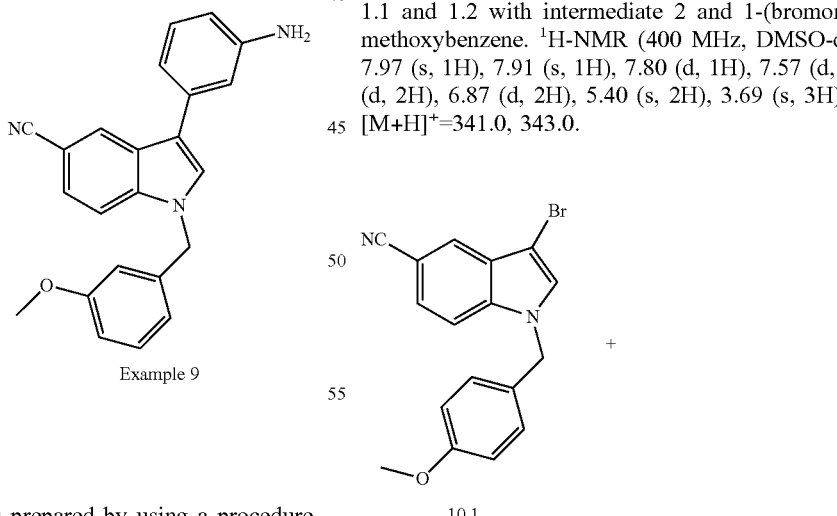

-continued

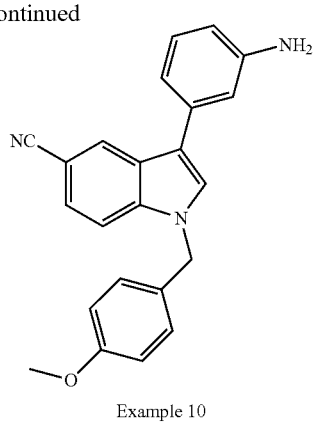

Example 10

The title compound was prepared by using a procedure similar to that of intermediate 1.1 by replacing intermediate 2 and (3-nitrophenyl)boronic acid with intermediate 10.1 and (3-aminophenyl)boronic acid. $^1$H-NMR (400 MHz, DMSO-d$_6$) δ ppm 8.27 (s, 1H), 7.93 (s, 1H), 7.75 (d, 1H), 7.51 (d, 1H), 7.26 (d, 2H), 7.08 (t, 1H), 6.93 (s, 1H), 6.87 (d, 2H), 6.79 (d, 1H), 6.49 (d, 1H), 5.42 (s, 2H), 3.69 (s, 3H). LC-MS: [M+H]$^+$=354.1.

Example 11

3-(3-aminophenyl)-1-(2-hydroxyethyl)-1H-indole-5-carbonitrile

Intermediate 11.1: 3-bromo-1-(2-((tert-butyldimethylsilyl)oxy)ethyl)-1H-indole-5-carbonitrile

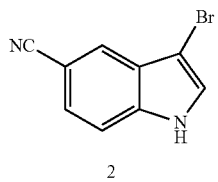 

2

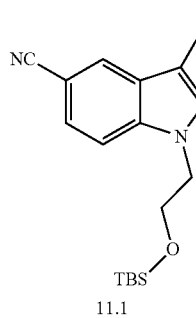

11.1

To a solution of compound 2 (200 mg, 0.905 mmol) in dry DMF (2.5 mL) was added NaH (60%, 55 mg, 1.358 mmol) in several portions under ice-water bath. Then the mixture was stirred at rt for 10 min and followed by addition of (2-bromoethoxy)(tert-butyl)dimethylsilane (433 mg, 1.810 mmol) and then it was stirred at 45° C. overnight. The mixture was diluted with water and extracted with EA for 3 times. The organic layer was combined and washed with brine for 3 times, dried over Na$_2$SO$_4$, concentrated and then purified by column chromatography on silica gel (eluent: PE~PE/EA=4:1) to give the title compound (200 mg 58%) as a yellow oil. $^1$H NMR (300 MHz, CDCl3) δ ppm 7.91 (s, 1H), 7.43 (q, 2H), 7.29 (s, 1H), 4.24 (t, 2H), 3.88 (t, 2H), 0.78 (s, 9H), −0.18 (s, 6H). LC-MS: [M+H]$^+$=378.8, 380.8.

Intermediate 11.2: 3-(3-aminophenyl)-1-(2-((tert-butyldimethylsilyl)oxy)ethyl)-1H-indole-5-carbonitrile

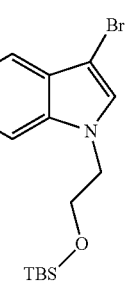 

11.1

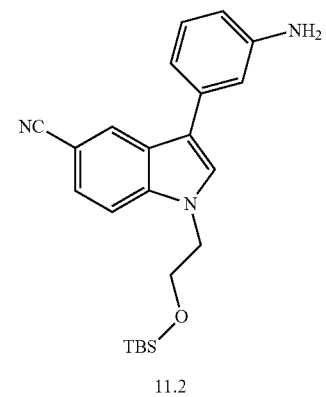

11.2

To a solution of 11.1 (150 mg, 0.395 mmol) and (3-aminophenyl)boronic acid (99 mg, 0.593 mmol) in DMF (4 mL) was added 2N Na$_2$CO$_3$ aq. (1.19 mL, 2.37 mmol) and Pd(dppf)Cl$_2$ (29 mg, 0.040 mmol). The mixture was stirred at 110° C. for 3.5 h under N$_2$ atmosphere. Water (20 mL) was added. The mixture was extracted with EA for three times. The combined organic phase was washed with brine and dried over Na$_2$SO$_4$, concentrated and purified by column chromatography on silica gel (eluent: PE/EA=10:1~4:1) to give the title compound (59 mg, 38%) as a yellow oil. $^1$H NMR (300 MHz, CDCl$_3$) δ ppm 8.25 (s, 1H), 7.41 (d, 3H), 7.27-7.21 (m, 1H), 6.98 (d, 1H), 6.92 (s, 1H), 6.68 (d, 1H), 4.28 (t, 2H), 3.95 (t, 2H), 0.79 (s, 9H), −0.16 (s, 6H). LC-MS: [M+H]$^+$=392.0.

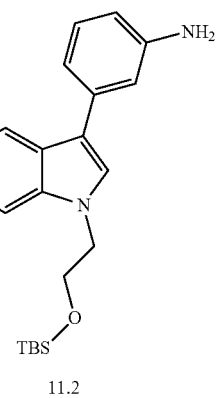 

11.2

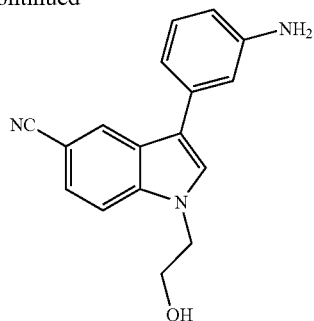

Example 11

The solution of 11.2 (40 mg, 0.102 mml) and TBAF (80 mg, 0.306 mmol) in THF (2 mL) was stirred at r.t overnight. Then it was purified by prep-TLC (eluent: DCM/MeOH=15:1) to give a mixture of product and TBAF. So it was purified by prep-HPLC (0.1% NH$_3$.H$_2$O/ACN/H$_2$O) and lyophilized to give the title compounds (10 mg, 36%) as a white solid. $^1$H NMR (400 MHz, DMSO) δ ppm 8.29 (d, 1H), 7.80 (s, 1H), 7.75 (d, 1H), 7.54 (d, 1H), 7.10 (t, 1H), 6.96 (t, 1H), 6.80 (d, 1H), 6.50 (d, 1H), 5.15 (s, 2H), 4.96 (t, 1H), 4.32 (t, 2H), 3.77 (q, 2H). LC-MS: [M+H]$^+$=278.1.

Example 12

3-(3-aminophenyl)-1-(pyridin-3-ylmethyl)-1H-indole-5-carbonitrile

Intermediate 12.1: 3-bromo-1-(pyridin-3-ylmethyl)-1H-indole-5-carbonitrile

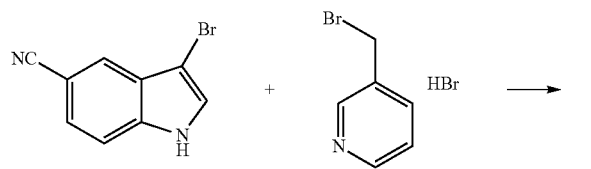

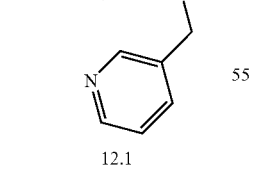

12.1

The title compound was prepared by using a procedure similar to that of intermediate 1.3 by replacing intermediate 1.1 and 1.2 with intermediate 2 and 3-(bromomethyl)pyridine hydrobromide. $^1$H-NMR (400 MHz, DMSO-d$_6$) δ ppm 8.59 (s, 1H), 8.48 (d, 1H), 8.02 (s, 1H), 7.93 (s, 1H), 7.84 (d, 1H), 7.60-7.65 (m, 2H), 7.32 (t, 1H), 5.54 (s, 2H). LC-MS: [M+H]$^+$=312.0, 314.0.

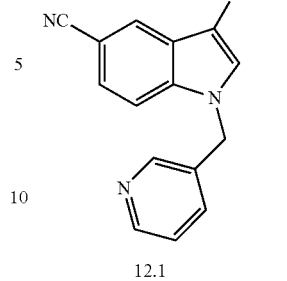

12.1

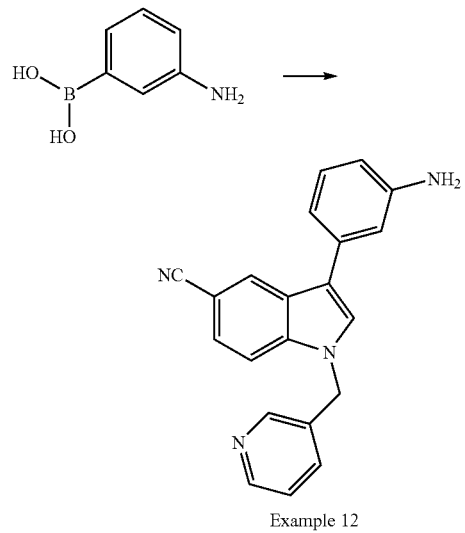

Example 12

The title compound was prepared by using a procedure similar to that of intermediate 1.1 by replacing intermediate 2 and (3-nitrophenyl)boronic acid with intermediate 12.1 and (3-aminophenyl)boronic acid. $^1$H-NMR (400 MHz, CD$_3$OD) δ ppm 8.46-8.50 (m, 2H), 8.28 (s, 1H), 7.71 (s, 1H), 7.48 (d, 1H), 7.39 (t, 1H), 7.20 (t, 1H), 7.05 (s, 1H), 6.98 (d, 1H), 6.70 (d, 1H), 5.58 (s, 2H). LC-MS: [M+H]$^+$=325.1.

Example 13

3-(3-aminophenyl)-1-(pyridin-4-ylmethyl)-1H-indole-5-carbonitrile

Intermediate 13.1: 3-bromo-1-(pyridin-4-ylmethyl)-1H-indole-5-carbonitrile

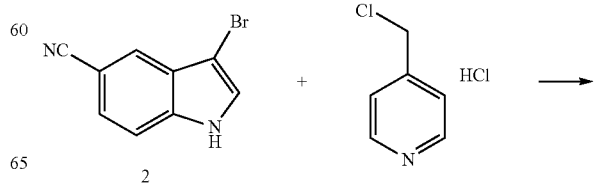

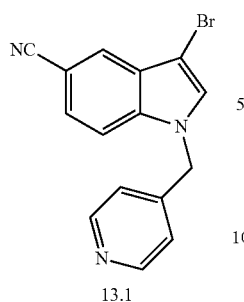

13.1

The title compound was prepared by using a procedure similar to that of intermediate 1.3 by replacing intermediate 1.1 and 1.2 with intermediate 2 and 4-(chloromethyl)pyridine hydrochloride. $^1$H-NMR (400 MHz, DMSO-$d_6$) δ ppm 8.49 (d, 2H), 8.01 (s, 1H), 7.96 (d, 1H), 7.72 (d, 1H), 7.58 (d, 1H), 7.11 (d, 2H), 5.57 (s, 2H). LC-MS: [M+H]$^+$=312.0, 314.0.

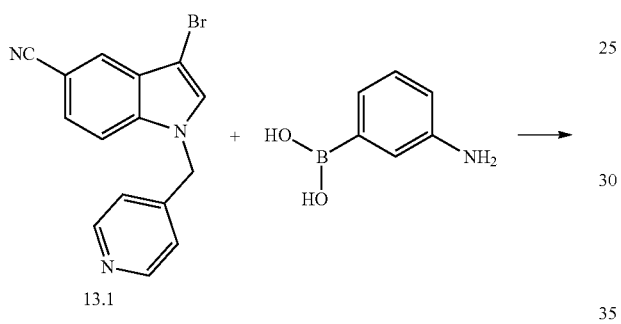

13.1

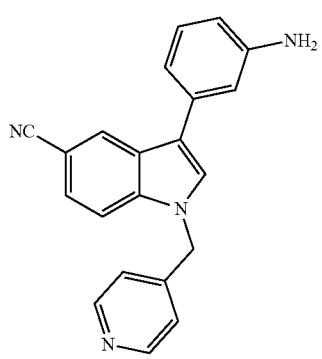

Example 13

The title compound was prepared by using a procedure similar to that of intermediate 1.1 by replacing intermediate 2 and (3-nitrophenyl)boronic acid with intermediate 13.1 and (3-aminophenyl)boronic acid. $^1$H-NMR (400 MHz, CD$_3$OD) δ ppm 8.45 (d, 2H), 8.27 (s, 1H), 7.66 (s, 1H), 7.41-7.47 (m, 2H), 7.20 (t, 1H), 7.14 (d, 2H), 7.06 (s, 1H), 6.97 (d, 1H), 6.71 (d, 1H), 5.56 (s, 2H). LC-MS: [M+H]$^+$=325.1.

Example 14

3-(3-amino-2-methylphenyl)-1-(pyridin-3-ylmethyl)-1H-indole-5-carbonitrile

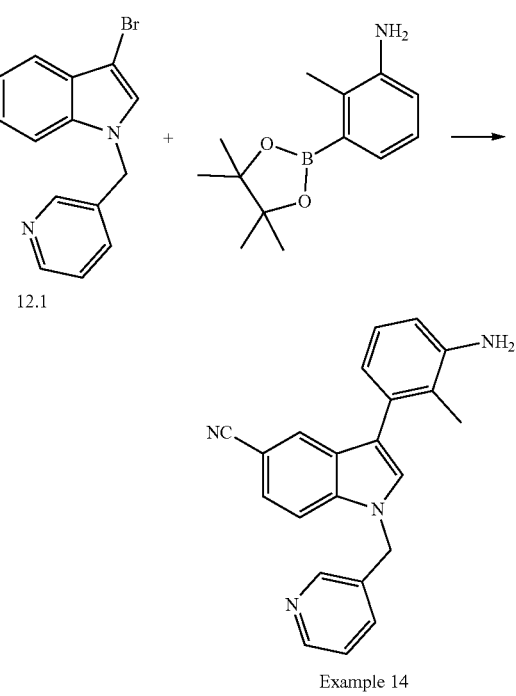

Example 14

The title compound was prepared by using a procedure similar to that of intermediate 1.1 by replacing intermediate 2 and (3-nitrophenyl)boronic acid with intermediate 13.1 and 2-methyl-3-(4,4,5,5-tetramethyl-1,3,2-dioxaborolan-2-yl)aniline. $^1$H-NMR (400 MHz, CD$_3$OD) δ ppm 8.54 (s, 1H), 7.70-7.76 (m, 2H), 7.53 (d, 1H), 7.46 (s, 1H), 7.41 (d, 1H), 7.31 (t, 1H), 7.03-7.09 (m, 2H), 6.80 (d, 1H), 6.74 (d, 1H), 5.58 (s, 2H), 2.07 (s, 3H). LC-MS: [M+H]$^+$=338.9.

Example 15

3-(3-aminophenyl)-1-((tetrahydro-2H-pyran-3-yl)methyl)-1H-indole-5-carbonitrile

Intermediate 15.1:
(tetrahydro-2H-pyran-3-yl)methanol

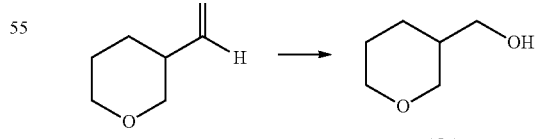

15.1

At −5° C.˜−10° C., to a solution of tetrahydro-2H-pyran-3-carbaldehyde (450 mg, 3.943 mmol) in the co-solvent of DCM/MeOH (6 mL, 15:1) was added NaBH$_4$ (90 mg, 2.366 mmol) in several portions. The mixture was stirred at rt for 4 h. Then at 0° C., to the mixture was added 1N HCl aq. until no bubble appeared. The mixture was extracted with DCM for 3 times. The organic layer was combined, dried over anhydrous Na$_2$SO$_4$, filtered and concentrated to give the title compound (416 mg, 91%) as colorless oil. $^1$H NMR (300 MHz, DMSO-d$_6$) δ ppm 4.05-3.57 (m, 2H), 3.45-3.22 (m, 4H), 3.17 (t, 1H), 1.89-1.43 (m, 4H), 1.37-1.08 (m, 1H). LC-MS: [M+H]$^+$=117.0.

Intermediate 15.2:
3-(bromomethyl)tetrahydro-2H-pyran

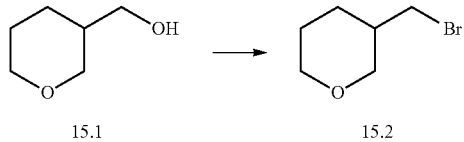 [SMILES: OCC1CCCOC1 ; BrCC1CCCOC1]

15.1          15.2

At rt, to a suspension of 4,5-dichloro-3,6-dioxocyclohexa-1,4-diene-1,2-dicarbonitrile (1.216 g, 5.356 mmol), TBAB (1.727 mg, 5.356 mmol) and PPh$_3$ (1.405 g, 5.356 mmol) in DCM (15 mL) was added a solution of 15.1 (360 mg, 3.151 mmol) in DCM (10 mL) dropwise quickly. After addition, the reaction mixture turned to a brown solution and was stirred at rt for another 1 h. Then it was purified by column chromatography on silica gel (pH=8-9, eluent: PE/EA=10:1) directly to give crude title compound (140 mg, 25%) as a colorless oil.

Intermediate 15.3: 3-bromo-1-((tetrahydro-2H-pyran-3-yl)methyl)-1H-indole-5-carbonitrile

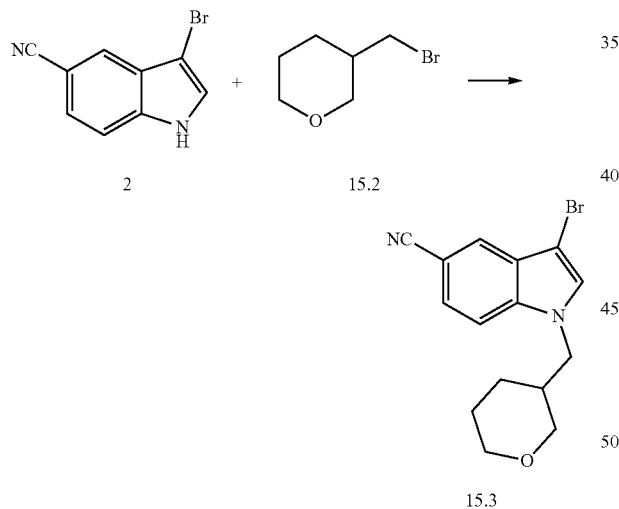

To a solution of 2 (100 mg, 0.452 mmol) in dry DMF (3 mL) was added NaH (60%, 27 mg, 0.678 mmol) in several portions under ice-water bath. Then the mixture was stirred at rt for 10 min and followed by addition of 15.2 (138 mg, 0.768 mmol) and then it was stirred at 50° C. overnight. The mixture was diluted with water and extracted with EA for 3 times. The organic layer was combined and washed with brine for 3 times, dried over Na$_2$SO$_4$, concentrated and then purified by prep-TLC (eluent: PE~PE/EA=2:1) to give the title compound (110 mg, 76%) as a yellow oil. $^1$H NMR (300 MHz, DMSO-d$_6$) δ ppm 7.99 (s, 1H), 7.91 (s, 1H), 7.87 (d, 1H), 7.66 (d, 1H), 4.22 (m, 2H), 3.74 (d, 1H), 3.66-3.61 (m, 1H), 3.35 (s, 1H), 3.26-3.15 (m, 1H), 2.11 (s, 1H), 1.64 (s, 2H), 1.52-1.39 (m, 1H), 1.38-1.22 (m, 1H). LC-MS: [M+H]$^+$=318.92, 320.87.

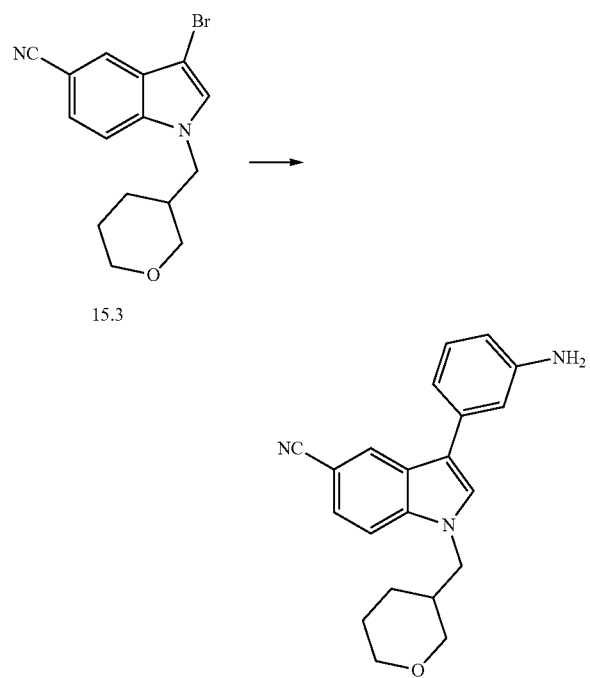

Example 15

To a solution of 15.3 (67 mg, 0.209 mmol) and (3-aminophenyl)boronic acid (52 mg, 0.313 mmol) in the co-solvent of i-PrOH/H$_2$O (2.5 mL, 10:1) was added 2N Na$_2$CO$_3$ aq. (0.627 mL, 1.254 mmol) and Pd(PPh$_3$)$_2$Cl$_2$ (15 mg, 0.021 mmol). The mixture was stirred at 100° C. for 40 min under N$_2$ atmosphere by microwave. Water (15 mL) was added. The mixture was extracted with EA for three times. The combined organic phase was washed with brine and dried over Na$_2$SO$_4$, concentrated and purified by prep-TLC (eluent: PE/EA=1:1) to give a crude product which was purified by prep-HPLC (0.1% NH$_3$.H$_2$O/ACN/H$_2$O) and lyophilized to give the title compound (18.9 mg, 27%) as a white solid. $^1$H NMR (400 MHz, DMSO-d$_6$) δ ppm 8.30 (d, 1H), 7.82 (s, 1H), 7.79 (d, 1H), 7.56 (dd, 1H), 7.09 (t, 1H), 6.95 (t, 1H), 6.81 (d, 1H), 6.50 (dd, 1H), 5.16 (s, 2H), 4.23 (dd, 1H), 4.15 (dd, 1H), 3.75-3.65 (m, 1H), 3.61 (dd, 1H), 3.37 (s, 1H), 3.20 (dd, 1H), 2.10 (s, 1H), 1.62 (d, 2H), 1.48-1.38 (m, 1H), 1.37-1.24 (m, 1H). LC-MS: [M+H]$^+$=332.19.

Example 19

2-((3-(3-amino-2-methylphenyl)-5-cyano-1H-indol-1-yl)methyl)benzamide

Intermediate 19.1: methyl 2-((3-bromo-5-cyano-1H-indol-1-yl)methyl)benzoate

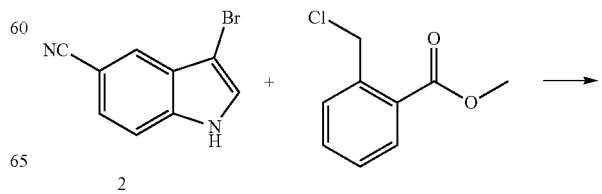

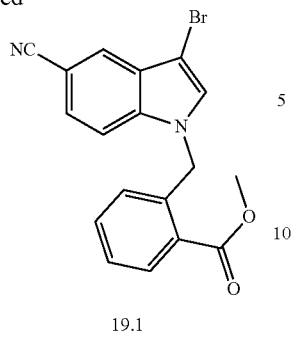

19.1

The title compound was prepared by using a procedure similar to that of intermediate 1.3 by replacing intermediate 1.1 and 1.2 with intermediate 2 and methyl 2-(chloromethyl)benzoate. $^1$H-NMR (400 MHz, DMSO-$d_6$) δ ppm 7.99-7.94 (m, 2H), 7.88 (s, 1H), 7.64 (d, 1H), 7.54 (d, 1H), 7.46-7.40 (m, 2H), 6.49 (d, 1H), 5.86 (s, 2H), 3.86 (s, 2H).

Intermediate 19.2: 2-((3-bromo-5-cyano-1H-indol-1-yl)methyl)benzoic acid

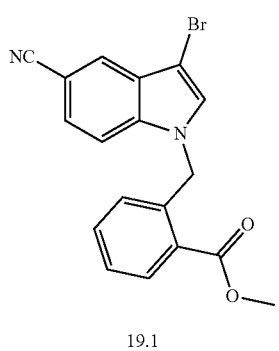

19.1

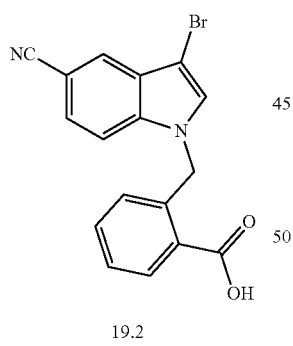

19.2

To a solution of 19.1 (140 mg, 0.379 mmol) in THF (5 mL) was added lithium hydroxide (45.4 mg, 1.896 mmol), then water (1 mL) was added. The mixture was stirred at 20° C. for 5 h. The mixture was concentrated under reduced pressure to remove the THF. Then the residue was treat with hydrochloric acid to pH=3. Collected the precipitate, dried to give the title compound (130 mg) as a white solid which was used directly for next step. $^1$H-NMR (400 MHz, DMSO-$d_6$) δ ppm 13.25 (b, 1H), 7.98-7.96 (m, 2H), 7.95 (s, 1H), 7.64 (d, 1H), 7.54 (d, 1H), 7.43-7.38 (m, 2H), 6.49 (d, 1H), 5.86 (s, 2H).

Intermediate 19.3: 2-((3-bromo-5-cyano-1H-indol-1-yl)methyl)benzamide

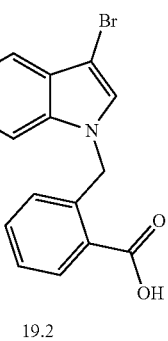

19.2

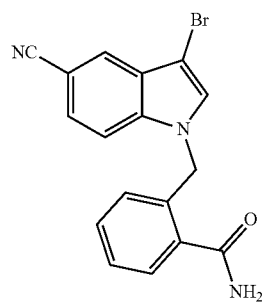

19.3

The title compound was prepared by using a procedure similar to that of Example 4 by replacing intermediate 4.2 with intermediate 19.2. LC-MS: [M−H]$^−$=351.6, 353.6.

19.3 +

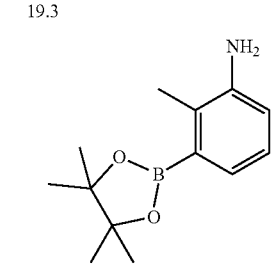

-continued

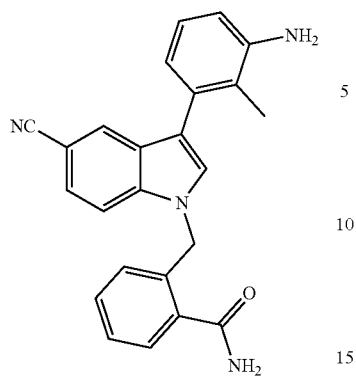

Example 19

The title compound was prepared by using a procedure similar to that of intermediate 1.1 by replacing intermediate 2 and (3-nitrophenyl)boronic acid with intermediate 19.3 and 2-methyl-3-(4,4,5,5-tetramethyl-1,3,2-dioxaborolan-2-yl)aniline. $^1$H-NMR (400 MHz, CD$_3$OD) δ ppm 8.00 (s, 1H), 7.72 (s, 1H), 7.71-7.65 (m, 1H), 7.63 (s, 1H), 7.62-7.51 (m, 2H), 7.48 (d, 1H), 7.45 (d, 1), 7.35-7.32 (m, 2H), 6.95 (t, 1H), 6.88 (t, 1H), 6.65 (d, 1H), 6.56 (d, 1H), 5.72 (s, 2H), 1.97 (s, 3H). LC-MS: [M+H]$^+$=380.9.

Example 20

3-(3-amino-2-methylphenyl)-1-(2-methoxybenzyl)-1H-indole-5-carbonitrile

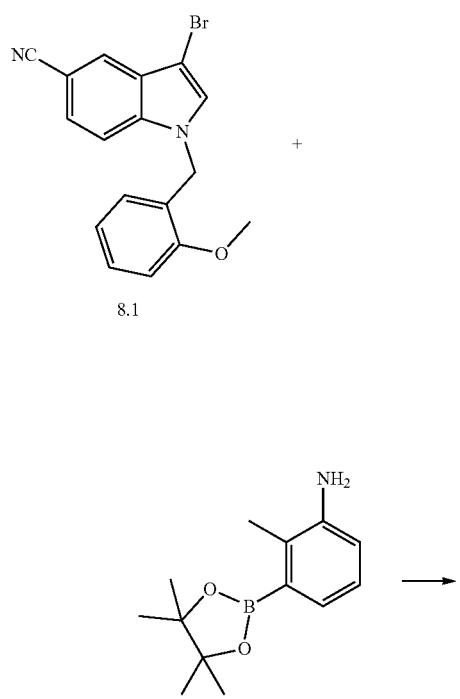

-continued

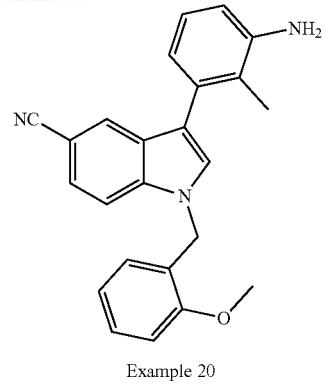

Example 20

The title compound was prepared by using a procedure similar to that of intermediate 1.1 by replacing intermediate 2 and (3-nitrophenyl)boronic acid with intermediate 8.1 and 2-methyl-3-(4,4,5,5-tetramethyl-1,3,2-dioxaborolan-2-yl)aniline. $^1$H-NMR (400 MHz, CD$_3$OD) δ ppm 7.69 (s, 1H), 7.57 (d, 1H), 7.40 (d, 1H), 7.35 (s, 1H), 7.28 (t, 1H), 7.05-6.97 (m, 3H), 6.87 (t, 1H), 6.78 (d, 1H), 6.71 (d, 1H), 5.42 (s, 2H), 3.86 (s, 3H), 2.05 (s, 3H). LC-MS: [M+H]$^+$=367.9.

Example 23

3-(3-amino-2-methylphenyl)-1-(2-methoxybenzyl)-6-methyl-1H-indole-5-carbonitrile Intermediate 23.1: 1-(2-methoxybenzyl)-6-methyl-1H-indole-5-carbonitrile

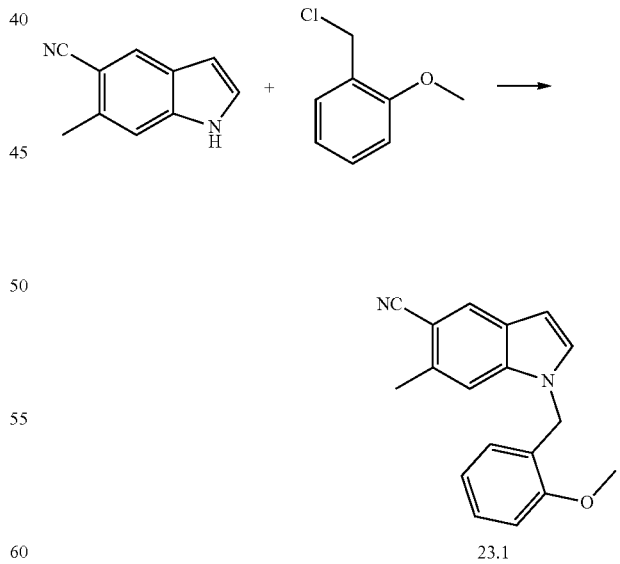

The title compound was prepared by using a procedure similar to that of intermediate 1.3 by replacing intermediate 1.1 and 1.2 with 6-methyl-1H-indole-5-carbonitrile and 1-(chloromethyl)-2-methoxybenzene. LC-MS: [M+H]$^+$=276.9.

Intermediate 23.2: 3-bromo-1-(2-methoxybenzyl)-6-methyl-1H-indole-5-carbonitrile

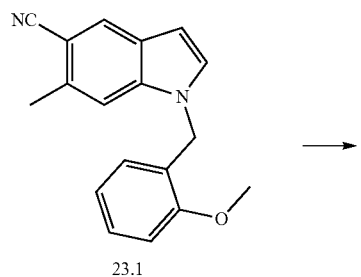

23.1

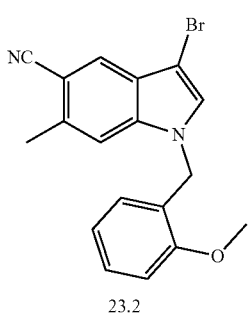

23.2

To a solution of 23.1 (110 mg, 0.398 mmol) in DMF (10 mL) was added NBS (78 mg, 0.438 mmol). The mixture was stirred at 20° C. for 1 h. Water (30 mL) was added. The mixture was extracted with ethyl acetate (10 mL×2), combined the organic layer, dried over Na$_2$SO$_4$, filtered and concentrated, the residue was purified by silica column to give the title compound (700 mg, 81%) as a white solid. LC-MS: [M+H]$^+$=354.8, 356.8.

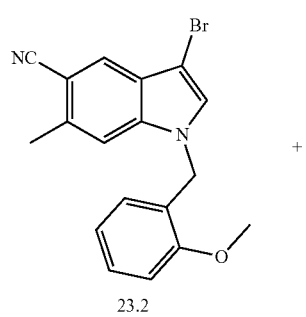

23.2

+

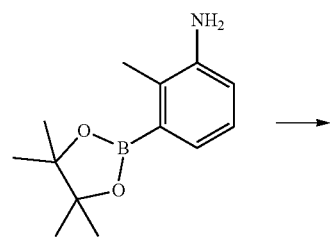

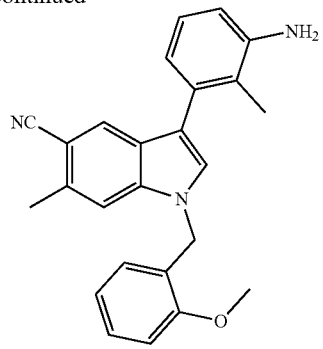

Example 23

The title compound was prepared by using a procedure similar to that of intermediate 1.1 by replacing intermediate 2 and (3-nitrophenyl)boronic acid with intermediate 23.2 and 2-methyl-3-(4,4,5,5-tetramethyl-1,3,2-dioxaborolan-2-yl)aniline. $^1$H-NMR (400 MHz, DMSO-d$_6$) δ ppm 7.65 (s, 1H), 7.57 (s, 1H), 7.50 (s, 1H), 7.25 (t, 1H), 7.04 (d, 1H), 6.96-6.86 (m, 2H), 6.64 (d, 1H), 6.54 (d, 1H), 5.40 (s, 2H), 3.86 (s, 3H), 2.49 (s, 3H), 1.96 (s, 3H). LC-MS: [M+H]$^+$=381.9.

Example 24

3-(3-amino-2-methylphenyl)-1-(3-hydroxypropyl)-1H-indole-5-carbonitrile

Intermediate 24.1: 3-bromo-1-(3-((tert-butyldimethylsilyl)oxy)propyl)-1H-indole-5-carbonitrile

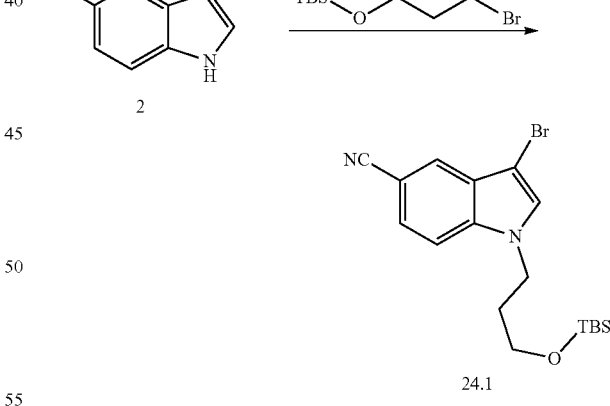

24.1

To a solution of compound 2 (200 mg, 0.905 mmol) in dry DMF (2.5 mL) was added NaH (60%, 55 mg, 1.358 mmol) in several portions under ice-water bath. Then the mixture was stirred at rt for 10 min and followed by addition of (3-bromopropoxy)(tert-butyl)dimethylsilane (458 mg, 1.810 mmol) and then it was stirred at 50° C. overnight. The mixture was diluted with water and extracted with EA for 3 times. The organic layer was combined and washed with brine for 3 times, dried over Na$_2$SO$_4$, concentrated and then purified by flash column chromatography on silica gel (eluent: EA %=5~10%) to give the title compound (246 mg, 69%) as a yellow oil. $^1$H-NMR (300 MHz, DMSO-$d_6$) δ ppm 7.98 (s, 1H), 7.88 (s, 1H), 7.79 (d, 1H), 7.64 (d, 1H), 4.36 (t, 2H), 3.56 (t, 2H), 2.01 (m, 2H), 0.90 (s, 9H), 0.03 (s, 6H). LC-MS: [M+H]$^+$=393.0, 395.0.

Intermediate 24.2: 3-(3-amino-2-methylphenyl)-1-(3-((tert-butyldimethylsilyl)oxy)propyl)-1H-indole-5-carbonitrile

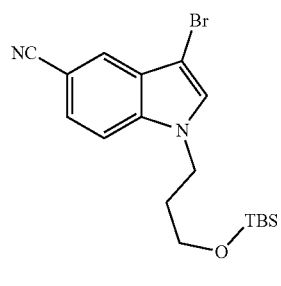

24.1

+

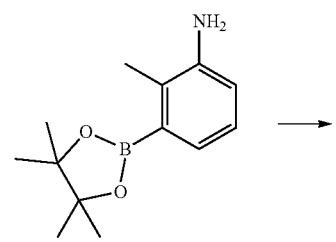

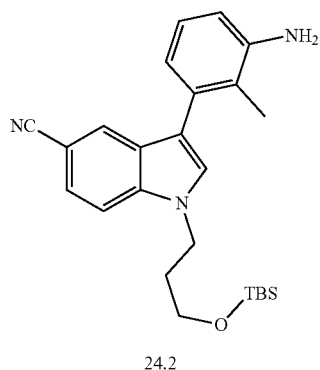

24.2

To a solution of 24.1 (100 mg, 0.254 mmol) and 2-methyl-3-(4,4,5,5-tetramethyl-1,3,2-dioxaborolan-2-yl)aniline (90 mg, 0.381 mmol) in the co-solvent of i-PrOH/H$_2$O (4 mL, 10:1) was added 2N Na$_2$CO$_3$ aq. (0.76 mL, 1.524 mmol) and Pd(PPh$_3$)$_2$Cl$_2$ (18 mg, 0.025 mmol). The mixture was stirred at 100° C. for 40 min under N$_2$ atmosphere by microwave. It was diluted with brine and extracted with EA for three times. The combined organic phase was washed with brine and dried over Na$_2$SO$_4$, concentrated and purified by prep-TLC (eluent: PE/EA=2:1) to give the title compound (58 mg, 55%) as a brown oil. $^1$H-NMR (400 MHz, DMSO-$d_6$) δ ppm 7.76 (d, 2H), 7.58 (d, 2H), 7.02 (t, 1H), 6.72 (d, 1H), 6.61 (d, 1H), 4.97 (s, 2H), 4.40 (t, 2H), 3.60 (t, 2H), 2.03 (s, 3H), 0.91 (s, 9H), 0.05 (s, 6H). LC-MS: [M+H]$^+$=419.6.

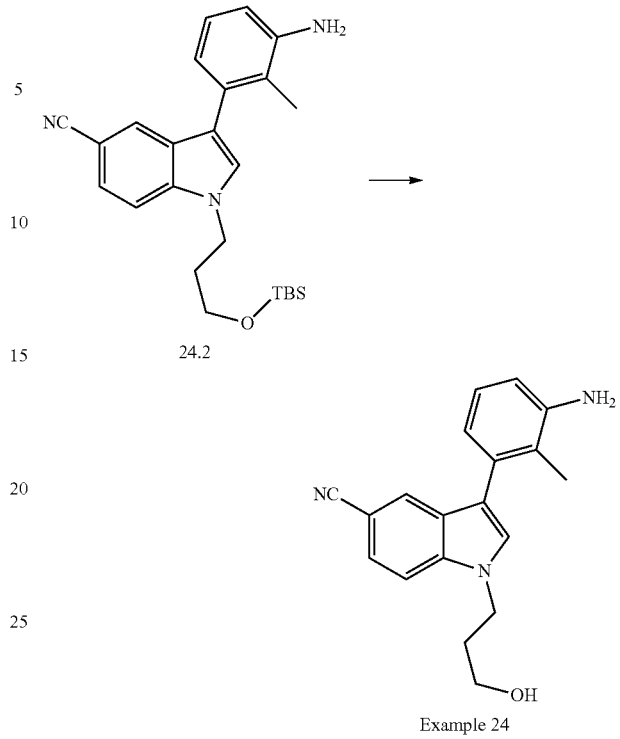

24.2

Example 24

The solution of Compound 24.2 (50 mg, 0.119 mmol) and TBAF (93 mg, 0.357 mmol) in THF (1 mL) was stirred at rt for 3 h. The reaction mixture was purified by ion exchange resin (NH$_3$.H$_2$O/MeOH=1:1) to remove most TBAF. Then the crude product was purified by prep-HPLC (0.1% NH$_3$.H$_2$O/ACN/H$_2$O) and lyophilized to give the title compound (13.7 mg, 38%) as a white solid. $^1$H NMR (300 MHz, DMSO-$d_6$) δ ppm 7.74 (d, 2H), 7.58 (s, 1H), 7.53 (dd, 1H), 6.97 (t, 1H), 6.66 (d, 1H), 6.56 (d, 1H), 4.93 (s, 2H), 4.69 (s, 1H), 4.35 (t, 2H), 3.39 (t, 2H), 1.98 (s, 3H), 1.94 (t, 2H). LC-MS: [M+H]$^+$=306.1.

Example 26

3-(3-amino-2-methylphenyl)-1-(3-methoxypropyl)-1H-indole-5-carbonitrile

Intermediate 26.1: 3-bromo-1-(3-hydroxypropyl)-1H-indole-5-carbonitrile

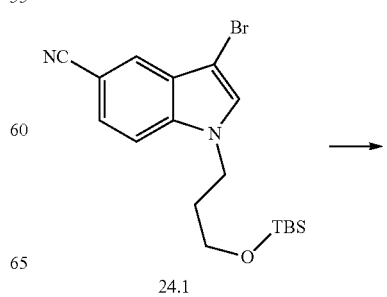

24.1

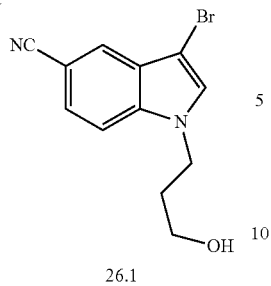

26.1

The solution of Compound 24.1 (88 mg, 0.224 mmol) and TBAF (175 mg, 0.671 mmol) in THF (2 mL) was stirred at rt overnight. Then the reaction mixture was purified by prep-TLC (eluent: DCM/MeOH=20:1) to give the title compound (63 mg, 100%) as a white solid. ¹H NMR (300 MHz, DMSO-d₆) δ ppm 7.98 (s, 1H), 7.91 (s, 1H), 7.82 (d, 1H), 7.65 (d, 1H), 4.36 (t, 2H), 3.52 (s, 1H), 3.39 (t, 2H), 1.99-1.91 (m, 2H). LC-MS: [M+H]⁺=279.0.

Intermediate 26.2: 3-bromo-1-(3-methoxypropyl)-1H-indole-5-carbonitrile

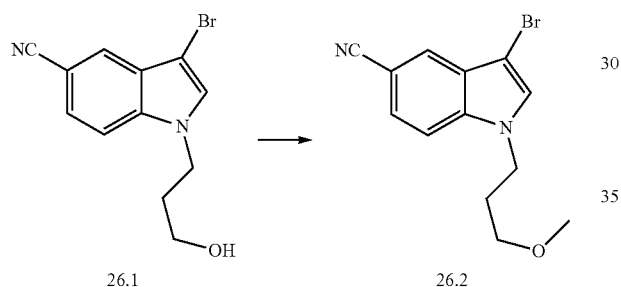

To a solution of compound 26.1 (55 mg, 0.197 mmol) in dry THF (1 mL) was added NaH (60%, 12 mg, 0.296 mmol) in several portions under ice-water bath. Then the mixture was stirred at rt for 10 min and followed by addition of CH₃I (84 mg, 0.591 mmol) and then it was stirred at 45° C. overnight. Some white precipitate appeared. The mixture was diluted with water and extracted with EA for 3 times. The organic layer was combined and washed with brine for 3 times, dried over Na₂SO₄, concentrated to give the title compound (48 mg, 83%) as a yellow solid. ¹H NMR (300 MHz, DMSO-d₆) δ ppm 7.98 (s, 1H), 7.91 (s, 1H), 7.80 (d, 1H), 7.65 (d, 1H), 4.35 (t, 2H), 3.27 (t, 2H), 3.24 (s, 3H), 2.08-1.98 (m, 2H). LC-MS: [M+H]⁺=292.9, 294.9.

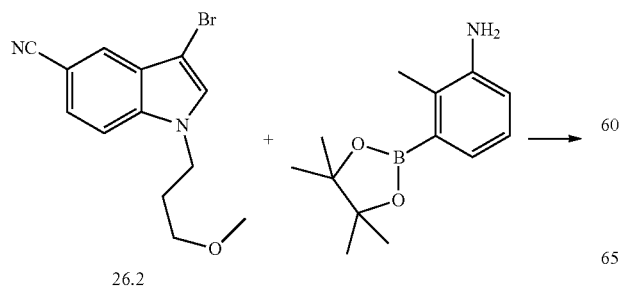

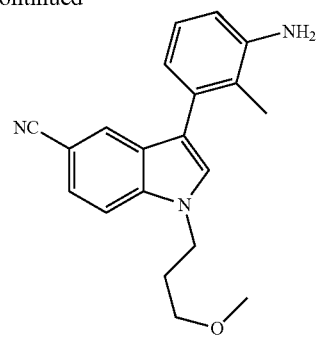

Example 26

To a solution of compound 26.2 (40 mg, 0.136 mmol) and 2-methyl-3-(4,4,5,5-tetramethyl-1,3,2-dioxaborolan-2-yl) aniline (48 mg, 0.205 mmol) in the co-solvent of i-PrOH/H₂O (1.5 mL, 10:1) was added 2N Na₂CO₃ aq. (0.4 mL, 0.816 mmol) and Pd(PPh₃)₂Cl₂ (10 mg, 0.014 mmol). The mixture was stirred at 100° C. for 40 min under N₂ atmosphere by microwave. The mixture was diluted with brine and extracted with EA for three times. The combined organic phase was washed with brine and dried over Na₂SO₄, concentrated and purified by prep-HPLC (0.1% NH₃.H₂O/ACN/H₂O) to give the title compound (10.6 mg, 26%) as a brown solid. ¹H NMR (400 MHz, DMSO-d₆) δ ppm 7.72 (d, 1H), 7.71 (d, 1H), 7.57 (s, 1H), 7.53 (dd, 1H), 6.97 (t, 1H), 6.67 (dd, 1H), 6.56 (dd, 1H), 4.92 (s, 2H), 4.34 (t, 2H), 3.27 (t, 2H), 3.22 (s, 3H), 2.04 (m, 2H), 1.98 (s, 3H). LC-MS: [M+H]⁺=320.3.

Example 27

(E)-3-(3-amino-2-methylphenyl)-1-(4-hydroxybut-2-en-1-yl)-1H-indole-5-carbonitrile Intermediate 27.1: (E)-3-bromo-1-(4-bromobut-2-en-1-yl)-1H-indole-5-carbonitrile

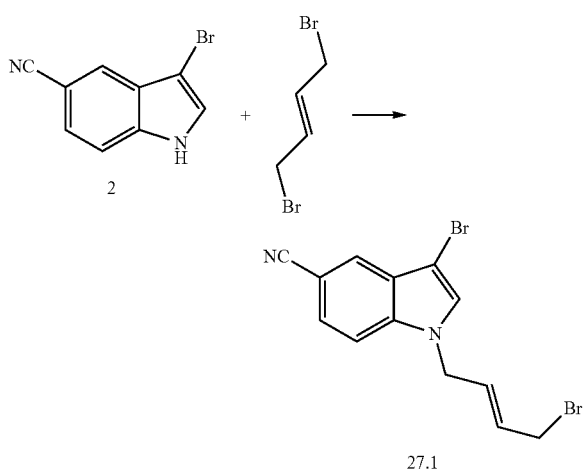

To the mixture of 2 (300 mg, 1.357 mmol) and DMF (10 mL) was added NaH (65.1 mg, 1.629 mmol) at 0° C. The mixture was stirred at rt for 30 min. To the mixture was added (E)-1,4-dibromobut-2-ene (435 mg, 2.036 mmol) at 0° C. The mixture was stirred for another 3 h. The reaction was finished and then quenched by 10% citric acid. The solvent was evaporated and the residue was extracted by EA. The combined organic layers are washed successively with water and a brine solution, dried over $Na_2SO_4$ and concentrated. The residue was purified by column (eluted by EA/Hexane 0/100 to 20/80) to give the title compound (200 mg, 40%). LC-MS: $[M+H]^+=354.9$.

Intermediate 27.2: (E)-4-(3-bromo-5-cyano-1H-indol-1-yl)but-2-en-1-yl acetate

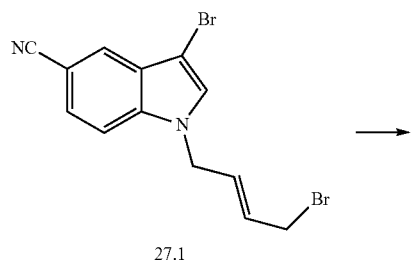

27.1

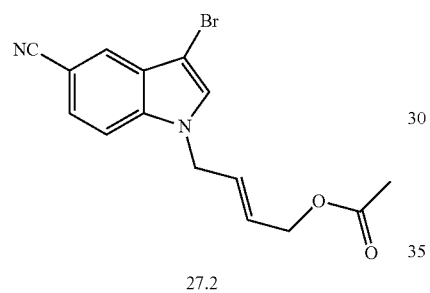

27.2

A mixture of 27.1 (50 mg, 0.141 mmol), potassium acetate (139 mg, 1.412 mmol) and DMF (2 mL) was stirred at 100° C. for 1 h. The solvent was evaporated. The residue was extracted by EA. The organic layer was washed by brine, dried over $Na_2SO_4$ and concentrated. The residue was purified by silica column (eluent: EA/Hexane from 0/100 to 30/70) to give the title compound (45 mg, 91%). $^1$H NMR (400 MHz, DMSO-$d_6$) δ ppm 7.90 (s, 1H), 7.46 (d, 1H), 7.35 (d, 1H), 7.25 (d, 1H), 5.93-5.86 (m, 1H), 5.69-5.62 (m, 1H), 4.76 (d, 2H), 4.56 (d, 2H), 2.05 (s, 3H).

Intermediate 27.3: (E)-3-bromo-1-(4-hydroxybut-2-en-1-yl)-1H-indole-5-carbonitrile

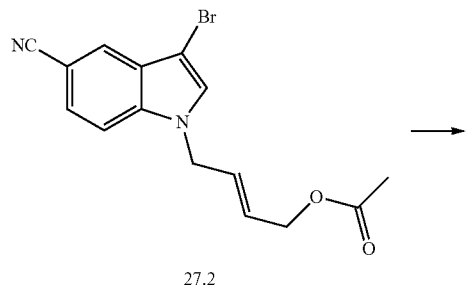

27.2

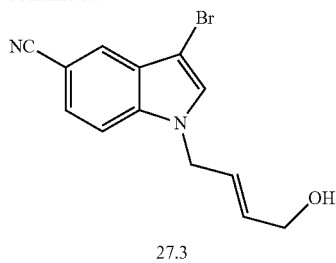

27.3

A mixture of 27.2 (45 mg, 0.135 mmol), $K_2CO_3$ (200 mg, 1.447 mmol) and MeOH (8 mL) was stirred at rt for 2 h. The mixture was added 20 ml EA and the mixture was filtered. The filtrate was collected and concentrated. The residue was used directly in next step without further purification. LC-MS: $[M+H]^+=291.0, 293.0$.

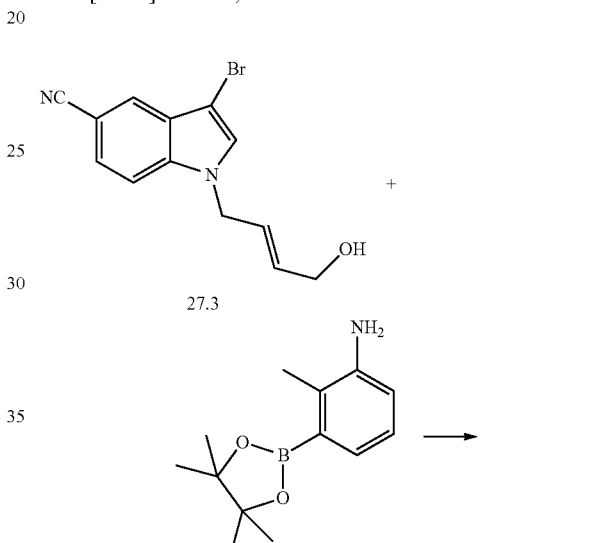

Example 27

A mixture of 27.3 (40 mg, 0.137 mmol), 2-methyl-3-(4,4,5,5-tetramethyl-1,3,2-dioxaborolan-2-yl)aniline (48.0 mg, 0.206 mmol), $PdCl_2(PPh_3)_2$ (7.71 mg, 10.99 μmol), $Na_2CO_3$ (29.1 mg, 0.275 mmol), 2-propanol (2 mL) and Water (0.2 mL) was stirred at 100° C. for 40 min under microwave and $N_2$. The reaction was monitored by LCMS. The mixture was extracted by EA and washed by brine. The organic layer was dried, filtered and evaporated to dryness. The residue was purified by silica column (eluent: EA/Hexane from 0/100 to 70/30) to give the title compound (10 mg, 22%). $^1$H NMR (400 MHz, CD$_3$OD) δ ppm 7.70 (s, 1H), 7.61 (d, 1H), 7.46 (d, 1H), 7.37 (s, 1H), 7.04 (t, 1H), 6.80 (d, 1H), 6.73 (d, 1H), 5.95 (m, 1H), 5.75 (m, 1H), 4.92 (m, 2H), 4.07 (m, 2H), 2.06 (s, 3H). LC-MS: [M+H]⁺=318.1.

Example 28

3-(3-amino-2-methylphenyl)-1-(4-hydroxybutyl)-1H-indole-5-carbonitrile

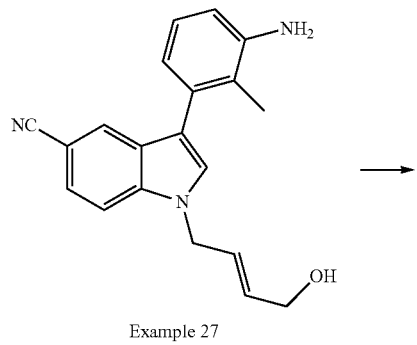

Example 27

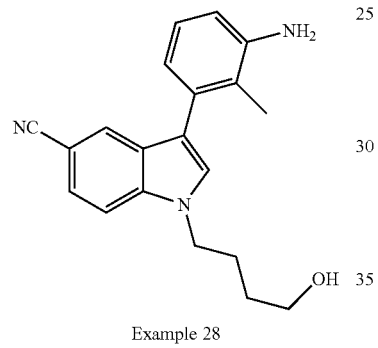

Example 28

A mixture of Example 27 (15 mg, 0.047 mmol), Pd/C (5.03 mg, 4.73 μmol) and EtOH (10 mL) was stirred under hydrogen atmosphere (1 atm) at rt for 3 h. The mixture was filtered and the filtrate was concentrated. The residue was purified by prep-HPLC (0.1% TFA/ACN/H₂O) and lyophilized to give the title compound (3.5 mg, 22%). LC-MS: [M+H]⁺=319.9.

Example 29 methyl 3-(3-(3-amino-2-methylphenyl)-5-cyano-1H-indol-1-yl)propanoate

Intermediate 29.1: methyl 3-(3-bromo-5-cyano-1H-indol-1-yl)propanoate

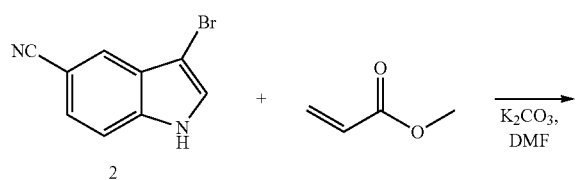

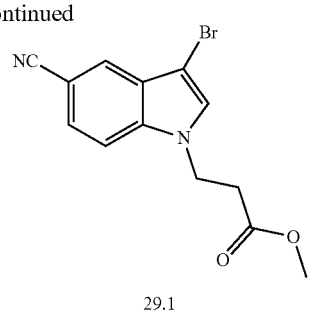

29.1

To a stirred solution of 2 (80 mg, 0.362 mmol) in DMF (6 mL) was added methyl acrylate (50 mg, 0.543 mmol) and K₂CO₃ (150 mg, 1.09 mmol). The reaction was stirred at rt overnight. The mixture was extracted with EA, washed with water and brine. The organic layers was dried over anhydrous Na₂SO₄, filtered and the filtrate was concentrated to give the crude product which was purified by prep-TLC (PE:EA=2:1) to give the title compound (180 mg, 87%). ¹H NMR (300 MHz, DMSO-d₆) δ ppm 7.97 (s, 1H), 7.90 (s, 1H), 7.87 (d, 1H), 7.66 (d, 1H), 4.56 (t, 2H), 3.61 (s, 3H), 2.96 (t, 2H). LC-MS: [M+H]⁺=307.2, 309.2.

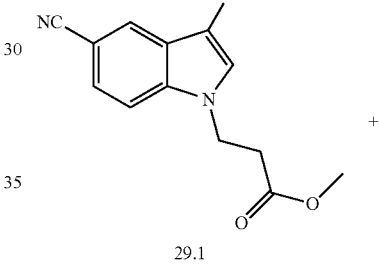

29.1

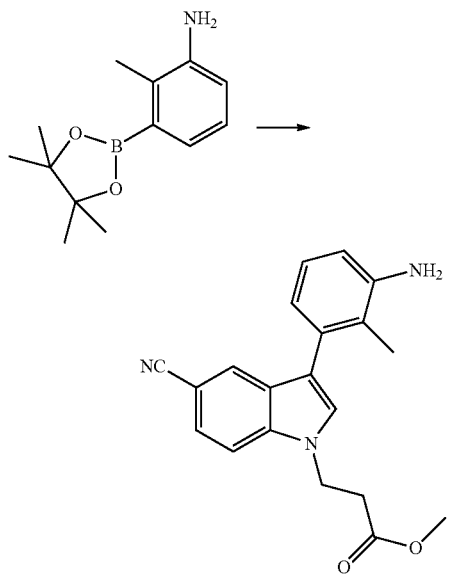

Example 29

A mixture of 29.1 (135 mg, 0.437 mmol), 2-methyl-3-(4,4,5,5-tetramethyl-1,3,2-dioxaborolan-2-yl)aniline (254 mg, 1.05 mmol) and Cs₂CO₃ (673 mg, 2.05 mmol) in DME (15 mL) was degassed with N₂. Then Pd(dppf)Cl₂CH₂Cl₂ (36 mg, 0.044 mmol) was added to. The reaction suspension was degassed with N₂ and heated at 150° C. for 30 min by microwave reactor. The reaction mixture was diluted with EA and washed with water and brine. The combined organic layers was dried over anhydrous Na₂SO₄ and filtered. The filtrate was evaporated to give the crude which was purified by prep-HPLC (0.1% NH₃H₂O/ACN/H₂O) to give the title compound (5.8 mg, 4%). ¹H NMR (400 MHz, DMSO-d₆) δ ppm 7.78 (d, 1H), 7.72 (d, 1H), 7.57 (s, 1H), 7.54 (dd, 1H), 6.97 (t, 1H), 6.67 (d, 1H), 6.55 (d, 1H), 4.91 (s, 2H), 4.55 (t, 2H), 3.57 (s, 3H), 2.94 (t, 2H), 1.97 (s, 3H). LC-MS: [M+H]⁺=334.0.

Example 30

3-(3-(3-amino-2-methylphenyl)-5-cyano-1H-indol-1-yl)propanamide

Intermediate 30.1:
3-(3-bromo-5-cyano-1H-indol-1-yl)propanoic acid

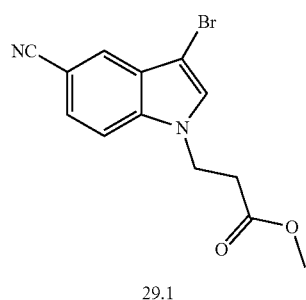

29.1

LiOH, MeOH
H₂O, r.t.

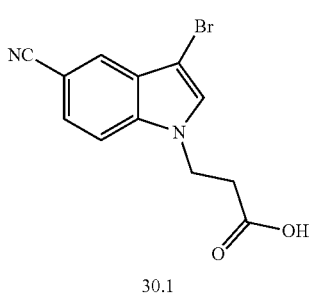

30.1

To a solution of 29.1 (100 mg, 0.326 mmol) in MeOH (3 mL) was added an aqueous solution of LiOH H₂O (2 N, 330 uL). The reaction was stirred ar rt overnight. The solvent of reaction was removed to give the residue, which was dissolved in 1.5 mL of water and neutralized with 1 N HCl aqueous solution to pH 3~4. Solid precipitated. The suspension was extracted with EA, washed with water and brine. The combined organic layers were dried over anhydrous Na₂SO₄, filtered and the filtrate was concentrated in reduce pressure to give the crude product (90 mg) which was used in next step without purification. ¹H NMR (300 MHz, DMSO-d₆) δ ppm 12.48 (s, 1H), 7.97 (s, 1H), 7.92-7.83 (m, 2H), 7.66 (d, 1H), 4.52 (t, 2H), 2.86 (t, 2H). LC-MS: [M+H]⁺=293.1, 295.1.

Intermediate 30.2:
3-(3-bromo-5-cyano-1H-indol-1-yl)propanamide

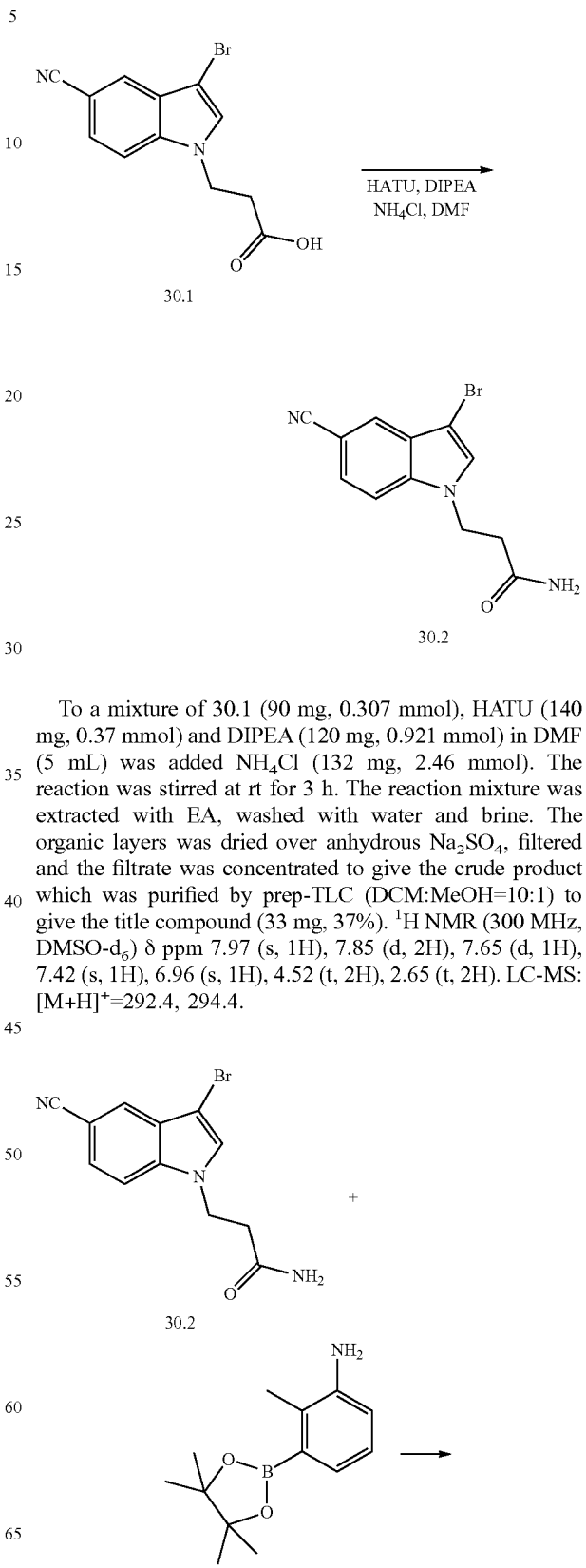

To a mixture of 30.1 (90 mg, 0.307 mmol), HATU (140 mg, 0.37 mmol) and DIPEA (120 mg, 0.921 mmol) in DMF (5 mL) was added NH₄Cl (132 mg, 2.46 mmol). The reaction was stirred at rt for 3 h. The reaction mixture was extracted with EA, washed with water and brine. The organic layers was dried over anhydrous Na₂SO₄, filtered and the filtrate was concentrated to give the crude product which was purified by prep-TLC (DCM:MeOH=10:1) to give the title compound (33 mg, 37%). ¹H NMR (300 MHz, DMSO-d₆) δ ppm 7.97 (s, 1H), 7.85 (d, 2H), 7.65 (d, 1H), 7.42 (s, 1H), 6.96 (s, 1H), 4.52 (t, 2H), 2.65 (t, 2H). LC-MS: [M+H]⁺=292.4, 294.4.

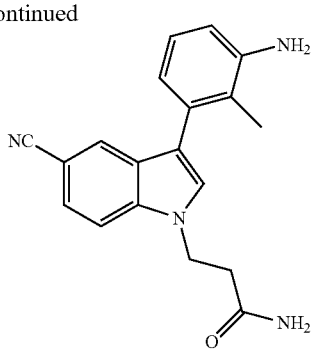

Example 30

A mixture of 30.1 (25 mg, 0.086 mmol), 2-methyl-3-(4,4,5,5-tetramethyl-1,3,2-dioxaborolan-2-yl)aniline (26 mg, 0.111 mmol) and aqueous Na$_2$CO$_3$ solution (2 N, 0.52 mmol) in i-PrOH/H$_2$O (10:1, 3 mL) was degassed with N$_2$. Then Pd(PPh$_3$)$_2$Cl$_2$ (6 mg, 0.0086 mmol) was added. The reaction suspension was degassed with N$_2$ and heated at 100° C. for 30 min by microwave reactor. The reaction mixture was diluted with EA and washed with water. The combined organic layers was dried over anhydrous Na$_2$SO$_4$ and filtered. The filtrate was evaporated to give the crude product which was purified by prep-HPLC (0.1% TFA/ACN/H$_2$O) to give the title compound (10.9 mg, 44%). $^1$H NMR (400 MHz, DMSO-d$_6$) δ ppm 7.80 (d, 1H), 7.73 (s, 1H), 7.61 (d, 1H), 7.56 (d, 1H), 7.39 (s, 1H), 7.23 (s, 1H), 7.07 (s, 2H), 6.93 (s, 1H), 4.52 (t, 2H), 3.46 (s, 2H), 2.65 (t, 2H), 2.13 (s, 3H). LC-MS: [M+H]$^+$=319.1.

Example 31

3-(3-amino-2-methylphenyl)-1-(3-hydroxy-3-methylbutyl)-1H-indole-5-carbonitrile

Intermediate 31.1: 3-bromo-1-(3-hydroxy-3-methylbutyl)-1H-indole-5-carbonitrile

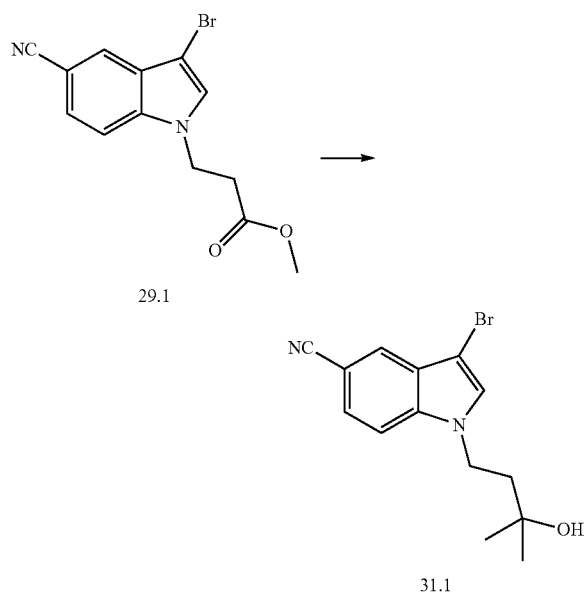

At 0° C., to a solution of compound 29.1 (100 mg, 0.325 mmol) in THF (4 mL) was added a solution of 1 M CH$_3$MgBr in THF (0.98 mL, 0.977 mmol) dropwise. After addition, the reaction was stirred at rt for 1 h. The reaction mixture was diluted with water and extracted with EA for 4 times. The organic layer was combined and dried over anhydrous Na$_2$SO$_4$, filtered and concentrated to give a crude oil which was purified by prep-TLC (eluent: PE/EA=2:1) to give the title compound (38.5 mg, 38%) as a yellow oil. $^1$H NMR (300 MHz, DMSO-d$_6$) δ ppm 7.98 (s, 1H), 7.92 (s, 1H), 7.78 (d, 1H), 7.66 (d, 1H), 4.35 (t, 2H), 1.90 (t, 2H), 1.21 (s, 6H). LC-MS: [M+H]$^+$=307.2, 309.2.

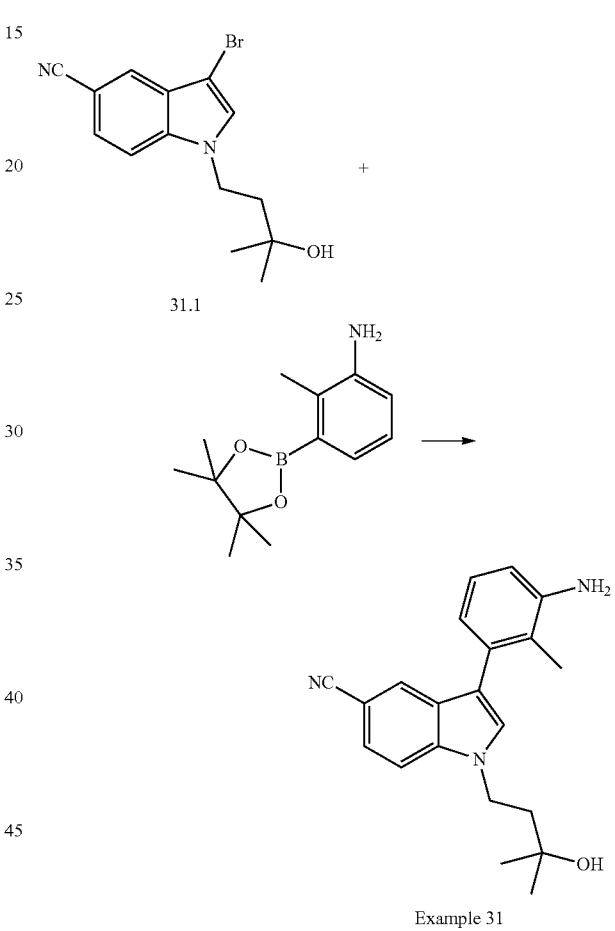

Example 31

To a mixture of compound 31.1 (35 mg, 0.114 mmol) and 2-methyl-3-(4,4,5,5-tetramethyl-1,3,2-dioxaborolan-2-yl)aniline (34.5 mg, 0.330 mmol) in the co-solvent of i-PrOH/H$_2$O (1.5 mL, 10:1) was added 2 N Na$_2$CO$_3$ aq. (340 uL, 0.68 mmol) and Pd(PPh$_3$)$_2$Cl$_2$ (7.7 mg, 0.011 mmol). The mixture was stirred at 100° C. for 30 min under N$_2$ atmosphere by microwave. It was diluted with brine and extracted with EA for three times. The combined organic phase was washed with brine and dried over Na$_2$SO$_4$, concentrated to give a crude product which was purified by prep-TLC (eluent: PE/EA=1:1) to give a crude product which contained POPh$_3$. It was purified by prep-HPLC (0.1% NH$_3$.H$_2$O/ACN/H$_2$O) and lyophilized to give the title compound (3.6 mg, 9.5%) as a white solid. $^1$H NMR (400 MHz, DMSO-d$_6$) δ ppm 7.72 (d, 1H), 7.69 (d, 1H), 7.59 (s, 1H), 7.56-7.52 (dd, 1H), 6.97 (t, 1H), 6.67 (d, 1H), 6.59-6.53 (m, 1H), 4.90 (s, 2H), 4.53 (s, 1H), 4.41-4.31 (m, 2H), 1.98 (s, 3H), 1.95-1.85 (m, 2H), 1.18 (s, 6H).

Example 32

3-(3-amino-2-methylphenyl)-1-(2-(1-hydroxycyclo-propyl)ethyl)-1H-indole-5-carbonitrile Intermediate 32.1: 1-(2-bromoethyl)cyclopropan-1-ol

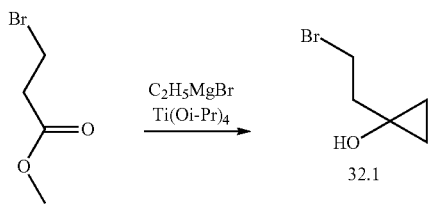

To a solution of methyl 3-bromopropanoate (2.0 g, 12.0 mmol) and titanium tetraisopropanolate (3.4 g, 12.0 mmol) in dry THF (40 mL) was added C₂H₅MgBr (26 mL, 1.0 M) dropwise at 0° C.-5° C. under N₂ atmosphere. The mixture was stirred at rt for 2 h. The reaction mixture was quenched with saturated ammonium chloride solution and then extracted with EA. The EA phase was washed with brine, dried over Na₂SO₄, concentrated and then purified by column chromatography on silica gel (PE:EA=5:1) to give the title compound (250 mg, yield:12%) as a brown oil. ¹H NMR (300 MHz, CDCl₃) δ ppm 3.62 (t, 2H), 2.12 (t, 2H), 1.97 (s, 1H), 0.82 (t, 2H), 0.55 (q, 2H).

Intermediate 32.2: (1-(2-bromoethyl)cyclopropoxy)(tert-butyl)dimethylsilane

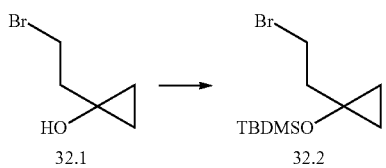 [SMILES: OC1(CCBr)CC1 ; CC(C)(C)[Si](C)(C)OC1(CCBr)CC1]

To a solution of compound 32.1 (250 mg, 1.5 mmol) and imidazole (204 mg, 3.0 mmol) in DCM (5 mL) was added TBDMSCl (340 mg, 2.75 mmol) under an ice-bath. The mixture was stirred at rt overnight. To the mixture was added water (5 mL). After separated, the organic phase was washed with brine, dried over Na₂SO₄, concentrated and then purified by column chromatography on silica gel (with 100% PE) to give the title compound (260 mg, 61%) as a colorless oil. ¹H NMR (300 MHz, CDCl₃) δ ppm 3.63-3.49 (m, 2H), 2.09-1.97 (m, 2H), 0.85 (s, 9H), 0.74 (t, 2H), 0.49 (t, 2H), 0.09 (s, 6H).

Intermediate 32.3: 3-bromo-1-(2-(1-((tert-butyldimethylsilyl)oxy)cyclopropyl)ethyl)-1H-indole-5-carbonitrile

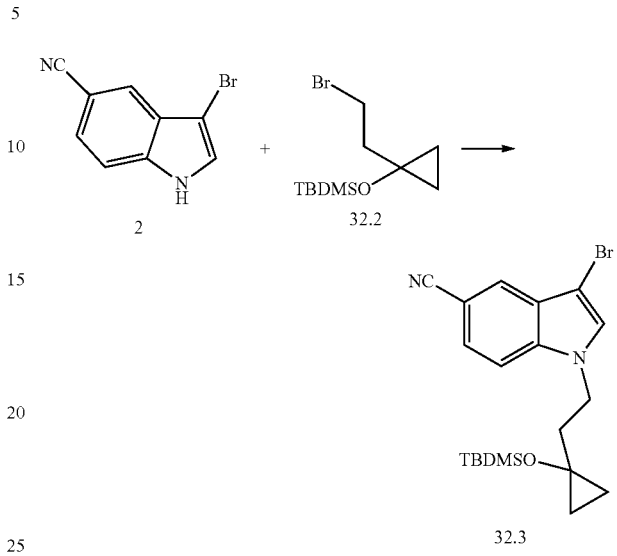

A mixture of compound 32.2 (240 mg, 0.86 mmol), compound 2 (158 mg, 0.72 mmol) and K₂CO₃ (298 mg, 2.16 mmol) in dry DMF (6.5 mL) was heated at 80° C. for 3 h. To the cooled mixture was added water (45 mL) and EA (15 mL). After separated, the aqueous layer was extracted with EA (15 mL×3). The combined organic phases were washed with brine, dried over Na₂SO₄, concentrated and then purified by column chromatography on silica gel (PE:EA=10:1) to give the title compound (302 mg, yield: 95%) as a white solid. ¹H NMR (300 MHz, CDCl₃) δ ppm 7.90 (s, 1H), 7.47-7.39 (m, 2H), 7.26 (s, 1H), 4.39 (t, 2H), 1.89 (t, 2H), 0.92 (s, 9H), 0.61 (t, 2H), 0.15-0.06 (m, 8H).

Intermediate 32.4: 3-bromo-1-(2-(1-hydroxycyclo-propyl)ethyl)-1H-indole-5-carbonitrile

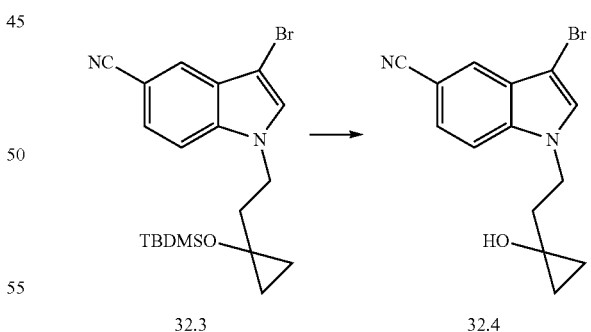

To a solution of compound 32.3 (140 mg, 0.33 mmol) in THF (7 mL) was added tetrabutylammonium fluoride trihydrate (315 mg, 1.00 mmol). The mixture was stirred at rt for 20 min. To the mixture was added EA (15 mL) and water (20 mL). After separated, the aqueous layer was extracted with EA (15 mL×2). The combined organic phases were washed with brine, dried over Na₂SO₄, concentrated and then purified by column chromatography on silica gel (PE:EA=2:1) to give the title compound (100 mg, yield: 95%) as a white solid. ¹H NMR (300 MHz, CDCl₃) δ ppm 7.91 (s, 1H), 7.48-7.41 (m, 2H), 7.30 (s, 1H), 4.43 (t, 2H), 2.00 (t, 2H), 1.74 (s, 1H), 0.67 (t, 2H), 0.21 (t, 2H).

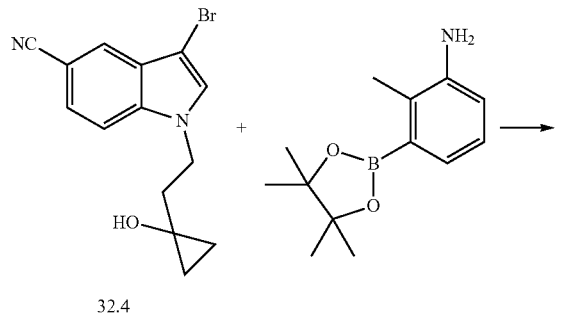

32.4

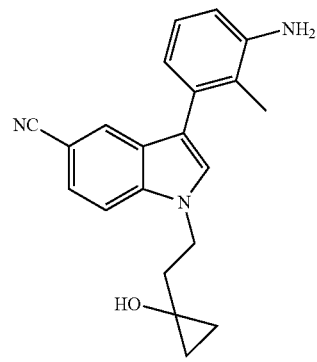

Example 32

To a mixture of compound 32.4 (50 mg, 0.164 mmol) and 2-methyl-3-(4,4,5,5-tetramethyl-1,3,2-dioxaborolan-2-yl) aniline (50 mg, 0.213 mmol) in the co-solvent of i-PrOH/H₂O (2 mL, 10:1) was added 2N Na₂CO₃ aq. (0.5 mL, 0.983 mmol) and Pd(PPh₃)₂Cl₂ (12 mg, 0.016 mmol). The mixture was stirred at 100° C. for 30 min under N₂ atmosphere by microwave. The cooled mixture was diluted with brine and extracted with EA for three times. The combined organic phase was washed with brine and dried over Na₂SO₄, concentrated and purified by prep-HPLC (0.1% NH₄OH/ACN/H₂O) to give the title compound (5.7 mg, 10%) as a light yellow solid. ¹H NMR (400 MHz, DMSO-d₆) δ ppm 7.71 (dd, 2H), 7.58 (s, 1H), 7.52 (dd, 1H), 6.96 (t, 1H), 6.67 (d, 1H), 6.55 (d, 1H), 5.34 (s, 1H), 4.91 (s, 2H), 4.47 (t, 2H), 2.02-1.89 (m, 5H), 0.46 (q, 2H), 0.13 (q, 2H). LC-MS: [M+H]⁺=332.2.

Example 33

3-(3-amino-2-methylphenyl)-1-((1-(hydroxymethyl)cyclopropyl)methyl)-1H-indole-5-carbonitrile Intermediate 33.1: (1-(((tert-butyldimethylsilyl)oxy)methyl)cyclopropyl)methanol

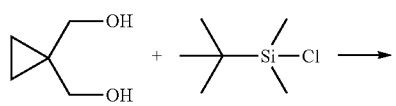

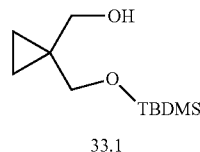

33.1

To a solution of cyclopropane-1,1-diyldimethanol (1.53 g, 15 mmol) in DMF (30 mL) was added tert-butylchlorodimethylsilane (2.26 g, 15 mmol) and imidazole (1.53 g, 22.4 mmol). The mixture was stirred at rt overnight. EA (10 mL) was added and the mixture was washed with water. The organic layer was separated and the aqueous layer was extracted with EA (2×10 mL). The combined organic layers were washed with water and brine, dried over Na₂SO₄, concentrated and concentrated and purified by column chromatography on silica gel (PE:EA=10:1) to give the title compound (1.6 g, 49%). ¹H NMR (300 MHz, CDCl₃) δ ppm 3.61 (s, 2H), 3.56 (s, 2H), 2.19 (s, 1H), 0.90 (s, 9H), 0.51 (t, 2H), 0.44 (t, 2H), 0.06 (s, 6H). LC-MS: [M+H]⁺=217.4.

Intermediate 33.2: (1-(((tert-butyldimethylsilyl)oxy)methyl)cyclopropyl)methyl 4-methylbenzenesulfonate

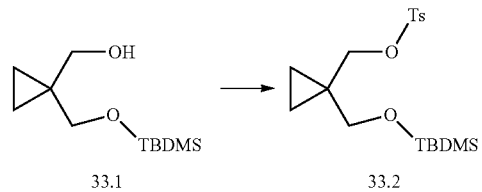

To a solution of 33.1 (972 mg, 4.492 mmol) in DCM (20 mL) was added DMAP (658 mg, 5.390 mmol). The mixture was cooled to 0° C. and the solution of TsCl (942 mg, 4.941 mmol) in DCM (2 mL) was added dropwise to the mixture at 0° C. The mixture was warmed to rt and stirred at rt for 3 h. The mixture was washed with water. The organic layer was separated and the aqueous layer was extracted with DCM (15 mL×2). The combined organic layers were washed with water and brine, dried over Na₂SO₄ and concentrated to give the title compound (1.4 g, 84%) which was used in next step without purification. LC-MS: [M+H]⁺=371.5.

Intermediate 33.3: 3-bromo-1-((1-(((tert-butyldimethylsilyl)oxy)methyl)cyclopropyl)methyl)-1H-indole-5-carbonitrile

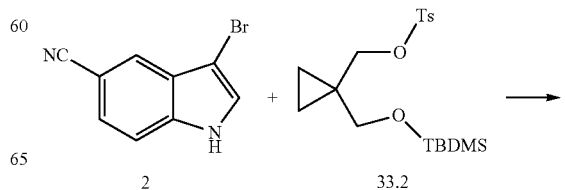

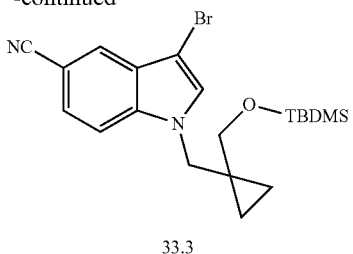

33.3

To a solution of 2 (221 mg, 1 mmol) in DMF (10 mL) was added 33.2 (741 mg, 2 mmol) and Cs$_2$CO$_3$ (1301 mg, 4 mmol). The mixture was stirred at 90° C. overnight under N$_2$ atmosphere. After cooled to rt, EA (20 mL) was added and the mixture was filtered. The filtrate was washed with water (100 mL) and the aqueous layer was extracted with EA (2×20 mL). The combined organic layers were washed with water and brine, dried over Na$_2$SO$_4$, concentrated and purified by column chromatography on silica gel (PE: EA=40:1) to give the title compound (350 mg, 94%). $^1$H NMR (300 MHz, DMSO-d$_6$) δ ppm 7.97 (d, 1H), 7.85 (t, 2H), 7.62 (dd, 1H), 4.28 (s, 2H), 3.23 (s, 2H), 0.88-0.86 (m, 9H), 0.79 (q, 2H), 0.54 (q, 2H), 0.02--0.09 (m, 6H). LC-MS: [M+H]$^+$=419.5, 421.5.

Intermediate 33.4: 3-(3-amino-2-methylphenyl)-1-((1-(((tert-butyldimethylsilyl)oxy)methyl)cyclopropyl)methyl)-1H-indole-5-carbonitrile

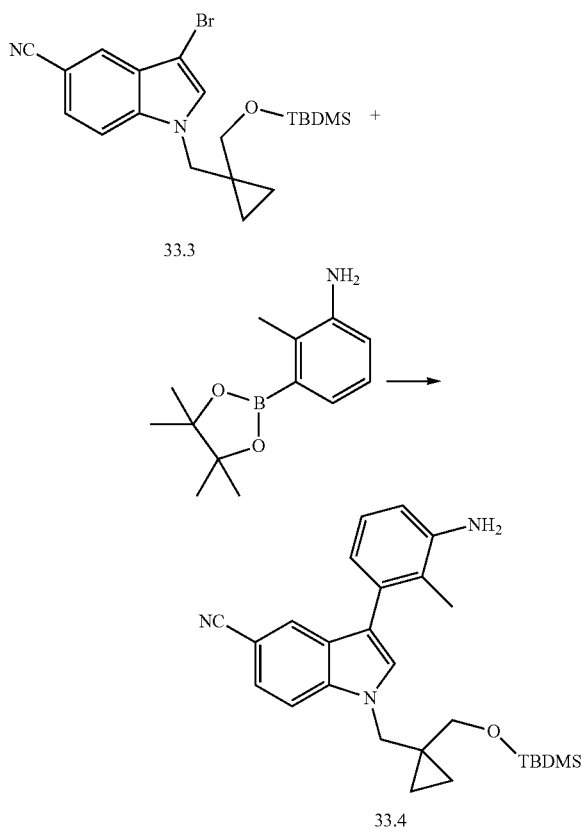

33.4

To a solution of compound 33.3 (140 mg, 0.3338 mmol) in i-PrOH/H$_2$O (10:1, 3 mL) was added 2-methyl-3-(4,4,5,5-tetramethyl-1,3,2-dioxaborolan-2-yl)aniline (96 mg, 0.4106 mmol) and 2 N Na$_2$CO$_3$ (1 mL, 2.0028 mmol). The mixture was degassed with N$_2$ for 0.5 min. Pd(PPh$_3$)$_2$Cl$_2$ (23 mg, 0.03338 mmol) was added and the mixture was degassed with N$_2$ for 0.5 min. The mixture was stirred at 100° C. for 30 min in microwave condition. After the reaction mixture was cooled to rt, EA (15 mL) was added and the mixture was filtered. The organic layer was separated and the aqueous layer was extracted with EA (2×15 mL). The combined organic layers were washed with brine, dried over Na$_2$SO$_4$, concentrated and purified by prep-TLC (PE:EA=6:1) to give the title compound (100 mg, 67%). $^1$H NMR (300 MHz, DMSO-d$_6$) δ ppm 7.84-7.76 (m, 2H), 7.62-7.52 (m, 2H), 7.03 (t, 1H), 6.73 (d, 1H), 6.62 (d, 1H), 4.32 (s, 2H), 3.31 (s, 2H), 2.03 (s, 3H), 1.29 (s, 2H), 0.89 (s, 9H), 0.79 (s, 2H), 0.56 (s, 2H), −0.01 (s, 6H). LC-MS: [M+H]$^+$=446.4.

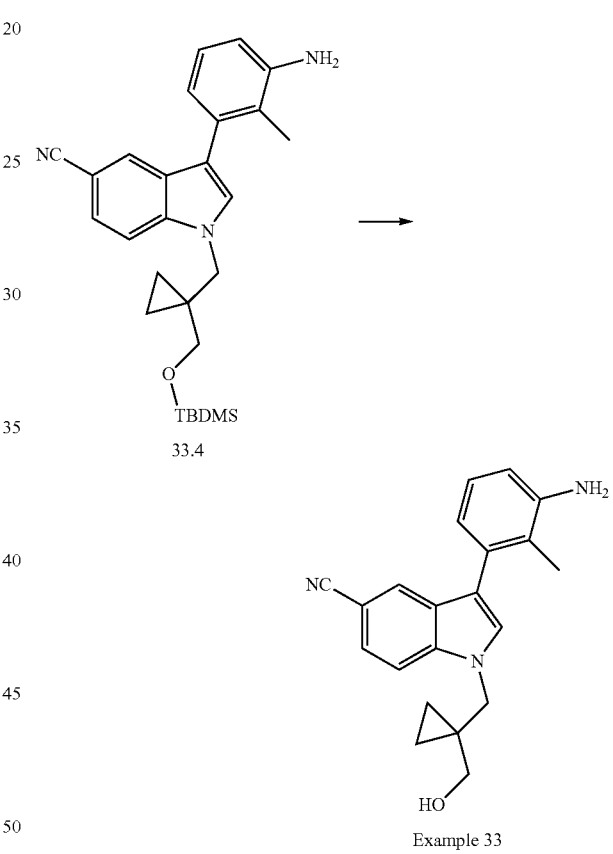

Example 33

To a solution of 33.4 (97 mg, 0.2176 mmol) in THF (3 mL) was added TBAF.3H$_2$O (247 mg, 0.7828 mmol). The mixture was stirred at rt for 30 min. EA (15 mL) was added and the mixture was washed with water. The organic layer was separated and the aqueous layer was extracted with EA (2×15 mL). The combined organic layers were washed with brine, dried over Na$_2$SO$_4$, concentrated and purified by prep-HPLC (0.1% NH$_3$.H$_2$O/CH$_3$CN/H$_2$O) to give the title compound (40 mg, 55%). $^1$H NMR (400 MHz, DMSO-d$_6$) δ ppm 7.81 (d, 1H), 7.72 (d, 1H), 7.58 (s, 1H), 7.52 (dd, 1H), 6.97 (t, 1H), 6.67 (d, 1H), 6.57 (d, 1H), 4.92 (s, 2H), 4.81 (t, 1H), 4.29 (s, 2H), 3.10 (d, 2H), 1.99 (s, 3H), 0.67 (t, 2H), 0.48 (q, 2H). LC-MS: [M+H]$^+$=332.2.

Example 34

3-(3-aminophenyl)-1-(4-(2-methoxyethoxy)phenyl)-1H-indole-5-carbonitrile

Intermediate 34.1: 1-(4-(2-methoxyethoxy)phenyl)-1H-indole-5-carbonitrile

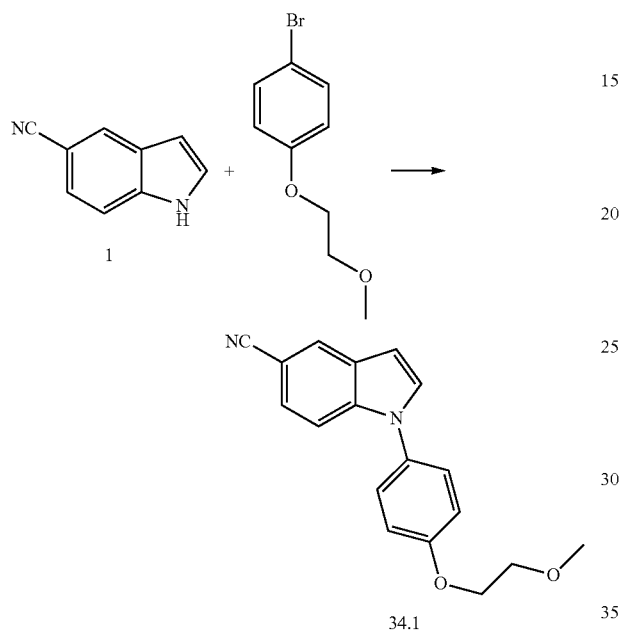

34.1

A mixture of 1,10-phenanthroline (0.127 g, 0.703 mmol), 1 mol/L TBAF (10.55 ml, 10.55 mmol), Cu₂O (0.05 g, 0.352 mmol), 1-bromo-4-(2-methoxyethoxy)benzene (0.975 g, 4.22 mmol) and compound 1 (0.5 g, 3.52 mmol) was concentrated in high vacuum. The solvent free residue was warmed to 150° C. under nitrogen protection for 2 hr. The mixture was dissolved in DCM (30 mL), filtered and the filtrate was purified by silica column to afford the title compound (450 mg, 42%) as a white solid. LC-MS: [M+H]⁺=293.1.

Intermediate 34.2: 3-bromo-1-(4-(2-methoxyethoxy)phenyl)-1H-indole-5-carbonitrile

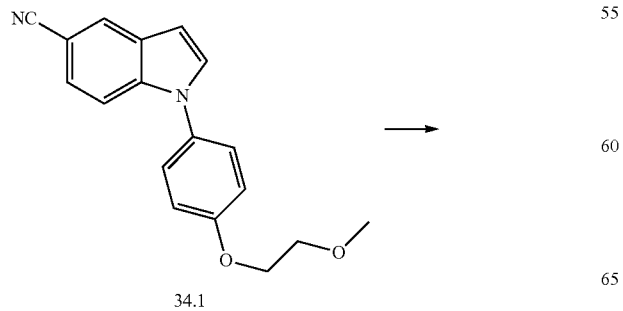

34.1

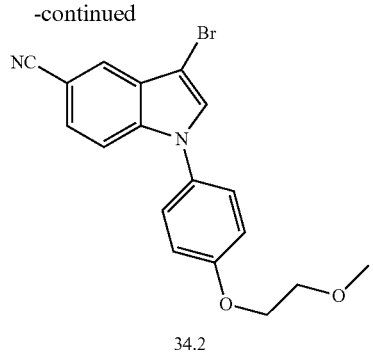

34.2

To a solution of 34.1 in DMF (5 mL) was added bromine (0.144 mL, 2.79 mmol). The mixture was stirred at 20° C. for 30 min, then was poured into water (20 mL). The precipitate was collected and dried in high vacuum to afford the title compound (900 mg, 83%) as a brown solid. LC-MS: [M+H]⁺=371.0, 373.0.

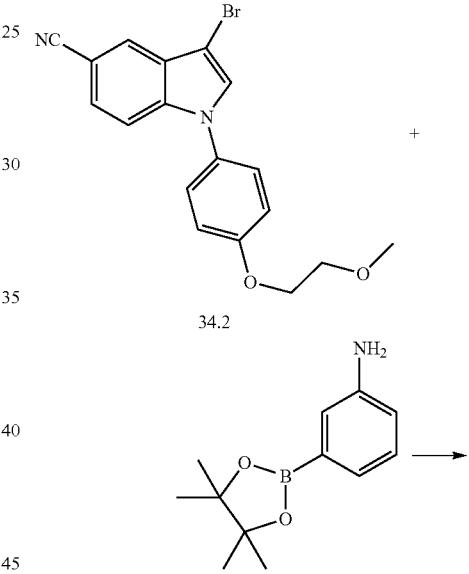

34.2

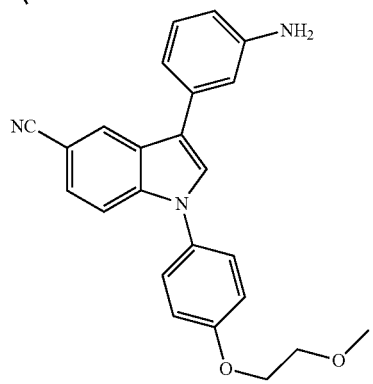

Example 34

The title compound was prepared by using a procedure similar to that of intermediate 1.1 by replacing intermediate 2 and (3-nitrophenyl)boronic acid with intermediate 34.2 and (3-aminophenyl)boronic acid. ¹H NMR (400 MHz, METHANOL-d₄) δ ppm 9.13-9.13 (m, 1H), 8.27 (d, 1H), 7.63 (s, 1H), 7.36-7.53 (m, 4H), 7.21 (m, 1H), 7.04-7.15 (m, 3H), 6.95-7.02 (m, 1H), 6.72 (m, 1H), 4.17 (m, 2H), 3.74-3.83 (m, 2H), 3.45 (s, 3H). LC-MS: [M+H]$^+$=384.2.

Example 48

3-(3-amino-2-methylphenyl)-1-(4-hydroxyphenyl)-1H-indole-5-carbonitrile

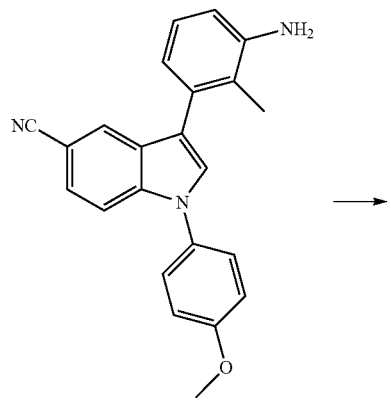

Example 38

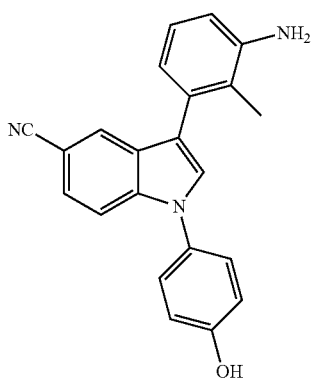

Example 48

At rt, to a solution of Example 38 (50 mg, 0.141 mmol) in DCM (2.5 mL) was added a solution of 1N BBr$_3$ in DCM (1.41 mL, 1.41 mmol) dropwise. Some precipitate appeared. The reaction was heated to 40° C. for 4 h. The reaction mixture was quenched with water and extracted with DCM for 3 times. The organic layer was dried over anhydrous Na$_2$SO$_4$, filtered and concentrated to give a crude product which was purified by prep-HPLC (0.1% TFA/ACH/H$_2$O) and lyophilized to give the title compound (11 mg, 30%). $^1$H NMR (400 MHz, DMSO-d$_6$) δ ppm 9.89 (s, 1H), 7.85 (s, 1H), 7.82 (s, 1H), 7.64-7.55 (m, 2H), 7.47 (d, 2H), 7.22 (t, 1H), 7.06 (t, 2H), 6.99 (d, 2H), 3.70 (s, 2H), 2.17 (s, 3H). LC-MS: [M+H]$^+$=340.3.

Example 49

3-(3-amino-2-(trifluoromethyl)phenyl)-1-(4-methoxyphenyl)-1H-indole-5-carbonitrile Intermediate 49.1:
1-(4-methoxphenyl)-1H-indole-5-carbonitrile

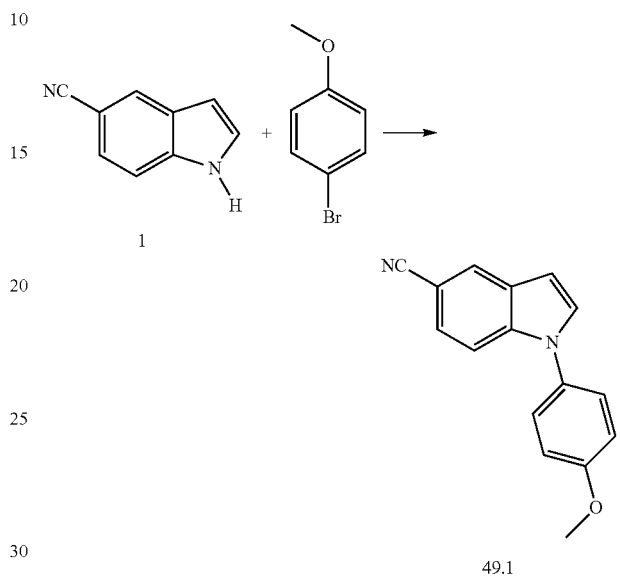

The mixture of compound 1 (3 g, 21.103 mmol), 1-bromo-4-methoxybenzene (5.920 g, 31.654 mmol), 1,10-phenanthroline (1.521 g, 8.441 mmol), Cu$_2$O (604 mg, 4.221 mmol) and 63 mL 1 N solution of TBAF in THF was concentrated under vacuo to remove solvent. The residue was then heated to 150° C. for 6 h. Then the reaction mixture was cooled down and diluted with water and extracted with EA for 3 times. The organic layer was dried over anhydrous Na$_2$SO$_4$, filtered and concentrated to give a crude product which was purified by column chromatography on silica gel (eluent: PE/EA=40:1~10:1) to give the title compound (3.087 g, 59%) as a white solid. $^1$H NMR (300 MHz, CDCl$_3$) δ ppm 8.02 (s, 1H), 7.44 (d, 2H), 7.38 (d, 2H), 7.35 (s, 1H), 7.05 (d, 2H), 6.72 (d, 1H), 3.89 (s, 3H). LC-MS: [M+H]$^+$=249.2.

Intermediate 49.2: 3-bromo-1-(4-methoxyphenyl)-1H-indole-5-carbonitrile

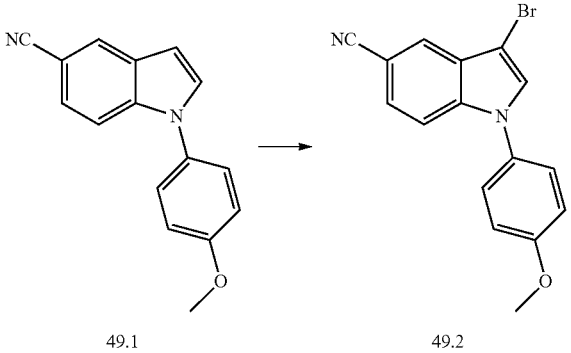 [SMILES: COc1ccc(-n2ccc3cc(C#N)ccc32)cc1 ; COc1ccc(-n2cc(Br)c3cc(C#N)ccc32)cc1]

At 20° C., to a solution of 49.1 (2.4 g, 9.667 mmol) in DMF (48 mL) was added a solution of NBS (1.892 g, 10.633 mmol) in DMF (6 mL) dropwise. After addition, the reaction was stirred at 20° C. for 1 h. Then it was diluted with EA and washed with brine for 3 times. The organic layer was dried over anhydrous $Na_2SO_4$, filtered and concentrated to give a crude product which was purified by column chromatography on silica gel (eluent: PE/EA=20:1~10:1) to give the title compound (2.107 g, 66%) as a white solid. $^1$H NMR (300 MHz, $CDCl_3$) δ ppm 7.98 (s, 1H), 7.50-7.40 (m, 3H), 7.34 (d, 2H), 7.07 (d, 2H), 3.89 (s, 3H). LC-MS: [M+H]$^+$=327.3, 329.3.

Intermediate 49.3: 1-(4-methoxyphenyl)-3-(4,4,5,5-tetramethyl-1,3,2-dioxaborolan-2-yl)-1H-indole-5-carbonitrile

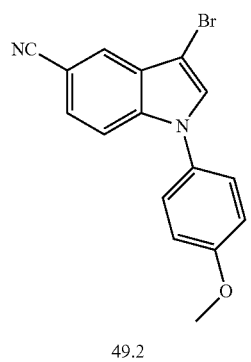

49.2

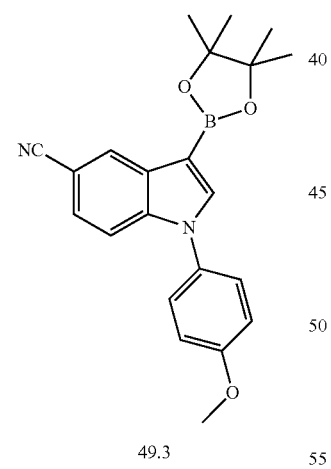

49.3

To a mixture of 49.2 (560 mg, 1.712 mmol), bis(pinacolato)diboron (652 mg, 2.567 mmol) and AcOK (336 mg, 3.424 mmol) in dioxane (15 mL) was added Pd(dppf)$Cl_2 \cdot CH_2Cl_2$ (140 mg, 0.171 mmol). The mixture was heated to 100° C. for 20 h under $N_2$ atmosphere. The mixture was diluted with brine and extracted with EA for 3 times. The organic layer was dried over anhydrous $Na_2SO_4$, filtered and concentrated to give a crude product which was purified by flash column chromatography on silica gel (eluent: PE/EA, EA %=3%) to give the title compound (158 mg, 25%) as a white solid. $^1$H NMR (300 MHz, DMSO-$d_6$) δ ppm 8.30 (s, 1H), 8.08 (s, 1H), 7.66-7.56 (m, 4H), 7.20 (d, 2H), 3.90 (s, 3H), 1.40 (s, 12H). LC-MS: [M+H]$^+$=375.1.

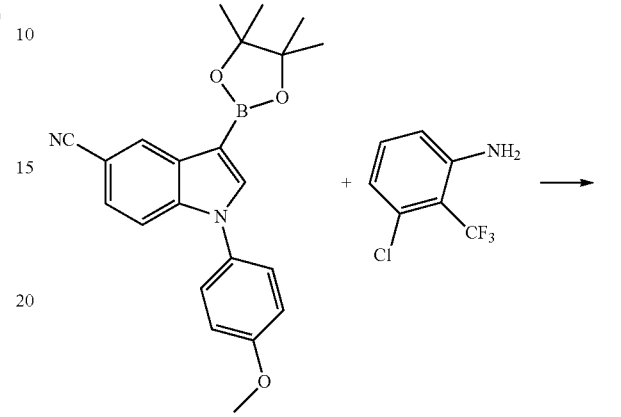

49.3

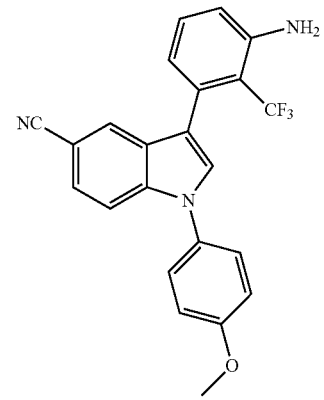

Example 49

A mixture of 49.3 (50 mg, 0.134 mmol), 3-chloro-2-(trifluoromethyl)aniline (40 mg, 0.2 mmol) and aqueous $Na_2CO_3$ solution (2 N, 0.80 mmol) in i-PrOH/$H_2O$ (10:1, 4 mL) was degassed with $N_2$. Then $Pd(PPh_3)_2Cl_2$ (10 mg, 0.0134 mmol) was added to. The reaction suspension was degassed with $N_2$ and heated at 100° C. for 30 min by microwave reactor. The reaction mixture was diluted with EA and washed with water. The combined organic layers was dried over anhydrous $Na_2SO_4$ and filtered. The filtrate was evaporated to give the crude which was purified by prep-HPLC (0.1% TFA/ACN/$H_2O$) to give the title compound (4.6 mg, 5%). $^1$H NMR (300 MHz, DMSO-$d_6$) δ ppm 7.76 (d, 2H), 7.63-7.53 (m, 4H), 7.31 (t, 1H), 7.17 (dd, 2H), 6.93 (d, 1H), 6.62 (d, 1H), 3.85 (s, 3H), 3.63 (s, 2H). LC-MS: [M+H]$^+$=407.8.

Example 55

3-(5-amino-4-methylpyridin-3-yl)-1-(4-methoxyphenyl)-1H-indole-5-carbonitrile

Intermediate 55.1: 1-(4-methoxphenyl)-3-(4-methyl-5-nitropyridin-3-yl)-1H-indole-5-carbonitrile

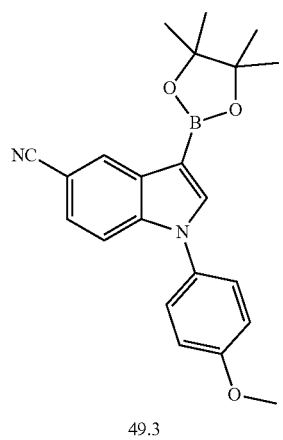

49.3

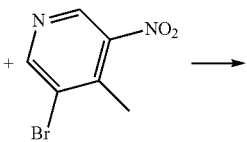

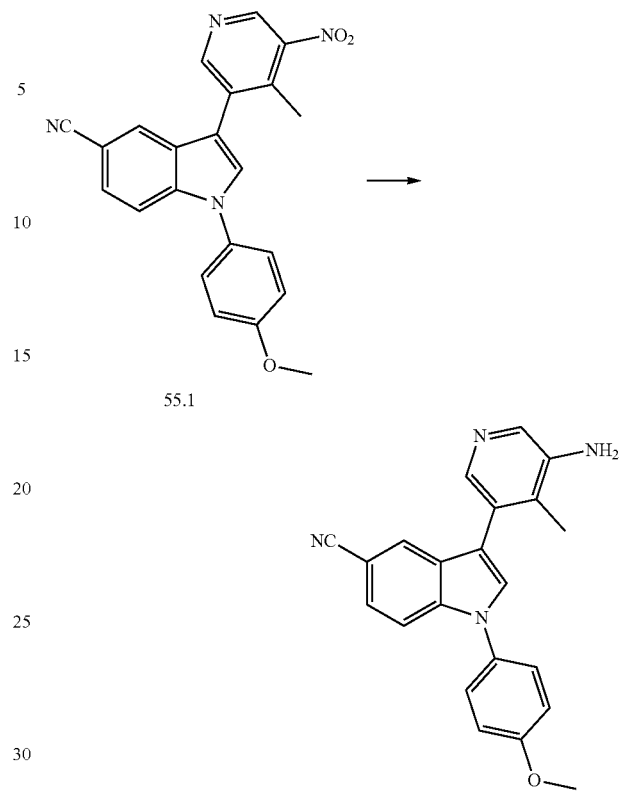

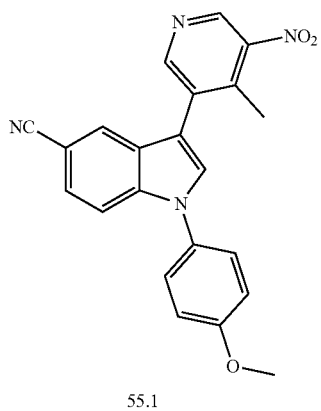

55.1

A mixture of 49.3 (100 mg, 0.267 mmol), 3-bromo-4-methyl-5-nitropyridine (87 mg, 0.4 mmol) and aqueous $Na_2CO_3$ solution (2N, 1.6 mmol) in i-PrOH/$H_2O$ (10:1, 10 mL) was degassed with $N_2$. Then Pd(PPh$_3$)$_2$Cl$_2$ (20 mg, 0.0267 mmol) was added. The reaction suspension was degassed with $N_2$ and heated at 100° C. for 30 min by microwave reactor. The reaction mixture was diluted with EA and washed with water. The combined organic layers was dried over anhydrous $Na_2SO_4$ and filtered. The filtrate was evaporated to give the crude which was purified by Prep-TLC (PE:EA=2:1) to give the title compound (25 mg, 24.3%). $^1$H NMR (400 MHz, DMSO-d$_6$) δ ppm 9.18 (s, 1H), 8.95 (s, 1H), 8.19 (d, 2H), 7.69 (d, 4H), 7.25 (d, 2H), 3.92 (s, 3H), 2.56 (s, 3H). LC-MS: [M+H]$^+$=385.4.

Example 55

To a solution of 55.1 (25 mg, 0.065 mmol) in MeOH (1 mL) was added Pd/C (10%, 3 mg). The reaction suspension was stirred at rt in $H_2$ atmosphere for 2 h. The reaction mixture was filtered and the filtrate was purified by prep-HPLC (0.1% NH$_3$.H$_2$O/ACN/H$_2$O) to give the title compound (1.8 mg, 8%). $^1$H NMR (400 MHz, DMSO-d$_6$) δ ppm 7.98 (s, 1H), 7.91 (s, 1H), 7.88 (s, 1H), 7.83 (s, 1H), 7.66-7.56 (m, 4H), 7.18 (d, 2H), 5.22 (s, 2H), 3.86 (s, 3H), 2.07 (s, 3H). LC-MS: [M+H]$^+$=355.0.

Example 56 methyl 2-(3-(3-amino-2-methylphenyl)-5-cyano-1H-indol-1-yl)-5-methoxybenzoate

Intermediate 56.1: methyl 2-(5-cyano-1H-indol-1-yl)-5-methoxybenzoate

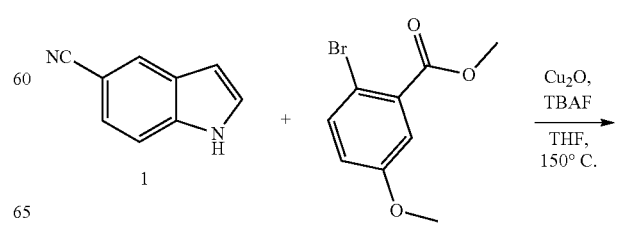

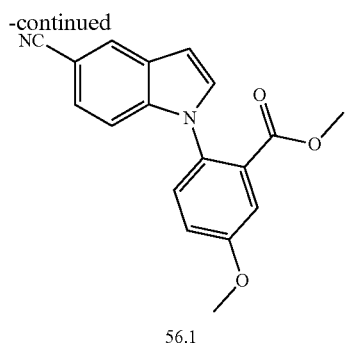

56.1

To a mixture of 1 (1 g, 7.03 mmol), methyl 2-bromo-5-methoxybenzoate (2.6 g, 10.55 mmol), 1,10-phenanthroline (506 mg, 2.8 mmol), $Cu_2O$ (200 mg, 1.4 mmol) in THF (20 mL) was added TBAF $3H_2O$ (5.5 g, 21.1 mmol). The solvent was removed after TBAF $3H_2O$ was dissolved completely. The reaction was stirred at 150° C. for 5 h in $N_2$ atmosphere. The reaction mixture was extracted with EA, washed with water and brine. The combined organic layers was dried over anhydrous $Na_2SO_4$ and filtered. The filtrate was concentrated to give the crude which was purified by column chromatography on silica gel (PE:EA=40:1~15:1) to give the title compound (560 mg, 21.7%). $^1$H NMR (300 MHz, DMSO-$d_6$) δ ppm 8.24 (s, 1H), 7.67 (d, 1H), 7.61-7.49 (m, 3H), 7.43 (dd, 1H), 7.17 (d, 1H), 6.84 (d, 1H), 3.96 (s, 3H), 3.48 (s, 3H). LC-MS: [M+H]$^+$=307.4.

Intermediate 56.2: methyl 2-(3-bromo-5-cyano-1H-indol-1-yl)-5-methoxybenzoate

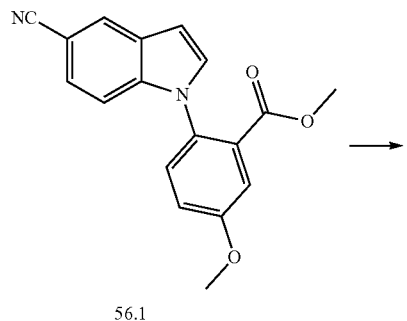

56.1

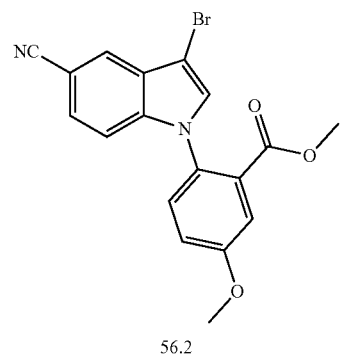

56.2

To a solution of 56.1 (0.56 g, 1.83 mmol) in DMF (8 mL) was added NBS (358 mg, 2.01 mmol). The reaction was stirred at rt for 1 h. The reaction mixture was extracted with EA, washed with water and brine. The organic layers were dried over anhydrous $Na_2SO_4$, filtered and the filtrate was concentrated to give the crude product which was purified by column chromatography on silica gel (PE:EA=30:1~15:1) to give the title compound (620 mg, 88%). $^1$H NMR (300 MHz, DMSO-$d_6$) δ ppm 8.08 (s, 1H), 8.01 (s, 1H), 7.66-7.57 (m, 3H), 7.44 (dd, 1H), 7.21 (d, 1H), 3.96 (s, 3H), 3.53 (s, 3H). LC-MS: [M+H]$^+$=307.4.

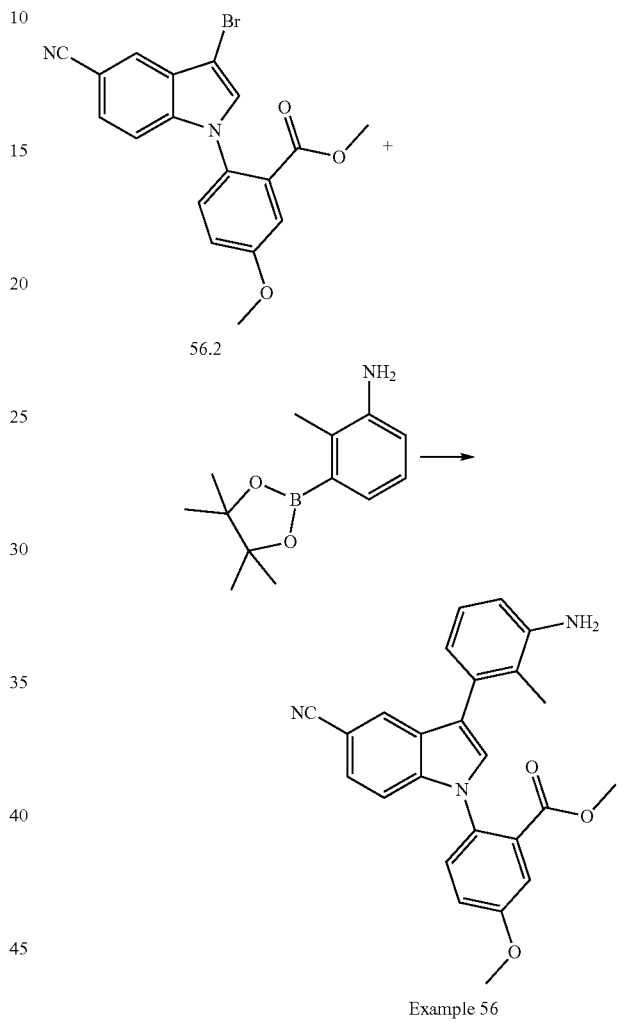

Example 56

A mixture of 56.2 (100 mg, 0.26 mmol), 2-methyl-3-(4,4,5,5-tetramethyl-1,3,2-dioxaborolan-2-yl)aniline (91 mg, 0.39 mmol) and $Cs_2CO_3$ (212 mg, 0.65 mmol) in DME (10 mL) was degassed with $N_2$. Then $PdCl_2(dppf)CH_2Cl_2$ (22 mg, 0.026 mmol) was added. The reaction suspension was degassed with $N_2$ and heated at 140° C. for 30 min by microwave reactor. Three batches were carried out. The reaction mixtures were combined and diluted with EA and washed with water. The combined organic layers were dried over anhydrous $Na_2SO_4$ and filtered. The filtrate was evaporated to give the crude product, which was purified by prep-HPLC (0.1% $NH_3H_2O$/ACN/$H_2O$) to give the title compound (68.4 mg, 67%). $^1$H NMR (400 MHz, DMSO-$d_6$) δ ppm 7.79 (d, 1H), 7.64 (d, 1H), 7.60 (s, 1H), 7.50 (dd, 2H), 7.39 (dd, 1H), 7.18 (d, 1H), 7.00 (t, 1H), 6.69 (d, 1H), 6.63 (d, 1H), 4.94 (s, 2H), 3.91 (s, 3H), 3.46 (s, 3H), 2.03 (s, 3H). LC-MS: [M+H]$^+$=412.5.

Example 62

3-(3-amino-2-methylphenyl)-1-(2-(hydroxymethyl)-4-methoxyphenyl)-1H-indole-5-carbonitrile

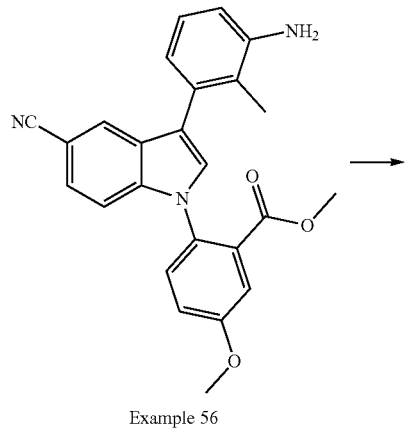

Example 56

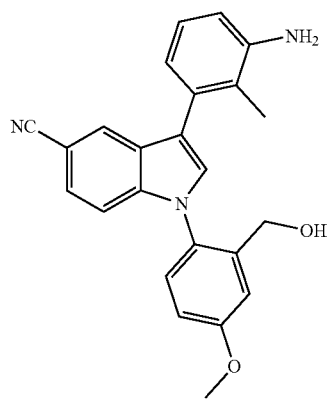

Example 62

At 0° C., to a solution of Example 56 (50 mg, 0.12 mmol) in a mixed solvent of EtOH/THF (1:10, 8 mL) was added LiBH$_4$ (50 mg, 2.3 mmol). The reaction was stirred at 60° C. for 2 h. The reaction mixture was quenched with ice, extracted with EA and washed with water. The combined organic layers were dried over anhydrous Na$_2$SO$_4$ and filtered. The filtrate was evaporated to give the crude product, which was purified by prep-HPLC (0.1% NH$_3$H$_2$O/ACN/H$_2$O) to give the title compound (17.3 mg, 20%). $^1$H NMR (400 MHz, DMSO-d$_6$) δ ppm 7.83 (d, 1H), 7.66 (s, 1H), 7.51 (dd, 1H), 7.42 (d, 1H), 7.27 (d, 1H), 7.17 (d, 1H), 7.04 (dd, 1H), 7.00 (t, 1H), 6.67 (dd, 2H), 5.28 (s, 1H), 4.95 (s, 2H), 4.19 (d, 2H), 3.87 (s, 3H), 2.04 (s, 3H). LC-MS: [M+H]$^+$=384.0.

Example 64

3-(3-amino-2-methylphenyl)-1-(2-(2-hydroxyethyl)-4-methoxyphenyl)-1H-indole-5-carbonitrile Intermediate 64.1: 2-(2-bromo-5-methoxyphenyl)ethan-1-ol

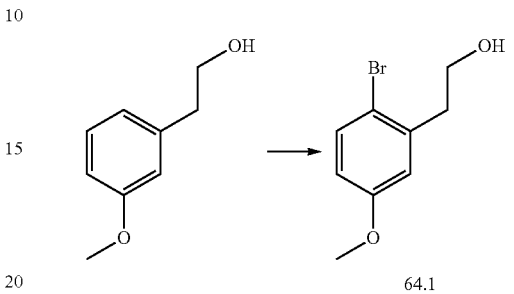

64.1

At 0° C., to a solution of 2-(3-methoxyphenyl)ethan-1-ol (1 g, 6.571 mmol) and pyridine (634 uL, 7.885 mmol) in DCM (8.5 mL) was added a solution of Br$_2$ (2.415 g, 15.113 mmol) in DCM (1.5 mL) dropwise. After addition, the solution was stirred at rt for 4 h. The reaction mixture was quenched with sat. NaHSO$_3$ aq. The organic layer was washed with brine, dried over anhydrous Na$_2$SO$_4$, filtered and concentrated to give a crude product which was purified by flash column chromatography on silica gel (eluent: PE/EA, EA %=5%~8%~10%) to give the title compound (893 mg, 64%) as a colorless oil. $^1$H NMR (300 MHz, CDCl$_3$) δ ppm 7.43 (d, 1H), 6.83 (d, 1H), 6.66 (dd, 1H), 3.87 (t, 2H), 3.78 (s, 3H) 2.98 (t, 2H). LC-MS: [M+H]$^+$=384.3.

Intermediate 64.2: (2-bromo-5-methoxyphenethoxy)(tert-butyl)dimethylsilane

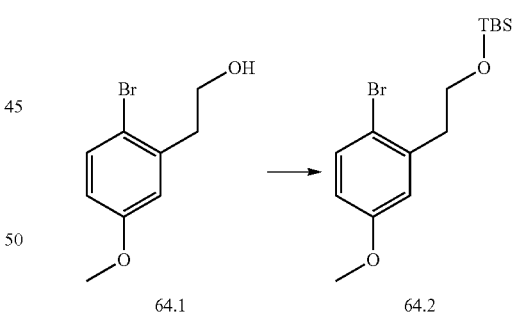

64.1    64.2

At 0° C., to a stirred solution of compound 64.1 (2 g, 8.655 mmol) and imidazole (1.178 g, 17.310 mmol) in DCM (30 mL) was added TBS-Cl (1.435 g, 9.520 mmol) in several portions. Some white solid precipitated. The reaction was stirred at rt overnight. Then the reaction mixture was washed with 10% HCl aq. and brine twice. The organic layer was dried over anhydrous Na$_2$SO$_4$, filtered and concentrated to give a crude product which was purified by column chromatography on silica gel (eluent: PE) to give the title compound (2.568 g, 85%) as a light yellow oil. $^1$H NMR (300 MHz, CDCl$_3$) δ ppm 7.40 (d, 1H), 6.82 (d, 1H), 6.64 (dd, 1H), 3.82 (t, 2H), 3.77 (s, 3H), 2.93 (t, 2H), 0.87 (s, 9H), −0.01 (s, 6H). LC-MS: [M+H]$^+$=213.1, 215.1.

Intermediate 64.3: 1-(2-(2-((tert-butyldimethylsilyl)oxy)ethyl)-4-methoxphenyl)-1H-indole-5-carbonitrile

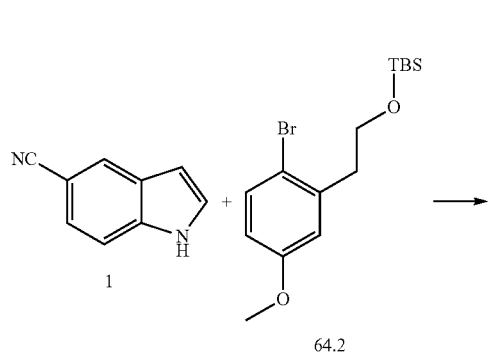

64.2

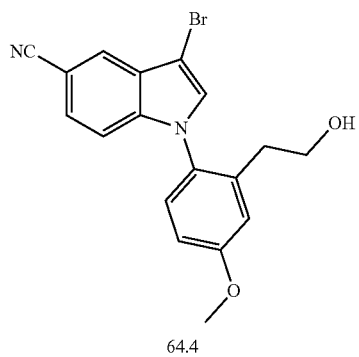

64.4

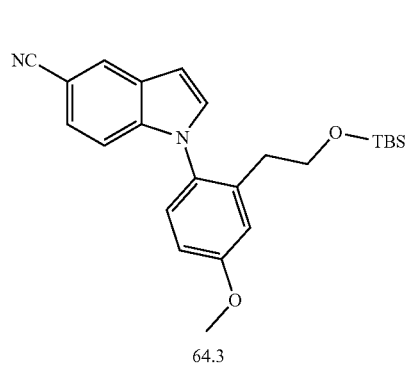

64.3

The mixture of compound 64.2 (364 mg, 1.055 mmol), 1H-indole-5-carbonitrile (100 mg, 0.703 mmol), K$_2$CO$_3$ (146 mg, 1.055 mmol), CuI (40 mg, 0.211 mmol) and pyridine (1 mL) in nitrobenzene (5 mL) was heated to 180° C. for 40 min by microwave under N$_2$ atmosphere. Then the reaction mixture was cooled down and purified by column chromatography on silica gel directly (eluent: PE~PE/EA=50:1-40:1) to give the title compound (122 mg, 43%) as a yellow solid. $^1$H NMR (300 MHz, DMSO-d$_6$) δ ppm 8.25 (s, 1H), 7.66 (d, 1H), 7.51 (d, 1H), 7.32 (d, 1H), 7.18-7.07 (m, 2H), 7.06-7.00 (m, 1H), 6.87 (d, 1H), 3.88 (s, 3H), 3.67 (s, 2H), 2.50-2.37 (m, 2H), 0.73 (s, 9H), −0.21 (s, 6H). LC-MS: [M+H]$^+$=407.3.

Intermediate 64.4: 3-bromo-1-(2-(2-hydroxyethyl)-4-methoxyphenyl)-1H-indole-5-carbonitrile

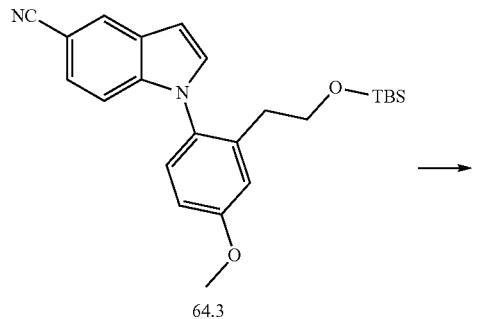

64.3

At rt, to a solution of compound 64.3 (90 mg, 0.221 mmol) in DMF (2 mL) was added NBS (43 mg, 0.243 mmol) in one portion. The solution was stirred at rt overnight. The reaction mixture was diluted with water and extracted with EA for 3 times. The organic layer was dried over anhydrous Na$_2$SO$_4$, filtered and concentrated to give a crude product which was purified by prep-TLC (eluent: PE/EA=2:1) to give the title compound (47 mg, 57%) as a gel. $^1$H NMR (300 MHz, DMSO-d$_6$) δ ppm 8.08 (s, 1H), 7.98 (s, 1H), 7.62 (dd, 1H), 7.33 (d, 1H), 7.17 (d, 1H), 7.13 (d, 1H), 7.02 (dd, 1H), 4.72 (s, 1H), 3.88 (s, 3H), 3.42 (m, 2H), 2.47 (m, 1H), 2.46-2.27 (m, 1H). LC-MS: [M+H]$^+$=371.5, 373.5.

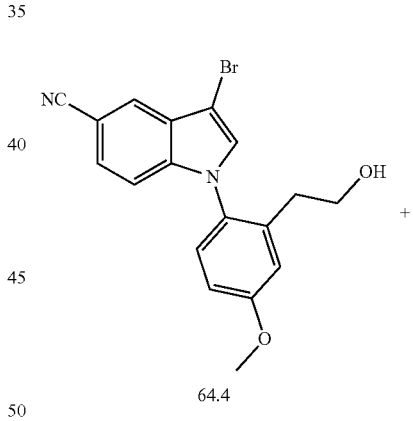

64.4

+

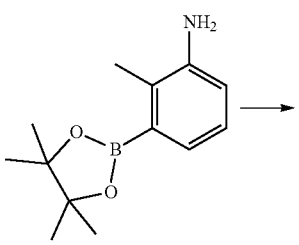

-continued

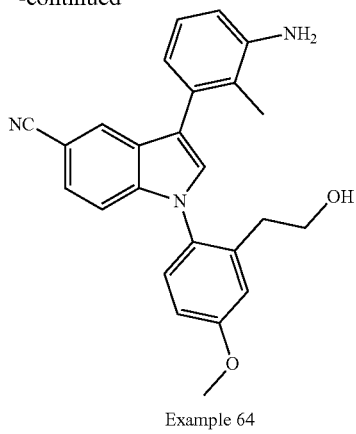

Example 64

To a mixture of compound 64.4 (47 mg, 0.127 mmol) and 2-methyl-3-(4,4,5,5-tetramethyl-1,3,2-dioxaborolan-2-yl) aniline (45 mg, 0.193 mmol) in the co-solvent of i-PrOH/H₂O (2.5 mL, 10:1) was added 2 N Na₂CO₃ aq. (0.38 mL, 0.762 mmol) and Pd(PPh₃)₂Cl₂ (7.7 mg, 0.012 mmol). The mixture was stirred at 100° C. for 30 min under N₂ atmosphere by microwave. Then the reaction mixture was diluted with brine and extracted with EA for three times. The combined organic phase was washed with brine and dried over Na₂SO₄, concentrated and purified by prep-HPLC (0.1% TFA/ACH/H₂O) and lyophilized to give the title compound (19.9 mg, 39%) as a white solid. ¹H NMR (400 MHz, DMSO-d₆) δ ppm 7.86 (d, 1H), 7.77 (s, 1H), 7.54 (dd, 1H), 7.38 (d, 1H), 7.23 (t, 1H), 7.16 (d, 1H), 7.12 (d, 1H), 7.12-7.03 (m, 2H), 7.01 (dd, 1H), 4.04 (s, 2H), 3.86 (s, 3H), 3.41 (m, 2H), 2.56-2.52 (m, 1H), 2.39 (dd, 1H), 2.19 (s, 3H). LC-MS: [M+H]⁺=398.2.

Example 65

3-(3-amino-2-methylphenyl)-1-(4-methoxyphenyl)-6-methyl-1H-indole-5-carbonitrile Intermediate 65.1: 1-(4-methoxyphenyl)-6-methyl-1H-indole-5-carbonitrile

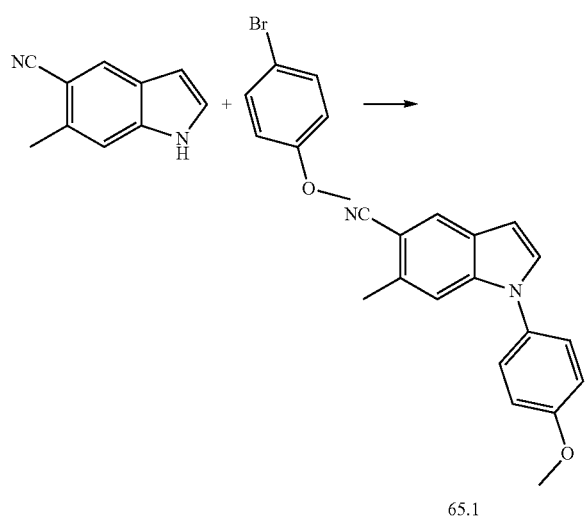

A mixture of 6-methyl-1H-indole-5-carbonitrile (1 g, 6.403 mmol), 1-bromo-4-methoxybenzene (1.8 g, 9.605 mmol), 1,10-phenanthroline (461 mg, 2.561 mmol), Cu₂O (183 mg, 1.281 mmol) and 19.2 mL 1 N solution of TBAF in THF was concentrated under vacuum to remove solvent. The residue was then heated to 150° C. for 6.5 h under N₂ atmosphere. Then the mixture was cooled down and diluted with water and EA, and filtered to remove inorganic solid. The filtrate was separated and the aq. was extracted with EA twice. The combined organic layer was dried over anhydrous Na₂SO₄, filtered and concentrated to give a crude product which was purified by column chromatography on silica gel (eluent: PE/EA=10:1~8:1) to give the title compound (486 mg, 29%) as a white solid. ¹H NMR (400 MHz, CDCl₃) δ ppm 7.99 (s, 1H), 7.45-7.34 (m, 2H), 7.32 (d, 1H), 7.29 (s, 1H), 7.13-7.02 (m, 2H), 6.68 (d, 1H), 3.92 (s, 3H), 2.62 (s, 3H). LC-MS: [M+H]⁺=263.2.

Intermediate 65.2: 3-bromo-1-(4-methoxphenyl)-6-methyl-1H-indole-5-carbonitrile

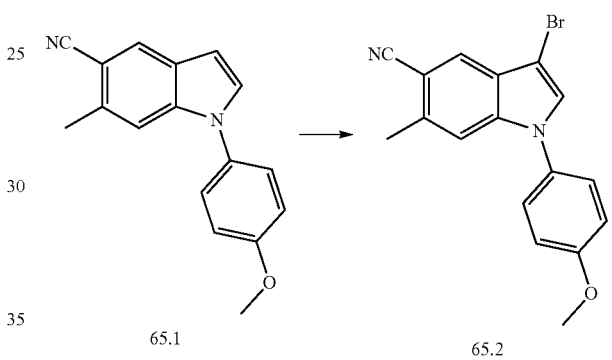

At 20° C., to a solution of compound 65.1 (485 mg, 1.849 mmol) in DMF (10 mL) was added NBS (362 mg, 2.034 mmol) portionwise. After addition, the solution was stirred at rt for 1 h. Then the reaction mixture was diluted with water and extracted with EA for 3 times. The organic layer was combined and washed with brine for 3 times. It was dried over anhydrous Na₂SO₄, filtered and concentrated to give a crude product which was purified by flash column chromatography on silica gel (eluent: PE/EA, EA %=8%) to give the title compound (526 mg, 83%) as a solid. ¹H NMR (400 MHz, CDCl₃) δ ppm 7.94 (s, 1H), 7.38-7.33 (m, 3H), 7.29 (s, 1H), 7.10-7.04 (m, 2H), 3.92 (s, 3H), 2.62 (s, 3H). LC-MS: [M+H]⁺=341.3, 343.3.

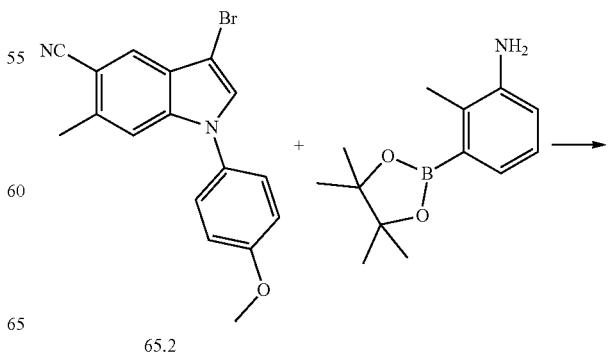

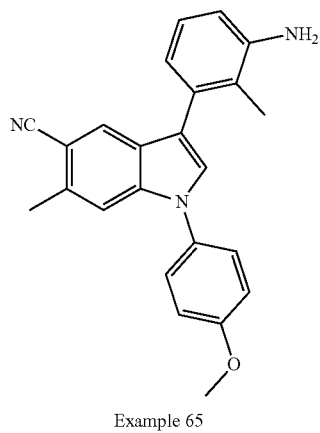

Example 65

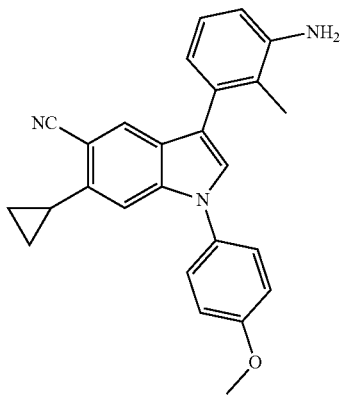

Example 69

To a mixture of compound 65.2 (500 mg, 1.465 mmol) and 2-methyl-3-(4,4,5,5-tetramethyl-1,3,2-dioxaborolan-2-yl)aniline (444 mg, 1.905 mmol) in the co-solvent of i-PrOH/H$_2$O (30 mL, 10:1) was added 2N Na$_2$CO$_3$ aq. (4.4 mL, 8.8 mmol) and Pd(PPh$_3$)$_2$Cl$_2$ (82 mg, 0.117 mmol). The mixture was stirred at 100° C. for 1.5 h under N$_2$ atmosphere. Then the reaction mixture was diluted with brine and extracted with EA for three times. The combined organic phase was dried over anhydrous Na$_2$SO$_4$, filtered, concentrated to give a crude product which was purified by column chromatography on silica gel (eluent: PE/EA=4:1~3:1) to give 500 mg crude product. 300 mg of the crude product was purified by prep-HPLC (0.1% NH$_3$.H$_2$O/ACN/H$_2$O) and lyophilized to give the title compound (125 mg, 39%) as a white solid. $^1$H NMR (400 MHz, DMSO-d$_6$) δ ppm 7.74 (s, 1H), 7.68 (s, 1H), 7.62-7.54 (m, 2H), 7.49 (s, 1H), 7.22-7.13 (m, 2H), 6.99 (t, 1H), 6.74-6.67 (m, 1H), 6.66-6.60 (m, 1H), 4.94 (s, 2H), 3.86 (s, 3H), 2.55 (s, 3H), 2.04 (s, 3H). LC-MS: [M+H]$^+$=368.2.

Example 69

3-(3-amino-2-methylphenyl)-6-cyclopropyl-1-(4-methoxyphenyl)-1H-indole-5-carbonitrile To the mixture of Example 68 (76 mg, 0.196 mmol), cyclopropylboronic acid (102 mg, 1.187 mmol), tricyclohexylphosphine (11 mg, 0.040 mmol) and K$_3$PO$_4$ (250 mg, 1.187 mmol) in toluene (2.5 mL) was added Pd(OAc)$_2$ (10 mg, 0.04 mmol). Then the mixture was heated to 140° C. for 40 min by microwave under N$_2$ atmosphere. After the reaction was completed, it was diluted with water and extracted with EA for 3 times. The combined organic phase was washed with brine and dried over anhydrous Na$_2$SO$_4$, filtered and concentrated to give a residue which was purified by prep-TLC (eluent: PE/EA=2:1) to give 60 mg crude product and it was purified by prep-HPLC (0.1% NH$_3$.H$_2$O/ACN/H$_2$O) and lyophilized to give the title compound (11 mg) as a white solid. $^1$H NMR (400 MHz, DMSO-d$_6$) δ ppm 7.74 (s, 1H), 7.69 (s, 1H), 7.62-7.53 (m, 2H), 7.21-7.13 (m, 2H), 7.11 (s, 1H), 6.99 (t, 1H), 6.69 (d, 1H), 6.63 (d, 1H), 4.95 (s, 2H), 3.86 (s, 3H), 2.30-2.20 (m, 1H), 2.03 (s, 3H), 1.09-1.00 (m, 2H), 0.81-0.71 (m, 2H). LC-MS: [M+H]$^+$=394.2.

Example 70

N-(3-(5-cyano-1-(4-methoxphenyl)-1H-indol-3-yl)phenyl)acetamide

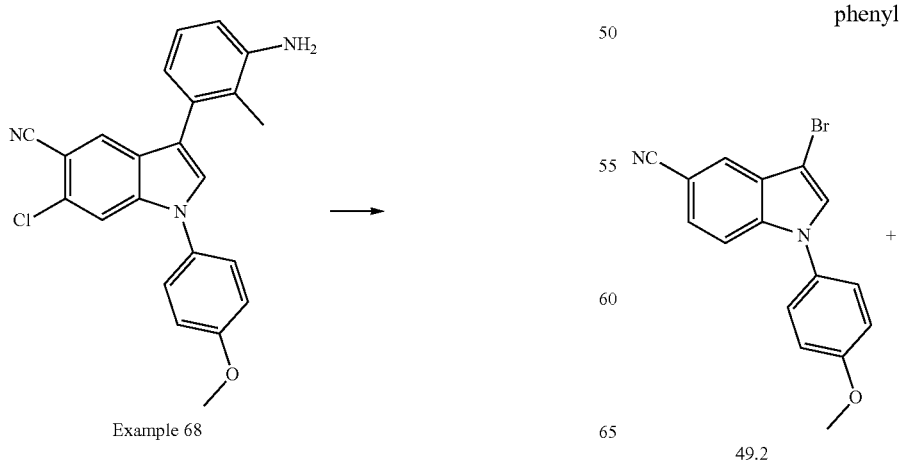

Example 68

49.2

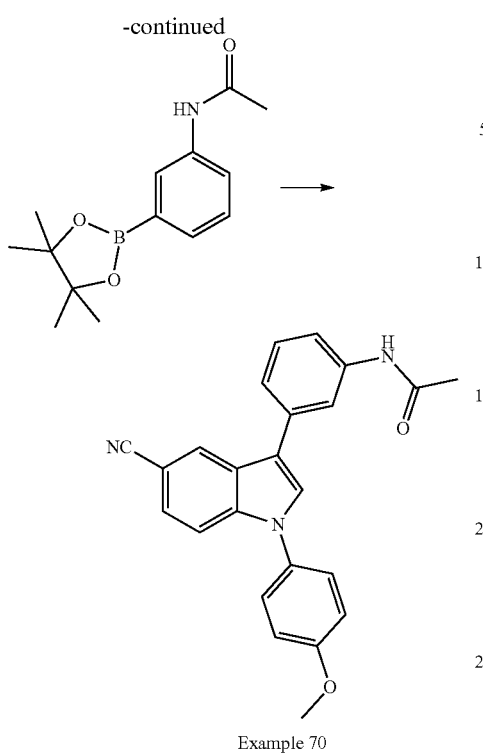

Example 70

The title compound was prepared by using a procedure similar to that of intermediate 1.1 by replacing intermediate 2 and (3-nitrophenyl)boronic acid with intermediate 49.2 and N-(3-(4,4,5,5-tetramethyl-1,3,2-dioxaborolan-2-yl)phenyl)acetamide. $^1$H-NMR (400 MHz, DMSO-d$_6$) δ ppm 8.40 (s, 1H), 8.11 (s, 1H), 7.99 (s, 1H), 7.54-7.67 (m, 5H), 7.40 (m, 2H), 7.08-7.23 (m, 2H), 3.85 (s, 3H), 2.09 (s, 3H). LC-MS: [M+H]$^+$=382.1.

Example 71

3-(5-amino-4-methylpyridin-3-yl)-1-(4-methoxyphenyl)-6-methyl-1H-indole-5-carbonitrile Intermediate 71.1:
(4-methyl-5-nitropyridin-3-yl)boronic acid

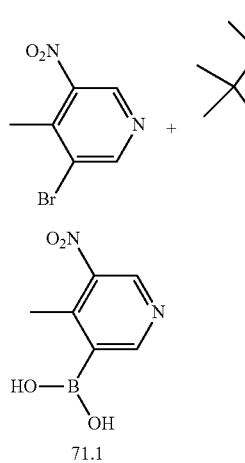

To a solution of 3-bromo-4-methyl-5-nitropyridine (350 mg, 1.61 mmol) and 4,4,4',4',5,5,5',5'-octamethyl-2,2'-bi(1,3,2-dioxaborolane) (614 mg, 2.42 mmol) in dioxane (10 mL) was added PdCl$_2$(dppf).CH$_2$Cl$_2$ (105 mg, 0.13 mmol) and AcOK (316 mg, 3.22 mmol). After addition, the mixture was stirred at 100° C. under nitrogen atmosphere overnight. The mixture was diluted with EA (100 mL) and filtered. The organic phase was washed with water (50 mL) and brine (50 mL), dried and concentrated under reduced pressure. The crude product was purified by prep-HPLC (0.1% TFA/ACN/H$_2$O) to give the title compound (150 mg, 51%). $^1$H NMR (400 MHz, CD$_3$OD) δ ppm 9.03 (s, 1H), 8.68 (s, 1H), 2.62 (s, 3H). LC-MS: [M+H]$^+$=182.9.

Intermediate 71.2:
(5-amino-4-methylpyridin-3-yl)boronic acid

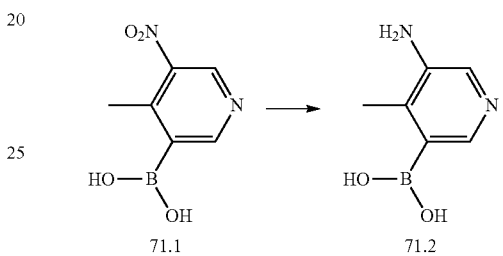

Compound 71.1 (31 mg, 0.17 mmol) was added to a solution of ammonia in methanol (5 mL) and Raney Nickel as a slurry in water. A balloon containing hydrogen was attached and the vessel was purged with vacuum/hydrogen gas several times. The reaction mixture was stirred at rt under hydrogen atmosphere. After 1 h, the crude reaction mixture was diluted with methanol, filtered and concentrated to give the title compound (30 mg) which was directly used to next step without further purification. LC-MS: [M+H]$^+$=153.1.

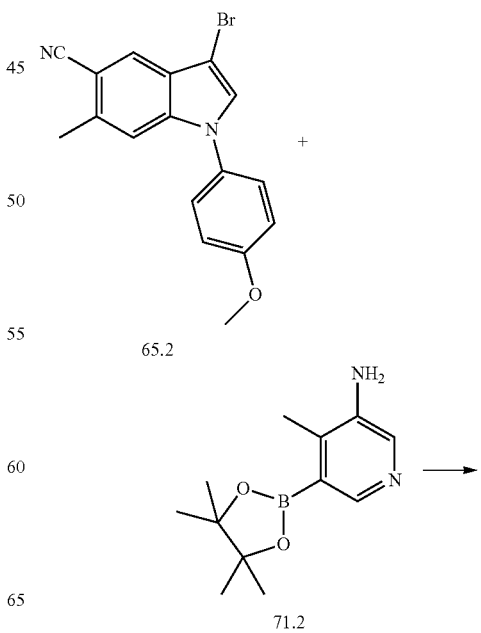

Example 71

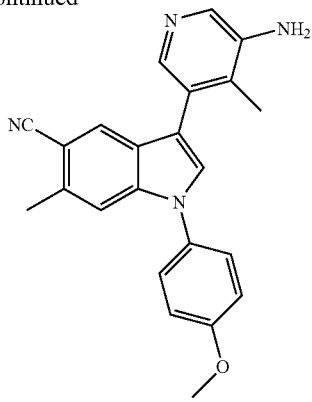

Example 71

Compound 65.2 (49 mg, 0.144 mmol), compound 71.2 (61 mg, 0.401 mmol) and Pd(PPh₃)₂Cl₂ (10 mg, 0.0142 mmol) were added to a mixture solvent (IPA:H₂O=10:1, 2 mL). Then 2 N Na₂CO₃ aqueous solution (0.5 mL) was added to the mixture. After addition, the mixture was stirred at 100° C. for 35 min in microwave condition. The mixture was diluted with EA (50 mL) and brine (20 mL). The organic phase was separated. The aqueous phase was further extracted with EA (20 mL×3). The organic phase was dried and concentrated under reduced pressure. The crude product was purified by prep-HPLC (0.1% NH₃/ACN/H₂O) to give the title compound (23 mg, 43%). $^1$H NMR (400 MHz, DMSO-d₆) δ ppm 7.97 (s, 1H), 7.81 (d, 3H), 7.60 (d, 2H), 7.51 (s, 1H), 7.18 (d, 2H), 5.20 (s, 2H), 3.86 (s, 3H), 2.56 (s, 3H), 2.07 (s, 3H). LC-MS: [M+H]⁺=369.1.

Example 72

3-(3-amino-2-methylphenyl)-1-(tetrahydro-2H-pyran-4-yl)-1H-indole-5-carbonitrile Intermediate 72.1: tetrahydro-2H-pyran-4-yl 4-methylbenzenesulfonate

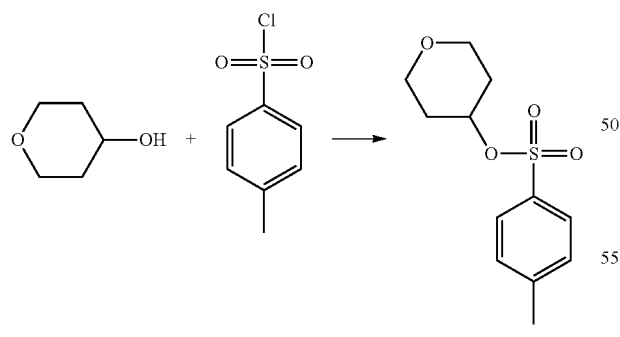

72.1

To a solution of tetrahydro-2H-pyran-4-ol (200 mg, 1.96 mmol) in pyridine (5 mL) was added p-toluenesulfonylchloride (560 mg 2.94 mmol) portion wise at 10° C. After completing addition, the reaction was allowed to warm to rt and stirred for 18 h. The reaction was dissolved in DCM (50 mL) and was washed with 1M aqueous HCl solution (30 mL), followed by saturated aqueous NaHCO₃ solution (30 mL). The organic phase was then dried over Na₂SO₄, filtered and concentrated under reduced pressure to give the title compound (360 mg 72%) as orange oil. LC-MS: [M+H]⁺=257.1.

Intermediate 72.2: 3-bromo-1-(tetrahydro-2H-pyran-4-yl)-1H-indole-5-carbonitrile

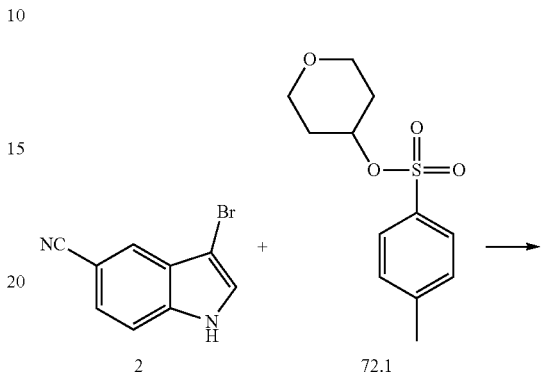

Cs₂CO₃ (553 mg, 1.70 mmol) was added to a mixture of compound 2 (150 mg, 0.68 mmol) and 72.1 (348 mg, 1.36 mmol) in DMF (3 mL) and under N₂ atmosphere. The reaction mixture was heated to 70° C. for 24 h. After cooling, the reaction mixture was diluted with EA (50 mL) and washed with brine (20 mL×2). The organic phase was then dried over Na₂SO₄, filtered and concentrated under reduced pressure. The residue was purified by column chromatography on silica gel (PE:EA=2:1) to give the title compound (120 mg, 58%). $^1$H NMR (300 MHz, DMSO-d₆) δ ppm 8.11 (s, 1H), 7.99-7.96 (m, 2H), 7.66 (d, 1H), 4.90-4.82 (m, 1H), 4.05 (d, 2H), 3.61 (t, 2H), 2.18-2.01 (m, 2H), 1.95-1.92 (m, 2H). LC-MS: [M+H]⁺=306.8.

-continued

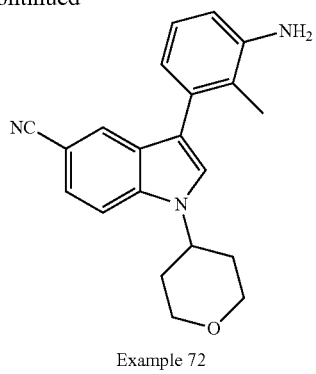

Example 72

A mixture of 72.2 (80 mg, 0.262 mmol), 2-methyl-3-(4,4,5,5-tetramethyl-1,3,2-dioxaborolan-2-yl)aniline (61 mg, 0.262 mmol) and 2 N Na$_2$CO$_3$ aqueous solution (0.5 mL) in i-PrOH/H$_2$O (10:1, 1 mL) was degassed with N$_2$. Then Pd(PPh$_3$)$_2$Cl$_2$ (19 mg, 0.0271 mmol) was added. The reaction suspension was degassed with N$_2$ and heated at 110° C. for 30 min. After cooling, the reaction mixture was diluted with EA and washed with water. The combined organic layer was dried over anhydrous Na$_2$SO$_4$ and filtered. The filtrate was evaporated to give the crude which was purified by prep-HPLC (0.1% NH$_3$/ACN/H$_2$O) to give the title compound (22.6, 26%). $^1$H NMR (400 MHz, DMSO-d$_6$) δ ppm 7.88 (d, 1H), 7.79-7.65 (m, 2H), 7.53 (dd, 1H), 6.97 (t, 1H), 6.67 (d, 1H), 6.57 (d, 1H), 4.91 (s, 2H), 4.86-4.63 (m, 1H), 4.02 (dd, 2H), 3.60 (t, 2H), 2.10 (qd, 2H), 2.00-1.84 (m, 5H). LC-MS: [M+H]$^+$=332.2.

Example 74

3-(3-amino-2-methylphenyl)-1-(4-hydroxycyclohexyl)-1H-indole-5-carbonitrile

Intermediate 74.1: 1,4-dioxaspiro[4.5]decan-8-yl 4-methylbenzenesulfonate

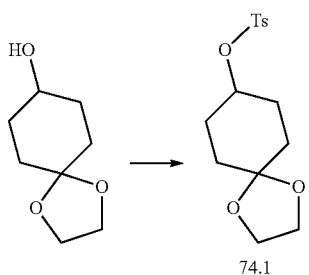 [SMILES: OC1CCC2(CC1)OCCO2 ; Cc1ccc(S(=O)(=O)OC2CCC3(CC2)OCCO3)cc1]

74.1

At 0° C., to a solution of 1,4-dioxaspiro[4.5]decan-8-ol (500 mg, 3.16 mmol) in pyridine (5 mL) was add TsCl (904 mg, 4.741 mmol) portionwise. After addition, the reaction was stirred at rt overnight. Then the reaction mixture was washed with water and extracted with EA for 3 times. The combined organic phase was washed with brine for 3 times and dried over Na$_2$SO$_4$, filtered and concentrated to give the title compound (860 mg, 89%) as a yellow solid. $^1$H NMR (300 MHz, DMSO-d$_6$) δ ppm 7.86 (d, 2H), 7.53 (d, 2H), 4.73-4.63 (m, 1H), 3.86 (s, 4H), 2.47 (s, 3H), 1.72-1.49 (m, 8H). LC-MS: [M+Na]$^+$=335.3.

Intermediate 74.2: 3-bromo-1-(1,4-dioxaspiro[4.5]decan-8-yl)-1H-indole-5-carbonitrile

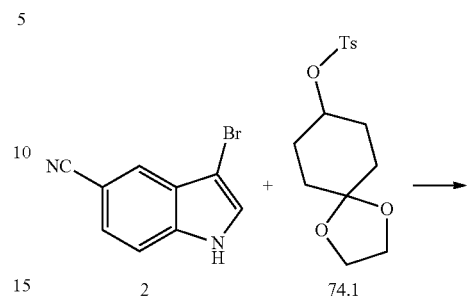

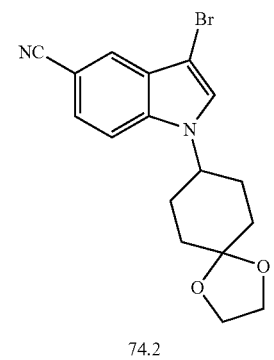

74.2

A mixture of compound 74.1 (736 mg, 2.356 mmol), compound 2 (300 mg, 1.357 mmol) and Cs$_2$CO$_3$ (1.326 g, 4.071 mmol) in DMF (5 mL) was heated to 100° C. overnight. Then the mixture was diluted with water and extracted with EA for three times. The combined organic phase was washed with brine and dried over Na$_2$SO$_4$, filtered and concentrated to give a crude product which was purified by flash column chromatography on silica gel (eluent: PE/EA, EA %=10~20%) to give the title compound (293 mg) as a white solid with 80% purity which was used for next step directly. LC-MS: [M+H]$^+$=361.2, 363.2.

Intermediate 74.3: 3-bromo-1-(4-oxocyclohexyl)-1H-indole-5-carbonitrile

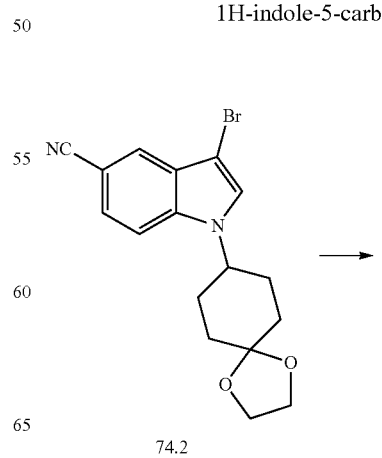

74.2

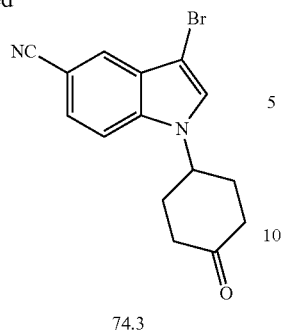

74.3

A mixture of compound 74.2 (244 mg, 0.676 mmol) in the co-solvent of AcOH (5 mL) and H$_2$O (1 mL) was heated to 60° C. overnight. After cooling down, 2 mL water was added. Much solid precipitated, which was filtered and washed with water to give the title compound (138 mg, 65%) as a white solid. $^1$H NMR (300 MHz, CDCl$_3$) δ ppm 7.94 (s, 1H), 7.49 (q 2H), 7.33 (s, 1H), 4.77 (m, 1H), 2.69-2.58 (m, 4H), 2.44 (m, 2H), 2.22 (m, 2H). LC-MS: [M+H]$^+$=317.0, 319.0.

Intermediate 74.3: 3-bromo-1-(4-hydroxycyclo-hexyl)-1H-indole-5-carbonitrile

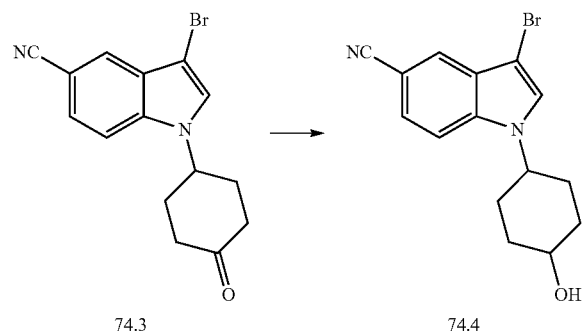 [SMILES: N#Cc1ccc2c(c1)c(Br)cn2C1CCC(=O)CC1 ; N#Cc1ccc2c(c1)c(Br)cn2C1CCC(O)CC1]

74.3    74.4

At rt, to a mixture of compound 74.3 (130 mg, 0.410 mmol) in methanol (3.5 mL) was added NaBH$_4$ (46.5 mg, 1.300 mmol) in several portions. The mixture gradually turned clear, then was stirred at rt for another 1 h. The solvent was removed under vacuum and the residue was dissolved in EA and washed with brine twice. The organic layer was dried over Na$_2$SO$_4$, filtered and concentrated to give the title compound (125 mg, 95%) as a white solid. $^1$H NMR (300 MHz, DMSO-d$_6$) δ ppm 8.02 (s, 1H), 7.96 (s, 1H), 7.93 (d, 1H), 7.63 (d, 1H), 4.78 (d, 1H), 4.56 (m, 1H), 3.59 (m, 1H), 2.04-1.88 (m, 6H), 1.51 (m, 2H). LC-MS: [M+H]$^+$=319.2, 321.2.

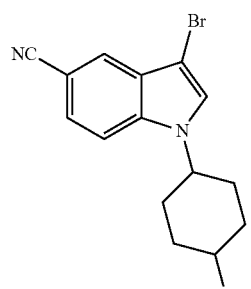

74.4

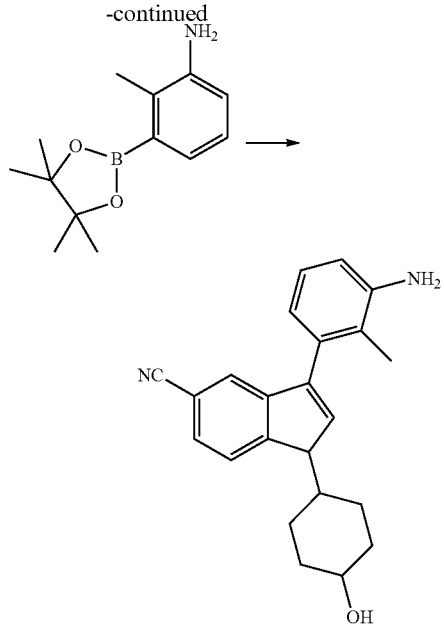

Example 74

To a mixture of compound 74.4 (70 mg, 0.219 mmol) and 2-methyl-3-(4,4,5,5-tetramethyl-1,3,2-dioxaborolan-2-yl) aniline (77 mg, 0.330 mmol) in the co-solvent of i-PrOH/ H$_2$O (2.5 mL, 10:1) was added 2 N Na$_2$CO$_3$ aq. (653 uL, 1.306 mmol) and Pd(PPh$_3$)$_2$Cl$_2$ (15 mg, 0.021 mmol). The mixture was stirred at 100° C. for 30 min under N$_2$ atmosphere by microwave. The same reaction was was repeated for twice. Then the three batches were combined and diluted with brine and extracted with EA for three times. The combined organic phase was washed with brine and dried over Na$_2$SO$_4$, concentrated and purified by prep-TLC (eluent: PE/EA=1:1) to give a crude product which was a mixture with Ph$_3$P═O. It was purified by prep-HPLC (0.1% TFA/ACN/H$_2$O) and lyophilized to give the title compound (30 mg, 40%) as a pink solid. $^1$H NMR (400 MHz, DMSO-d$_6$) δ ppm 7.88 (d, 1H), 7.78 (s, 1H), 7.72 (d, 1H), 7.54 (dd, 1H), 7.21 (t, 1H), 7.05 (t, 2H), 4.54 (m, 2H), 3.88 (s, 1H), 3.58 (t, 2H), 2.12 (s, 3H), 2.08-1.88 (m, 6H), 1.50 (m, 2H). LC-MS: [M+H]$^+$=346.0.

Example 75

3-(3-amino-2-methylphenyl)-1-(4-oxocyclohexyl)-1H-indole-5-carbonitrile

Intermediate 75.1: 3-(3-amino-2-methylphenyl)-1-(1,4-dioxaspiro[4.5]decan-8-yl)-1H-indole-5-carbonitrile

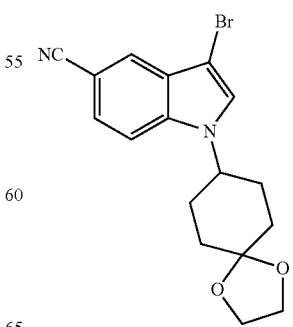

74.2

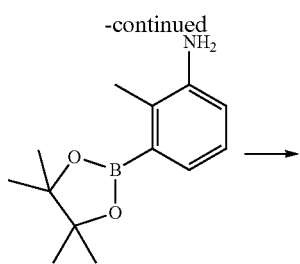

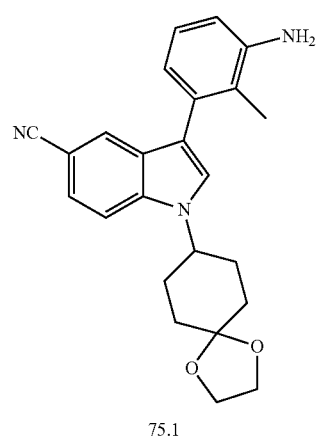

75.1

To a mixture of compound 74.2 (100 mg, 0.277 mmol) and 2-methyl-3-(4,4,5,5-tetramethyl-1,3,2-dioxaborolan-2-yl)aniline (97 mg, 0.417 mmol) in the co-solvent of i-PrOH/H₂O (3.6 mL, 10:1) was added 2 N Na₂CO₃ aq. (826 uL, 1.650 mmol) and Pd(PPh₃)₂Cl₂ (21 mg, 0.030 mmol). The mixture was stirred at 100° C. for 30 min under N₂ atmosphere by microwave. The cooled mixture was diluted with brine and extracted with EA for three times. The combined organic phase was washed with brine and dried over Na₂SO₄, concentrated and purified by prep-TLC (eluent: PE/EA=2:1) to give the title compound (60 mg, 40%) as a yellow foam. ¹H NMR (300 MHz, CDCl₃) δ ppm 7.82 (s, 1H), 7.46 (s, 2H), 7.30 (s, 1H), 7.09 (t, 1H), 6.75 (dd, 2H), 4.38 (dd, 1H), 4.01 (s, 4H), 2.21-2.11 (m, 4H), 2.07 (s, 3H), 1.96 (d, 2H), 1.91-1.80 (m, 2H). LC-MS: [M+H]⁺=388.4.

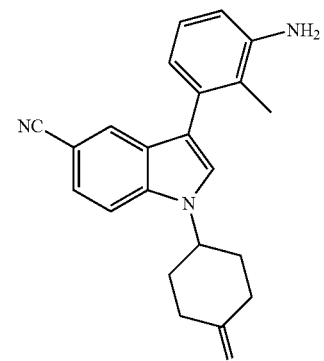

Example 75

A mixture of compound 75.1 (30 mg, 0.08 mmol) and water (0.12 mL) in AcOH (0.6 mL) was heated at 60° C. overnight. To the cooled mixture was added water (10 mL) and then basified by NH₄OH to pH=8 under an ice bath. The mixture was extracted with EA (5 mL×3). The combined organic phases were dried over Na₂SO₄, concentrated and then purified by prep-HPLC (0.1% NH₄OH/ACN/H₂O) to give the title compound (16 mg, 60%) as a white solid. ¹H NMR (400 MHz, DMSO-d₆) δ ppm 7.97 (d, 1H), 7.85 (s, 1H), 7.76 (d, 1H), 7.61 (dd, 1H), 7.22 (t, 1H), 7.08 (d, 2H), 5.17 (t, 1H), 3.61 (s, 2H), 2.85-2.74 (m, 2H), 2.34 (dt, 6H), 2.13 (s, 3H). LC-MS: [M+H]⁺=344.3.

Examples 76 & 77 trans/cis-3-(3-amino-2-methylphenyl)-1-(4-(methyl-amino)cyclohexyl)-1H-indole-5-carbonitrile

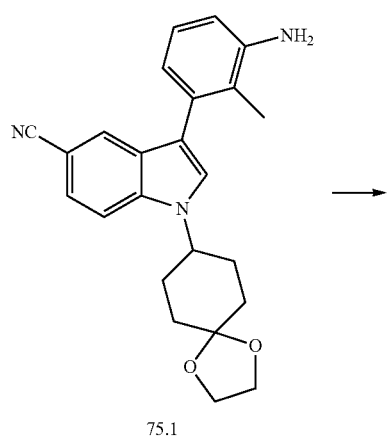

75.1

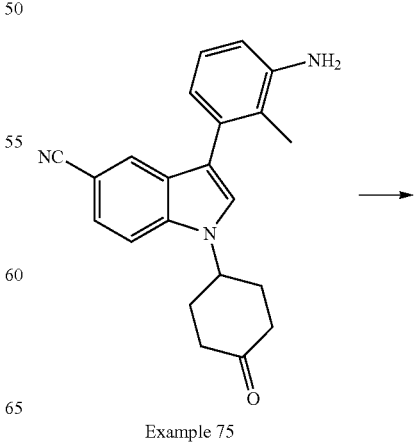

Example 75

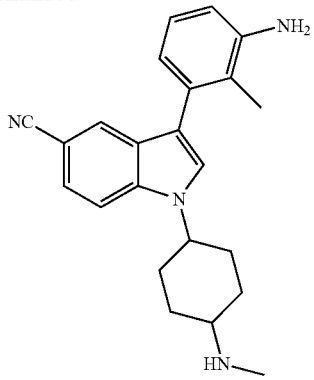

Example 76 & 77

A mixture of Example 75 (56 mg, 0.163 mmol), methylamine hydrochloride (33 mg, 0.489 mmol), NaBH$_3$CN (31 mg, 0.489 mmol) and CH$_3$COONa (40 mg, 0.489 mmol) in MeOH (5 mL) was stirred at rt for 2 h. To the mixture was added water (1 mL). The mixture was filtrated. The filtrate was purified by prep-HPLC (0.1% TFA/ACN/H$_2$O) to give two isomers.

Example 76

Trans-3-(3-amino-2-methylphenyl)-1-(4-(methylamino)cyclohexyl)-1H-indole-5-carbonitrile 27.2 mg of Example 76 was produced as a white solid (yield: 36%). $^1$H NMR (400 MHz, DMSO-d$_6$) δ ppm 8.58 (s, 2H), 7.89 (d, 1H), 7.76-7.70 (m, 2H), 7.55 (dd, 1H), 7.11 (t, 1H), 6.88 (dd, 2H), 4.58 (t, 1H), 3.63 (s, 2H), 3.09 (s, 1H), 2.62 (t, 3H), 2.16 (dd, 4H), 2.06 (s, 3H), 1.98 (dd, 2H), 1.70-1.56 (m, 2H). LC-MS: [M+H]$^+$=359.4.

Example 77

Cis-3-(3-amino-2-methylphenyl)-1-(4-(methylamino)cyclohexyl)-1H-indole-5-carbonitrile 12.2 mg of Example 76 was produced as a white solid (yield: 16%). $^1$H NMR (400 MHz, DMSO-d$_6$) δ ppm 8.58 (s, 2H), 7.87 (d, 1H), 7.75-7.67 (m, 2H), 7.57 (dd, 1H), 7.12 (t, 11H), 6.88 (dd, 2H), 4.70 (s, 1H), 3.66 (s, 2H), 3.39 (s, 1H), 2.67 (t, 3H), 2.16-2.01 (m, 7H), 1.96 (t, 4H). LC-MS: [M+H]$^+$=359.4.

Examples 89 & 90

The title compounds are two enantiomers which are obtained by chiral separation of Example 85. The absolute stereo was not determined.
Chiral separation: UV visualization at 254 nm
  Column: AD-H, 30×250 mm 4.6 µm
  Flow rate: 3.0 mL/min
  Pressure: 100 bar
  Solvent A: MeOH
  Modifer: 30%

Example 89

$^1$H NMR (400 MHz, METHANOL-d$_4$) δ ppm 7.62 (s, 1H), 7.52 (s, 1H), 7.37 (s, 1H), 7.03 (m, 1H), 6.79 (d, 1H), 6.72 (d, 1H), 5.13-5.26 (m, 1H), 4.44-4.60 (m, 1H), 2.64 (s, 3H), 2.39-2.57 (m, 1H), 2.12-2.35 (m, 4H), 2.05 (s, 3H), 1.92-2.03 (m, 1H), 1.74-1.87 (m, 1H). LC-MS: [M+H]$^+$=345.9.

Example 90

$^1$H NMR (400 MHz, METHANOL-d$_4$) δ ppm 7.62 (s, 1H), 7.52 (s, 1H), 7.37 (s, 1H), 7.03 (m, 1H), 6.79 (d, 1H), 6.72 (d, 1H), 5.21 (m, 1H), 4.47-4.60 (m, 1H), 2.64 (s, 3H), 2.40-2.55 (m, 1H), 2.11-2.34 (m, 3H), 2.05 (s, 3H), 1.91-2.01 (m, 1H), 1.75-1.87 (m, 1H). LC-MS: [M+H]$^+$=346.0.

Examples 91 & 92

The title compounds are two enantiomers which are obtained by chiral separation of Example 86. The absolute stereo was not determined.
Chiral separation: UV visualization at 254 nm
  Column: AD-H, 30×250 mm 4.6 µm
  Flow rate: 3.0 mL/min
  Pressure: 100 bar
  Solvent A: MeOH
  Modifer: 30%

Example 91

$^1$H NMR (400 MHz, METHANOL-d$_4$) δ ppm 7.63 (s, 1H), 7.57 (s, 1H), 7.55 (s, 1H), 7.04 (m, 1H), 6.80 (s, 1H), 6.74 (d, 1H), 4.98-5.10 (m, 1H), 4.40-4.50 (m, 1H), 2.55-2.70 (m, 4H), 2.24-2.37 (m, 1H), 2.14-2.24 (m, 1H), 2.07 (s, 3H), 1.88-2.01 (m, 3H). LC-MS: [M+H]$^+$=345.9.

Example 92

$^1$H NMR (400 MHz, METHANOL-d$_4$) δ ppm 7.63 (s, 1H), 7.49-7.59 (m, 2H), 7.04 (t, 1H), 6.75-6.83 (m, 1H), 6.73 (dd, 1H), 4.98-5.12 (m, 1H), 4.39-4.50 (m, 1H), 2.55-2.70 (m, 4H), 2.30 (dd 1H), 2.13-2.25 (m, 1H), 2.07 (s, 3H), 1.95 (td, 3H). LC-MS: [M+H]$^+$=345.9.

Example 93

Trans-3-(3-amino-2-methylphenyl)-1-(4-hydroxycyclohexyl)-6-methyl-1H-indole-5-carbonitrile Intermediate 93.1: 3-bromo-6-methyl-1-(1,4-dioxaspiro[4.5]decan-8-yl)-1H-indole-5-carbonitrile

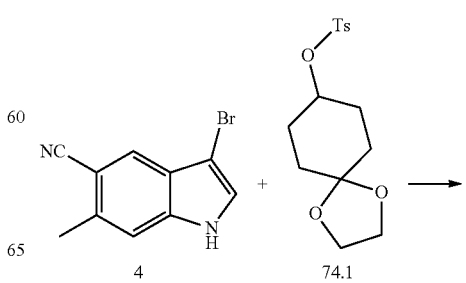

-continued

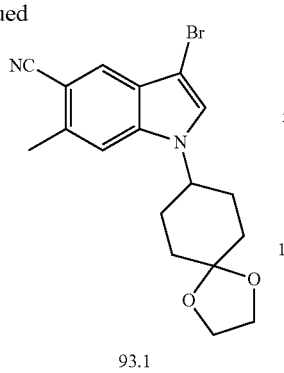

93.1

The mixture of compound 74.1 (960 mg, 3.07 mmol), compound 4 (415 mg, 1.77 mmol) and Cs$_2$CO$_3$ (1.73 g, 5.31 mmol) in DMF (10 mL) was heated to 100° C. overnight. Then it was diluted with water and extracted with EA for three times. The combined organic phase was washed with brine and dried over Na$_2$SO$_4$, filtered and concentrated to give a crude product which was purified by flash column chromatography on silica gel (eluent: PE/EA, EA %=10~20%) to give the title compound (726 mg) with 80% purity as a white solid. $^1$H NMR (300 MHz, CDCl$_3$) δ ppm 7.84 (s, 1H), 7.29 (s, 1H), 7.26 (s, 1H), 4.35-4.20 (m, 1H), 4.00 (s, 4H), 2.66 (s, 3H), 2.06 (dd, 4H), 1.93 (d, 2H), 1.84-1.76 (m, 2H). LC-MS: [M+H]$^+$=375.29, 377.24.

Intermediate 93.2: 3-bromo-6-methyl-1-(4-oxocyclohexyl)-1H-indole-5-carbonitrile

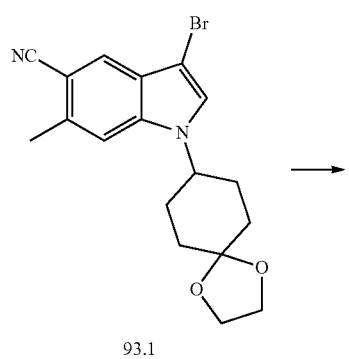

The mixture of compound 93.1 (480 mg, 1.28 mmol) in the co-solvent of AcOH (7.5 mL) and H$_2$O (1.5 mL) was heated to 60° C. for 3.5 h. After cooling to rt, 10 mL of water was added. Much solid precipitated, which was filtered and washed with water to give the title compound (357 mg, 84%) as a white solid. $^1$H NMR (300 MHz, CDCl$_3$) δ ppm 7.87 (s, 1H), 7.30 (s, 1H), 7.24 (s, 1H), 4.73 (m, 1H), 2.67 (s, 3H), 2.65-2.60 (m, 4H), 2.46-2.39 (m, 2H), 2.20 (dd, 2H). LC-MS: [M+H]$^+$=331.2.

Intermediate 93.3: 3-bromo-1-(4-hydroxycyclohexyl)-6-methyl-1H-indole-5-carbonitrile

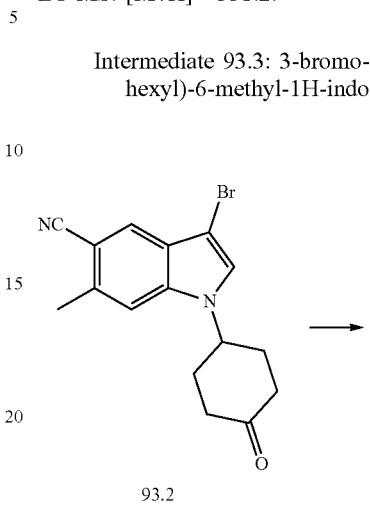

93.2

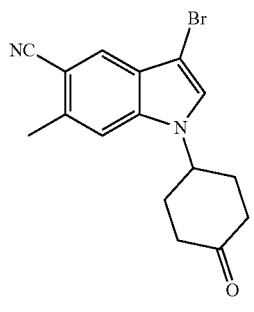

93.3

At rt, to a mixture of compound 93.2 (340 mg, 1.03 mmol) in methanol (10 mL) was added NaBH$_4$ (156 mg, 4.1 mmol) in several portions. The mixture gradually turned clear and was stirred at rt for 1 h. The solvent was removed under vacuum and the residue was dissolved in EA and washed with brine twice. The organic layer was dried over Na$_2$SO$_4$, filtered and concentrated to give the title compound (345 mg) as a white solid. $^1$H NMR (300 MHz, CDCl$_3$) δ ppm 7.85 (s, 1H), 7.23 (s, 2H), 4.22 (m, 1H), 3.78 (m, 1H), 2.66 (s, 3H), 2.16 (t, 4H), 1.80 (d, 2H), 1.64 (s, 2H). LC-MS: [M+H]$^+$=333.2, 335.3.

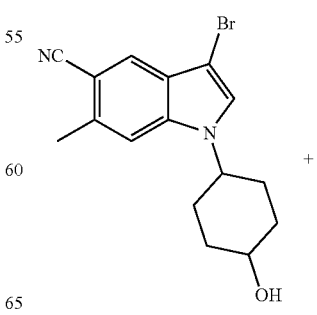

93.3

-continued

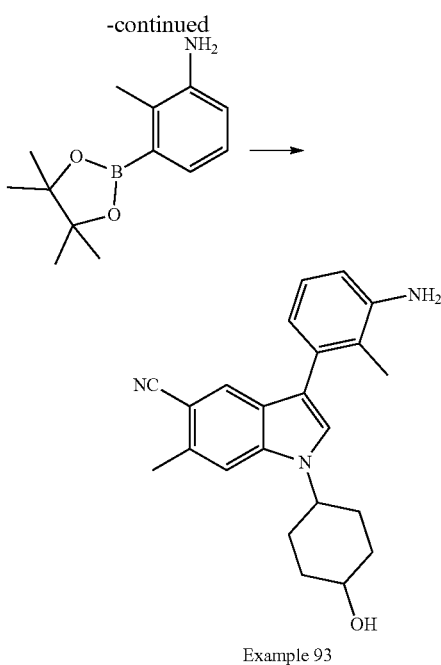

Example 93

To a mixture of compound 93.3 (200 mg, 0.6 mmol) and 2-methyl-3-(4,4,5,5-tetramethyl-1,3,2-dioxaborolan-2-yl)aniline (168 mg, 0.72 mmol) in the co-solvent of i-PrOH/H$_2$O (6 mL, 10:1) was added 2N Na$_2$CO$_3$ aq. (1.8 mL, 3.6 mmol) and Pd(PPh$_3$)$_2$Cl$_2$ (42 mg, 0.06 mmol). The mixture was stirred at 100° C. for 30 min under N$_2$ atmosphere by microwave reactor. The reaction mixture was diluted with water and extracted with EA for three times. The combined organic phase was washed with brine and dried over Na$_2$SO$_4$, concentrated and purified by column chromatography on silica gel (PE:EA=10:1~2:1) to give a crude product which contained Ph$_3$P=O. It was purified by prep-HPLC (0.1% TFA/ACN/H$_2$O) and lyophilized to give the title compound (73.2 mg, 34%) as a pink solid. $^1$H NMR (400 MHz, DMSO-d$_6$) δ ppm 7.76 (s, 1H), 7.69 (d, 1H), 7.64 (s, 1H), 7.21 (t, 1H), 7.07 (d, 2H), 4.47 (d, 2H), 3.84 (s, 1H), 3.58 (t, 2H), 2.59 (s, 3H), 2.13 (d, 3H), 1.94 (t, 6H), 1.53-1.44 (m, 2H). LC-MS: [M+H]$^+$=360.3.

Example 95

Cis-3-(3-amino-2-methylphenyl)-1-(4-hydroxycyclohexyl)-6-methyl-1H-indole-5-carbonitrile Intermediate 95.1: 3-(3-amino-2-methylphenyl)-6-methyl-1-(1,4-dioxaspiro[4.5]decan-8-yl)-1H-indole-5-carbonitrile

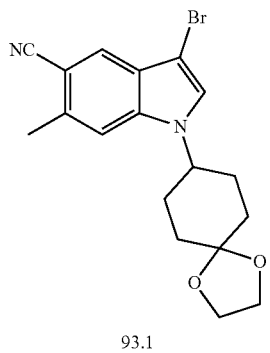

93.1

-continued

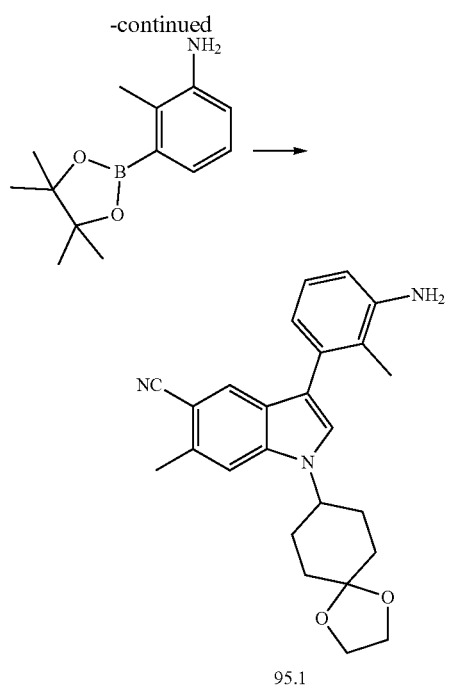

95.1

To a mixture of compound 93.1 (690 mg, 1.84 mmol) and 2-methyl-3-(4,4,5,5-tetramethyl-1,3,2-dioxaborolan-2-yl)aniline (471 mg, 2.02 mmol) in the co-solvent of i-PrOH/H$_2$O (35 mL, 10:1) was added 2 N Na$_2$CO$_3$ aq. (5.5 mL, 11.03 mmol) and Pd(PPh$_3$)$_2$Cl$_2$ (129 mg, 0.18 mmol). The mixture was stirred at 100° C. for 40 min under N$_2$ atmosphere by microwave. The cooled mixture was diluted with brine and extracted with EA for three times. The combined organic phase was washed with brine and dried over Na$_2$SO$_4$, concentrated and purified by column chromatography on silica gel (eluent: PE/EA=2:1) to give the title compound (472 mg, 64%) as a brown solid. $^1$H NMR (400 MHz, CDCl$_3$) δ ppm 7.76 (s, 1H), 7.29 (s, 1H), 7.22 (s, 1H), 7.09 (t, 1H), 6.76 (dd, 2H), 4.38-4.26 (m, 1H), 4.01 (s, 4H), 2.66 (s, 3H), 2.18-2.10 (m, 4H), 2.08 (s, 3H), 1.96 (d, 2H), 1.86 (dd, 2H). LC-MS: [M+H]$^+$=402.5.

Intermediate 95.2: 3-(3-amino-2-methylphenyl)-6-methyl-1-(4-oxocyclohexyl)-1H-indole-5-carbonitrile

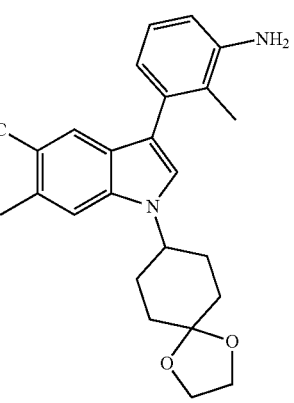

95.1

113
-continued

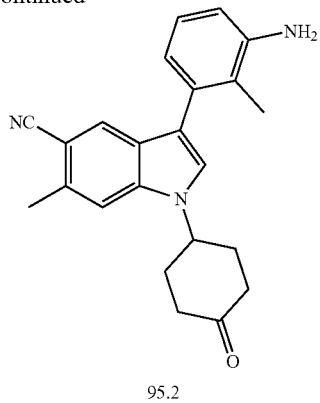

95.2

A mixture of compound 95.1 (400 mg, 1.0 mmol) and water (1.6 mL) in AcOH (8 mL) was heated at 70° C. overnight. To the cooled mixture was added water (20 mL) and then basified by NH₄OH to pH=8 under an ice bath. The mixture was extracted with EA three times. The combined organic phases were dried over Na₂SO₄, concentrated and then purified by flash chromatography (PE/EA, EA:30%-40%) to give the title compound (230 mg, 58%) as a yellow solid. ¹H NMR (300 MHz, CDCl₃) δ ppm 7.77 (s, 1H), 7.33 (s, 1H), 7.16 (s, 1H), 7.08 (t, 1H), 6.79-6.70 (m, 2H), 4.78 (ddd, 1H), 2.69-2.62 (m, 7H), 2.50 (d, 2H), 2.34-2.24 (m, 2H), 2.15-1.99 (m, 5H). LC-MS: [M+H]⁺=358.4.

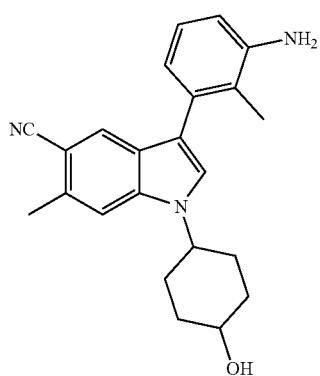

95.2

Example 95

Under N₂ atmosphere, to a solution of compound 95.2 (140 mg, 0.4 mmol) in dry THF (10 mL) was added 1.0 M LS-selectridereg (1.0 mL, THF solution, 1.0 mmol) drop-

114 wised and the temperature was controlled at −55° C. After addition completed, the mixture was stirred at −55° C. for 1 h. To the mixture was added saturated NH₄Cl solution (20 mL) dropwised at −55° C. After addition completed, the mixture was stirred for 15 min and then extracted with EA three times. The organic phases were washed with brine, dried over Na₂SO₄ and concentrated. The residue was dissolved in MeOH (5 mL) and then purified by prep-HPLC (0.1% NH₄OH/ACN/H₂O) to give the title compound (21 mg, yield: 15%) as a white solid. ¹H NMR (400 MHz, DMSO-d₆) δ ppm 7.68 (s, 1H), 7.64 (s, 1H), 7.52 (s, 1H), 6.95 (t, 1H), 6.65 (d, 1H), 6.55 (d, 1H), 4.88 (s, 2H), 4.53 (d, 1H), 4.46 (t, 1H), 3.93 (s, 1H), 2.57 (s, 3H), 2.18 (dd, 2H), 1.98 (s, 3H), 1.76 (dt, 6H). LC-MS: [M+H]⁺=360.1.

Example 96

Trans 3-(3-amino-2-methylphenyl)-6-fluoro-1-(4-hydroxycyclohexyl)-1H-indole-5-carbonitrile Intermediate 96.1:
4-amino-2-fluoro-5-iodobenzonitrile

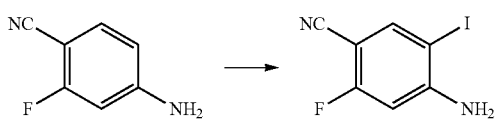

96.1

The aniline 4-amino-2-fluorobenzonitrile (500 mg, 3.7 mmol) was dissolved in AcOH (8 mL) and cooled in an ice bath. NIS (827 mg, 3.7 mmol) was added, and the reaction mixture was stirred at rt for 3 h. The reaction mixture was then concentrated to about one-quarter of the volume, then solid material was collected by filtration. The solid was washed with petroleum ether and dried to give the title compound (1.2 g) as a tan solid. ¹H NMR (300 MHz, DMSO-d₆) δ ppm 8.01 (d, J) 7.7 Hz, 1H), 6.61-6.55 (m, 3H). LC-MS: [M+H]⁺=263.2.

Intermediate 96.2: 4-amino-2-fluoro-5-(((trimethylsilyl)ethynyl)benzonitrile

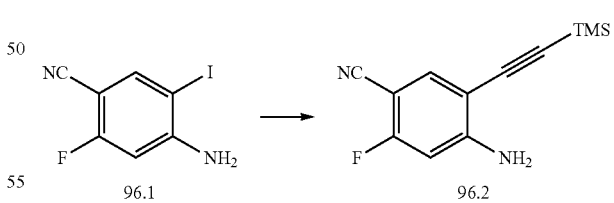

96.1   96.2

To a solution of compound 96.1 (730 mg, 2.79 mmol), Et₃N (7 mL), Pd(PPh₃)₂Cl₂ (20 mg, 0.028 mmol), and CuI (4 mg, 0.021 mmol) in THF (17 mL), trimethylsilylacetylene (329 mg, 3.35 mmol) was added. The resulting mixture was stirred for 24 h at et. Then 70 mL of EA was added and the mixture was washed with brine (50 mL×2). The organic phase was dried and filtered. The solvent was removed in vacuo, and the residue was purified by column chromatography on silica gel using PE/EA (20:1) to give the title compound (460 mg, 71%). ¹H NMR (300 MHz, DMSO-d₆)

δ ppm 7.65 (d, J=7.4 Hz, 1H), 6.64-6.60 (m, 3H), 0.24 (s, 9H). LC-MS: [M+H]⁺=233.3.

Intermediate 96.3:
4-amino-5-ethynyl-2-fluorobenzonitrile

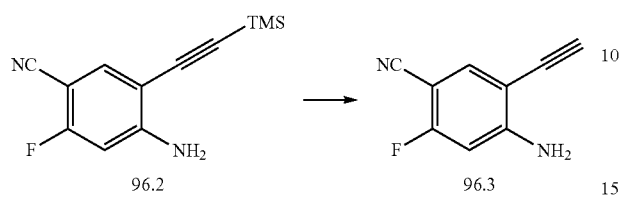

A mixture of compound 96.2 (510 mg, 2.20 mmol) and K₂CO₃ (1500 mg, 10.85 mmol) in 10 mL of MeOH was stirred at rt for 1 h. Then the mixture was diluted with EA (80 mL) and washed with brine (40 mL*3). The organic phase was dried and concentrated to give the title compound (340 mg, 97%). ¹H NMR (300 MHz, DMSO-d₆) δ ppm 7.69 (d, 1H), 6.73 (s, 2H), 6.61 (d, 1H), 4.47 (s, 1H). LC-MS: [M+H]⁺=161.2.

Intermediate 96.4: 6-fluoro-1H-indole-5-carbonitrile

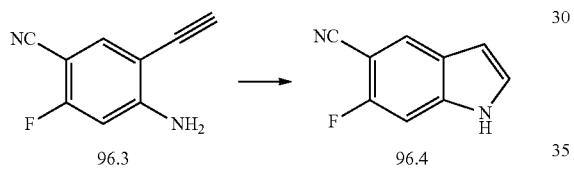

A mixture of compound 96.3 (340 mg, 2.12 mmol) and CpRu(PPh₃)₂Cl (154 mg, 0.21 mmol) in pyridine (12 mL) was stirred under nitrogen at 98° C. for 3 h. The mixture was diluted with EA (100 mL) and washed with saturated NH₄Cl (50 mL×3). The organic phase was dried over anhydrous Na₂SO₄, filtered and evaporated under vacuum. Purification by flash column chromatography through silica gel to give the title compound (240 mg, 70). ¹H NMR (300 MHz, DMSO-d₆) δ ppm 11.71 (s, 1H), 8.11 (d, 1H), 7.54 (s, 1H), 7.44 (d, 1H), 6.58 (s, 1H). LC-MS: [M+H]⁺=161.3.

Intermediate 96.5:
3-bromo-6-fluoro-1H-indole-5-carbonitrile

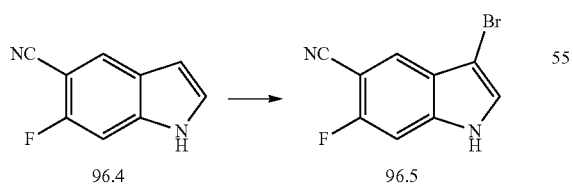

To a solution of compound 96.4 (200 mg, 1.25 mmol) in DMF (4 mL) was added NBS (245 mg, 1.38 mmol) in several portions. After addition, the reaction was stirred at rt for 1 h. Then it was diluted with EA and washed with brine for 3 times. The organic layer was dried over anhydrous Na₂SO₄, filtered and concentrated to give the title compound (300 mg, 100%). ¹H NMR (300 MHz, DMSO-d₆) δ ppm 12.01 (s, 1H), 7.89 (d, 1H), 7.70 (d, 1H), 7.45 (d, 1H).

Intermediate 96.6: 3-bromo-6-fluoro-1-(1,4-dioxaspiro[4.5]decan-8-yl)-1H-indole-5-carbonitrile

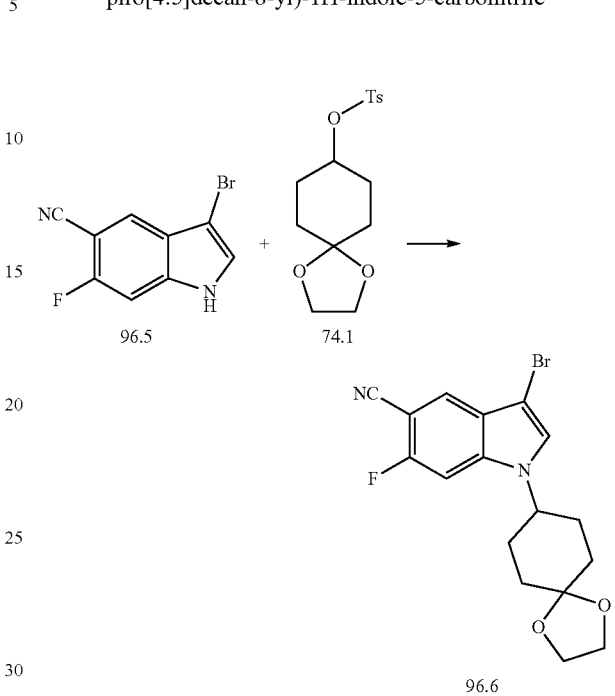

A mixture of compound 96.5 (243 mg, 1.02 mmol), compound 74.1 (635 mg, 2.03 mmol) and Cs₂CO₃ (998 mg, 3.06 mmol) in DMF (10 mL) was stirred under nitrogen at 140° C. for 1.5 h. Another portion of compound 74.1 (210 mg, 0.67 mmol) and Cs₂CO₃ (333 mg, 1.02 mmol) was added, then the mixture was still stirred at 140° C. for 1.5 hours. After cooling to rt, the mixture was diluted with EA (200 mL) and washed with brine (50 mL×3). The organic phase was dried over anhydrous Na₂SO₄, filtered and evaporated under vacuum. The residue was purification by column chromatography through silica gel to give the title compound (170 mg, 44%). ¹H NMR (300 MHz, CDCl₃) δ ppm 7.81 (d, 1H), 7.34 (s, 1H), 7.18 (d, 1H), 4.31-4.08 (m, 1H), 4.00 (s, 4H), 2.12-2.04 (m, 4H), 1.95-1.91 (m, 2H), 1.84-1.78 (m, 2H).

Intermediate 96.7: 3-bromo-6-fluoro-1-(4-oxocyclohexyl)-1H-indole-5-carbonitrile

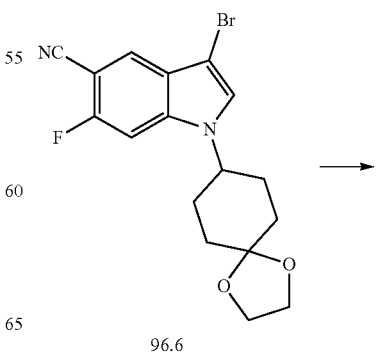

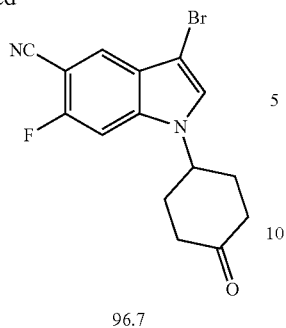
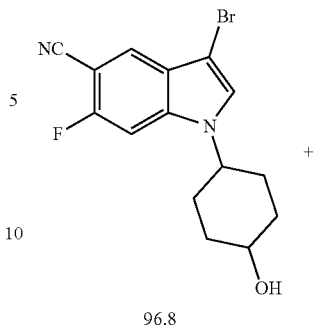

A mixture of compound 96.6 (130 mg, 0.34 mmol) in AcOH (8 mL) and H₂O (1.5 mL) was stirred at 60° C. for 7 h. After cooling to rt, ice-water (60 mL) was added to the mixture. The precipitate was washed with water to yield a white solid which was dried to give the title compound (100 mg, 87%). ¹H NMR (300 MHz, CDCl₃) δ ppm 7.85 (d, 1H), 7.29 (s, 1H), 7.23 (d, 1H), 5.15-4.34 (m, 1H), 2.86-2.54 (m, 4H), 2.50-2.35 (m, 2H), 2.30-2.17 (m, 2H). LC-MS: [M+H]⁺=335.1, 337.1.

Intermediate 96.8: 3-bromo-6-fluoro-1-(4-hydroxy-cyclohexyl)-1H-indole-5-carbonitrile

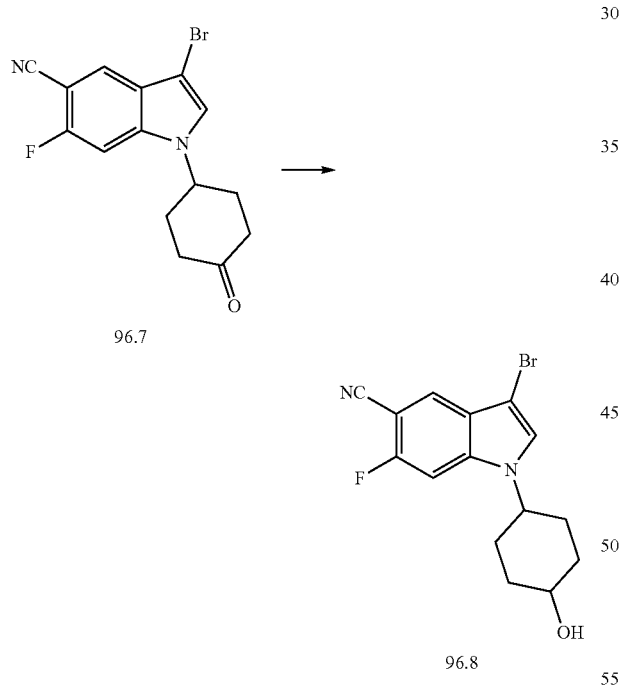

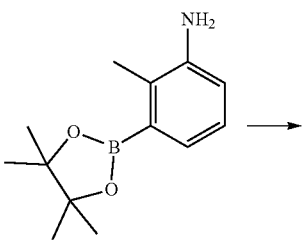

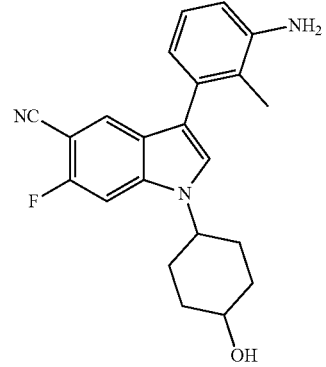

Example 96

To a solution of compound 96.7 (85 mg, 0.25 mmol) in MeOH (1.5 mL) was added NaBH₄ (38 mg, 1.0 mmol) under ice-cold. After addition, it was stirred at rt for 1 h. Then the mixture was diluted with DCM and washed with water for 2 times. The aqueous phase was extracted with EA. The combined organic layer was dried over anhydrous Na₂SO₄, filtered and concentrated to give the title compound (85 mg., 100%). ¹H NMR (300 MHz, DMSO-d₆) δ ppm 8.16-7.90 (m, 3H), 4.91-4.67 (m, 1H), 4.61-4.35 (m, 1H), 3.75-3.49 (m, 1H), 2.10-1.80 (m, 6H), 1.60-1.38 (m, 2H). LC-MS: [M+H]⁺=337.2, 339.2.

To a mixture of compound 1 (85 mg, 0.25 mmol) and compound J (88 mg, 0.38 mmol) in the co-solvent of i-PrOH/H₂O (5 mL, 10:1) was added 2 N Na₂CO₃ aq. (1.2 mL) and Pd(PPh₃)₂Cl₂ (18 mg, 0.026 mmol). The mixture was stirred at 100° C. for 30 min under N₂ atmosphere. Then the mixture was diluted with brine and extracted with EA for three times. The combined organic phase was washed with brine and dried over Na₂SO₄, concentrated and purified by prep-HPLC (ACN/H₂O) to give the title compound (33.2 mg, 36%). ¹H NMR (400 MHz, DMSO-d₆) δ ppm 7.90 (d, 1H), 7.71 (d, 1H), 7.68 (s, 1H), 6.96 (t, 1H), 6.66 (d, 1H), 6.54 (d, 1H), 4.92 (s, 2H), 4.72 (d, 1H), 4.62-4.30 (m, 1H), 3.72-3.42 (m, 1H), 2.04-1.76 (m, 9H), 1.64-1.38 (m, 2H). LC-MS: [M+H]⁺=364.1.

Example 97

3-(3-amino-2-methylphenyl)-6-methyl-1-(piperidin-4-yl)-1H-indole-5-carbonitrile

Intermediate 97.1: tert-butyl 4-(tosyloxy)piperidine-1-carboxylate

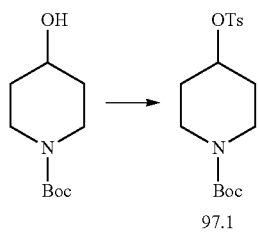 [SMILES: CC(C)(C)OC(=O)N1CCC(O)CC1 ; Cc1ccc(S(=O)(=O)OC2CCN(C(=O)OC(C)(C)C)CC2)cc1]

At 0° C., to a solution of tert-butyl 4-hydroxypiperidine-1-carboxylate (500 mg, 2.48 mmol) in pyridine (2.5 mL) was added TsCl (567 mg, 2.98 mmol) in several portions. The reaction was warmed to rt and stirred at rt overnight. The suspension was diluted with EA, washed with water and brine for 3 times. The organic layer was dried over anhydrous $Na_2SO_4$, filtered and concentrated in reduced pressure to give the title compound (910 mg), which was used directly in next step without further purification. $^1$H NMR (300 MHz, $CDCl_3$) δ ppm 7.81-7.78 (d, 2H), 7.36-7.33 (d, 2H), 4.69-4.64 (m, 1H), 3.62-3.54 (m, 2H), 3.29-3.20 (m, 2H), 2.45 (s, 3H), 1.79-1.64 (m, 4H), 1.43 (s, 9H). LC-MS: $[M+H]^+$=356.2.

Intermediate 97.2: tert-butyl 4-(3-bromo-5-cyano-6-methyl-1H-indol-1-yl)piperidine-1-carboxylate

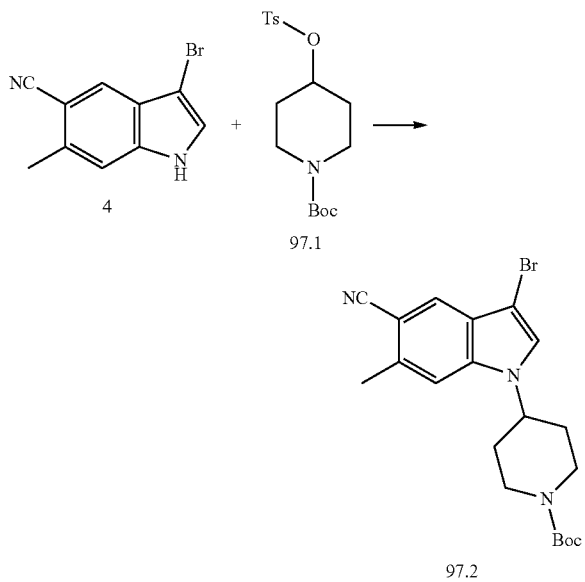 [SMILES: Cc1cc2[nH]cc(Br)c2cc1C#N ; Cc1ccc(S(=O)(=O)OC2CCN(C(=O)OC(C)(C)C)CC2)cc1 ; Cc1cc2c(cc1C#N)c(Br)cn2C1CCN(C(=O)OC(C)(C)C)CC1]

To a solution of compound 97.1 (300 mg, 1.28 mmol) in DMF (5 mL) was added 4 (909.9 mg, 2.56 mmol) and $Cs_2CO_3$ (1.251 g, 3.84 mmol). The mixture was stirred at 90° C. for 2.5 h under $N_2$ atmosphere. After cooled to rt, Water (15 mL) was added. The mixture was extracted with EA (3*5 mL). The combined organic layers were washed brine, dried over $Na_2SO_4$, concentrated and purified by column chromatography on silica gel (PE/EA, EA=0 to 30%) to give the title compound (270 mg, 51%). $^1$H NMR (300 MHz, DMSO-$d_6$) δ ppm 7.94 (s, 1H), 7.83 (s, 1H), 7.77 (s, 1H), 4.08 (t, J=17.5 Hz, 1H), 2.57 (s, 4H), 1.86 (d, J=18.2 Hz, 4H), 1.42 (s, 9H). LC-MS: $[M+H]^+$=418.1.

Intermediate 97.3: tert-butyl 4-(3-(3-amino-2-methylphenyl)-5-cyano-6-methyl-1H-indol-1-yl)piperidine-1-carboxylate

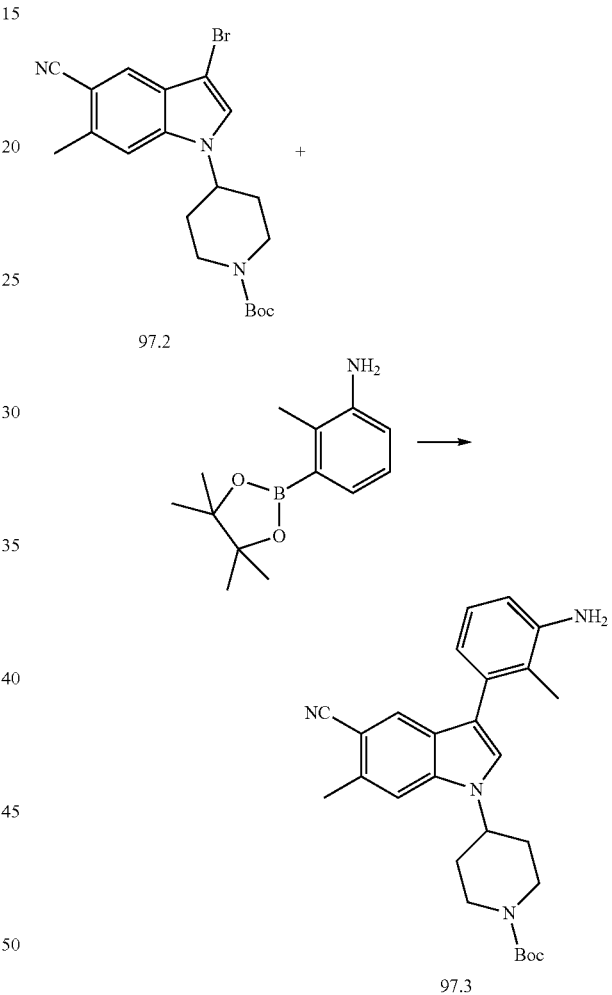

To a solution of compound 97.2 (250 mg, 0.6 mmol), (3-amino-2-methylphenyl)boronic acid (108 mg, 0.72 mmol) and 2 N. aqueous $Na_2CO_3$ solution (1.8 mL) in i-PrOH/$H_2O$ (10:1, 10 mL) was added Pd(PPh3)$_2$Cl$_2$ (42 mg, 0.06 mmol) under nitrogen. The mixture was stirred at 110° C. in microwave condition for 1 h. Water (20 mL) was added and the mixture was extracted with EA (3×10 mL). The combined organic layers were washed with brine, concentrated in vacuum to dryness. The residue was purified by prep-HPLC (0.1% $NH_3.H_2O$/$CH_3CN$/$H_2O$) to give the desired compound (125 mg, 47%). LC-MS: $[M+H]^+$=445.5.

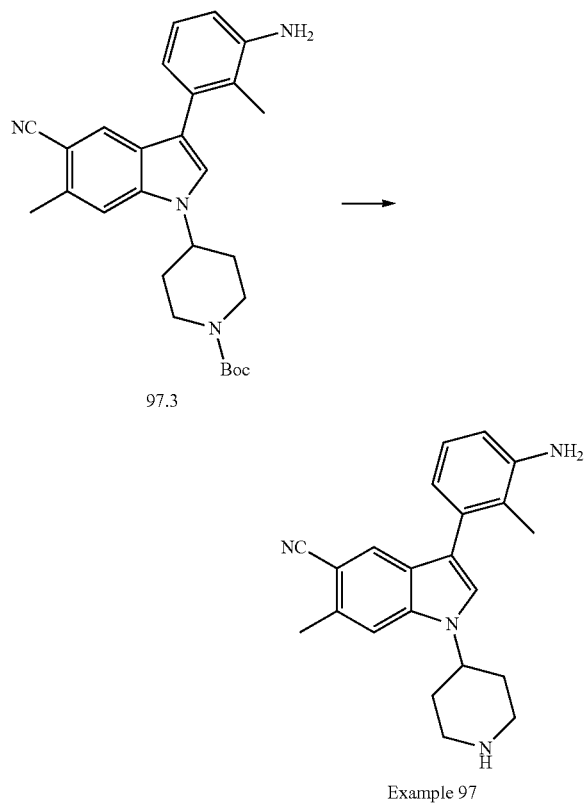 [SMILES: Cc1cc2c(cc1C#N)c(-c1cccc(N)c1C)cn2C1CCN(C(=O)OC(C)(C)C)CC1 ; Cc1cc2c(cc1C#N)c(-c1cccc(N)c1C)cn2C1CCNCC1]

97.3

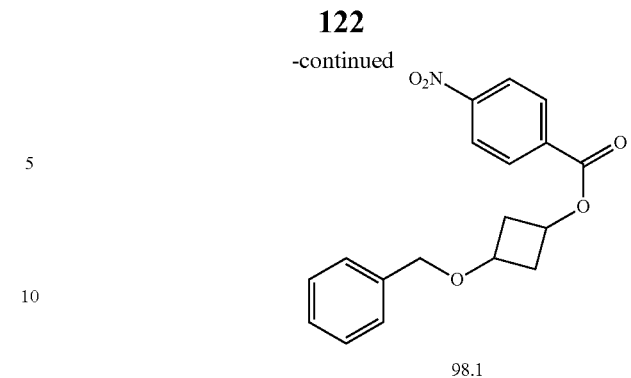

98.1

To a solution of 3-(benzyloxy)cyclobutan-1-ol (500 mg, 2.8 mmol, cis/trans 85%:15%), 4-nitrobenzoic acid (935 mg, 5.6 mmol) and PPh₃ (2.2 g, 8.4 mmol) in dry THF (25 mL) was added DIAD (1.7 g, 8.4 mmol) dropwise at 0° C. under N₂ atmosphere. After addition was completed, the mixture was stirred at 0° C. for 15 min and then allowed to room temperature overnight. The mixture was concentrated and then purified by column chromatography on silica gel (PE:EA=10:1) to give the title compound (900 mg, 98%) as a yellow solid. ¹H NMR (300 MHz, CDCl₃) δ ppm 8.31-8.26 (m, 2H), 8.23-8.18 (m, 2H), 7.39-7.27 (m, 5H), 5.44 (dq, 1H), 4.47 (d, 2H), 4.37 (tt, 1H), 2.67-2.56 (m, 2H), 2.55-2.44 (m, 2H).

Intermediate 98.2:
Cis-3-(benzyloxy)cyclobutan-1-ol

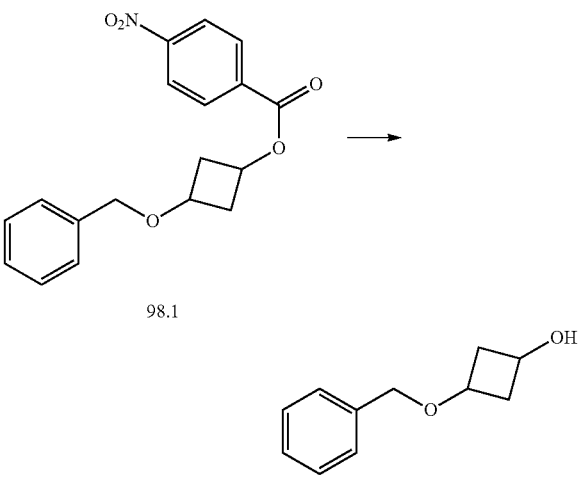

Example 97

To a mixture of compound 97.3 (80 mg, 0.18 mmol) in DCM (1.5 mL) was added TFA (300 uL). The reaction mixture was stirred at rt for 1 h. After removing solvent, the residue was purified by prep-HPLC (0.1% NH₃·H₂O/CH₃CN/H₂O) to give the title compound (18.2 mg, 29%) as a light grey solid. ¹H NMR (400 MHz, DMSO-d₆) δ ppm 7.72 (s, 1H), 7.67 (s, 1H), 7.52 (s, 1H), 6.96 (t, 1H), 6.66 (d, 1H), 6.55 (d, 1H), 4.92 (s, 2H), 4.73 (s, 1H), 3.37 (s, 2H), 3.02 (s, 2H), 2.59 (s, 3H), 2.10 (s, 4H), 1.97 (s, 3H). LC-MS: [M+H]⁺=345.3.

Example 98

Cis-3-(3-amino-2-methylphenyl)-1-(3-hydroxycyclobutyl)-6-methyl-1H-indole-5-carbonitrile Intermediate 98.1: 3-(benzyloxy)cyclobutyl 4-nitrobenzoate

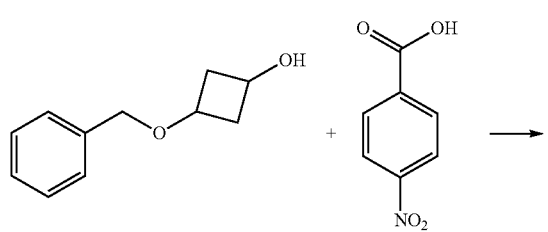

To a solution of compound 98.1 (850 mg, 2.5968 mmol) in dioxane (18 mL) was added 0.4 N NaOH (13 mL, 5.1935 mmol). The mixture was stirred at rt for 1 h. HOAc (234 mg, 3.8952 mmol) was added and the mixture was concentrated. EA (15 mL) and saturated NaHCO₃ (30 mL) was added to the residue. The organic layer was washed with saturated NaHCO₃ and separated. The aqueous layer was extracted with EA (2×10 mL). The combined organic layers were washed with water and brine, dried over Na₂SO₄ and concentrated to give the title compound (435 mg, 94%). ¹H NMR (300 MHz, CDCl₃) δ ppm 7.37-7.28 (m, 5H), 4.56 (tt, 1H), 4.43 (s, 2H), 4.34-4.26 (m, 1H), 2.44-2.33 (m, 2H), 2.24-2.16 (m, 2H), 2.12 (s, 1H). LC-MS: [M+Na]⁺=201.2.

Intermediate 98.3: Cis-3-(benzyloxy)cyclobutyl 4-methylbenzenesulfonate

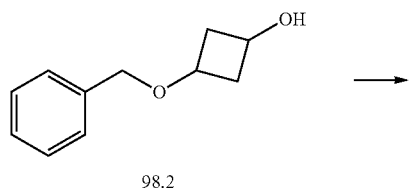

98.2

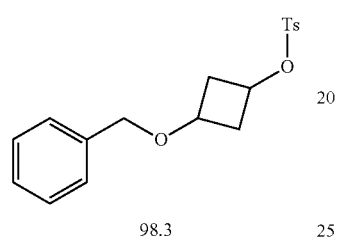

98.3

To a solution of compound 98.2 (433 mg, 2.4294 mmol) in DCM (5 mL) was added DMAP (445 mg, 3.6441 mmol). The mixture was cooled to 0° C. and the solution of TsCl (509 mg, 2.6724 mmol) in DCM (1 mL) was added dropwise to the mixture. The mixture was warned to rt and stirred at rt overnight. The mixture was washed with 1 N HCl (2*20 mL). the organic layer was separated and washed with water and brine, dried over Na$_2$SO$_4$ and concentrated to give the title compound (716 mg, 88%). $^1$H NMR (400 MHz, CDCl$_3$) δ ppm 7.79 (d, 2H), 7.37-7.29 (m, 7H), 5.01 (dq, 1H), 4.38 (s, 2H), 4.28-4.20 (m, 1H), 2.47 (s, 3H), 2.46-2.32 (m, 4H). LC-MS: [M+Na]$^+$=355.2.

Intermediate 98.4: Cis-1-(3-(benzyloxy)cyclobutyl)-3-bromo-6-methyl-1H-indole-5-carbonitrile

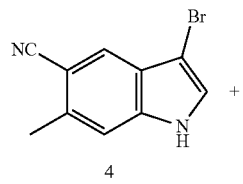

4

+

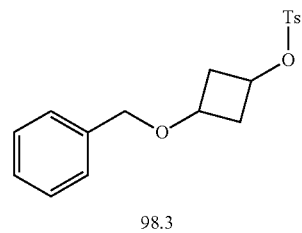

98.3

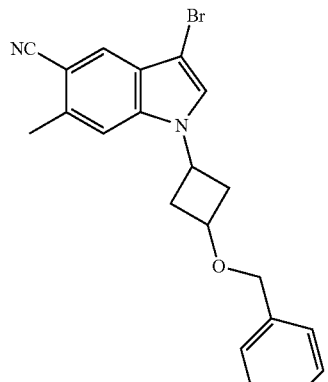

98.4

To a solution of compound 4 (180 mg, 0.657 mmol) in DMF (6 mL) was added compound 98.3 (382 mg, 1.1485 mmol) and Cs$_2$CO$_3$ (1684 mg, 5.1683 mmol). The mixture was stirred at 100° C. overnight. After cooling to rt, EA (100 mL) was added and the mixture was filtered. The filtrate was washed with water and brine, dried over Na$_2$SO$_4$ and concentrated to give the crude product, which was washed with tert-butyl methyl ether/PE (1:1, 2×25 mL) to give the title compound (192 mg, 63%). $^1$H NMR (400 MHz, DMSO-d$_6$) δ ppm 8.00 (s, 1H), 7.85 (s, 1H), 7.64 (s, 1H), 7.39-7.35 (m, 4H), 7.33-7.28 (m, 1H), 4.75-4.59 (m, 1H), 4.47 (s, 2H), 3.96 (p, 1H), 2.97-2.85 (m, 2H), 2.57 (s, 3H), 2.41-2.30 (m, 2H). LC-MS: [M+H]$^+$=395.1.

Intermediate 98.5: Cis-3-(3-amino-2-methylphenyl)-1-(3-(benzyloxy)cyclobutyl)-6-methyl-1H-indole-5-carbonitrile

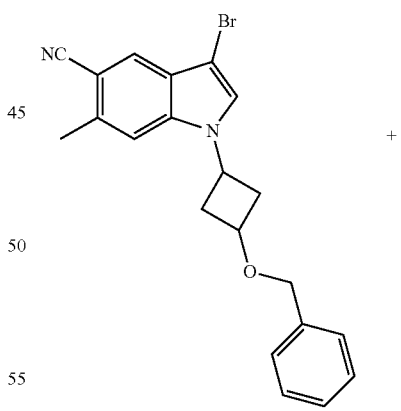

98.4

+

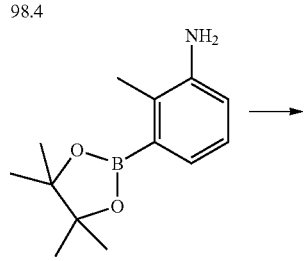

125
-continued

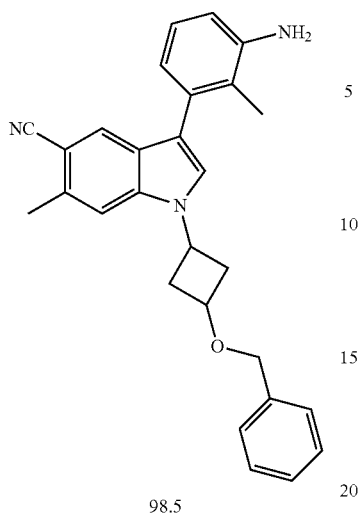

98.5

To a solution of compound 98.4 (148 mg, 0.374 mmol) in i-PrOH/H₂O (10:1, 3 mL) was added (3-amino-2-methylphenyl)boronic acid (105 mg, 0.449 mmol) and 2 N Na₂CO₃ (1.12 mL, 2.244 mmol). The mixture was degassed with N₂ for 0.5 min. Pd(PPh₃)₂Cl₂ (26 mg, 0.037 mmol) was added and the mixture was degassed with N2 for 0.5 min. The mixture was stirred at 100° C. for 30 min in microwave condition. After cooling to rt, EA was added and the mixture was filtered. The filtrate was washed with water and brine, dried over Na₂SO₄, concentrated and purified by column chromatography on silica gel (PE:EA=5:1) to give the title compound (98 mg, 62%). ¹H NMR (400 MHz, DMSO-d₆) δ ppm 7.63 (dd, 3H), 7.43-7.34 (m, 4H), 7.33-7.26 (m, 1H), 6.96 (t, 1H), 6.70-6.64 (m, 1H), 6.57 (dd, 1H), 4.90 (s, 2H), 4.76-4.63 (m, 1H), 4.48 (s, 2H), 4.05-3.97 (m, 1H), 3.02-2.88 (m, 2H), 2.57 (s, 3H), 2.41 (ddd, 2H), 1.98 (s, 3H). LC-MS: [M+H]⁺=422.3.

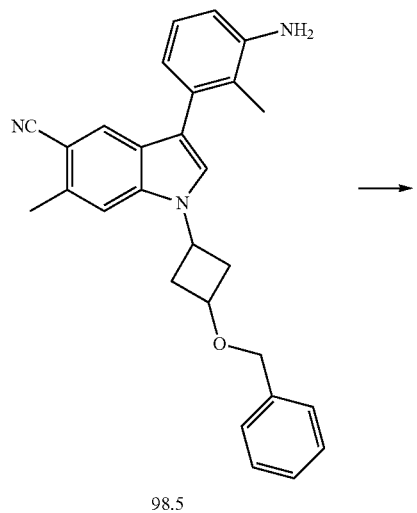

98.5

126
-continued

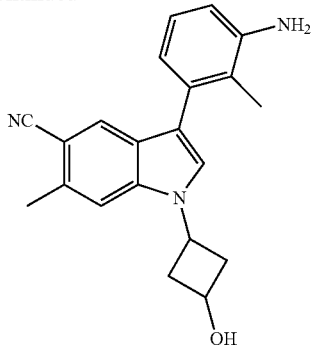

Example 98

To a solution of compound 98.5 (90 mg, 0.2135 mmol) in DCM (5 mL) was added BBr₃ (432 uL, 4.4835 mmol). The mixture was stirred at rt for 1.5 h under N₂ atmosphere. MeOH (10 mL) was added and the mixture was concentrated. The crude product was purified by prep-HPLC (0.1% NH₃.H₂O/CH₃CN/H₂O) to give the title compound (32, 45%). ¹H NMR (400 MHz, DMSO-d₆) δ ppm 7.63 (d, 2H), 7.59 (s, 1H), 6.96 (t, 1H), 6.66 (d, 1H), 6.56 (d, 1H), 5.31 (t, 1H), 4.91 (s, 2H), 4.65-4.51 (m, 1H), 4.11-3.98 (m, 1H), 2.98-2.86 (m, 2H), 2.57 (s, 3H), 2.31 (ddd, 2H), 1.98 (s, 3H). LC-MS: [M+H]⁺=332.0.

Example 100

Trans-3-(3-amino-2-methylphenyl)-1-(3-hydroxycyclobutyl)-6-methyl-1H-indole-5-carbonitrile Intermediate 100.1: Trans-3-(benzyloxy)cyclobutyl 4-methylbenzenesulfonate

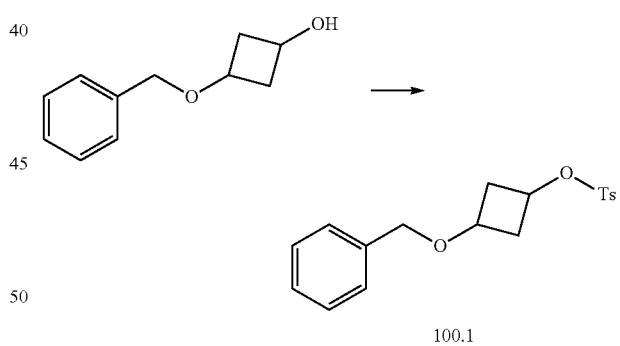

100.1

To a solution of trans-3-(benzyloxy)cyclobutan-1-ol (400 mg, 2.244 mmol) in DCM (10 mL) was added DMAP (411 mg, 3.366 mmol). The mixture was cooled to 0° C. and the solution of TsCl (471 mg, 2.469 mmol) in DCM (3 mL) was added dropwise to the mixture at 0° C. The mixture was warmed to rt and stirred at rt overnight. The mixture was washed with 1 N HCl (2×10 mL) and the aqueous layer was extracted with DCM (2×15 mL). The combined organic layers were washed with water and brine, dried over Na₂SO₄ and concentrated to give the title compound (730 mg, 98%). ¹H NMR (300 MHz, DMSO-d₆) δ ppm 7.83 (d, 2H), 7.56-7.50 (m, 2H), 7.38-7.30 (m, 5H), 4.55 (p, 1H), 4.37 (s, 2H), 3.69 (p, 1H), 2.61 (ddd, 2H), 2.48 (s, 3H), 2.07-1.93 (m, 2H). LC-MS: [M+H]⁺=333.4.

127

Intermediate 100.2: Trans-1-(3-(benzyloxy)cyclobutyl)-3-bromo-6-methyl-1H-indole-5-carbonitrile

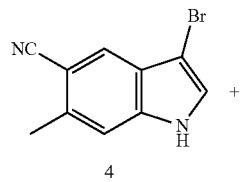
4

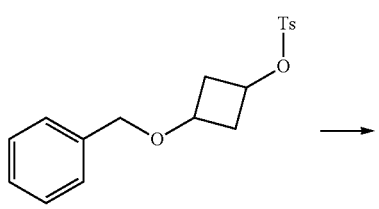
100.1

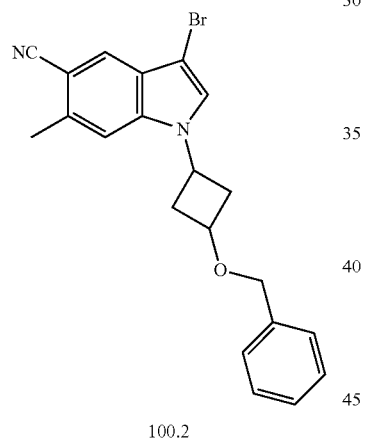
100.2

128

Intermediate 100.3: Trans-3-(3-amino-2-methylphenyl)-1-(3-(benzyloxy)cyclobutyl)-6-methyl-1H-indole-5-carbonitrile

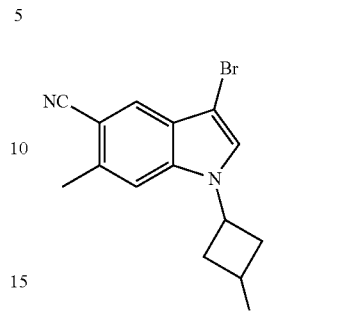
100.2

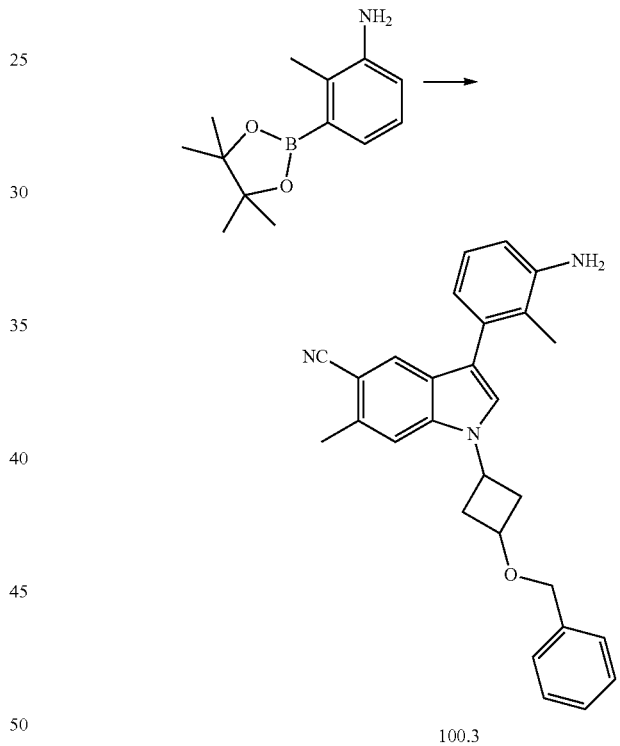
100.3

To a solution of compound 100.1 (150 mg, 0.638 mmol) in DMF (25 mL) was added compound 4 (382 mg, 1.148 mmol) and Cs$_2$CO$_3$ (935 mg, 2.871 mmol). The mixture was stirred at 100° C. overnight under N$_2$ atmosphere. After cooling to rt, EA (100 mL) was added and the mixture was filtered. The filtrate was washed with water and brine, dried over Na$_2$SO$_4$, concentrated to give 400 mg of crude product, which was washed with tert-butyl methyl ether/petroleum ether (1:1, 2×20 mL) to give the title compound (170 mg, 67%). $^1$H NMR (300 MHz, DMSO-d$_6$) δ ppm 8.03 (s, 1H), 7.84 (s, 1H), 7.66 (s, 1H), 7.38 (d, 4H), 7.34-7.30 (m, 1H), 5.29-5.16 (m, 1H), 4.47 (s, 2H), 4.33 (t, 1H), 2.66 (t, 4H), 2.57 (s, 3H). LC-MS: [M+H]$^+$=395.3, 397.3.

To a solution of compound 100.3 (148 mg, 0.374 mmol) in i-PrOH/H$_2$O (10:1, 3 mL) was added (3-amino-2-methylphenyl)boronic acid (105 mg, 0.449 mmol) and 2 N Na$_2$CO$_3$ (1.12 mL, 2.244 mmol). The mixture was degassed with N$_2$ for 0.5 min, then Pd(PPh$_3$)$_2$Cl$_2$ (26.3 mg, 0.037 mmol) was added and the mixture was degassed again with N$_2$ for 0.5 min. The mixture was stirred at 100° C. for 30 min in microwave condition. After cooling to rt, EA (60 mL) was added and the mixture was filtered. The filtrate was washed with water and brine, dried over Na$_2$SO$_4$, concentrated and purified by column chromatography on silica gel (PE:EA 5:1) to give the title compound (100 mg, 63%). $^1$H NMR (300 MHz, DMSO-d$_6$) δ ppm 7.79 (s, 1H), 7.68 (d, 2H), 7.50-7.42 (m, 4H), 7.37 (s, 1H), 7.02 (t, 1H), 6.72 (d, 1H), 6.62 (d, 1H), 5.32 (t, 1H), 4.94 (s, 2H), 4.54 (s, 2H), 4.42 (s, 1H), 2.77 (s, 4H), 2.63 (s, 3H), 2.04 (s, 3H). LC-MS: [M+H]⁺=422.5.

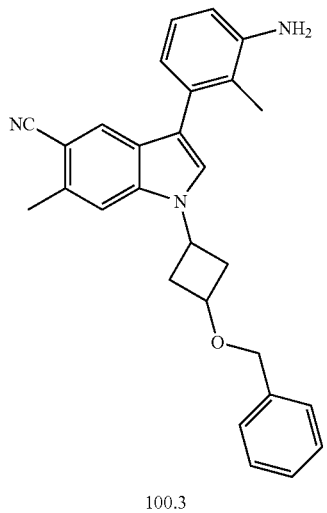

100.3

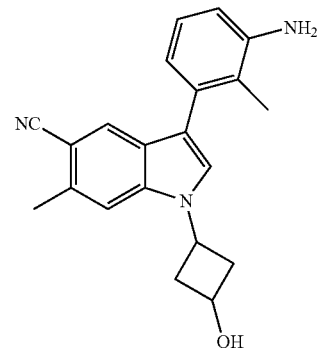

Example 100

To a solution of compound 100.4 (80 mg, 0.1898 mmol) in DCM (5 mL) was added BBr₃ (400 uL, 4.1514 mmol). The mixture was stirred at rt for 1.5 h under N₂ atmosphere. MeOH (10 mL) was added and the mixture was concentrated. The residue was dissolved in DCM and washed with saturated NaHCO₃, brine and water, dried over Na₂SO₄ and concentrated, purified by prep-HPLC (0.1% NH₃/ACN/H₂O) to give the title compound (22 mg, 35%). ¹H NMR (400 MHz, DMSO-d₆) δ ppm 7.70 (s, 1H), 7.63 (s, 1H), 7.56 (s, 1H), 6.96 (t, 1H), 6.66 (dd, 1H), 6.56 (dd, 1H), 5.30 (d, 1H), 5.26-5.17 (m, 1H), 4.90 (s, 2H), 4.46 (d, 1H), 2.74-2.64 (m, 2H), 2.57 (s, 3H), 2.50-2.46 (m, 2H), 1.98 (s, 3H). LC-MS: [M+H]⁺=332.2.

Example 102

3-(3-amino-2-methylphenyl)-1-(3-chloro-4-methoxyphenyl)-1H-indole-5-carbonitrile Intermediate 102.1: 1-(3-chloro-4-methoxyphenyl)-1H-indole-5-carbonitrile

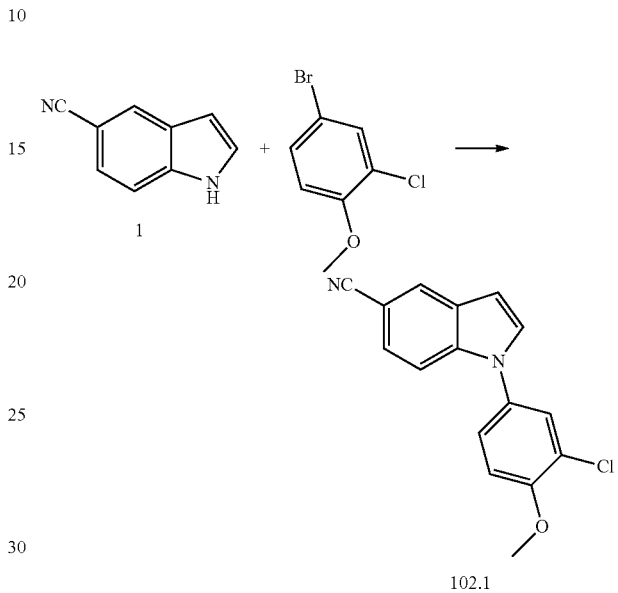

102.1

The mixture of compound 1 (300 mg, 2.11 mmol), 4-bromo-2-chloro-1-methoxybenzene (701 mg, 3.165 mmol), 1,10-phenanthroline (152 g, 0.844 mmol), Cu₂O (60 mg, 0.419 mmol) and the solution of TBAF in THF (1N, 6.4 mL) was concentrated under vacuo to remove solvent. The residue was then heated to 150° C. for 5 h. After cooling down, the residue was diluted with water and extracted with EA for 3 times. The organic layer was dried over anhydrous Na₂SO₄, filtered and concentrated to give a crude product which was purified by column chromatography on silica gel (PE/EA=4:1) to give the title compound (280 mg, 47%). ¹H NMR (300 MHz, DMSO-d₆) δ ppm 8.26 (s, 1H), 7.87 (d, 1H), 7.77 (d, 1H), 7.68-7.54 (m, 3H), 7.41 (d, =1H), 6.89 (d, 1H), 4.00 (s, 3H). LC-MS: [M+H]⁺=283.3.

Intermediate 102.2: 3-bromo-1-(3-chloro-4-methoxyphenyl)-1H-indole-5-carbonitrile

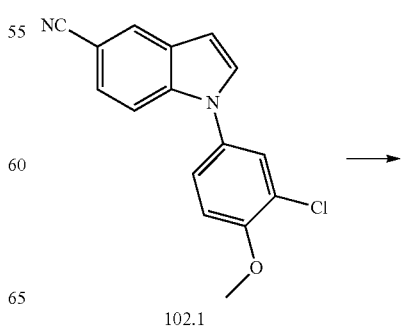

102.1

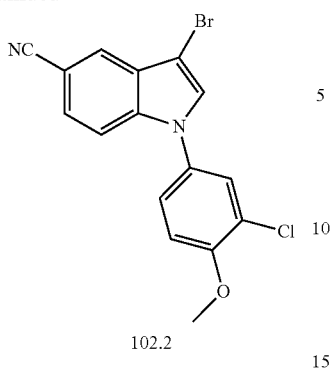

102.2

To a solution of compound 102.1 (50 mg, 0.177 mmol) in DMF (2 mL) was added a solution of NBS (35 mg, 0.197 mmol) in DMF (1 mL) dropwise. After addition, the reaction mixture was stirred at rt for 1 h. Then the mixture was diluted with EA and washed with brine for 3 times. The organic layer was dried over anhydrous $Na_2SO_4$, filtered and concentrated to give the title compound (48 mg, 75%). $^1$H NMR (300 MHz, DMSO-$d_6$) δ ppm 8.16 (s, 1H), 8.09 (s, 1H), 7.80 (d, 1H), 7.71-7.59 (m, 3H), 7.40 (d, 1H), 4.00 (s, 3H). LC-MS: [M+H]$^+$=363.3.

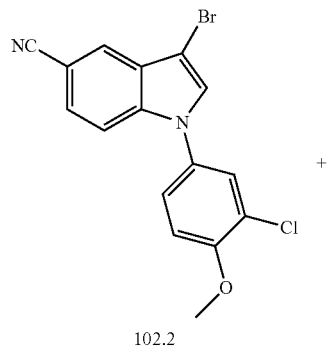

102.2

+

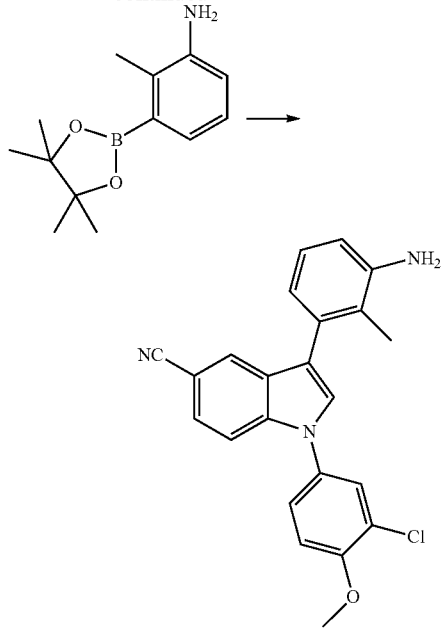

Example 102

To a mixture of compound 102.2 (100 mg, 0.277 mmol) and (4-hydroxy-2-methylphenyl)boronic acid (97 mg, 0.416 mmol) in the co-solvent of i-PrOH/$H_2O$ (2 mL, 10:1) was added 2N $Na_2CO_3$ aq. (0.9 mL) and Pd(PPh$_3$)$_2$Cl$_2$ (20 mg, 0.0285 mmol). The mixture was stirred at 100° C. for 30 min under $N_2$ atmosphere. Then the mixture was diluted with brine and extracted with EA for three times. The combined organic phase was washed with brine and dried over $Na_2SO_4$, concentrated and purified by prep-HPLC (0.1% $NH_3$/ACN/$H_2O$) to give the title compound (34.9 mg, 33%). $^1$H NMR (400 MHz, DMSO-$d_6$) δ ppm 7.87-7.78 (m, 3H), 7.67-7.64 (m, 2H), 7.59 (dd, 1H), 7.38 (d, 1H), 7.01 (t, 1H), 6.71 (d, 1H), 6.65 (d, 1H), 4.99 (s, 2H), 3.96 (s, 3H), 2.04 (s, 3H). LC-MS: [M+H]$^+$=388.2.

The following compounds, as identified in Table 1, were prepared using the general procedures as well as the procedures from the examples described above with the appropriate starting materials and reagents.

TABLE 1

| Ex # | Structure | $^1$H NMR and LC-MS Data |
|---|---|---|
| 16 | 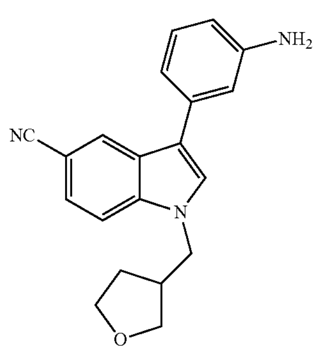 [SMILES: N#Cc1ccc2c(c1)c(-c1cccc(N)c1)cn2CC1CCOC1] | $^1$H NMR (400 MHz, DMSO-$d_6$) δ ppm 8.30 (d, 1H), 7.90 (s, 1H), 7.81 (d, 1H), 7.56 (dd, 1H), 7.09 (t, 1H), 6.96 (t, 1H), 6.81 (d, 1H), 6.50 (dd, 1H), 5.16 (s, 2H), 4.38-4.18 (m, 2H), 3.84 (m, 1H), 3.64 (q, 2H), 3.47 (dd, 1H), 2.87-2.73 (m, 1H), 1.89 (m, 1H), 1.63 (m, 1H). LC-MS: [M + H]$^+$ = 318.2. |

TABLE 1-continued
| Ex # | Structure | ¹H NMR and LC-MS Data |
|---|---|---|
| 17 | 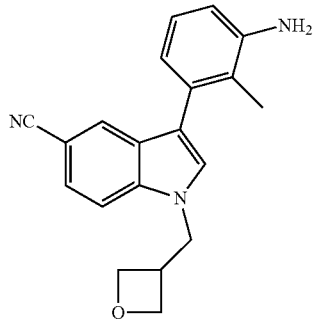 [SMILES: Cc1c(N)cccc1-c1cn(CC2COC2)c2ccc(C#N)cc12] | ¹H-NMR (400 MHz, CD₃OD) δ ppm 7.81 (d, 1H), 7.73 (d, 1H), 7.66 (s, 1H), 7.54 (dd, 1H), 6.97 (t, 1H), 6.67 (d, 1H), 6.56 (d, 1H), 4.92 (s, 2H), 4.69-4.56 (m, 4H), 4.45 (t, 2H), 3.60-3.44 (m, 1H), 1.97 (s, 3H).<br>LC-MS: [M + H]⁺ = 318.0. |
| 18 | 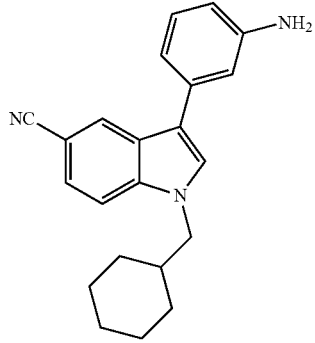 [SMILES: N#Cc1ccc2c(c1)c(-c1cccc(N)c1)cn2CC1CCCCC1] | ¹H-NMR (400 MHz, CD₃OD) δ ppm 8.24 (s, 1H), 7.59-7.53 (m, 2H), 7.44 (d, 1H), 7.19 (t, 1H), 7.04 (s, 1H), 6.96 (d, 1H), 6.69 (d, 2H), 4.06 (d, 2H), 1.91-1.84 (m, 1H), 1.73-1.58 (m, 5H), 1.24-1.06 (m, 3H), 1.20-1.04 (m, 2H).<br>LC-MS: [M + H]⁺ = 330.2. |
| 21 | 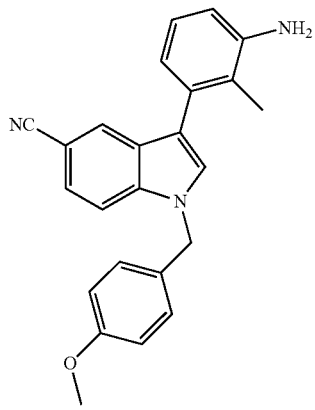 [SMILES: COc1ccc(Cn2cc(-c3cccc(N)c3C)c3cc(C#N)ccc32)cc1] | ¹H NMR (400 MHz, CDCl₃) δ ppm 7.84 (s, 1H), 7.44-7.38 (m, 2H), 7.27 (s, 1H), 7.20-7.05 (m, 3H), 6.88 (d, 2H), 6.81-6.73 (m, 2H), 5.33 (s, 2H), 3.80 (s, 3H), 2.09 (s, 3H).<br>LC-MS: [M + H]⁺ = 368.2. |
| 22 | 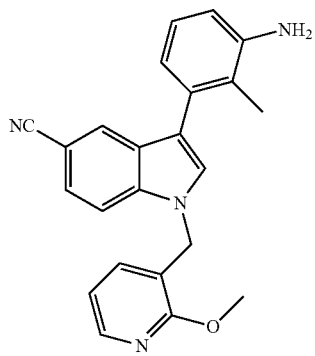 [SMILES: COc1ncccc1Cn1cc(-c2cccc(N)c2C)c2cc(C#N)ccc21] | ¹H-NMR (400 MHz, CD₃OD) δ ppm 8.06 (d, 1H), 7.71 (s, 1H), 7.56 (d, 1H), 7.44-7.40 (m, 2H), 7.26 (d, 1H), 7.03 (t, 1H), 6.86 (t, 1H), 6.79 (d, 1H), 6.72 (d, 1H), 5.42 (s, 2H), 3.99 (s, 3H), 2.06 (s, 3H).<br>LC-MS: [M + H]⁺ = 368.9. |

TABLE 1-continued

| Ex # | Structure | ¹H NMR and LC-MS Data |
|---|---|---|
| 25 | 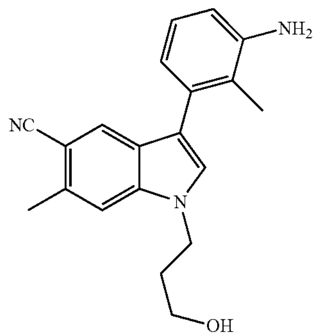 [SMILES: Cc1cc2c(cc1C#N)c(-c1cccc(N)c1C)cn2CCCO] | ¹H NMR (400 MHz, CD₃OD) δ ppm 7.63 (s, 1H), 7.50 (s, 1H), 7.28 (s, 1H), 7.03 (t, 1H), 6.78 (t, 1H), 6.72 (d, 1H), 4.35 (t, 2H), 3.57 (t, 2H), 2.63 (s, 3H), 2.08-2.01 (m, 5H). LC-MS: [M + H]⁺ = 319.9. |
| 35 | 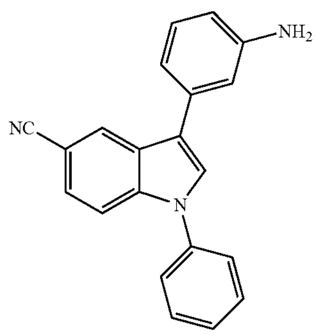 [SMILES: N#Cc1ccc2c(c1)c(-c1cccc(N)c1)cn2-c1ccccc1] | ¹H NMR (400 MHz, METHANOL-d₄) δ ppm 8.30 (s, 1H), 7.75 (s, 1H), 7.54-7.68 (m, 5H), 7.40-7.54 (m, 2H), 7.22 (m, 1H), 7.09 (s, 1H), 7.02 (d, 1H), 6.73 (m, 1H). LC-MS: [M + H]⁺ = 310.1. |
| 36 | 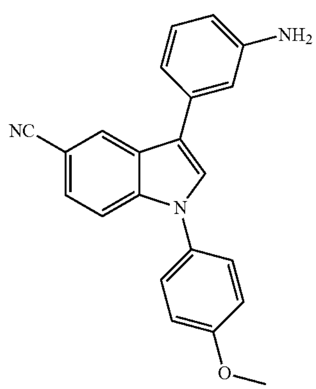 [SMILES: COc1ccc(-n2cc(-c3cccc(N)c3)c3cc(C#N)ccc32)cc1] | ¹H NMR (400 MHz, METHANOL-d₄) δ ppm 8.31 (s, 1H), 7.71 (s, 1H), 7.51-7.58 (m, 1H), 7.48 (d, 3H), 7.22 (s, 1H), 7.14 (d, 2H), 7.10 (s, 1H), 7.02 (d, 1H), 6.69-6.77 (m, 1H), 6.73 (m, 1H), 3.89 (s, 3H). LC-MS: [M + H]⁺ = 340.2. |
| 37 | 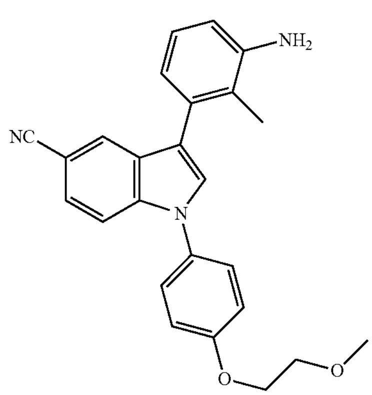 [SMILES: COCCOc1ccc(-n2cc(-c3cccc(N)c3C)c3cc(C#N)ccc32)cc1] | ¹H NMR (400 MHz, CHLOROFORM-d) δ ppm 7.88 (s, 1H), 7.42-7.56 (m, 4H), 7.36 (s, 1H), 7.07-7.20 (m, 3H), 6.88 (d, 1H), 6.82 (d, 1H), 4.15-4.28 (m, 2H), 3.83 (d, 2H), 3.50 (s, 3H), 2.17 (s, 3H). LC-MS: [M + H]⁺ = 398.2. |

TABLE 1-continued

| Ex # | Structure | ¹H NMR and LC-MS Data |
|---|---|---|
| 38 | 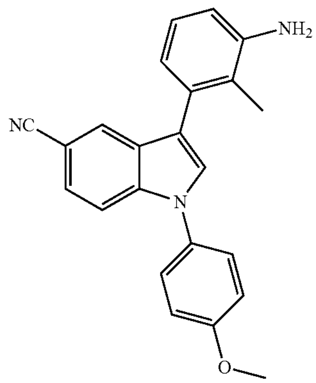 [SMILES: COc1ccc(-n2cc(-c3cccc(N)c3C)c3cc(C#N)ccc32)cc1] | ¹H NMR (CHLOROFORM-d) δ ppm 7.88 (br s, 1H), 7.51 (d, 1H), 7.45 (br m, 3H), 7.36 (d, 1H), 7.27 (d, 1H), 7.04-7.20 (m, 3H), 6.73-6.92 (m, 2H), 3.91 (d, 4H), 2.16 (d, 3H).<br>LC-MS: [M + H]⁺ = 354.2. |
| 39 | 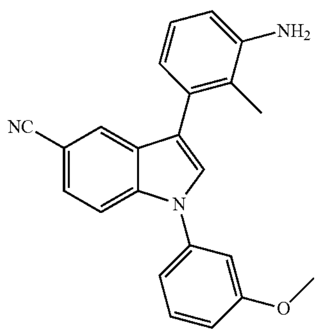 [SMILES: COc1cccc(-n2cc(-c3cccc(N)c3C)c3cc(C#N)ccc32)c1] | ¹H NMR (400 MHz, METHANOL-d₄) δ ppm 7.74 (d, 1H), 7.67 (d, 1H), 7.54 (s, 1H), 7.44-7.52 (m, 2H), 7.09-7.18 (m, 2H), 6.98-7.09 (m, 2H), 6.83 (d, 1H), 6.77 (d, 1H), 3.87 (s, 3H), 2.10 (s, 3H).<br>LC-MS: [M + H]⁺ = 354.2. |
| 40 | 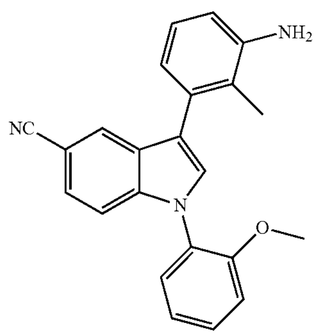 [SMILES: COc1ccccc1-n1cc(-c2cccc(N)c2C)c2cc(C#N)ccc21] | ¹H NMR (400 MHz, METHANOL-d₄) δ ppm 7.73 (d, 1H), 7.44-7.53 (m, 1H), 7.40 (m, 2H), 7.35 (s, 1H), 7.19-7.29 (m, 2H), 7.12 (d, 1H), 7.00-7.08 (m, 1H), 6.79 (m, 2H), 3.79 (s, 3H), 2.11 (s, 3H).<br>LC-MS: [M + H]⁺ = 354.1. |
| 41 | 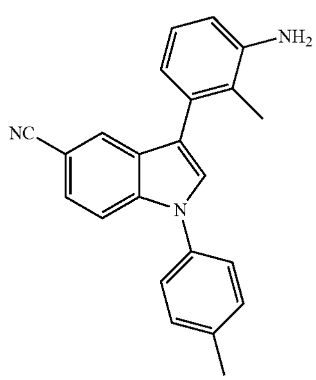 [SMILES: Cc1ccc(-n2cc(-c3cccc(N)c3C)c3cc(C#N)ccc32)cc1] | ¹H NMR (400 MHz, METHANOL-d₄) δ ppm 7.73 (d, 1H), 7.58 (d, 1H), 7.32-7.50 (m, 6H), 7.00-7.10 (m, 1H), 6.82 (d, 1H), 6.75 (d, 1H), 2.43 (s, 3H), 2.09 (s, 3H).<br>LC-MS: [M + H]⁺ = 338.1. |

TABLE 1-continued

| Ex # | Structure | ¹H NMR and LC-MS Data |
|---|---|---|
| 42 | 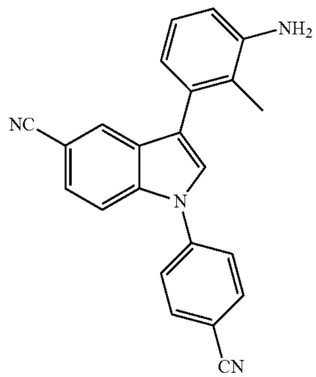 [SMILES: Cc1c(N)cccc1-c1cn(-c2ccc(C#N)cc2)c2ccc(C#N)cc12] | ¹H NMR (400 MHz, DMSO-d$_6$) δ ppm 8.11 (d, 2H), 7.98 (s, 1H), 7.94 (d, 2H), 7.86 (d, 1H), 7.81 (d, 2H), 7.65 (dd, 1H), 6.70 (d, 1H), 6.63 (d, 1H), 4.9 (s, 2H), 2.01 (s, 3H). LC-MS: [M + H]$^+$ = 349.1. |
| 43 | 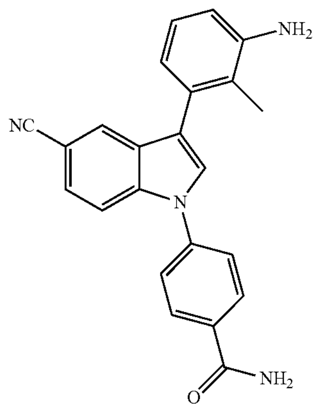 [SMILES: Cc1c(N)cccc1-c1cn(-c2ccc(C(N)=O)cc2)c2ccc(C#N)cc12] | ¹H NMR (400 MHz, METHANOL-d$_4$) δ ppm 8.10 (d, 2H), 7.67-7.82 (m, 4H), 7.63 (s, 1H), 7.46-7.56 (m, 1H), 6.99-7.10 (m, 1H), 6.71-6.87 (m, 2H), 2.09 (s, 3H). LC-MS: [M + H]$^+$ = 367.0. |
| 44 | 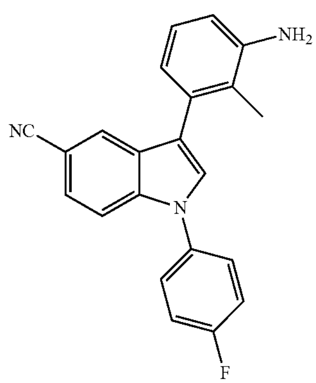 [SMILES: Cc1c(N)cccc1-c1cn(-c2ccc(F)cc2)c2ccc(C#N)cc12] | ¹H NMR (400 MHz, METHANOL-d$_4$) δ ppm 7.72 (d, 1H), 7.52-7.61 (m, 3H), 7.41-7.51 (m, 2H), 7.27-7.36 (m, 2H), 7.00-7.10 (m, 1H), 6.82 (d, 1H), 6.74 (d, 1H), 2.08 (s, 3H). LC-MS: [M + H]$^+$ = 341.9. |
| 45 | 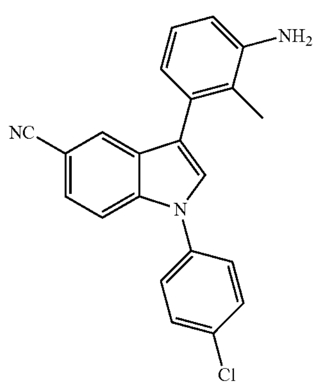 [SMILES: Cc1c(N)cccc1-c1cn(-c2ccc(Cl)cc2)c2ccc(C#N)cc12] | ¹H NMR (400 MHz, METHANOL-d$_4$) δ ppm 7.77 (s, 1H), 7.69 (d, 1H), 7.60-7.65 (m, 5H), 7.53 (d, 1H), 7.09 (br m, 1H), 6.86 (d, 1H), 6.81 (d, 1H), 2.12 (s, 3H). LC-MS: [M + H]$^+$ = 357.8. |

TABLE 1-continued

| Ex # | Structure | ¹H NMR and LC-MS Data |
|---|---|---|
| 46 | 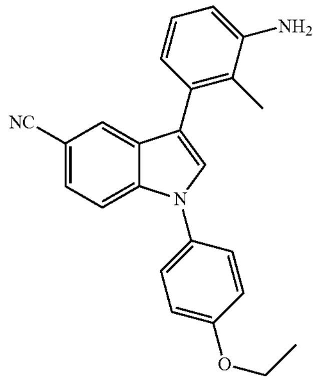 [SMILES: CCOc1ccc(-n2cc(-c3cccc(N)c3C)c3cc(C#N)ccc32)cc1] | ¹H NMR (400 MHz, DMSO-d$_6$) δ ppm 7.82 (s, 1H), 7.79 (s, 1H), 7.64-7.54 (m, 4H), 7.15 (d, 2H), 7.00 (t, 1H), 6.70 (d, 1H), 6.65 (d, 1H), 4.96 (s, 2H), 4.13 (q, 2H), 2.04 (s, 3H), 1.38 (t, 3H).<br>LC-MS: [M + H]$^+$ = 368.3. |
| 47 | 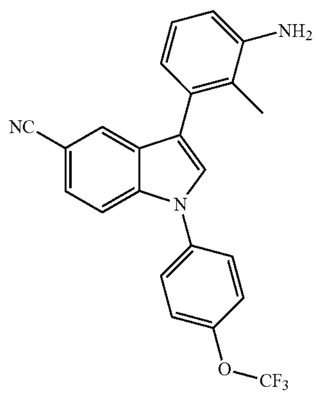 [SMILES: Cc1c(N)cccc1-c1cn(-c2ccc(OC(F)(F)F)cc2)c2ccc(C#N)cc12] | ¹H NMR (400 MHz, DMSO-d$_6$) δ ppm 7.92 (s, 1H), 7.88-7.82 (m, 3H), 7.76 (d, 1H), 7.62 (dd, 3H), 7.01 (t, 1H), 6.71 (d, 1H), 6.65 (d, 1H), 4.98 (s, 2H), 2.04 (s, 3H).<br>LC-MS: [M + H]$^+$ = 408.2. |
| 50 | 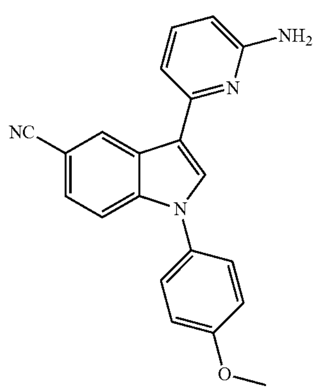 [SMILES: COc1ccc(-n2cc(-c3cccc(N)n3)c3cc(C#N)ccc32)cc1] | ¹H NMR (400 MHz, METHANOL-d$_4$) δ : 8.81 (s, 1H), 7.98 (s, 1H), 7.31-7.61 (m, 5H), 7.12 (d, 2H), 7.06 (d, 1H), 6.49 (d, 1H), 3.88 (s, 3H).<br>LC-MS: [M + H]$^+$ = 341.1. |
| 51 | 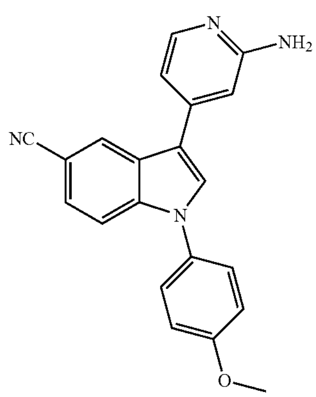 [SMILES: COc1ccc(-n2cc(-c3ccnc(N)c3)c3cc(C#N)ccc32)cc1] | ¹H NMR (400 MHz, METHANOL-d$_4$) δ ppm 8.42 (s, 1H), 8.00 (s, 1H), 7.89-7.97 (m, 1H), 7.42-7.62 (m, 4H), 7.16 (d, 2H), 6.94-7.07 (m, 2H), 3.90 (s, 3H).<br>LC-MS: [M + H]$^+$ = 341.1. |

| Ex # | Structure | ¹H NMR and LC-MS Data |
|---|---|---|
| 52 | 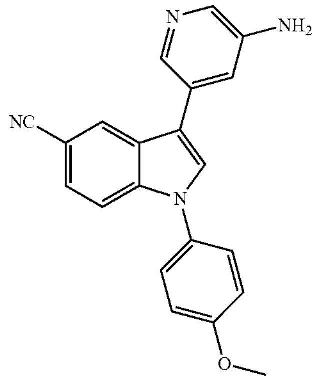 [SMILES: COc1ccc(-n2cc(-c3cncc(N)c3)c3cc(C#N)ccc32)cc1] | ¹H NMR (400 MHz, DMSO-d₆) δ ppm 8.39 (s, 1H), 8.17 (d, 2H), 7.91 (d, 1H), 7.61 (d, 4H), 7.38 (t, 1H), 7.18 (d, 2H), 5.41 (s, 2H), 3.86 (s, 3H).<br>LC-MS: [M + H]⁺ = 341.2. |
| 53 | 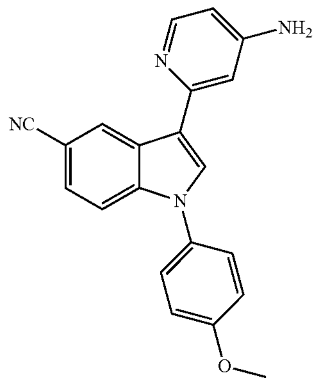 [SMILES: COc1ccc(-n2cc(-c3cc(N)ccn3)c3cc(C#N)ccc32)cc1] | ¹H NMR (400 MHz, DMSO-d₆) δ ppm 8.95 (s, 1H), 8.23 (s, 1H), 8.13 (d, 1H), 7.72-7.43 (m, 4H), 7.24-7.11 (m, 2H), 7.06 (d, 1H), 6.42 (dd, 1H), 5.99 (s, 2H), 3.86 (s, 3H).<br>LC-MS: [M + H]⁺ = 341.2. |
| 54 | 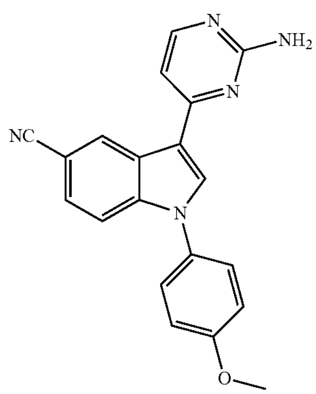 [SMILES: COc1ccc(-n2cc(-c3ccnc(N)n3)c3cc(C#N)ccc32)cc1] | ¹H NMR (400 MHz, DMSO-d₆) δ ppm 9.27 (d, 1H), 8.67 (s, 1H), 8.18 (d, 1H), 7.57-7.67 (m, 4H), 6.97-7.26 (m, 3H), 6.70 (br s, 2H), 3.85 (s, 3H).<br>LC-MS: [M + H]⁺ = 342.1. |
| 57 | 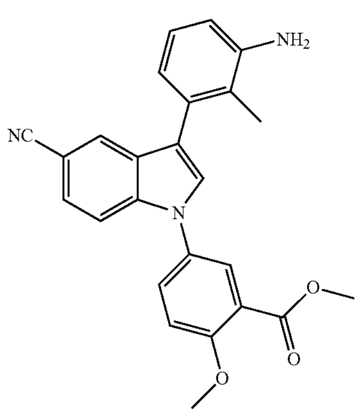 [SMILES: COC(=O)c1cc(-n2cc(-c3cccc(N)c3C)c3cc(C#N)ccc32)ccc1OC] | ¹H NMR (400 MHz, CD₃OD) δ ppm 7.92 (s, 1H), 7.88 (dt, 2H), 7.83 (s, 1H), 7.66-7.58 (m, 2H), 7.41 (d, 1H), 7.19 (t, 1H), 7.01 (d, 2H), 3.93 (s, 3H), 3.83 (s, 3H), 3.55 (s, 2H), 2.15 (s, 3H).<br>LC-MS: [M + H]⁺ = 412.3. |

TABLE 1-continued

| Ex # | Structure | ¹H NMR and LC-MS Data |
|---|---|---|
| 58 | 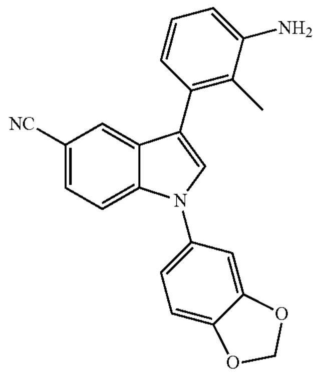 [SMILES: Cc1c(N)cccc1-c1cn(-c2ccc3c(c2)OCO3)c2ccc(C#N)cc12] | ¹H NMR (400 MHz, METHANOL-d$_4$) δ ppm 7.74 (s, 1H), 7.60 (d, 1H), 7.43-7.52 (m, 2H), 6.95-7.15 (m, 4H), 6.79 (m, 2H), 6.08 (s, 2H), 2.10 (s, 3H). LC-MS: [M + H]$^+$ = 367.8. |
| 59 | 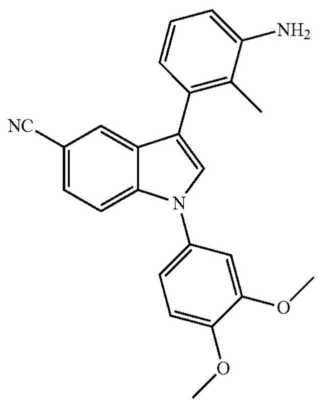 [SMILES: COc1ccc(-n2cc(-c3cccc(N)c3C)c3cc(C#N)ccc32)cc1OC] | ¹H NMR (400 MHz, METHANOL-d$_4$) δ ppm 7.73 (d, 1H), 7.59 (d, 1H), 7.50 (s, 1H), 7.45 (m, 1H), 6.95-7.19 (m, 4H), 6.82 (d, 1H), 6.76 (d, 1H), 3.89 (d, 6H), 3.91 (s, 3H), 3.88 (s, 3H), 2.01 (s, 3H). LC-MS: [M + H]$^+$ = 383.9. |
| 60 | 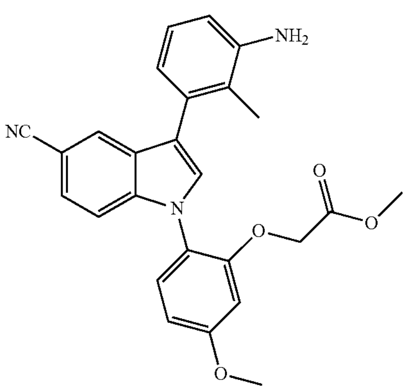 [SMILES: COC(=O)COc1cc(OC)ccc1-n1cc(-c2cccc(N)c2C)c2cc(C#N)ccc21] | ¹H NMR (400 MHz, DMSO-d$_6$) δ ppm 7.82 (s, 1H), 7.72 (s, 1H), 7.54 (dd, 1H), 7.48 (d, 1H), 7.39 (d, 1H), 7.21 (t, 1H), 7.06 (dd, 2H), 6.82 (d, 1H), 6.77 (dd, 1H), 4.92 (s, 2H), 3.85 (s, 3H), 3.67 (s, 3H), 3.43 (s, 2H), 2.18 (s, 3H). LC-MS: [M + H]$^+$ = 442.3. |
| 61 | 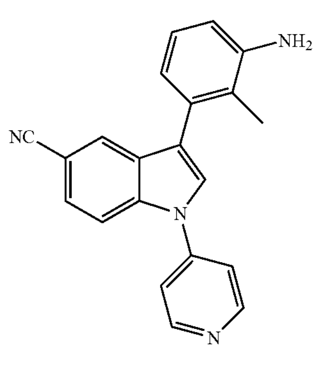 [SMILES: Cc1c(N)cccc1-c1cn(-c2ccncc2)c2ccc(C#N)cc12] | ¹H NMR (400 MHz, DMSO-d$_6$) δ ppm 8.70-8.82 (m, 2H), 7.91-8.06 (m, 2H), 7.73-7.86 (m, 3H), 7.66 (m, 1H), 6.95-7.05 (m, 1H), 6.71 (d, 1H), 6.63 (d, 1H), 4.96 (s, 2H), 2.01 (s, 3H). LC-MS: [M + H]$^+$ = 325.1. |

TABLE 1-continued

| Ex # | Structure | ¹H NMR and LC-MS Data |
|---|---|---|
| 63 | 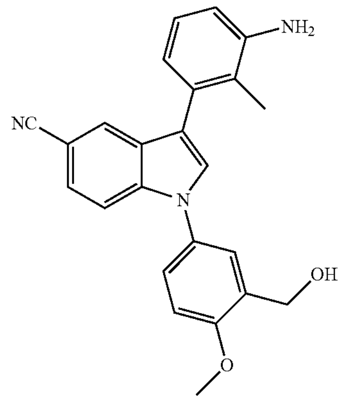 [SMILES: COc1ccc(-n2cc(-c3cccc(N)c3C)c3cc(C#N)ccc32)cc1CO] | ¹H NMR (400 MHz, DMSO-d₆) δ ppm 7.86 (s, 1H), 7.83 (s, 1H), 7.68-7.57 (m, 3H), 7.52 (dd, 1H), 7.24-7.16 (m, 2H), 7.09-6.98 (m, 2H), 4.60 (s, 2H), 3.88 (s, 3H), 3.64 (s, 2H), 2.16 (s, 3H). <br> LC-MS: [M + H]⁺ = 384.3. |
| 66 | 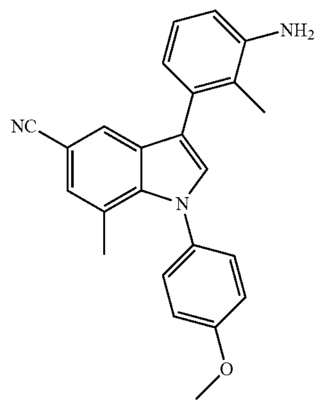 [SMILES: COc1ccc(-n2cc(-c3cccc(N)c3C)c3cc(C#N)cc(C)c32)cc1] | ¹H NMR (400 MHz, METHANOL-d₄) δ ppm 7.58 (d, 1H), 7.40 (d, 2H), 7.25 (s, 1H), 7.18 (s, 1H), 6.98-7.11 (m, 3H), 6.70-6.87 (m, 1H), 6.70-6.87 (m, 1H), 3.89 (s, 3H), 2.07 (d, 6H). <br> LC-MS: [M + H]⁺ = 367.9. |
| 67 | 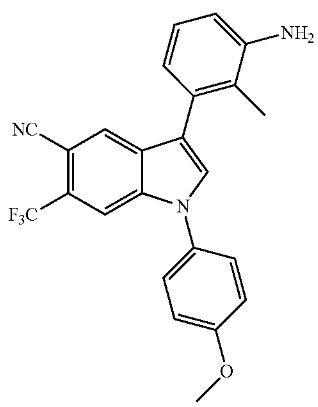 [SMILES: COc1ccc(-n2cc(-c3cccc(N)c3C)c3cc(C#N)c(C(F)(F)F)cc32)cc1] | ¹H NMR (400 MHz, METHANOL-d₄) δ ppm 7.99 (s, 1H), 7.83 (s, 1H), 7.72-7.78 (m, 1H), 7.43-7.60 (m, 2H), 7.19 (d, 2H), 7.09 (s, 1H), 6.81 (s, 1H), 6.71-6.90 (m, 1H), 3.91 (s, 3H), 2.12 (s, 3H). <br> LC-MS: [M + H]⁺ = 421.8. |
| 68 | 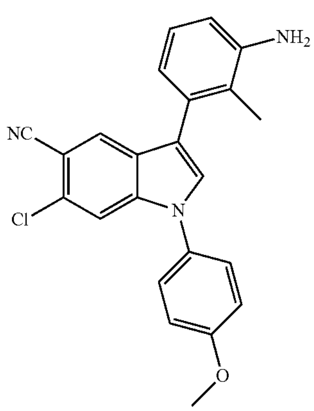 [SMILES: COc1ccc(-n2cc(-c3cccc(N)c3C)c3cc(C#N)c(Cl)cc32)cc1] | ¹H NMR (400 MHz, METHANOL-d₄) δ ppm 7.79 (s, 1H), 7.58 (s, 1H), 7.44-7.53 (m, 3H), 7.15 (d, 2H), 7.07 (m, 1H), 6.84 (s, 1H), 6.73-6.80 (m, 1H), 3.90 (s, 3H), 2.10 (s, 3H). <br> LC-MS: [M + H]⁺ = 387.8. |

TABLE 1-continued

| Ex # | Structure | ¹H NMR and LC-MS Data |
|---|---|---|
| 73 | 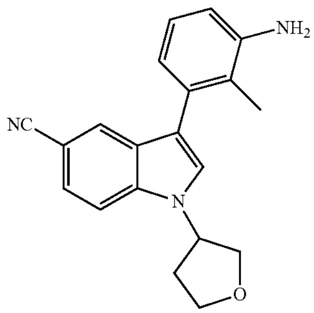 [SMILES: Cc1c(N)cccc1-c1cn(C2CCOC2)c2ccc(C#N)cc12] | ¹H NMR (400 MHz, DMSO-d₆) δ ppm 7.84 (d, 1H), 7.73 (d, 1H), 7.60-7.40 (m, 2H), 6.97 (t, 1H), 6.67 (d, 1H), 6.59-6.45 (m, 1H), 5.44-5.38 (m, 1H), 4.92 (s, 2H), 4.16-4.05 (m, 1H), 4.04-3.91 (m, 2H), 3.88-3.82(m, 1H), 2.64-2.53 (m, 1H), 2.24-2.16 (m, 1H), 1.97 (s, 3H). LC-MS: [M + H]⁺ = 318.2. |
| 78 | trans | ¹H NMR (400 MHz, DMSO-d₆) δ ppm 7.70 (s, 1H), 7.63 (s, 1H), 7.58 (s, 1H), 6.95 (t, 1H), 6.64 (d, 1H), 6.54 (d, 1H), 4.88 (s, 2H), 4.45 (t, 1H), 3.33 (s, 1H), 2.57 (s, 3H), 2.41 (t, 1H), 2.32 (s, 3H), 2.06-1.94 (m, 7H), 1.93-1.80 (m, 2H), 1.29 (dd, 2H). LC-MS: [M + H]⁺ = 373.1. |
| 79 | cis | ¹H NMR (400 MHz, MeOD) δ ppm 7.69 (s, 1H), 7.63 (s, 1H), 7.58 (s, 1H), 6.95 (t, 1H), 6.65 (d, 1H), 6.55 (d, 1H), 4.89 (s, 2H), 4.45 (t, 1H), 3.33 (s, 1H), 2.70 (s, 1H), 2.58 (s, 3H), 2.31 (s, 3H), 2.17-2.04 (m, 2H), 1.98 (s, 3H), 1.89 (d, 2H), 1.68 (dd, 4H). LC-MS: [M + H]⁺ = 373.1. |
| 94 | Trans | ¹H NMR (400 MHz, DMSO-d₆) δ ppm 7.92 (s, 1H), 7.74 (d, 2H), 7.69 (d, 2H), 5.16 (s, 2H), 4.73 (d, 1H), 4.57-4.36 (m, 1H), 3.60-3.53 (m, 1H), 2.59 (s, 3H), 1.99 (s, 3H), 1.98-1.78 (m, 6H), 1.61-1.36 (m, 2H). LC-MS: [M + H]⁺ = 361.3. |

TABLE 1-continued

| Ex # | Structure | ¹H NMR and LC-MS Data |
|------|-----------|------------------------|
| 99 | 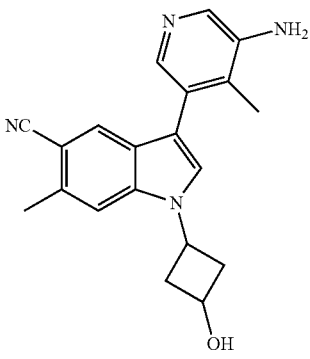<br>Cis | ¹H NMR (400 MHz, DMSO-d$_6$) δ ppm 7.94 (s, 1H), 7.75 (d, 2H), 7.69 (s, 1H), 7.62 (s, 1H), 5.33 (d, 1H), 5.19 (s, 2H), 4.64-4.52 (m, 1H), 4.04 (dd, 1H), 2.93 (dt, 2H), 2.58 (s, 3H), 2.32 (ddd, 2H), 2.01 (s, 3H).<br>LC-MS: [M + H]$^+$ = 333.1. |
| 101 | 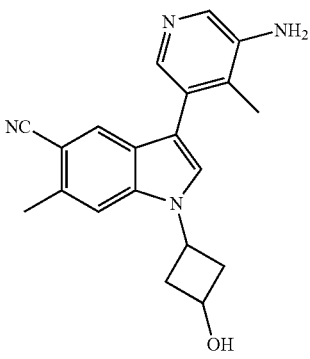<br>Trans | ¹H NMR (400 MHz, DMSO-d$_6$) δ ppm 7.94 (s, 1H), 7.82 (s, 1H), 7.75 (s, 1H), 7.69 (s, 1H), 7.59 (s, 1H), 5.33 (d, 1H), 5.23 (t, 1H), 5.18 (s, 2H), 4.46 (dd, 1H), 2.75-2.65 (m, 2H), 2.58 (s, 3H), 2.47 (d, 2H), 2.01 (s, 3H). ).<br>LC-MS: [M + H]$^+$ = 333.1. |

Example 80

Trans-3-(3-amino-2-methylphenyl)-1-(3-hydroxycyclopentyl)-1H-indole-5-carbonitrile Intermediate 80.1:
3-((tert-butyldimethylsilyl)oxy)cyclopentan-1-ol

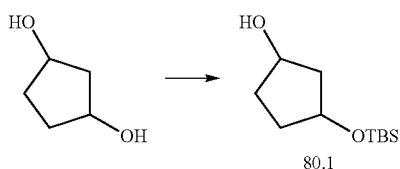 [SMILES: OC1CCC(O)C1 ; CC(C)(C)[Si](C)(C)OC1CCC(O)C1]

At 0° C., to a stirred solution of cyclopentane-1,3-diol (200 mg, 1.958 mmol) and imidazole (132 mg, 1.942 mmol) in DCM (5 mL) was added TBS-Cl (207 mg, 1.371 mmol) in several portions. Some white solid precipitated. The reaction mixture was was stirred at rt overnight. Then the mixture was washed with 10% HCl aq. and brine for twice. The organic layer was dried over anhydrous Na$_2$SO$_4$, filtered and concentrated to give a crude product which was purified by flash column chromatography on silica gel (eluent: PE/EA, EA %=0~5%~7%) to give the title compound (70 mg, 24%) as a colorless oil. ¹H NMR (300 MHz, CDCl$_3$) δ ppm 4.56-4.27 (m, 2H), 2.19-1.91 (m, 2H), 1.89-1.76 (m, 2H), 1.59-1.50 (m, 2H), 0.87 (s, 9H), 0.04 (s, 6H). LC-MS: [M+H]$^+$=217.4.

Intermediate 80.2:
3-((tert-butyldimethylsilyl)oxy)cyclopentyl 4-methylbenzenesulfonate

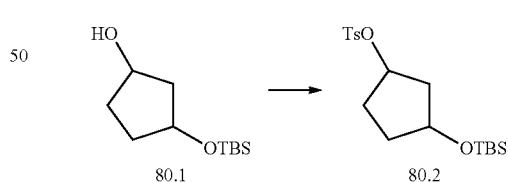

At 0° C., to a solution of compound 80.1 (230 mg, 1.063 mmol) and DMAP (156 mg, 1.276 mmol) in DCM (5 mL) was add Ts-Cl (223 mg, 1.169 mmol) portionwise. After addition, the reaction mixture was stirred at rt overnight. The mixture was washed with water and the organic phase was dried over anhydrous Na$_2$SO$_4$, filtered and concentrated to give crude title compound (528 mg) as light yellow oil. LC-MS: [M+H]$^+$=371.3.

Intermediate 80.3: 3-bromo-1-(3-((tert-butyldimethylsilyl)oxy)cyclopentyl)-1H-indole-5-carbonitrile

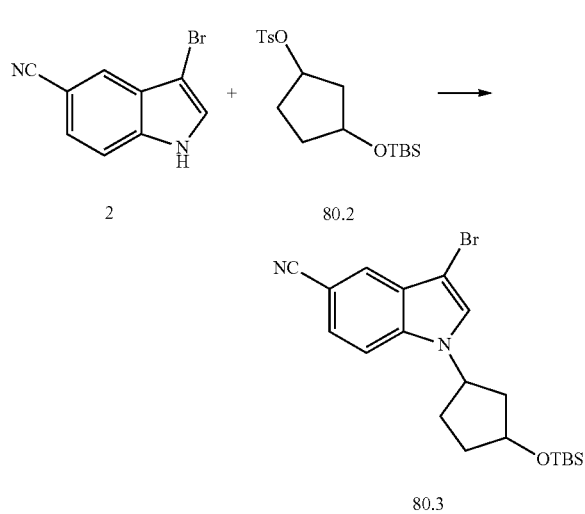

The mixture of compound 80.2 (528 mg crude, 1.063 mmol), compound 2 (235 mg, 1.063 mmol) and Cs$_2$CO$_3$ (519 mg, 1.595 mmol) in DMF (5 mL) was heated to 90° C. for 1 h. Then the mixture was diluted with water and extracted with EA for three times. The combined organic phase was washed with brine and dried over Na$_2$SO$_4$, filtered and concentrated to give a crude product which was purified by flash column chromatography on silica gel (eluent: PE/EA, EA %=5%~7%~9%) to give the title compound (127 mg, 29%) as a colorless oil. $^1$H NMR (300 MHz, CDCl$_3$) δ ppm 7.90 (s, 1H), 7.72 (s, 1H), 7.51-7.42 (m, 2H), 4.98-4.78 (m, 1H), 4.45 (m, 1H), 2.45 (m, 1H), 2.35-2.23 (m, 1H), 2.16-2.06 (m, 1H), 1.96-1.79 (m, 3H), 0.95 (s, 9H), 0.10 (d, 6H). LC-MS: [M+H]$^+$=419.2.

Intermediate 80.4: Trans-3-(3-amino-2-methylphenyl)-1-(3-((tert-butyldimethylsilyl)oxy)cyclopentyl)-1H-indole-5-carbonitrile

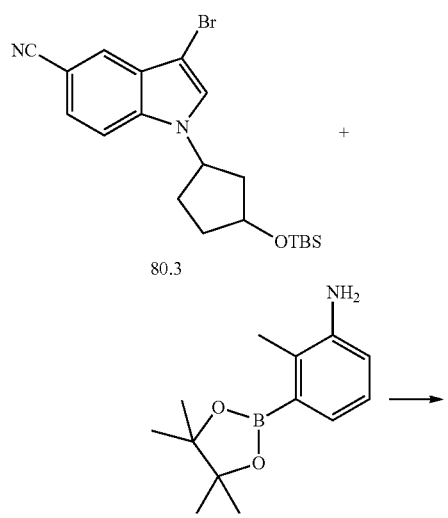

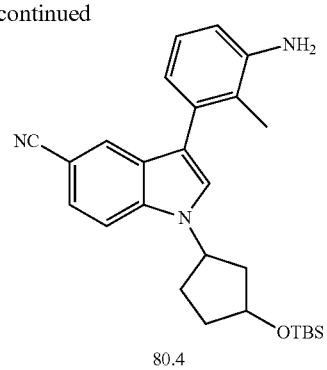

To a mixture of compound 80.3 (100 mg, 0.238 mmol) and 2-methyl-3-(4,4,5,5-tetramethyl-1,3,2-dioxaborolan-2-yl)aniline (83 mg, 0.358 mmol) in the co-solvent of i-PrOH/H$_2$O (4 mL, 10:1) was added 2 N Na$_2$CO$_3$ aq. (0.48 mL, 0.952 mmol) and Pd(PPh$_3$)$_2$Cl$_2$ (17 mg, 0.024 mmol). The mixture was stirred at 100° C. for 30 min under N$_2$ atmosphere by microwave. Then the mixture was diluted with water and extracted with EA for three times. The combined organic phase was washed with brine and dried over anhydrous Na$_2$SO$_4$, filtered and concentrated to give a crude product which was purified by prep-TLC (eluent: PE/EA=2:1) to give the title compound (70 mg, 60%) as a brown oil. $^1$H NMR (300 MHz, CDCl$_3$) δ ppm 7.80 (s, 1H), 7.56 (d, 1H), 7.52 (s, 1H), 7.42 (d, 1H), 7.10 (t, 1H), 6.79 (t, 2H), 5.01-4.78 (m, 1H), 4.46 (s, 1H), 2.63-2.47 (m, 1H), 2.27 (m, 2H), 2.10 (s, 3H), 2.05-1.99 (m, 1H), 1.92-1.83 (m, 2H), 0.89 (s, 9H), 0.09 (d, 6H). LC-MS: [M+H]$^+$=446.4.

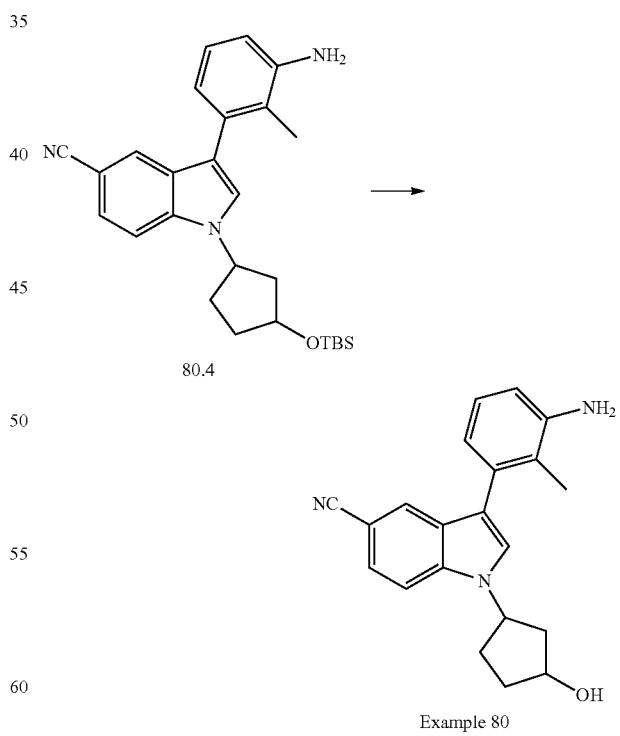

Example 80

The mixture of compound 80.4 (55 mg, 0.113 mmol) in the co-solvent of 1 N HCl (1.5 mL) and dioxane (1.5 mL) was heated to 100° C. for 1 h. Then the mixture was based with NH$_3$.H$_2$O to pH=8~9. It was extracted with EA for 3 times. The combined organic phase was washed with brine and dried over Na$_2$SO$_4$, concentrated to give a residue which was purified by prep-HPLC (0.1% NH$_3$.H$_2$O/ACN/H$_2$O) and lyophilized to give the title compound (12 mg, 29%) as a white solid. $^1$H NMR (400 MHz, DMSO-d$_6$) δ ppm 7.84 (d, 1H), 7.77 (s, 1H), 7.72 (d, 1H), 7.51 (dd, 1H), 6.97 (t, 1H), 6.67 (d, 1H), 6.57 (dd, 1H), 5.16-5.04 (m, 1H), 4.95 (d, 1H), 4.91 (s, 2H), 4.31 (m, 1H), 2.47 (m, 1H), 2.22 (m, 1H), 2.13-2.03 (m, 1H), 1.98 (s, 3H), 1.87 (m, 1H), 1.81 (m, 2H). LC-MS: [M+H]$^+$=332.2.

Examples 81 & 82

The title compounds are two enantiomers which are obtained by chiral separation of Example 80. The absolute stereo was not determined.
Chiral separation: UV visualization at 254 nm
  Column: AD-H, 30×150 mm 4.6 μm
  Flow rate: 3.0 mL/min
  Pressure: 100 bar
  Solvent A: MeOH
  Modifer: 25%

Example 81

$^1$H NMR (400 MHz, DMSO-d$_6$) δ ppm 7.82 (d, 1H), 7.74 (s, 1H), 7.70 (d, 1H), 7.49 (m, 1H), 6.95 (m, 1H), 6.66 (d, 1H), 6.56 (m, 1H), 4.99-5.16 (m, 1H), 4.83-4.95 (m, 3H), 4.29 (d, 1H), 2.42-2.48 (m, 1H), 2.20 (m, 1H), 2.00-2.13 (m, 1H), 1.97 (s, 3H), 1.72-1.90 (m, 3H). LC-MS: [M+H]$^+$=332.2.

Example 82

$^1$H NMR (400 MHz, DMSO-d$_6$) δ ppm 7.82 (d, 1H), 7.74 (s, 1H), 7.70 (d, 1H), 7.49 (m, 1H), 6.95 (m, 1H), 6.66 (d, 1H), 6.56 (m, 1H), 4.99-5.16 (m, 1H), 4.83-4.95 (m, 3H), 4.29 (d, 1H), 2.42-2.48 (m, 1H), 2.20 (m, 1H), 2.00-2.13 (m, 1H), 1.97 (s, 3H), 1.72-1.90 (m, 3H). LC-MS: [M+H]$^+$=332.2.

The following compounds, as identified in Table 2, were prepared using the general procedures as well as the procedures from the examples described as Example 80 with the appropriate starting materials and reagents. The product was purified by prep-HPLC (0.1% NH$_3$.H$_2$O/ACN/H$_2$O) to give below two isomers.

TABLE 2

| Ex # | Structure | $^1$H NMR (400 MHz, DMSO-d$_6$) and LC-MS Data |
|---|---|---|
| 83 | 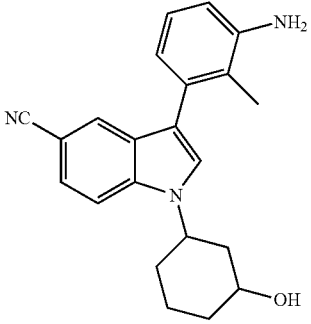<br>Trans | δ ppm 7.67 (d, 2H), 7.50-7.35 (m, 2H), 7.04 (t, 1H), 6.81 (d, 1H), 6.71 (d, 1H), 4.86-4.82 (m, 1H), 4.35-4.17 (m, 1H), 2.21-2.14 (m, 1H), 2.13-2.08 (m, 1H), 2.07-1.96 (m, 5H), 1.91-1.80 (m, 2H), 1.78-1.70 (m, 1H), 1.67-1.55 (t, 1H).<br>LC-MS: [M + H]$^+$ = 387.3. |
| 84 | 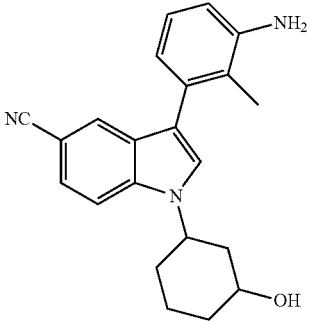<br>Cis | δ ppm 7.72-7.64 (m, 2H), 7.54-7.36 (m, 2H), 7.06 (t, 1H), 6.82 (d, 1H), 6.73 (d, 1H), 4.59-4.50 (m, 1H), 3.93-3.75 (m, 1H), 2.45-2.24 (m, 1H), 2.14-2.01 (m, 5H), 2.00-1.93 (m, 1H), 1.89-1.67 (m, 2H), 1.70-1.48 (m, 1H), 1.45-1.23 (m, 1H).<br>LC-MS: [M + H]$^+$ = 387.3. |

TABLE 2-continued
| Ex # | Structure | ¹H NMR (400 MHz, DMSO-$d_6$) and LC-MS Data |
|---|---|---|
| 85 | 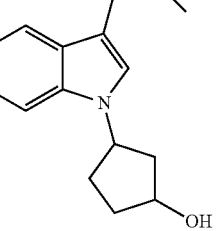 Trans | δ ppm 7.64 (d, 2H), 7.57 (s, 1H), 6.95 (t, 1H), 6.65 (d, 1H), 6.55 (d, 1H), 5.23-5.07 (m, 1H), 4.90 (s, 2H), 4.79 (d, 1H), 4.39 (m, 1H), 2.59 (s, 3H), 2.35 (m, 1H), 2.22-2.06 (m, 3H), 1.97 (s, 3H), 1.85 (m, 1H), 1.73-1.58 (m, 1H). LC-MS: [M + H]⁺ = 346.3. |
| 86 | 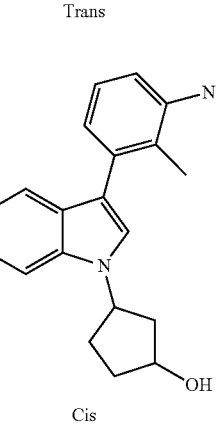 Cis | δ ppm 7.71 (s, 1H), 7.67 (s, 1H), 7.64 (s, 1H), 6.96 (t, 1H), 6.66 (d, 1H), 6.56 (d, 1H), 5.10-4.99 (m, 1H), 4.94 (d, 1H), 4.90 (s, 2H), 4.35-4.25 (m, 1H), 2.58 (s, 3H), 2.46 (dd, 1H), 2.27-2.15 (m, 1H), 2.11-2.02 (m, 1H), 1.98 (s, 3H), 1.85 (m, 1H), 1.80 (m, 2H). LC-MS: [M + H]⁺ = 346.3. |
| 87 | 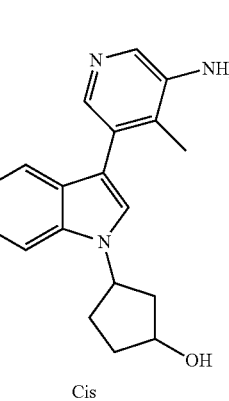 Cis | δ ppm 7.94 (s, 1H), 7.77 (s, 1H), 7.74 (d, 2H), 7.70 (s, 1H), 5.17 (s, 2H), 5.09-4.99 (m, 1H), 4.95 (d, 1H), 4.30 (dq, 1H), 2.58 (s, 3H), 2.46 (dd, 1H), 2.21 (td, 1H), 2.11-2.05 (m, 1H), 2.01 (s, 3H), 1.90-1.76 (m, 3H). LC-MS: [M + H]⁺ = 347.3. |
| 88 | 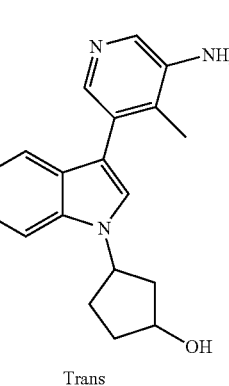 Trans | δ ppm 7.93 (s, 1H), 7.74 (s, 1H), 7.70 (s, 1H), 7.69 (s, 1H), 7.68 (s, 1H), 5.25-5.06 (m, 3H), 4.79 (d, 1H), 4.40 (m, 1H), 2.59 (s, 3H), 2.36 (m, 1H), 2.21-2.08 (m, 3H), 2.00 (s, 3H), 1.92-1.79 (m, 1H), 1.74-1.60 (m, 1H). LC-MS: [M + H]⁺ = 347.3. |

VI. Pharmacology and Utility

As a histone demethylase, LSD1 can directly binds to its substrates (e.g. methylated histones H3K4) and repress/promote corresponding gene transcription. Therefore, targeting LSD1 represents a highly attractive strategy for the development of a novel therapy for the treatment of many forms of cancers. In particular, the need exists for small molecules that inhibit the activity of LSD1.1t has now been found that LSD1 inhibitors as presently disclosed are useful to target LSD1 for the treatment of LSD1-mediated diseases or disorders, especially cancers.

The utility of the compounds of the present invention may be demonstrated using any one of the following test procedures. Compounds of the present invention were assessed for their ability to inhibit LSD1 activity to demethylate mono-methylated histone H3 lysine4 in presence of FAD in biochemical assays. The ability of compounds of the present invention to inhibit cellular activity of LSD1 was assessed by analyzing the expression level of genes that regulated by LSD1's demethylase activity (e.g. CD11b), or region specific histone H3 lysine 4 methylation in human cell lines. The ability of compounds of the present invention to inhibit cancers was derived from their ability to modulate activity in human cancer cell lines bearing specific dependence to LSD1 activity to maintain cancerous growth or maintain stem cell like phenotype (e.g. less differentiated).

FL-LSD1 LC-MS Assay

Representative compounds of the present invention were serially and separately diluted 3-fold in DMSO to obtain a total of twelve concentrations. Then the test compounds at each concentration (100 nL of each) were transferred into a 384-well Perkin Elmer ProxiPlate 384 plus plates by Mosquito™ Solutions (5 μL) of 0.8 nM, the full-length LSD1 and 0.5 μM FAD in reaction buffer (40 mM Tris-HCl, 0.01% Triton-X100, 10 mM KCl, 1 mM DTT) were added into the wells and then incubated with the test compound for 30 min. A 5 μL solution of 1 μM of the peptide substrate H3K4me1 (histone H3[1-21]-biotin) in reaction buffer was added to each initiate reaction. The final components in the reaction solution include 0.4 nM FL-LSD1, 0.25 μM FAD, and 0.5 μM H3K4me1 peptide with varying concentration of the compounds. A positive control consisted of the enzyme, 0.25 μM FAD and 0.5 μM substrate in the absence of the test compound, and a negative control consisted of 0.5 μM substrate only. Each reaction was incubated at room temperature for 60 min, and then stopped by the addition of 3 μL quench solution (2.5% TFA with 320 nM d4-SAH). The reaction mixture was centrifuged (Eppendorf centrifuge 5810, Rotor A-4-62) for 1 min at 2000 rpm and read on an API 4000 triple quadrupole mass spec with Turbulon Spray (Applied Biosystem) coupled with Prominence UFLC (Shimadzu). The conversion ratio of H3K4me1 substrate to the H3K4me0 product was calculated by dividing the peak area of the H3K4me0 peptide by the total peak area of all those two peptides on the assumption that the ionization efficiency of those peptides is the same. The data were then fit to a dose response equation using the program Helios to get the IC50 values of the test compound.

CD11b FACS Assay

Representative compounds of the present invention were serially and separately diluted 5-fold in DMSO to obtain a total of 6 concentrations. Then the compounds were added to Thp1 cell cultured in 96-well round bottom plate (Costar, Cat#3099) at 1:1000 dilution to obtain the highest concentration of 10 μM. The cells were further cultured for 96 hrs before FACS procedure.

FACS protocol: FACS was performed using standard flowcytometry. Cell was collected and washed with FACS buffer twice (2% heat inactivated FBS in PBS) in 96-well plate, and stained with antibody against CD11b, or isotype control, then washed with FACS buffer for 3 times before reading on Guava 8HT (Merck Millipore) Results were analyzed using Flowjo, and mean fluoreance was calculated and normalized to the cells treated with DMSO. The fold value were then analyzed via Graphpad Prism and fit to a dose response curve to get IC50 value of the test compound. Antibodies for FACS: PE mouse IgG1 k chain (BD Bioscience, #555749), PE mouse anti human CD11b (BD Bioscience, #555388)

CD11b qPCR Assay

Representative compounds of the present invention were serially and separately diluted 5-fold in DMSO to obtain a total of 6 concentrations. Then the compounds were added to Molm13 cell cultured in 24-well plate at 1:1000 dilution to obtain the highest concentration of 10 μM. The cells were further cultured overnight before RNA was collected for qPCR assay RNA was extracted using the RNeasy Mini Kit (Qiagen). RNA quality was confirmed with Nanodrop. Real-time RT-PCR analysis was performed on an ABI Prism 7900 Sequence Detection System using the SYBR Green PCR Master Mix (Applied Biosystems, Foster City, USA). The relative expression of CD11b was detected using sequence specific primers and normalized against Actin. The CD11b expression in compound treated cells were then normalized to ratio to DMSO treated cell. The increase of CD11b mRNA level after treatment of representative compounds of present invention will reflect the inhibition of LSD1 activity. qPCR primer sequence as following: For CD11b Forward primer TGATGCTGTTCTCTACGGGG; Reverse primer AGAGAGCTTGGAGCCTGCTA; For Actin, Forward primer GATCATTGCTCCTCCTGAGC; Reverse primer: ACTCCTGCTTGCTGATCCAC

Target Region ChIP-qPCR Assay

Molm13 cells were treated with representative compounds overnight. Cells were then treated with fresh culture medium containing 1% formaldehyde for 10 min and washed twice with ice-cold PBS containing protease inhibitors. Cell pellets were resuspended in SDS lysis buffer also containing protease inhibitors (200 μL lysis buffer for every 1×106 cells) and incubated on ice for 10 min. Cell lysate was sonicated (12 W for 10 sec, six times) to shear DNA to lengths between 100 and 500 bp. Subsequently, ChIP was performed according to the ChIP assay kit (Millipore, #17-295) instructions using antibodies against H3k4Me1 (Abcam, #ab8895) H3K4Me2(Millipore, #05-790), H3K4Me2 and total H3(Cell signaling, #2650). Eluted DNA was used for qPCR. For ChIP-qPCR analysis, the relative binding level of each gene with histone methylation was normalized against binding level with total H3. The relative binding level of H3K4Me1 to promoter region of CD11b/LILRA5 after compound treatment was normalized to ratio to cell treated with DMSO. The inhibition of LSD1 activity mediated by representative compounds will reflect on the decrease of H3K4Me1 binding level to the promoter/enhancer region of LSD1 target genes CD11b/LILRA5.

Anti-Proliferation Assay in Molm13 Cell

Acute myeloid leukemia cell Molm13 was cultured using standard cell culture conditions in RPMI-1640 (Invitrogen, cat #11875) supplemented with 10% FBS (Invitrogen, cat #10099-141) in humidified incubator at 37° C., 5% $CO_2$. To assess the effect of LSD1 inhibition on cell proliferation, exponentially growing cells were seeded at a density of 2×10³ cells/well in 96-well plate (Corning, cat #3603). After cell seeding, a compound of the present invention was added to the cell media (in concentrations ranging from 0 to 100 μM, 3× dilution series). After 6 days, 100 ul/well cell titer glow (Promega, cat#G7573) was added into the cell culture, and luminerence was read on Envision (Pelkin Elmer) to determine the viable cells. The percentage inhibition was calculated against the samples treated with DMSO. The data were then fit to a dose response curve using the program Prism to get the IC50.

Anti-Colony Formation Assay in Molm13 Cell

Molm13 cell was seeded for colony formation in 48-well plate using standard assay condition with human methycellulose base media (R&D systems, #HSC002), at density of 250 cell/well. The representative compounds of the present invention was serially diluted at 5 fold for 6 points, and added into the methycellulose media together with cells to give highest final concentration at 10 uM. Total volume of methylcellulose media in each well is 300 ul. The plates were incubated at 37 C incubator for 8 days before colony were counted. Inhibition of the colony formation at each dose was calculated by dividing the colony numbers in each compound treated well to DMSO treated well. Ratios were then input into the Graphpad prism software to generate a dose-response curve to get an IC50

Analysis of Pharmacokinetic Properties

Pharmacokinetic properties of the compounds as presently disclosed can be determined by using the below described protocol.

A representative compound of the present invention was dissolved in 10% PEG300, 10% Solutol HS 15 and 80% pH 4.65 Acetate buffer to yield a final concentration of 0.2 mg/mL for intravenous (IV) and oral administration (PO).

For rat PK studies, a total of three male Sprague Dawley rats each were used for rat IV and PO PK study, respectively. The formulation solution was administered via a single bolus IV at 1 mg/kg and a single oral gavage (PO) at 2 mg/kg, respectively. Blood samples (approximately 150 μL) were collected via jugular cannula at appropriate time points.

For mouse PK study, a total of twelve male ICR mice were used for IV and PO study, respectively. The formulation solution was administered via a single bolus IV at 1 mg/kg and a single oral gavage (PO) at 2 mg/kg, respectively. Blood samples (approximately 150 μL) were collected via retro-orbital puncture (~150 μL/mouse) after anesthetized by isoflurane or via cardiac puncture (terminal collection) at appropriate time points (n=3).

Samples were collected in tubes containing K3-EDTA and stored on ice until centrifuged. The blood samples were centrifuged at approximately 8000 rpm for 6 min at 2-8° C. and the resulting plasma was separated and stored frozen at approximately −80° C. After adding the internal standard, the plasma samples were quantified by LC-MS/MS using the calibration curve. PK parameters including area under concentration curve (AUC), mean residence time (MRT), plasma clearance (Cl), steady state volume of distribution (Vdss), elimination half-life ($t_{1/2}$), maximum concentration (Cmax), time of maximum concentration (Tmax) and oral bioavailability (F %) were calculated using the following equations:

$$AUC = \int_0^\infty C\,dt$$

$$MRT = \frac{\int_0^\infty tC\,dt}{\int_0^\infty C\,dt} = \frac{AUMC}{AUC}$$

t is time and C is plasma concentration at the time (t); $Dose_{iv}$ is the dose for intravenous administration; and $Dose_{oral}$ is the dose for oral administration.

$$Cl = Dose_{iv}/AUC$$

$$t_{1/2} = 0.693 \times MRT$$

$$Vdss = Cl \ast MRT$$

$$F\% = (Dose_{iv} \times AUC_{oral})/(Dose_{oral} \times AUC_{iv}) \times 100\%$$

Protocol for High-Throughput Equilibrium Solubility Assay

Compounds of the present invention were first solubilized at 10 mM in pure DMSO. 20 μL each of the DMSO stock solution was then transferred into 6 wells on 96-well plate. The DMSO solvent was dried with GeneVac solvent evaporator at 30° C., 1 mbar vacuum for 1 h. After the addition of 200 μL of buffer solutions (pH 6.8, or FaSSIF), the plate was sealed and shaken at 160 rpm for 24 h at rt. The plate was centrifuged at 3750 rpm for 20 min, 5 μL of supernatant is mixed with 495 μL of MeOH/H₂O (1:1). 0.01 μM, 0.1 μM, 1 μM, 10 μM stock solutions were prepared by series of dilution for the calibration curves. The supernatant was quantified by HPLC or LC/MS using the calibration curve. High-Throughput equilibrium solubility was determined based on the concentration of the supernatant.

Efficacy Studies in Mouse Xenograph Model

All experiments conducted were performed in female athymic Nude-nu mice in an AAALAC certificated facility. The animals were kept under SPF conditions in individual ventilation cages at constant temperature and humidity (i.e., 20-26° C.; 40-70%) with 5 or less animals in each cage. Animals had free access to irradiation sterilized dry granule food and sterile drinking water. All procedures and protocols were approved by the Institutional Animal Care and Use and interal committee.

The cells MV4:11 or HL60 leukemia were cultured in RPMI-1640 medium (Gibco; 11875-093) supplemented with 10% FBS (Gibco; 10099-141) and 1% Pen Strep (Gibco; 15140-122) at 37° C. in an atmosphere of 5% CO2 in air. Cells were maintained in suspension cultures at concentrations between 0.5-2×10⁶ cells/ml. Cells were split at 1:5 every 2-4 days. To establish xenograft tumor models the cells were collected, suspended in PBS, mixed with Matrigel (BD Bioscience) at a volume ratio of 1:1 at a concentration of 1×10⁸ cells/mL and then injected subcutaneously into the right flank of balb/c nude mice (Vital River) at a concentration of 5×10⁶ cells per animal.

The compound was formulated as a suspension in 0.5% methyl cellulose (MC) and 0.5% Tween 80 in 50 mM pH6.8 buffer (prepared in house according to the USP) and administered orally by gavage at specific doses.

Treatment was initiated when the average tumor volume reached 100-300 mm³. Tumor growth and body weights were monitored at regular intervals. The two largest diameters, width (W) and length (L), of the xenograft tumors were measured manually with calipers and the tumor volume was estimated using the formula: 0.5×L×W².

When applicable, results are presented as mean±SEM. Graphing and statistical analysis was performed using GraphPad Prism 6.00 (GraphPad Software). Tumor and body weight change data were analyzed statistically. If the variances in the data were normally distributed (Bartlett's test for equal variances), the data were analyzed using one-way ANOVA with post hoc Dunnet's test for comparison of treatment versus control group. The post hoc Tukey test was used for intragroup comparison. Otherwise, the Kruskal-Wallis ranked test post hoc Dunn's was used.

As a measure of efficacy the % T/C value is calculated at the end of the experiment according to:

($\Delta$tumor volume$^{treated}$/$\Delta$tumor volume$^{control}$)*100

Tumor regression was calculated according to:

$-$($\Delta$tumor volume$^{treated}$/tumor volume$^{treated\ at\ start}$)*100

Where $\Delta$tumor volumes represent the mean tumor volume on the evaluation day minus the mean tumor volume at the start of the experiment.

The exemplified Examples disclosed below were tested in the LC-MS assays and CD11b FACS assay described above and found having LSD1 inhibitory activity. A range of $IC_{50}$ values of 1 μM (1000 nM) was observed.

Table 3 below lists $IC_{50}$ values in the a) LC-MS Qualified assay and/or (b) anti proliferative assay in molm13 cell and or (c) CD11b FACS assay for the following examples:

glioblastoma, nasopharyngeal carcinoma colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

V. Pharmaceutical Compositions and Combinations

The compounds of the present invention are typically used as a pharmaceutical composition (e.g., a compound of the present invention and at least one pharmaceutically acceptable carrier). A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants,

TABLE 3

| Ex # | IUPAC name | (a) $IC_{50}$ (μM) | (b) $IC_{50}$ (μM) | (c) $IC_{50}$ (μM) |
|---|---|---|---|---|
| 38 | 3-(3-amino-2-methylphenyl)-1-(4-methoxyphenyl)-1H-indole-5-carbonitrile | 0.015 | 0.89 | |
| 55 | 3-(5-amino-4-methylpyridin-3-yl)-1-(4-methoxyphenyl)-1H-indole-5-carbonitrile | 0.009 | 0.57 | |
| 65 | 3-(3-amino-2-methylphenyl)-1-(4-methoxyphenyl)-6-methyl-1H-indole-5-carbonitrile | 0.003 | 0.123 | 0.315 |
| 71 | 3-(5-amino-4-methylpyridin-3-yl)-1-(4-methoxyphenyl)-6-methyl-1H-indole-5-carbonitrile | 0.003 | 0.051 | 0.801 |
| 78 | Trans-3-(3-amino-2-methylphenyl)-6-methyl-1-(4-(methylamino)cyclohexyl)-1H-indole-5-carbonitrile | 0.006 | 0.029 | |
| 79 | Cis-3-(3-amino-2-methylphenyl)-6-methyl-1-(4-(methylamino)cyclohexyl)-1H-indole-5-carbonitrile | 0.004 | 0.019 | |
| 80 | Trans-3-(3-amino-2-methylphenyl)-1-(3-hydroxycyclopentyl)-1H-indole-5-carbonitrile | 0.024 | 0.39 | |
| 83 | Trans-3-(3-amino-2-methylphenyl)-1-(3-hydroxycyclohexyl)-1H-indole-5-carbonitrile | 0.06 | 0.27 | |
| 85 | Trans-3-(3-amino-2-methylphenyl)-1-(3-hydroxycyclopentyl)-6-methyl-1H-indole-5-carbonitrile | 0.003 | 0.046 | |
| 86 | Cis-3-(3-amino-2-methylphenyl)-1-(3-hydroxycyclopentyl)-6-methyl-1H-indole-5-carbonitrile | 0.0025 | 0.046 | |
| 87 | Cis-3-(5-amino-4-methylpyridin-3-yl)-1-(3-hydroxycyclopentyl)-6-methyl-1H-indole-5-carbonitrile | 0.015 | 0.076 | |
| 88 | Trans-3-(5-amino-4-methylpyridin-3-yl)-1-(3-hydroxycyclopentyl)-6-methyl-1H-indole-5-carbonitrile | 0.015 | 0.09 | |
| 93 | Trans-3-(3-amino-2-methylphenyl)-1-(4-hydroxycyclohexyl)-6-methyl-1H-indole-5-carbonitrile | 0.003 | 0.022 | 0.073 |
| 94 | Trans-3-(5-amino-4-methylpyridin-3-yl)-1-(4-hydroxycyclohexyl)-6-methyl-1H-indole-5-carbonitrile | 0.016 | 0.073 | |
| 95 | Cis-3-(3-amino-2-methylphenyl)-1-(4-hydroxycyclohexyl)-6-methyl-1H-indole-5-carbonitrile | 0.005 | 0.049 | |
| 97 | 3-(3-amino-2-methylphenyl)-6-methyl-1-(piperidin-4-yl)-1H-indole-5-carbonitrile | 0.014 | 0.926 | |
| 98 | Cis-3-(3-amino-2-methylphenyl)-1-(3-hydroxycyclobutyl)-6-methyl-1H-indole-5-carbonitrile | 0.004 | 0.064 | |
| 100 | Trans-3-(3-amino-2-methylphenyl)-1-(3-hydroxycyclobutyl)-6-methyl-1H-indole-5-carbonitrile | 0.015 | 0.048 | |

Accordingly, the compounds of the present invention have been found to inhibit LSD1 and therefore useful in the treatment of diseases or disorders associated with LSD1, which include, but are not limited to, B cell lymphoma, acute myeloid leukemia, gastric cancer, hepatocellular carcinoma, prostate cancer, breast carcinoma, neuroblastoma, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012). For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The compound of the present invention is typically formulated into pharmaceutical dosage forms to provide an easily controllable dosage of the drug and to give the patient an elegant and easily handleable product. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. Compounds of this invention may be administered in a single daily dose, or the total daily dosage may be administered in divided doses of two, three, or four times daily.

In certain instances, it may be advantageous to administer the compound of the present invention in combination with at least one additional pharmaceutical (or therapeutic) agent, such as other anti-cancer agents, immunomodulators, anti-allergic agents, anti-nausea agents (or anti-emetics), pain relievers, cytoprotective agents, and combinations thereof.

The term "combination therapy" refers to the administration of two or more therapeutic agents to treat a therapeutic disease, disorder or condition described in the present invention. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. The compound of the present invention and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include:

Cyclin-Dependent Kinase (CDK) Inhibitors:

(Chen, S. et al., Nat Cell Biol., 12(11):1108-14 (2010); Zeng, X. et al., Cell Cycle, 10(4):579-83 (2011)) Aloisine A; Alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-Methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido[5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl)amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438, CAS 602306-29-6); Palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394).

Checkpoint Kinase (CHK) Inhibitors:

(Wu, Z. et al., *Cell Death Differ.*, 18(11):1771-9 (2011)) 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL), and CBP501 ((d-Bpa)sws(d-Phe-F5)(d-Cha)rrrqrr); and (αR)-α-amino-N-[5,6-dihydro-2-(1-methyl-1H-pyrazol-4-yl)-6-oxo-1H-pyrrolo[4,3,2-ef][2,3]benzodiazepin-8-yl]-Cyclohexaneacetamide (PF-0477736).

Histone Deacetylase (HDAC) Inhibitors:

(Yamaguchi, J. et al., *Cancer Sci.*, 101(2):355-62 (2010)) Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-η-oxo-L-α-aminooxiraneoctanoyl-D-prolyl] (HC-toxin); Cyclo[(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide); and Depudecin (4,5:8,9-dianhydro-1,2,6,7,11-pentadeoxy-D-threo-D-ido-Undeca-1,6-dienitol).

Anti-Tumor Antibiotics:

(Bai, J. et al., *Cell Prolif.*, 47(3):211-8 (2014)) Doxorubicin (Adriamycin® and Rubex®); Bleomycin (lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence™); Idarubicin (Idamycin®, Idamycin PFS®); Mitomycin C (Mutamycin®); Geldanamycin; Herbimycin; Ravidomycin; and Desacetylravidomycin.

Demethylating Agents:

(Musch, T. et al., *PLoS One*, (5):e10726 (2010)) 5-Azacitidine (Vidaza®); and Decitabine (Dacogen®).

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Immunomodulators of particular interest for combinations with the compounds of the present invention include one or more of: an activator of a costimulatory molecule or an inhibitor of an immune checkpoint molecule (e.g., one or more inhibitors of PD-1, PD-L1, LAG-3, TIM-3 or CTLA4) or any combination thereof.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy for treatment of a malignancy, the compound of the present invention and other anti-cancer agent(s) may be administered simultaneously, concurrently or sequentially with no specific time limits, wherein such administration provides therapeutically effective levels of the two compounds in the body of the subject.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The compounds of the present invention are also useful as standard or reference compounds, for example as a quality standard or control, in tests or assays involving LSD1. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving LSD1.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

What is claimed is:

1. A compound of Formula (I):

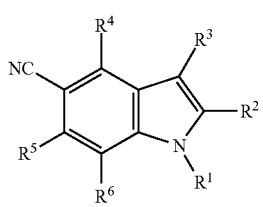

(I)

or a pharmaceutically acceptable salt, stereoisomer or tautomer thereof, wherein:

$R^1$ is selected from the group consisting of:

(i) $C_1$-$C_6$ alkyl, substituted with one or two $R^a$;

(ii) $C_2$-$C_6$ alkenyl, substituted with one or two $R^a$;

(iii) —$(CH_2)_n$—$C_3$-$C_6$cycloalkyl, substituted with one or two $R^d$;

(iv) —$(CH_2)_n$-phenyl, optionally substituted with one, two, or three $R^b$;

(v) —$(CH_2)_n$-6-membered heteroaryl, optionally substituted with one, two, or three $R^b$, wherein the 6-membered heteroaryl comprises one, two, three, four, or five carbon atoms and one or two heteroatoms selected from N and $NR^a$;

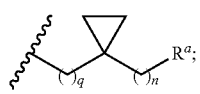

(vi)

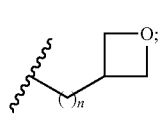

(vii)

(viii)

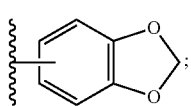

(ix)

$R^2$ is selected from the group consisting of H, halogen, and $C_1$-$C_4$ alkyl;

R³ is selected from the group consisting of:

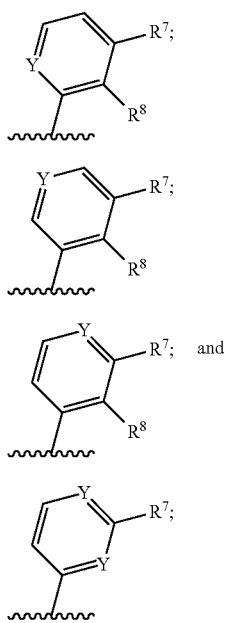

R⁴ is selected from the group consisting of H, halogen, and $C_1$-$C_4$ alkyl;
R⁵ is selected from the group consisting of H, halogen, $C_1$-$C_4$ alkyl, $C_1$-$C_4$ haloalkyl, and $C_3$-$C_6$ cycloalkyl;
R⁶ is selected from the group consisting of H, halogen, and $C_1$-$C_4$ alkyl;
R⁷ is selected from the group consisting of $NH_2$, $NH(C_1$-$C_4$ alkyl), and $NHCO(C_1$-$C_4$ alkyl);
R⁸ is selected from the group consisting of H, halogen, $C_1$-$C_4$ alkyl, and $C_1$-$C_4$ haloalkyl;
Y, at each occurrence, is independently selected from the group consisting of CH and N;
W is selected from the group consisting of —O— and —NH—;
$R^a$, at each occurrence, is independently selected from the group consisting of OH, $C_1$-$C_4$ alkoxy, $CO_2(C_1$-$C_4$ alkyl), $CONR^eR^f$, and $NHR^e$;
$R^b$, at each occurrence, is independently selected from the group consisting of:
(i) halogen;
(ii) $C_1$-$C_4$ haloalkoxy;
(iii) OH;
(iv) CN;
(v) $CO_2(C_1$-$C_4$ alkyl);
(vi) $CONR^eR^f$;
(vii) $NHR^e$;
(viii) $C_1$-$C_4$ alkyl, optionally substituted with one $R^c$; and
(ix) $C_1$-$C_4$ alkoxy, optionally substituted with one $R^c$;
$R^c$ is selected from the group consisting of OH, $C_1$-$C_4$ alkoxy, $CO_2(C_1$-$C_4$ alkyl), $CONR^eR^f$, and $NHR^e$;
$R^d$, at each occurrence, is independently selected from the group consisting of =O, OH, and $NH(C_1$-$C_4$ alkyl);
$R^e$, at each occurrence, is independently selected from the group consisting of H, $C_1$-$C_4$ alkyl, and $CO(C_1$-$C_4$ alkyl);

$R^f$, at each occurrence, is independently selected from the group consisting of H and $C_1$-$C_4$ alkyl;
m is selected from the group consisting of 1 and 2;
n, at each occurrence, is independently selected from the group consisting of 0 and 1; and
q is selected from the group consisting of 1, 2 and 3.

2. The compound according to claim 1, or a pharmaceutically acceptable salt, stereoisomer or tautomer thereof, wherein:
R¹ is selected from the group consisting of:
(i) $C_1$-$C_6$ alkyl, substituted with one $R^a$;
(ii) $C_2$-$C_6$ alkenyl, substituted with one $R^a$;
(iii) —$(CH_2)_n$—$C_3$-$C_6$ cycloalkyl, substituted with one $R^d$;
(iv) —$(CH_2)_n$-phenyl, optionally substituted with one or two $R^b$;
(v) —$(CH_2)_n$-6-membered heteroaryl, optionally substituted with one or two $R^b$, wherein the 6-membered heteroaryl comprises one, two, three, four, or five carbon atoms and one or two heteroatoms selected from N and $NR^a$;

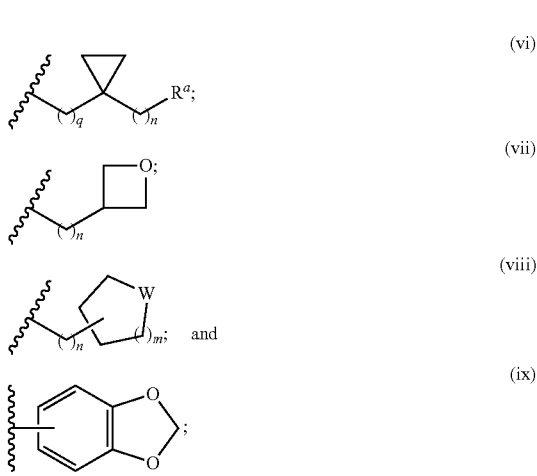

R⁸ is selected from the group consisting of H, $C_1$-$C_4$ alkyl, and $C_1$-$C_4$ haloalkyl;
$R^a$, at each occurrence, is independently selected from the group consisting of OH, $C_1$-$C_4$ alkoxy, $CO_2(C_1$-$C_4$ alkyl), and $CONH_2$;
$R^b$, at each occurrence, is independently selected from the group consisting of:
(i) halogen;
(ii) $C_1$-$C_4$ haloalkoxy;
(iii) OH;
(iv) CN;
(v) $CO_2(C_1$-$C_4$ alkyl);
(vi) $CONH_2$;
(vii) $C_1$-$C_4$ alkyl, optionally substituted with one $R^c$; and
(viii) $C_1$-$C_4$ alkoxy, optionally substituted with one $R^c$; and
$R^c$ is selected from the group consisting of OH, $C_1$-$C_4$ alkoxy, $CO_2(C_1$-$C_4$ alkyl), and $CONH_2$.

3. The compound according to claim 1, or a pharmaceutically acceptable salt, stereoisomer or tautomer thereof, wherein the compound is of Formula (I-1):

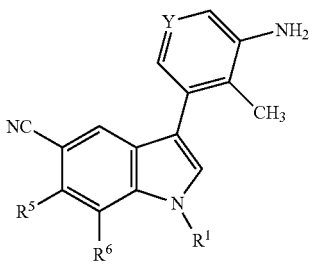

(I-1)

wherein:
R¹ is selected from the group consisting of:
(i) $C_2$-$C_6$ alkyl, substituted with one $R^a$;
(ii) $C_2$-$C_6$ alkenyl, substituted with one $R^a$;
(iii) —$(CH_2)_n$—$C_4$-$C_6$cycloalkyl, substituted with one $R^d$;
(iv) —$(CH_2)_n$-phenyl, optionally substituted with one or two $R^b$;
(v) —$(CH_2)_n$-pyridyl, optionally substituted with one or two $R^b$;

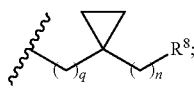
(vi)

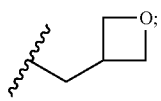
(vii)

piperidinyl; (viii)

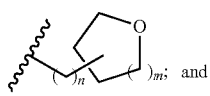
(ix)
and

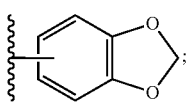
(x)

R⁵ is selected from the group consisting of H, halogen, $C_1$-$C_4$ alkyl, $CF_3$, and cyclopropyl;
R⁶ is selected from the group consisting of H and $C_1$-$C_4$ alkyl;
$R^a$, at each occurrence, is independently selected from the group consisting of OH, $C_1$-$C_4$ alkoxy, $CO_2(C_1$-$C_4$ alkyl), and $CONH_2$;
$R^b$, at each occurrence, is independently selected from the group consisting of:
(i) halogen;
(ii) $C_1$-$C_4$ haloalkoxy;
(iii) OH;
(iv) CN;
(v) $CO_2(C_1$-$C_4$ alkyl);
(vi) $CONH_2$;
(vii) $C_1$-$C_4$ alkyl, optionally substituted with one $R^c$; and
(viii) $C_1$-$C_4$ alkoxy, optionally substituted with one $R^c$; and
$R^c$ is selected from the group consisting of OH, $C_1$-$C_4$ alkoxy, $CO_2(C_1$-$C_4$ alkyl), and $CONH_2$.

4. The compound according to claim 1, or a pharmaceutically acceptable salt, stereoisomer or tautomer thereof, wherein:
R¹ is selected from the group consisting of:
(i) $C_1$-$C_6$ alkyl, substituted with one $R^a$;
(ii) $C_2$-$C_6$ alkenyl, substituted with one $R^a$;
(iii) $C_4$-$C_6$ cycloalkyl, substituted with one $R^d$;
(iv) —$(CH_2)_n$-phenyl, substituted with one or two $R^b$;
(v) —$(CH_2)_n$-pyridyl, substituted with one or two $R^b$;

(vi)

(vii)

piperidinyl; (viii)

(ix)
and (x)

R⁵ is selected from the group consisting of H, F, Cl, $CH_3$, $CF_3$, and cyclopropyl;
R⁶ is selected from the group consisting of H and $CH_3$;
$R^a$, at each occurrence, is independently selected from the group consisting of OH, $OCH_3$, $CO_2CH_3$, and $CONH_2$;
$R^b$, at each occurrence, is independently selected from the group consisting of:
(i) F;
(ii) Cl;
(iii) $OCF_3$;
(iv) OH;
(v) CN;
(vi) $CO_2CH_3$;
(vii) $CONH_2$;
(viii) $C_1$-$C_4$ alkyl, optionally substituted with one $R^c$; and
(ix) $C_1$-$C_4$ alkoxy, optionally substituted with one $R^c$;
$R^c$ is selected from the group consisting of OH, $OCH_3$, $CO_2CH_3$, and $CONH_2$;
$R^d$, at each occurrence, is independently selected from the group consisting of =O, OH, and $NHCH_3$; and
q is selected from the group consisting of 1 and 2.

5. The compound according to claim 1, or a pharmaceutically acceptable salt, stereoisomer or tautomer thereof, wherein:
R¹ is selected from the group consisting of:
(i) $C_4$-$C_6$ cycloalkyl, substituted with one $R^d$;
(ii) phenyl, substituted with one or two $R^b$; and
(iii) pyridyl, substituted with one or two $R^b$;
R⁵ is selected from the group consisting of H, F, Cl, and $CH_3$;
R⁶ is selected from the group consisting of H and $CH_3$;
$R^b$, at each occurrence, is independently selected from the group consisting of:

(i) F;
(ii) Cl;
(iii) OCF$_3$;
(iv) OH;
(v) CN;
(vi) CO$_2$CH$_3$;
(vii) CONH$_2$;
(viii) C$_1$-C$_4$ alkyl, optionally substituted with one R$^c$; and
(ix) C$_1$-C$_4$ alkoxy, optionally substituted with one R$^c$;
R$^c$ is selected from the group consisting of OH, OCH$_3$, CO$_2$CH$_3$, and CONH$_2$; and
R$^d$, at each occurrence, is independently selected from the group consisting of =O, OH, and NHCH$_3$.

6. The compound according to claim 1, or a pharmaceutically acceptable salt, stereoisomer or tautomer thereof, wherein:
R$^1$ is selected from the group consisting of:
(i) C$_4$-C$_6$ cycloalkyl, substituted with one R$^d$; and
(ii) phenyl, substituted with one or two R$^b$;
R$^5$ is selected from the group consisting of H, F, Cl, and CH$_3$;
R$^6$ is selected from the group consisting of H and CH$_3$;
R$^b$, at each occurrence, is independently selected from the group consisting of:
(i) F;
(ii) Cl;
(iii) OCF$_3$;
(iv) OH;
(v) CN;
(vi) C$_1$-C$_4$ alkyl; and
(vii) C$_1$-C$_4$ alkoxy; and
R$^d$, at each occurrence, is independently selected from the group consisting of OH and NHCH$_3$.

7. The compound according to claim 1, wherein the compound is selected from the group consisting of:

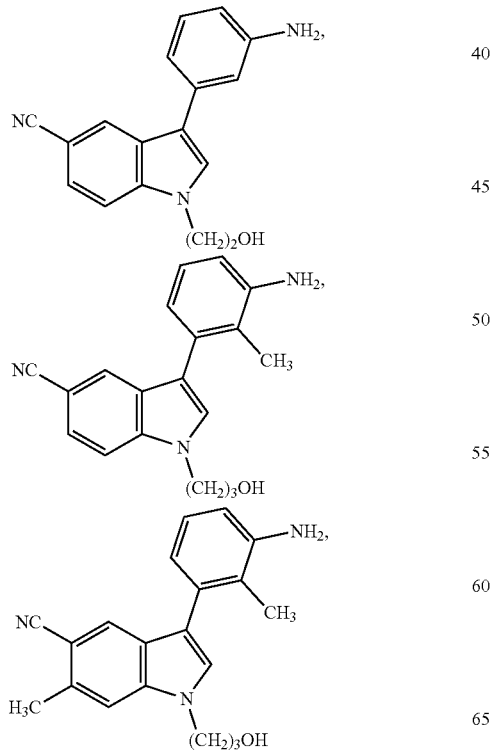

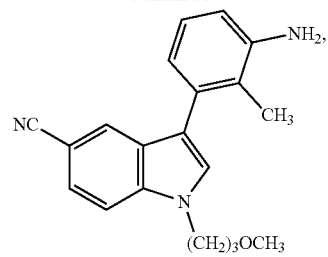

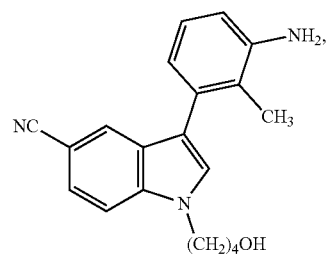

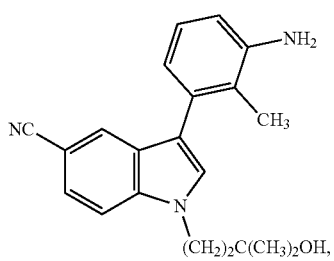

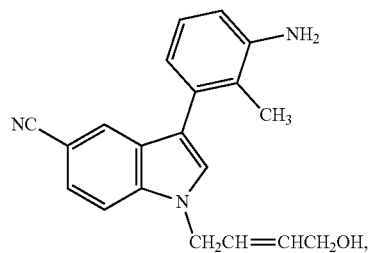

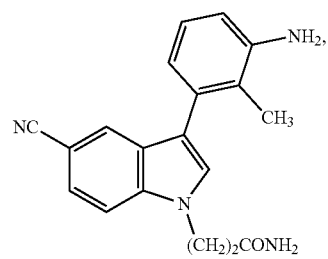

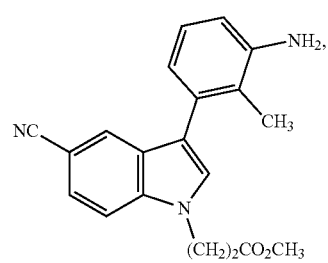

-continued
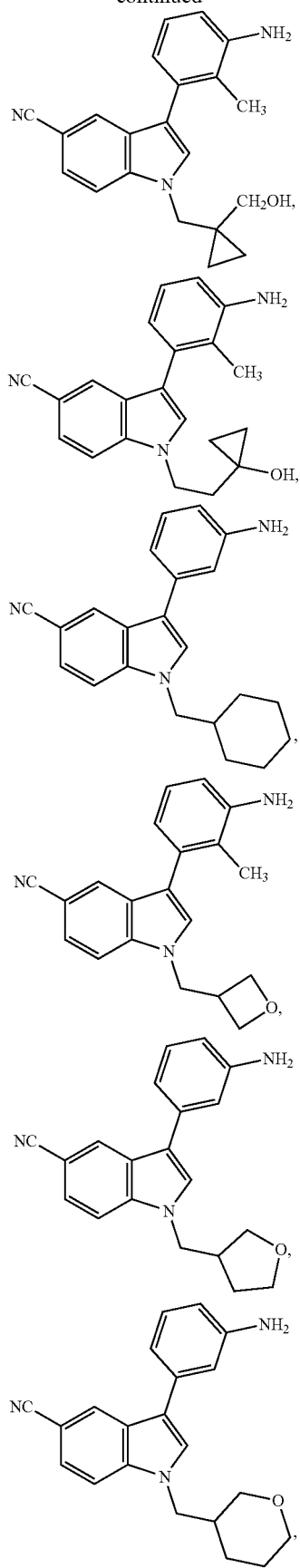
-continued
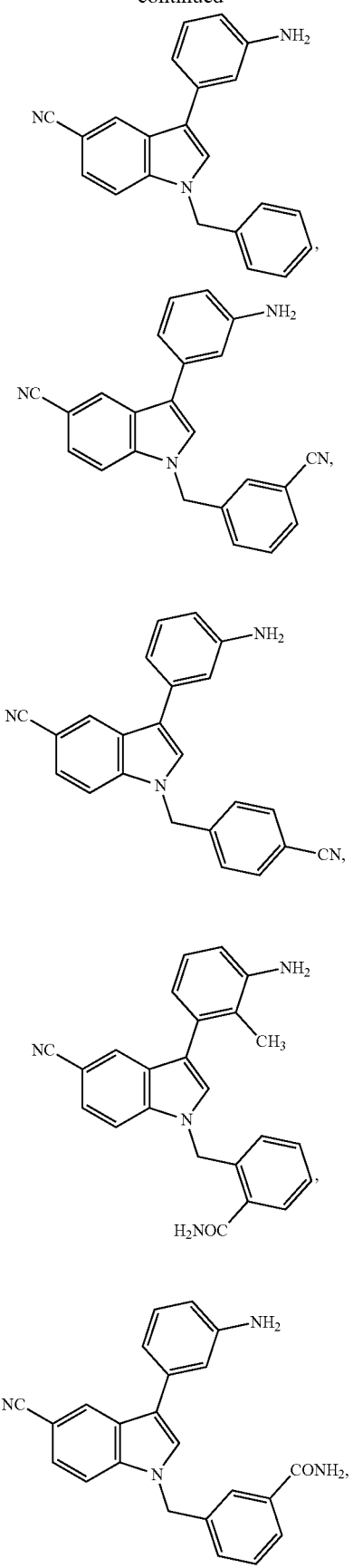

-continued
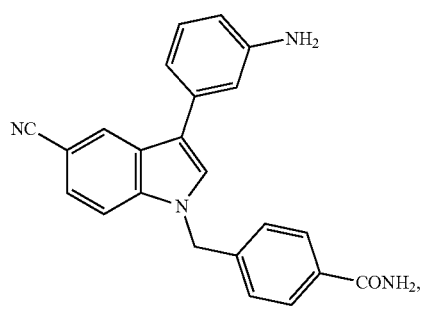
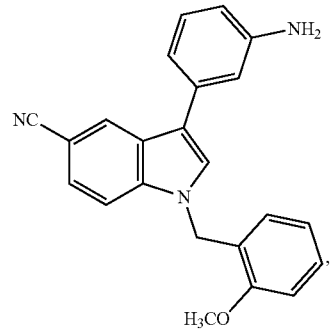
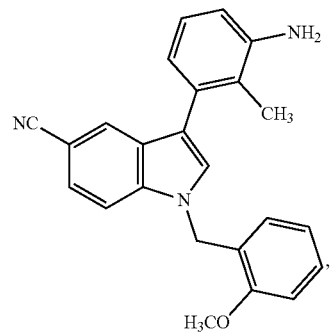
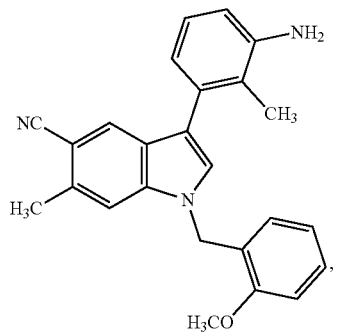
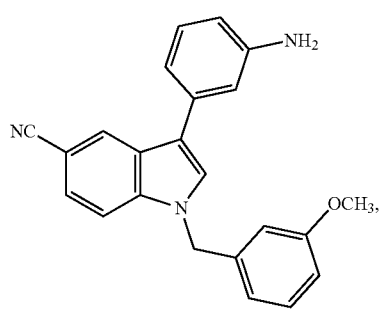
-continued
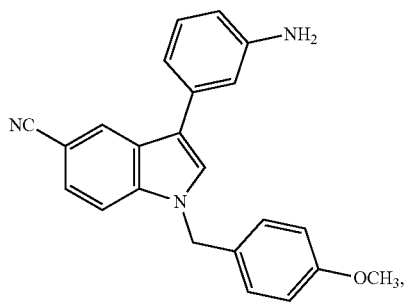
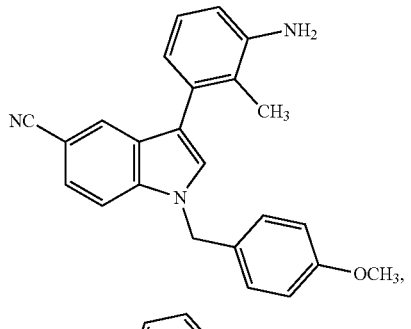
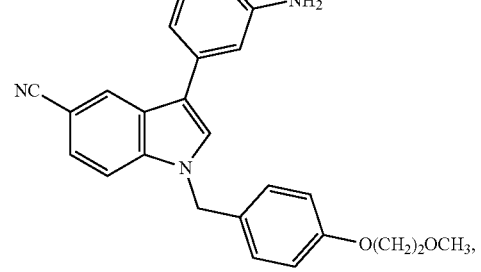
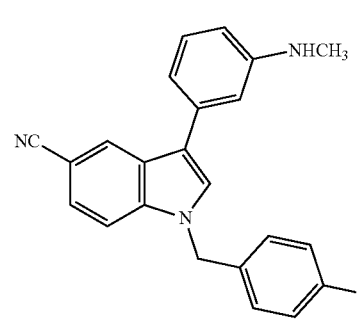
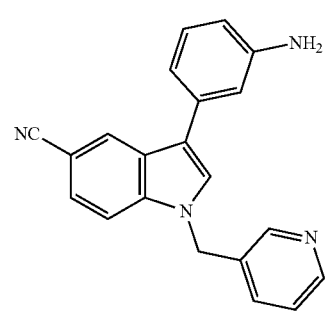

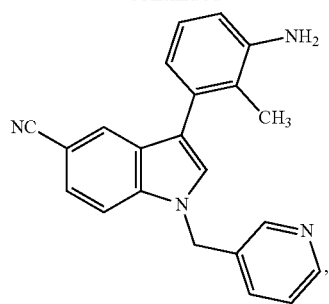
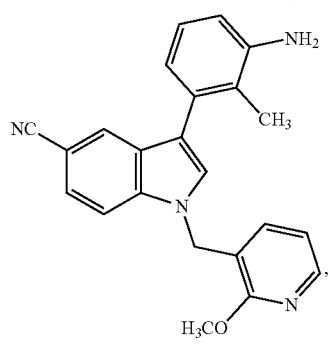
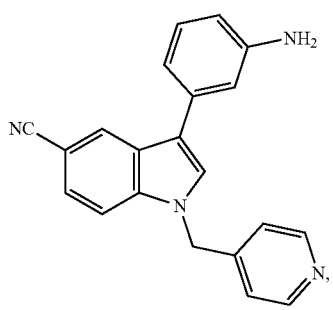
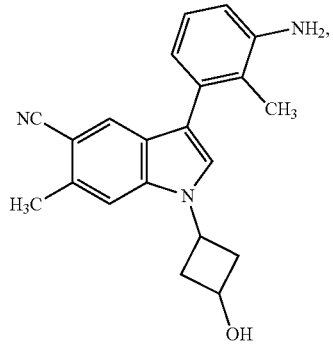
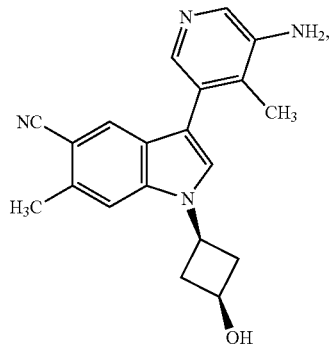
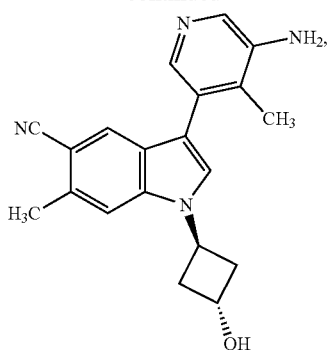
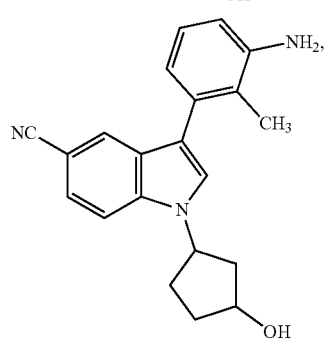
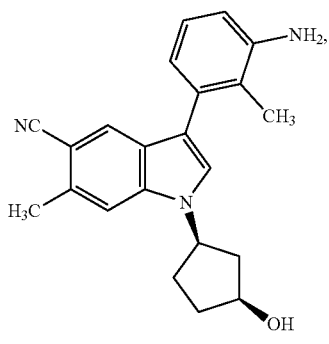
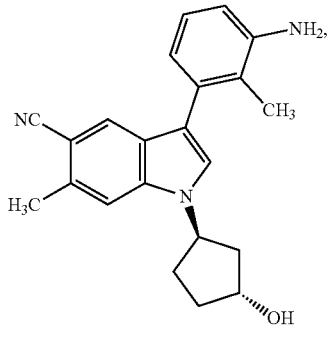
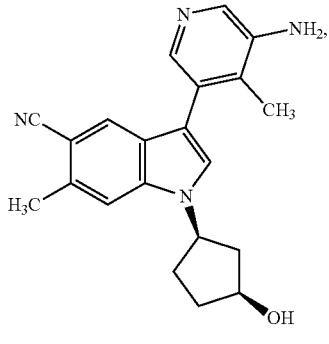

185
-continued
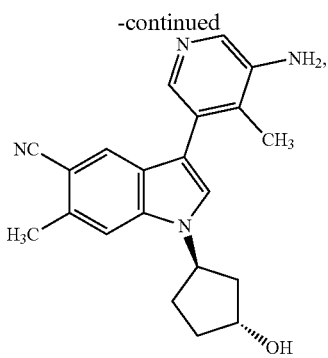
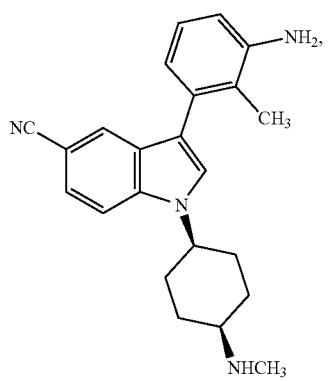
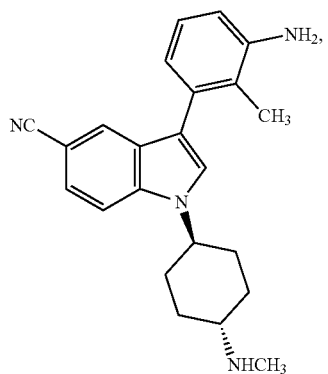
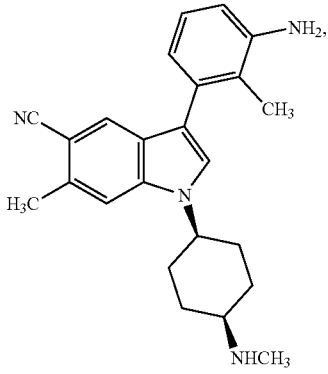
186
-continued
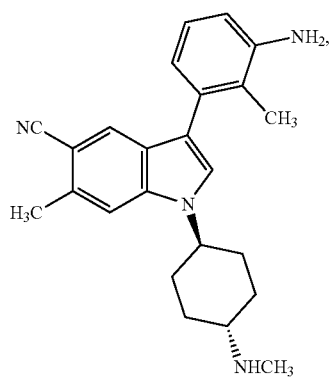
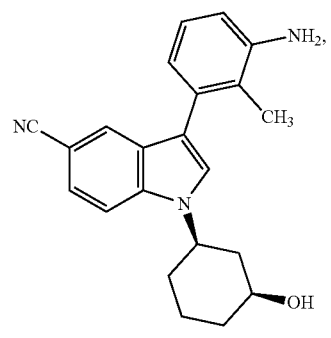
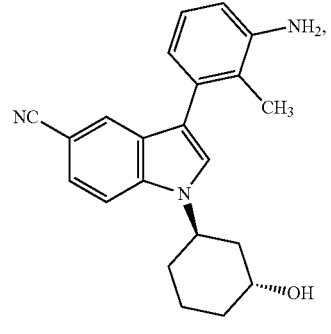
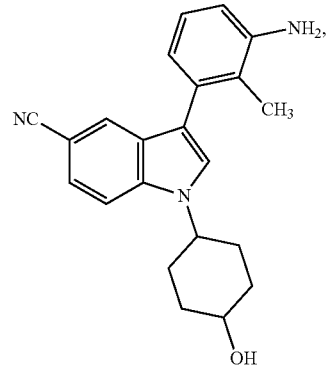

187
-continued
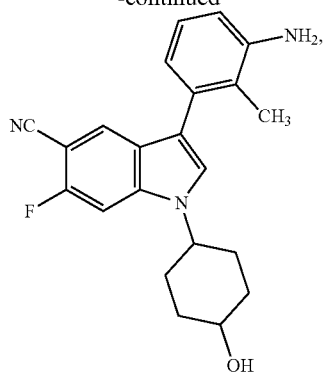
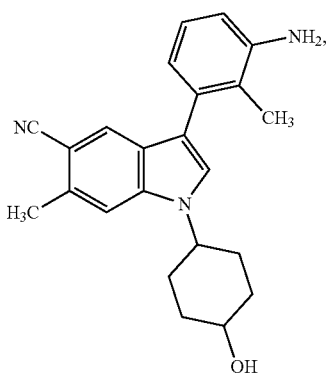
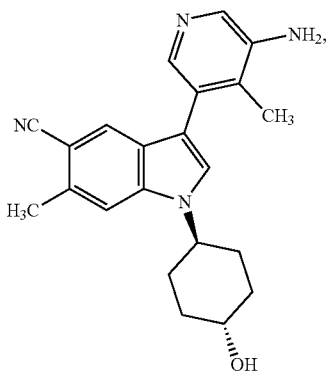
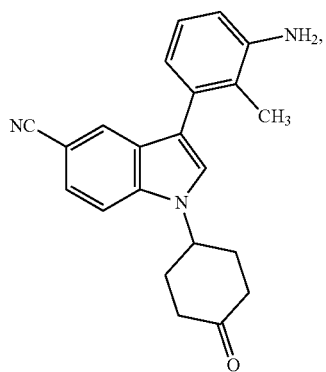
188
-continued
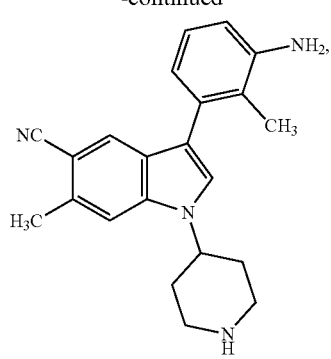
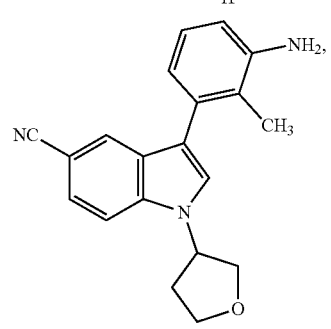
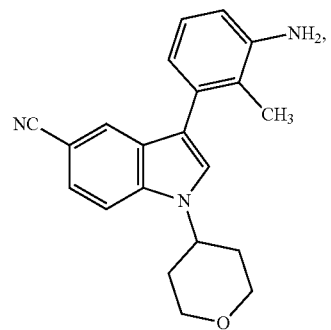
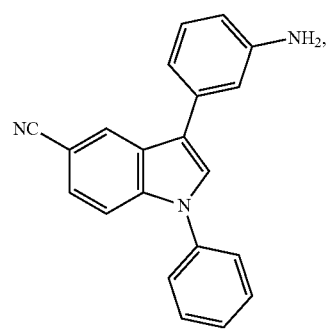
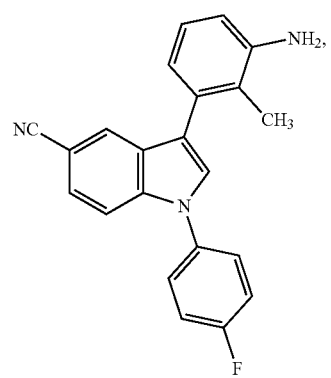

-continued

-continued
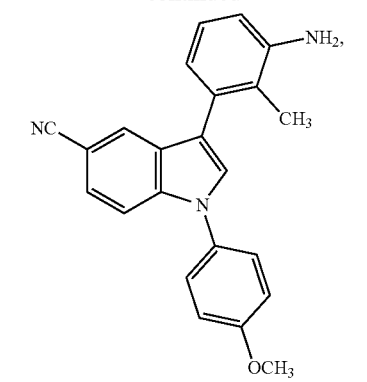
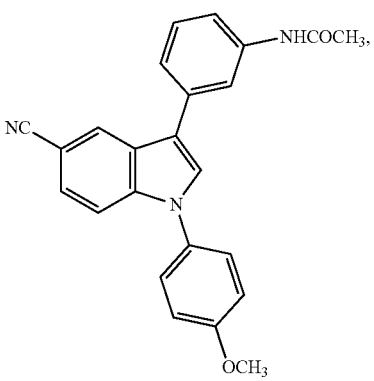
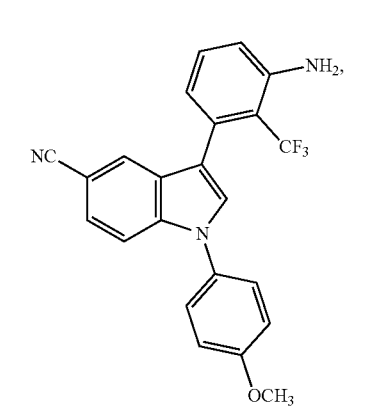
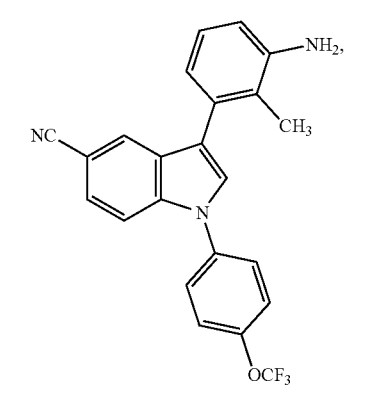
-continued
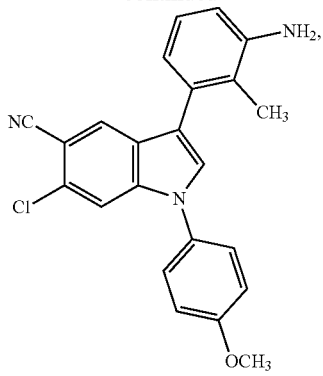
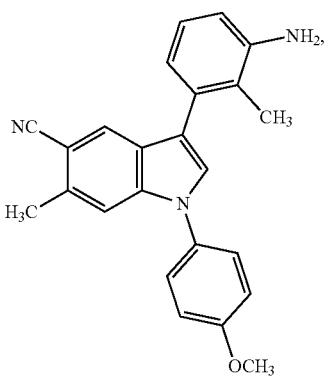 [SMILES: COc1ccc(-n2cc(-c3cccc(N)c3C)c3cc(C#N)c(C)cc32)cc1]
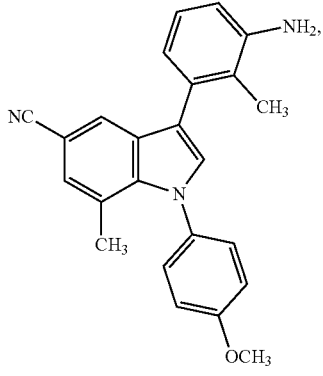
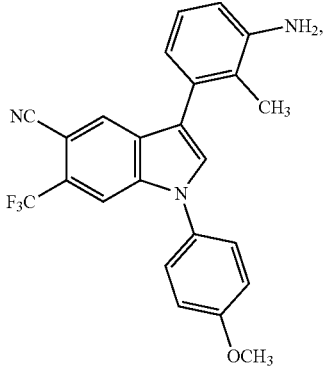

193
-continued
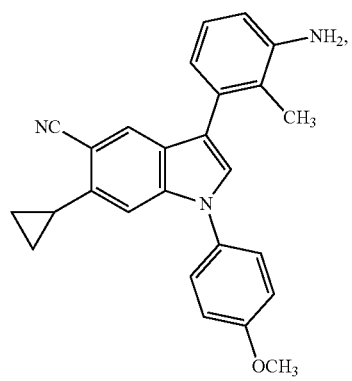
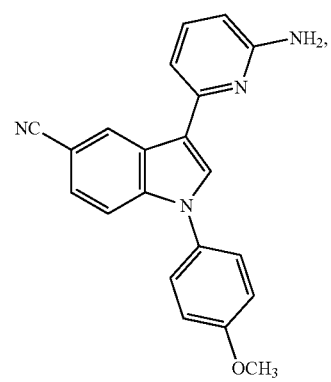
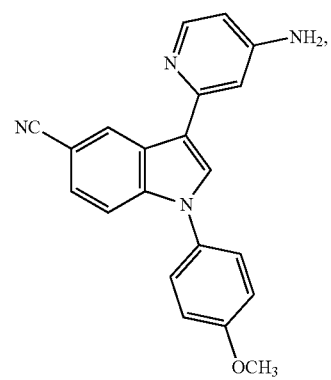
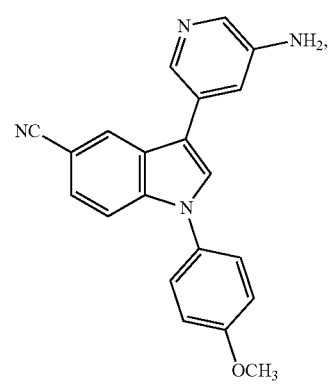
194
-continued
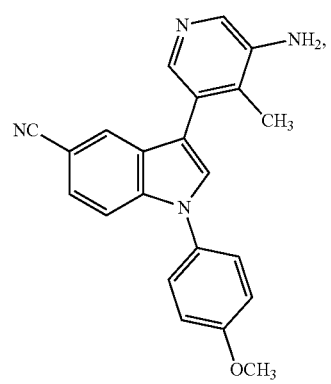
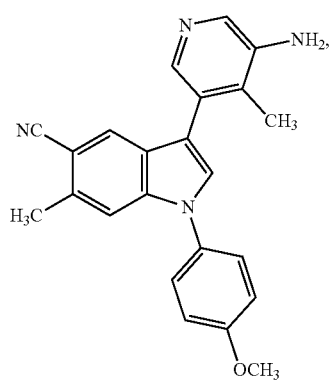
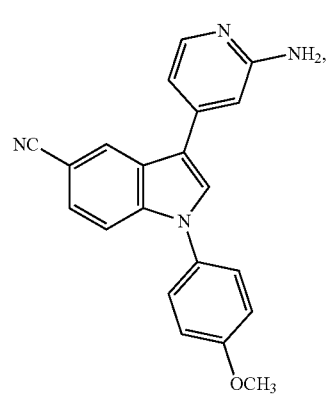
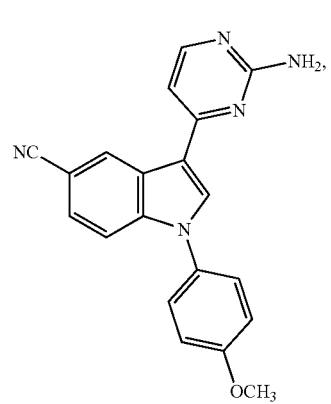

-continued
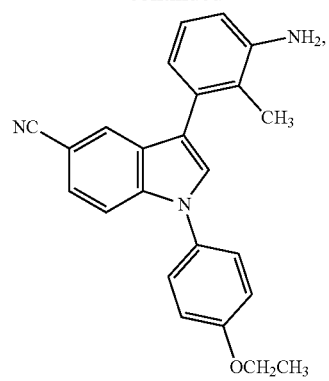
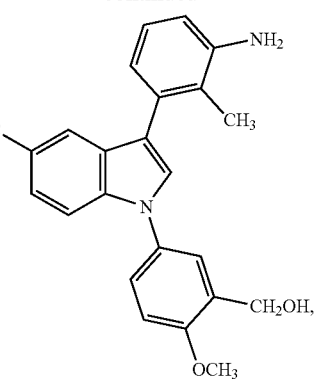
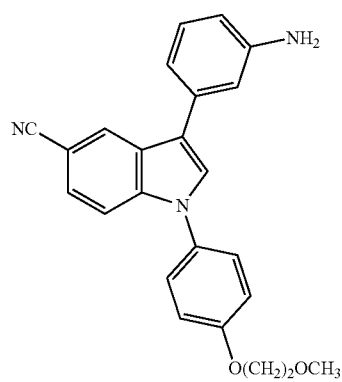
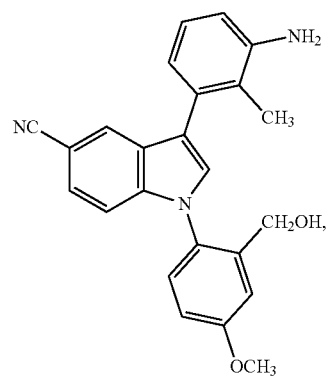
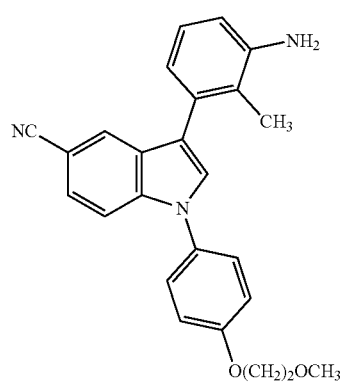
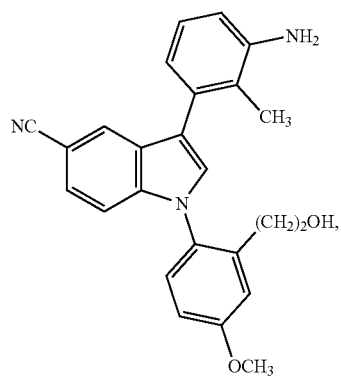
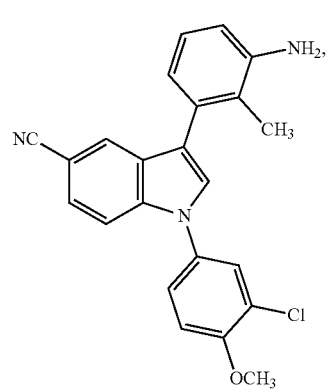
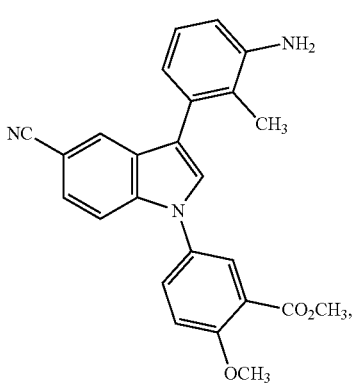

197
-continued
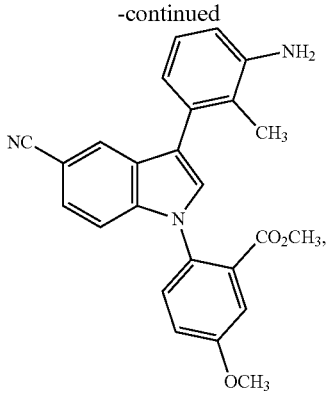
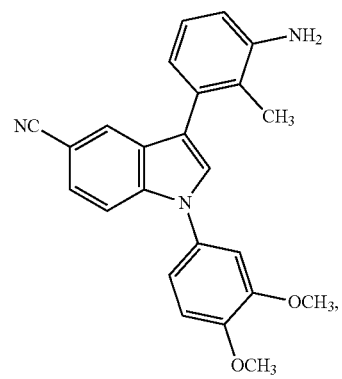
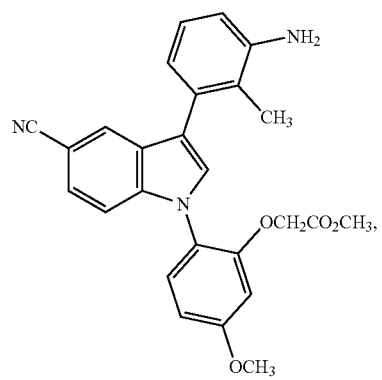
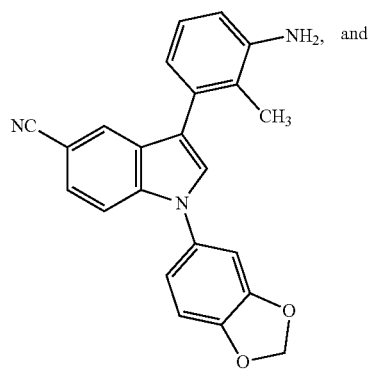
198
-continued
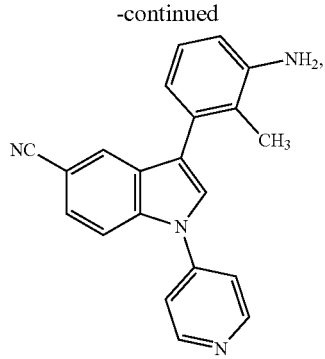
or a pharmaceutically acceptable salt, stereoisomer or tautomer thereof.
8. The compound according to claim 1, wherein the compound is selected from the group consisting of:
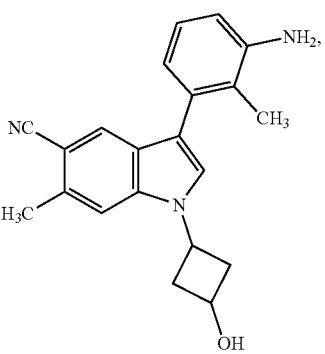
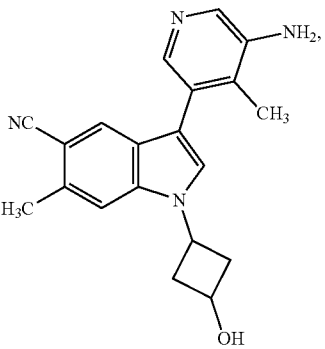
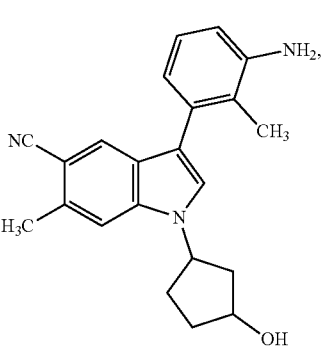

-continued
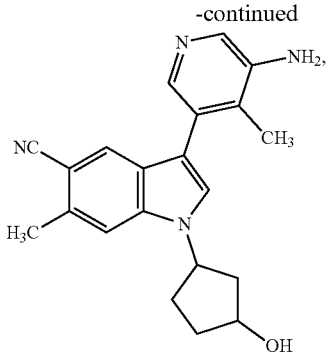
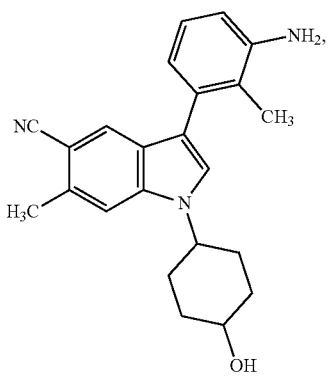
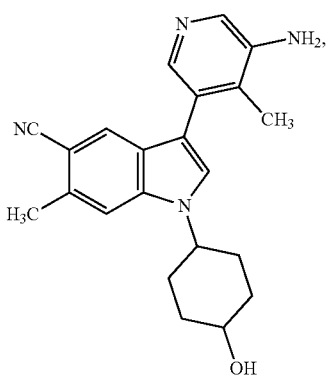
-continued
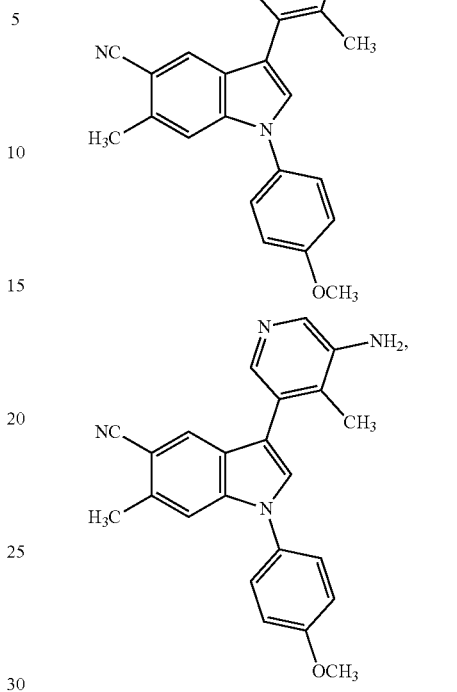
or a pharmaceutically acceptable salt, stereoisomer or tautomer thereof.
9. The compound according to claim 1, wherein the compound is selected from the group consisting of:
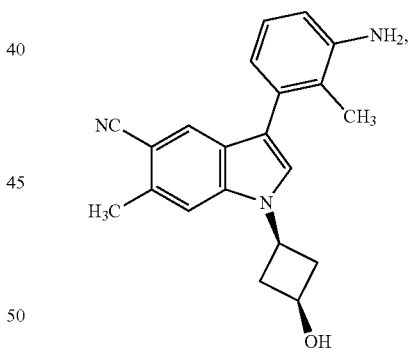
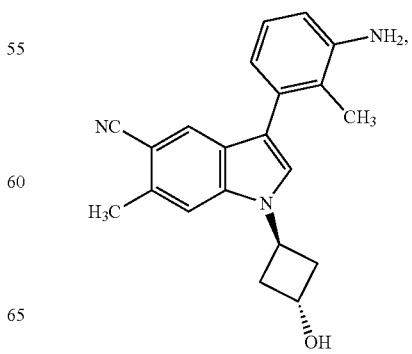

201
-continued
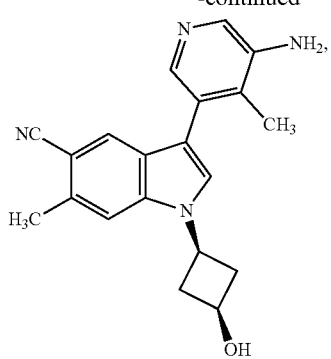
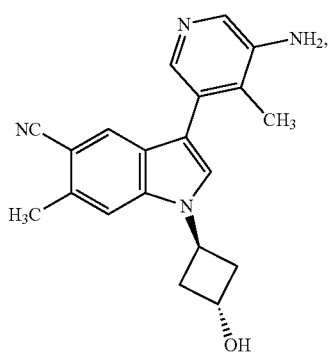
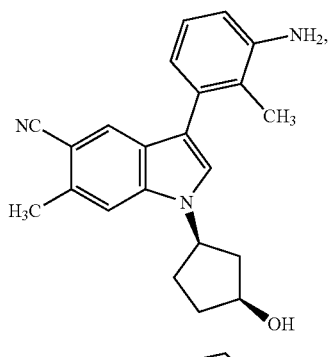
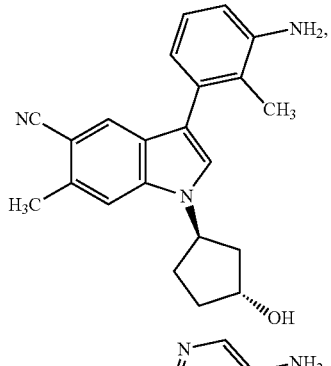
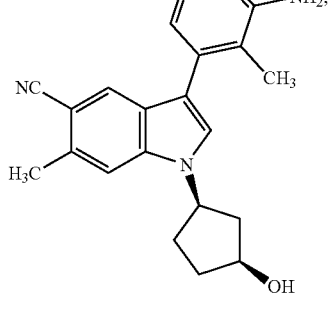
202
-continued
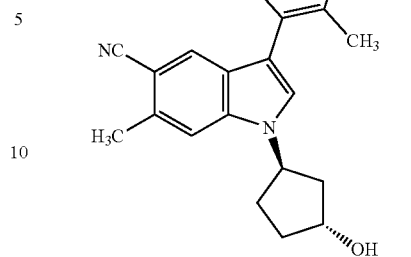
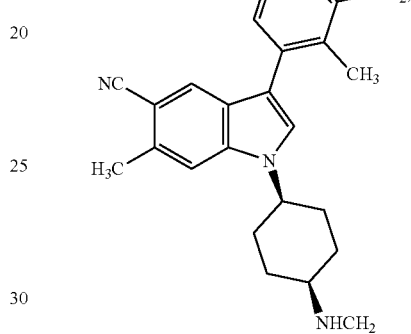
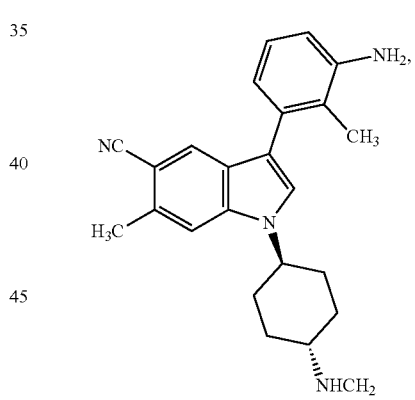
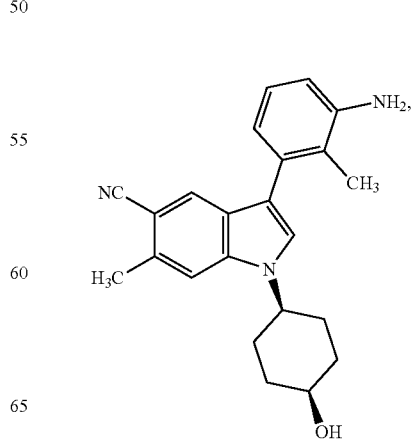

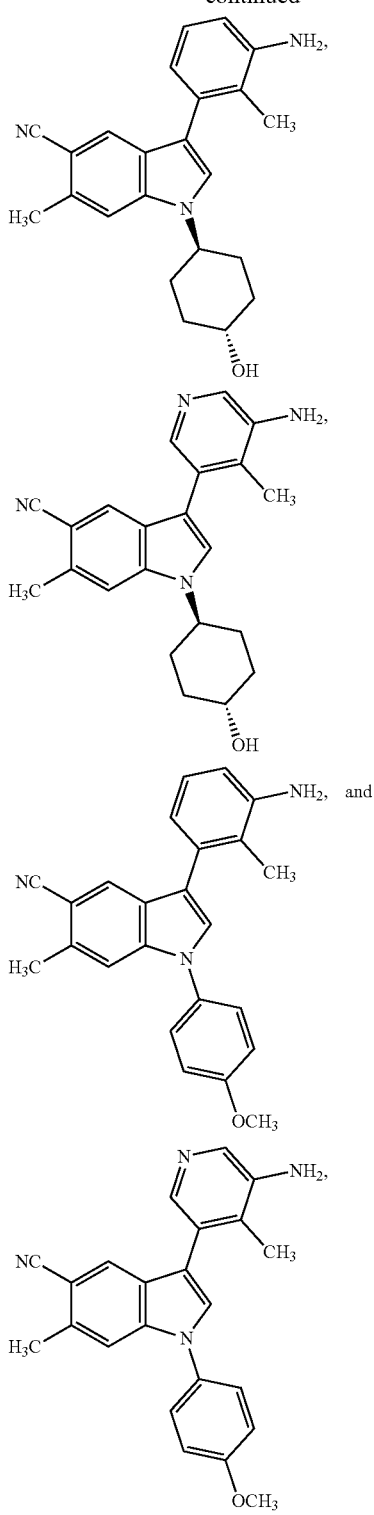

or a pharmaceutically acceptable salt, stereoisomer or tautomer thereof.

10. The compound according to claim 1, wherein the compound is selected from the group consisting of:

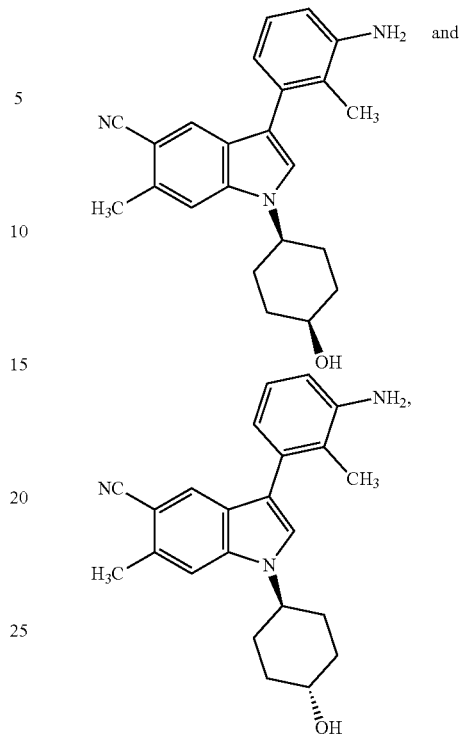

or a pharmaceutically acceptable salt, stereoisomer or tautomer thereof.

11. The compound according to claim 1, wherein the compound is:

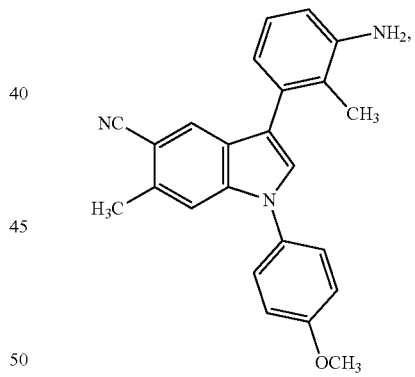

or a pharmaceutically acceptable salt, stereoisomer or tautomer thereof.

12. A pharmaceutical composition comprising one or more pharmaceutically acceptable carriers and a compound according to claim 1, or a pharmaceutically acceptable salt, stereoisomer or tautomer thereof.

13. The pharmaceutical composition according to claim 12, wherein the pharmaceutical composition further comprises at least one additional therapeutic agent.

14. The pharmaceutical composition according to claim 13, wherein the at least one additional therapeutic agent is selected from the group consisting of an anti-cancer agent, an immunomodulatory, an anti-allergic agent, an anti-emetic, a pain reliever, and a cytoprotective agent, or a combination thereof.

15. A method for inhibiting lysine-specific demethylase 1A activity in a subject, comprising administering to the subject a therapeutically effective amount of a compound according to claim 1, or a pharmaceutically acceptable salt, stereoisomer or tautomer thereof.

16. The method according to claim 15, wherein the subject has a disease or disorder selected from the group consisting of a soft tissue sarcoma, Ewing's sarcoma, acute myeloid leukemia, B-cell lymphoma, glioblastoma, neuroblastoma, breast carcinoma, endometrial carcinoma, hepatocellular carcinoma, nasopharyngeal carcinoma, colon cancer, esophageal cancer, gall bladder cancer, gastric cancer, head and neck cancer, lung cancer, ovarian cancer, pancreatic cancer, prostate cancer, liver fibrosis, and sickle cell disease.

* * * * *

SEQUENCE LISTING

<160> NUMBER OF SEQ ID NOS: 4

<210> SEQ ID NO 1
<211> LENGTH: 20
<212> TYPE: DNA

```
<213> ORGANISM: Artificial Sequence
<220> FEATURE:
<223> OTHER INFORMATION: synthesized

<400> SEQUENCE: 1
tgatgctgtt ctctacgggg                                         20

<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2
agagagcttg gagcctgcta                                         20

<210> SEQ ID NO 3
<211> LENGTH: 20
<212> TYPE: DNA
<213> ORGANISM: Artificial Sequence
<220> FEATURE:
<223> OTHER INFORMATION: synthesized

<400> SEQUENCE: 3
gatcattgct cctcctgagc                                         20

<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
actcctgctt gctgatccac                                         20
```